United States Patent
Coronella et al.

(10) Patent No.: US 12,060,427 B2
(45) Date of Patent: *Aug. 13, 2024

(54) DRUG CONJUGATES OF CMET MONOCLONAL BINDING AGENTS, AND USES THEREOF

(71) Applicant: MITSUBISHI TANABE PHARMA CORPORATION, Osaka (JP)

(72) Inventors: Julia Coronella, Carlsbad, CA (US); Marco Gymnopoulos, San Diego, CA (US); Vincent Blot, Seattle, WA (US); Ryo Fujita, Osaka (JP); Roland Newman, San Diego, CA (US)

(73) Assignee: MITSUBISHI TANABE PHARMA CORPORAT, Osaka (JP)

( * ) Notice: Subject to any disclaimer, the term of this patent is extended or adjusted under 35 U.S.C. 154(b) by 771 days.

This patent is subject to a terminal disclaimer.

(21) Appl. No.: 17/042,013

(22) PCT Filed: Mar. 27, 2019

(86) PCT No.: PCT/JP2019/013345
§ 371 (c)(1),
(2) Date: Sep. 25, 2020

(87) PCT Pub. No.: WO2019/189453
PCT Pub. Date: Oct. 3, 2019

(65) Prior Publication Data
US 2021/0163604 A1 Jun. 3, 2021

Related U.S. Application Data

(60) Provisional application No. 62/649,078, filed on Mar. 28, 2018.

(51) Int. Cl.
| | |
|---|---|
| C07K 16/28 | (2006.01) |
| A61K 31/5517 | (2006.01) |
| A61K 39/00 | (2006.01) |
| A61K 47/64 | (2017.01) |
| A61P 35/00 | (2006.01) |

(52) U.S. Cl.
CPC ...... C07K 16/2863 (2013.01); A61K 31/5517 (2013.01); A61K 47/6415 (2017.08); A61P 35/00 (2018.01); A61K 2039/505 (2013.01)

(58) Field of Classification Search
CPC ............ C07K 16/2863; C07K 2317/24; C07K 2317/33; C07K 2317/92; A61K 31/5517; A61K 47/6415; A61K 2039/505; A61K 47/6849; A61K 47/6803; A61P 35/00
See application file for complete search history.

(56) References Cited

U.S. PATENT DOCUMENTS

| | | | |
|---|---|---|---|
| 5,225,539 A | 7/1993 | Winter | |
| 5,530,101 A | 6/1996 | Queen et al. | |
| 5,565,332 A | 10/1996 | Hoogenboom et al. | |
| 5,585,089 A | 12/1996 | Queen et al. | |
| 5,693,761 A | 12/1997 | Queen et al. | |
| 5,693,762 A | 12/1997 | Queen et al. | |
| 5,707,622 A | 1/1998 | Fong et al. | |
| 5,859,205 A | 1/1999 | Adair et al. | |
| 5,990,296 A | 11/1999 | Pastan et al. | |
| 5,994,524 A | 11/1999 | Matsushima et al. | |
| 6,072,035 A | 6/2000 | Hardman et al. | |
| 6,054,297 A | 8/2000 | Carter et al. | |
| 6,099,842 A | 8/2000 | Pastan et al. | |
| 6,180,370 B1 | 1/2001 | Queen et al. | |
| 6,245,894 B1 | 6/2001 | Matsushima et al. | |
| 8,293,972 B2 * | 10/2012 | Kav ................. | G01N 33/56961 800/278 |
| 8,697,688 B2 | 4/2014 | Howard et al. | |
| 9,242,013 B2 | 1/2016 | Howard et al. | |
| 11,130,821 B2 * | 9/2021 | Rittenhouse-Olson ..................... | A61P 35/04 |
| 11,299,547 B2 * | 4/2022 | Coronella ............... | A61P 35/04 |
| 2006/0264622 A1 | 11/2006 | Howard et al. | |
| 2007/0072846 A1 | 3/2007 | Vishnuvajjala et al. | |
| 2008/0167293 A1 | 7/2008 | Howard et al. | |
| 2009/0285807 A1 | 11/2009 | Comoglio et al. | |
| 2010/0113425 A1 | 5/2010 | Howard et al. | |
| 2011/0196148 A1 | 8/2011 | Howard et al. | |
| 2011/0201803 A1 | 8/2011 | Howard et al. | |
| 2011/0256157 A1 | 10/2011 | Howard et al. | |
| 2013/0028919 A1 | 1/2013 | Howard et al. | |
| 2013/0035484 A1 | 2/2013 | Howard et al. | |
| 2013/0059800 A1 | 3/2013 | Howard et al. | |
| 2013/0266595 A1 | 10/2013 | Flygare | |
| 2013/0274091 A1 | 10/2013 | Maparu et al. | |

(Continued)

FOREIGN PATENT DOCUMENTS

| | | |
|---|---|---|
| CN | 102014913 A | 4/2011 |
| CN | 107613974 A | 1/2018 |

(Continued)

OTHER PUBLICATIONS

Almagro et. al., Front. Immunol. 2018; 8:1751 (Year: 2018).*
Brown et al., J. Immunol., 1996 156(9):3285-91 (Year: 1996).*
Janeway, Immuno Biology The immune system in Health and Disease, 5th edition, 2001, section 7.8 (Year: 2001).*
Lydard et. al., Immunology, 2011, D3 Generation of Diversity pp. 76-85 (Year: 2011).*
Patent Cooperation Treaty, International Search Report issued in PCT/JP2019/013345, Jul. 2, 2019, pp. 1-3.
Patent Cooperation Treaty, International Preliminary Report on Patentability issued in PCT/JP2019/013345, Sep. 29, 2020, pp. 1-7.
Tiberghien et al., ACS Medicinal Chemistry Letters, 2016, pp. 983-987, vol. 7.

(Continued)

*Primary Examiner* — Julie Wu
*Assistant Examiner* — John J Skoko, III
(74) *Attorney, Agent, or Firm* — Pillsbury Winthrop Shaw Pittman LLP

(57) ABSTRACT

Presented herein are novel monoclonal cMET binding agents that are conjugated to pyrrolobenzodiazepine toxins, composition thereof and uses thereof for the treatment of cancer.

16 Claims, 54 Drawing Sheets

Specification includes a Sequence Listing.

(56) References Cited

U.S. PATENT DOCUMENTS

| | | |
|---|---|---|
| 2014/0088089 A1 | 3/2014 | Chari |
| 2014/0120118 A1 | 5/2014 | Howard |
| 2014/0127239 A1 | 5/2014 | Howard |
| 2014/0234346 A1 | 8/2014 | Howard |
| 2014/0274907 A1 | 9/2014 | Howard et al. |
| 2014/0275522 A1 | 9/2014 | Howard et al. |
| 2014/0286970 A1 | 9/2014 | Jeffrey et al. |
| 2014/0294868 A1 | 10/2014 | Howard et al. |
| 2014/0302066 A1 | 10/2014 | Jeffrey et al. |
| 2015/0071950 A1 | 3/2015 | Chae et al. |
| 2015/0110815 A1 | 4/2015 | Park et al. |
| 2015/0111880 A1 | 4/2015 | Howard et al. |
| 2015/0125474 A1 | 5/2015 | Smith et al. |
| 2015/0133435 A1 | 5/2015 | Howard et al. |
| 2015/0158869 A1 | 6/2015 | Howard |
| 2015/0209444 A1 | 7/2015 | Chari et al. |
| 2015/0250896 A1 | 9/2015 | Zhao |
| 2015/0315196 A1 | 11/2015 | Howard |
| 2015/0344482 A1 | 12/2015 | Howard |
| 2016/0015828 A1 | 1/2016 | Torgov et al. |
| 2016/0031887 A1 | 2/2016 | Howard |
| 2016/0106861 A1 | 4/2016 | Beau-Iarvor |
| 2016/0136300 A1 | 5/2016 | Kim et al. |
| 2016/0144052 A1 | 5/2016 | Howard et al. |
| 2016/0250344 A1 | 9/2016 | Howard et al. |
| 2016/0250345 A1 | 9/2016 | Howard et al. |
| 2016/0331842 A1 | 11/2016 | Bregeon et al. |
| 2017/0002096 A1 | 1/2017 | Kellogg et al. |
| 2017/0080103 A1 | 3/2017 | Ariaans |
| 2017/0095570 A1 | 4/2017 | Dragovich et al. |
| 2017/0152274 A1 | 6/2017 | Zhao et al. |
| 2017/0157264 A1 | 6/2017 | Chari et al. |
| 2017/0281796 A1 | 10/2017 | Zhu et al. |
| 2017/0348429 A1 | 12/2017 | Reilly et al. |
| 2018/0100021 A1* | 4/2018 | Blankenship ............ A61P 35/00 |
| 2018/0327500 A1 | 11/2018 | Bouquin et al. |

FOREIGN PATENT DOCUMENTS

| | | | |
|---|---|---|---|
| RU | 2613906 C2 | 3/2017 | |
| WO | 2007/090807 A1 | 8/2007 | |
| WO | 2009/111691 A2 | 11/2009 | |
| WO | 2012/153193 A2 | 11/2012 | |
| WO | 2014/057074 A1 | 4/2014 | |
| WO | 2014/057115 A1 | 4/2014 | |
| WO | WO-2014062659 A2 * | 4/2014 | ............ C07K 16/18 |
| WO | 2015/052322 A1 | 4/2015 | |
| WO | WO-2015052322 A1 * | 4/2015 | ......... A61K 31/5517 |
| WO | 2016/042412 A1 | 3/2016 | |
| WO | 2016/094455 A1 | 6/2016 | |
| WO | 2016/149265 A1 | 9/2016 | |
| WO | 2017/0137553 A1 | 8/2017 | |
| WO | 2017/137555 A1 | 8/2017 | |
| WO | 2017/186894 A1 | 11/2017 | |
| WO | 2017/201204 A1 | 11/2017 | |
| WO | WO-2017201204 A1 * | 11/2017 | ........... A61K 31/517 |
| WO | 2018/050733 A1 | 3/2018 | |
| WO | 2018/062402 A1 | 4/2018 | |

OTHER PUBLICATIONS

UniProtKB—P08581 (Met_Human), accessed on May 5, 2016, https://www.uniprot.org/uniprot/P08581, pp. 1-19.

Daugherty et al., Polymerase chain reaction facilitates the cloning, CDR-grafting, and rapid expression of a murine monoclonal antibody directed against the CD18 component of leukocyte integrins, Nucleic Acids Research, 1991, pp. 2471-2476, vol. 19(9).

Marks et al., By-passing Immunization Human Antibodies from V-gene Libraries Displayed on Phage, J. Mol Biol, 1991, pp. 581-597, vol. 222.

Edelman et al., The Covalent Structure of an Entire Gimmunoglobulin Molecule, PNAS, 1969, pp. 78-85, vol. 63.

Chothia et al., Canonical Structures for the Hypervariable Regions of Immunoglobulins, J. Mol. Biol., 1987, pp. 901-917, vol. 196.

Al-Lazikani et al., Standard Conformations for the Canonical Structures of Immunoglobulins, J. Mol. Biol., 1997, pp. 927-948, vol. 273.

Martin et al., Modeling antibody hypervariable loops: A combined algorithm, PNAS, Dec. 1989, pp. 9268-9272, vol. 86.

Samudrala et al., Ab Initio Protein Structure Prediction Using a Combined Hierarchical Approach, Proteins: Structure, Function, and Genetics Suppl, 1999, pp. 194-198, vol. 3.

Jones et al., Replacing the complementarity-determining regions in a human antibody with those from a mouse, Nature, May 29, 1986, pp. 522-525, vol. 321.

Winter, Synthetic human antibodies and a strategy for protein engineering, FEBS Letters, 1997, pp. 92-94, vol. 430.

Queen et al., A humanized antibody that binds to the interleukin 2 receptor, Proc. Natl. Acad. Sci., Dec. 1989, pp. 10029-10033, vol. 86.

Roguska et al., A comparison of two murine monoclonal antibodies humanized by CDR-grafting and variable domain resurfacing, Protein Engineering, 1996, pp. 895-904, vol. 9(10).

Gilliland et al., Elimination of the Immunogenicity of Therapeutic Antibodies, J Immunol, 1999, pp. 3663-3671, vol. 162.

Portolano et al., "Lack of promiscuity in autoantigen-specific H and L chain combinations as revealed by human H and L chain "roulette"", The Journal of Immunology, 1993, pp. 880-887, vol. 150.

Clackson et al., "Making antibody fragments using phage display libraries", Nature, Aug. 15, 1991, pp. 624-628, vol. 352.

European Patent Office, Extended European Search Report issued in EP Patent Application No. 19775335.3, Dec. 1, 2021, pp. 1-9.

Jeffrey et al., "A Potent Anti-CD70 Antibody-Drug Conjugate Combining a Dimeric Pyrrolobenzodiazepine Drug with Site-Specific Conjugation Technology", Bioconjugate Chemistry, 2013, pp. 1256-1263, vol. 24.

Tiberghien et al., "Design and Synthesis of Tesirine, a Clinical Antibody-Drug Conjugate Pyrrolobenzodiazepine Dimer Payload", ACS Medicinal Chemistry Letters, 2016, pp. 983-987, vol. 7.

Linking Group, Academician, Scientific and technical encyclopedic dictionary, accessed at https://dic.academic.ru/dic.nsf/ntes/4202/%D0%A1%D0%92%D0%AF%D0%97%D0%AB%D0%92%D0%90%D0%AE%D0%A9%D0%90%D0%AF, 2000-2022, pp. 1-2, Machine English translation.

* cited by examiner

②

| PLATE 3 | | | |
|---|---|---|---|
| Well name | Description | FACS Geom. Mean | MET BINDING ELISA OD450nm |
| Well_E01.fcs | negative control | 103000 | NA |
| Well_F01.fcs | negative control | 116000 | NA |
| Well_A01.fcs | positive control | 83500 | NA |
| Well_B01.fcs | positive control | 81800 | NA |
| Well_E09.fcs | hybridoma | 61000 | 4.5319 |
| Well_D12.fcs | hybridoma | 67200 | 4.3803 |
| Well_E02.fcs | hybridoma | 69800 | 4.596 |
| Well_F04.fcs | hybridoma | 77300 | 3.0801 |
| Well_B10.fcs | hybridoma | 97200 | 0.0211 |
| Well_H06.fcs | hybridoma | 97600 | 6.1209 |
| Well_F06.fcs | hybridoma | 97800 | -0.0005 |
| Well_G10.fcs | hybridoma | 98800 | 0.0078 |
| Well_E07.fcs | hybridoma | 98900 | 0.0011 |
| Well_H10.fcs | hybridoma | 98900 | 1.7238 |
| Well_E06.fcs | hybridoma | 99300 | 5.2925 |
| Well_F10.fcs | hybridoma | 99700 | 0.0185 |
| Well_F07.fcs | hybridoma | 99800 | 0.235 |

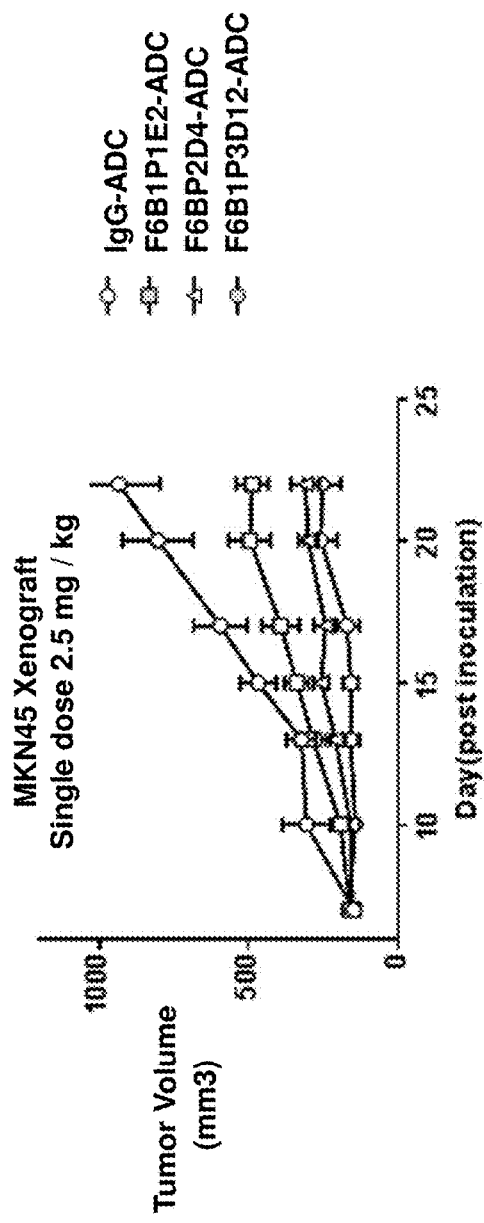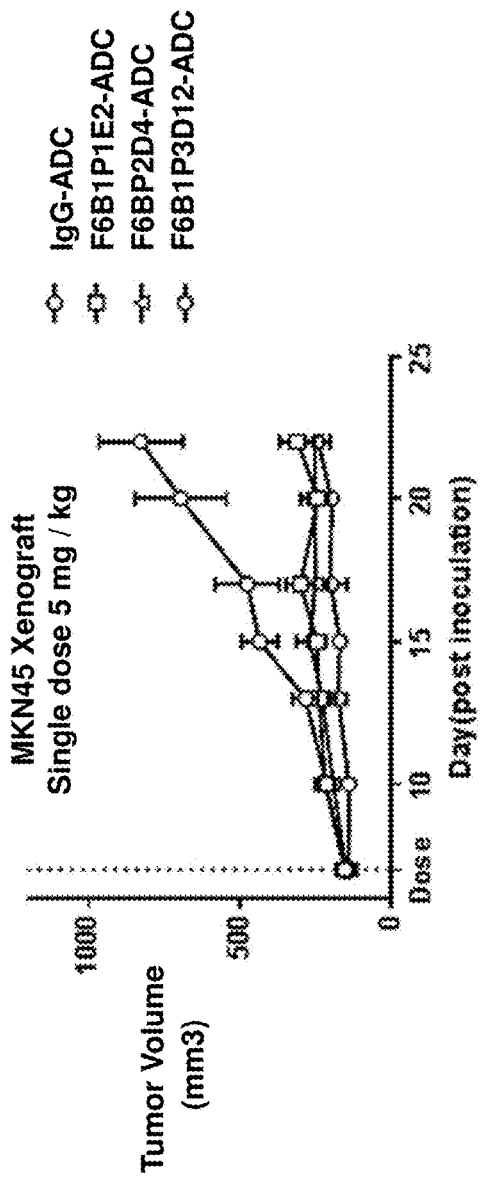
Fig. 9A
Fig. 9B

HUMANIZED LIGHT CHAIN VARIABLE REGIONS

```
SEQ ID NO:      1                                                          50
P3D12 VL        45  (1)    QIVLTQSPAINSASPGEKVTLTCSASSSVTSNYLYWYQQRPGSSPKLWIY
P3D12 VL-ven    46  (1)    QIVLTQSPATMSASPGERVTLSCSASSSVTSNYLYWYQQRPGSSPKLWIY
P3D12 VL-fra    47  (1)    QIVLTQSPAILSISPGERATLSCSASSSVTSNYLYWYQQRPGSSPKLLIY
P3D12 VL-abb/sdr 48 (1)    QIVLTQSPATLSLSPGERATLSCRASQSVTSNYLYWYQQRPGSSPRLLIY
P3D12 VL-cdr    49  (1)    QIVLTQSPATLSLSPGERATLSCSASSSVTSNYLYWYQQRPGSSPRLLIY 51                                                         100
P3D12 VL        (51)   STSNLASGVPARFSGSGSGTSYSLTISSMEAEDAASYFCHQWSSYPPTFG
P3D12 VL-ven    (51)   STSNLASGVPARFSGSGSGTSYTLTISRMEPEDAASYFCHQWSSYPPTFG
P3D12 VL-fra    (51)   STSNLASGVPARFSGSGSGTSYTLTISSLEAEDAASYFCHQWSSYPPTFG
P3D12 VL-abb/sdr (51)  STSNLASGVPARFSGSGSGTDYTLTISRLEPEDFASYFCHQWSSYPPTFG
P3D12 VL-cdr    (51)   STSNLASGVPARFSGSGSGTDYTLTISRLEPEDFASYFCHQWSSYPPTFG 101
P3D12 VL        (101)  SGTKLEIKR
P3D12 VL-ven    (101)  SGTKLEIKR
P3D12 VL-fra    (101)  SGTKLEIKR
P3D12 VL-abb/sdr (101) SGTKLEIKR
P3D12 VL-cdr    (101)  SGTKLEIKR
```

FIG. 13

HUMANIZED HEAVY CHAIN VARIABLE REGIONS

③

```
SEQ ID NO:       1                                                          50
    p3D12 VH 104 (1)    QVQLQQSGAELARPGASVKMSCKASGYTFTSYWMHWVKQRPGQGLDWIGY
p3D12 VH-fra 105 (1)    QVQLQQSGAEVKRPGASVKVSCKASGYTFTSYWMHWVKQRPGQGLDWIGY
p3D12 VH-ven 106 (1)    QVQLVQSGAEVAKPGASVKMSCKASGYTFTSYWMHWVKQAPGQGLDWIGY
p3D12 VH-abb/sdr 107 (1) QVQLVQSGAEVKKPGASVKVSCKASGYTFTSYWMHWVKQAPGQGLDWMGY
p3D12 VH-cdr 108 (1)    QVQLVQSGAEVKKPGASVKVSCKASGYTFTSYWMHWVKQAPGQGLDWIGY
                        51                                                  100
         p3D12 VH  (51)  IKPSTDNTEYNQKFKDKATLTADKSSSTAYMQLSSLTSEDSAVYYCARSY
     p3D12 VH-fra (51)  IKPSTDNTEYNQKFKDRVTLTADKSTSTAYMQLSNLISEDTAVYYCARSY
     p3D12 VH-ven (51)  IKPSTDNTEYNQKFKDKATITALKSTSTAYMQLSSIRSEDTAVYYCARSY
 p3D12 VH-abb/sdr (51)  IKPSTDNTEYAQKFQGRVTLTADKSTSTAYMELSSLRSEDTAVYYCARSY
     p3D12 VH-cdr (51)  IKPSTDNTEYNQKFKDRATLTADKSTSTAYMELSSLRSEDTAVYYCARSY
                        101         119
         p3D12 VH  (101) GNYPLMDYWGQGTSVTVSS
     p3D12 VH-fra (101) GNYPLMDYWGQGTSVTVSS
     p3D12 VH-ven (101) GNYPLMDYWGQGTTVTVSS
 p3D12 VH-abb/sdr (101) GNYPLMDYWGQGTTVTVSS
     p3D12 VH-cdr (101) GNYPLMDYWGQGTTVTVSS
```

FIG. 14

| Antibody | hD12 | hD12 | hD12 | hD12 | hD12 |
|---|---|---|---|---|---|
| Payload | VI | II | VII | IV | XI |
| SNU-1 | Max %kill / IC50 (uM) | 19% / --- | 47% / --- | 39% / --- | 3% / --- | 52% / --- |
| SNU-16 | Max %kill / IC50 (uM) | 76% / 27.3 | 80% / 30.9 | 81% / 9.0 | 78% / 58.7 | 86% / 13.5 |
| SNU-620 | Max %kill / IC50 (uM) | 84% / 338.4 | 90% / 174.8 | 89% / 363.5 | 81% / 326.6 | 80% / 405.9 |
| MKN-45 | Max %kill / IC50 (uM) | 74% / 47.7.9 | 77% / 86.9 | 81% / 64.2 | 71% / 72.2 | 73% / 82.0 |
| | Ave DAR (HIC): | 1.82 | 1.98 | 0.84 | 1.88 | 2.99 |
| | DAR 0% (HIC): | 35.82% | 23.25% | 58.02% | 23.95% | 5.88% |
| | Free Drug (RP): | 1.61% | 0.71% | 1.89-1.98% | N/A | N/A |

FIG. 18E

| Antibody | Payload | hD12 VI | hD12 II | hD12 VII | hD12 IV | Denosumab XI |
|---|---|---|---|---|---|---|
| H441 | Max %kill / IC50 (uM) | 58% / 1.3 | 68% / 3.8 | 63% / 2.1 | 43% / 38.5 | 54% / 8.0 |
| H1373 | Max %kill / IC50 (uM) | 47% / 16.7 | 68% / 35.6 | 75% / 42.66 | 35% / 19.7 | 68% / --- |
| H1573 | Max %kill / IC50 (uM) | 16% / 2.0 | 50% / 8.7 | 47% / 49.5 | 4% / 14.4 | 29% / 6.2 |
| H1975 | Max %kill / IC50 (uM) | 64% / 111.8 | 81% / 311.1 | 94% / 33.8 | 50% / 174.3 | 82% / 622.9 |
| SNU-5 | Max %kill / IC50 (uM) | 81% / 17.1 | 83% / 22.4 | 84% / 5.9 | 76% / 30.5 | 77% / 22.3 |
| | Ave DAR (HIC): | 1.82 | 1.98 | 0.84 | 1.88 | 2.99 |
| | DAR 0% (HIC): | 35.82% | 23.25% | 58.02% | 23.95% | 5.88% |
| | Free Drug (RP): | 1.61% | 0.71% | 1.89-1.98% | N/A | N/A |

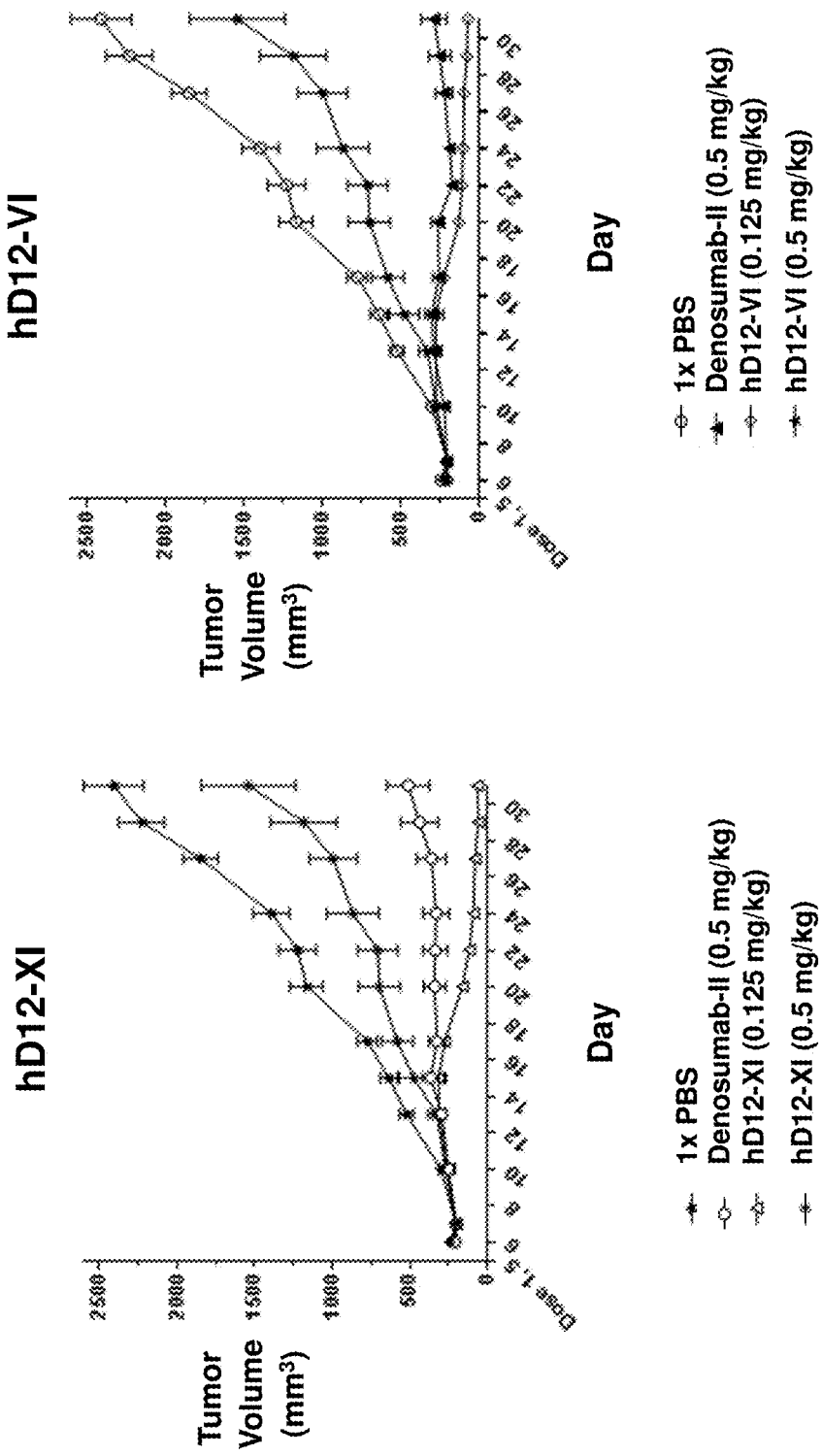

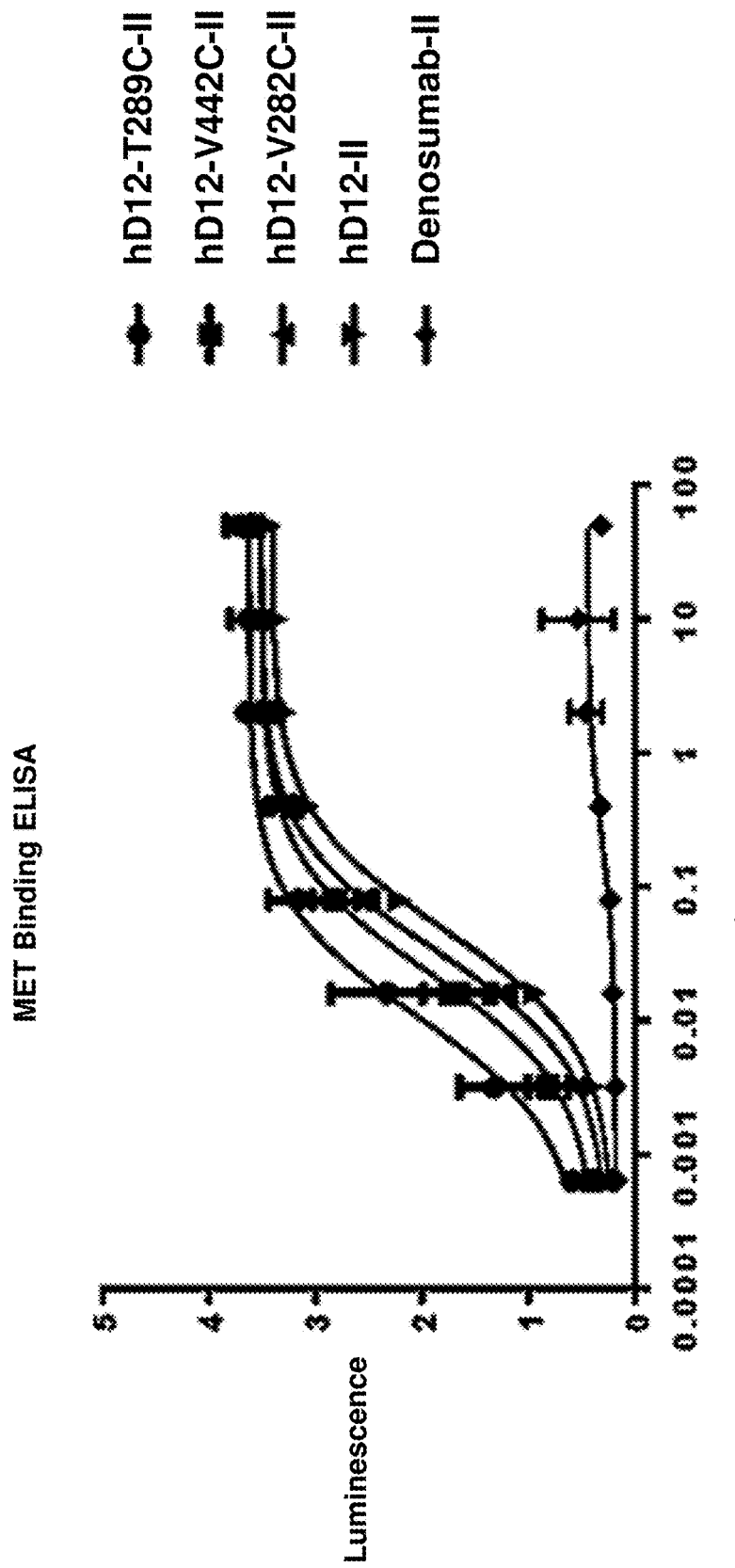

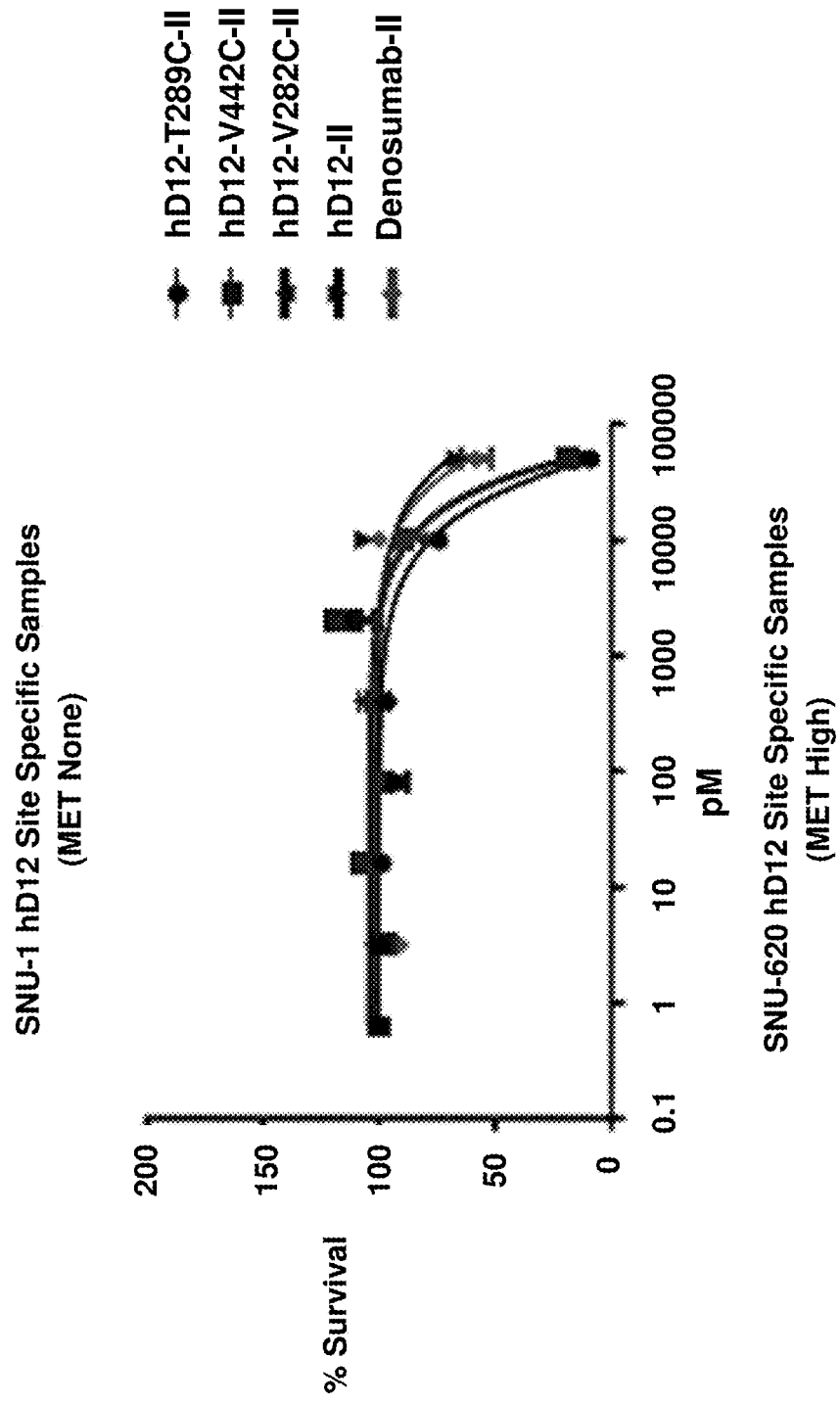

| Antibody | | hD12 | hD12 | hD12 | hD12 | hD12 | Denosumab |
|---|---|---|---|---|---|---|---|
| | | T289C | V442C | V282C | | Vc-PBD | Vc-PBD |
| | Payload | = | = | = | | = | = |
| SNU-1 | Max %kill / IC50 (uM) | 91% / --- | 81% / --- | 84% / --- | | 33% / --- | 42% / --- |
| SNU-16 | Max %kill / IC50 (uM) | 95% / 100.3 | 94% / 91.9 | 95% / 140.9 | | 90% / 51.6 | 80% / --- |
| SNU-620 | Max %kill / IC50 (uM) | 99% / 122.9 | 99% / 116.3 | 99% / 123.7 | | 98% / 155.1 | 5% / --- |
| MKN-45 | Max %kill / IC50 (uM) | 99% / 34.9 | 99% / 46.6 | 99% / 54.5 | | 96% / 72.9 | 36% / --- |
| N87 | Max %kill / IC50 (uM) | 96% / 440.0 | 96% / 518.3 | 97% / 472.2 | | 86% / 979.8 | 86% / --- |
| | DAR: | 2 | 2 | 2 | | | |
| | Ave DAR (HIC): | --- | --- | --- | | 1.98 | 2.31 |
| | DAR 0% (HIC): | --- | --- | --- | | 23.25% | 5.88% |
| | Free Drug (RP): | --- | --- | --- | | 0.71% | 0.43% |
| | Batch #: | SPADC3118.01 | SPADC3117.01 | SPADC3119.01 | | SG3249.019 | SG3249.019 |

FIG. 25F

| pM |
|---|
| 50000 |
| 10000 |
| 2000 |
| 400 |
| 80 |
| 16 |
| 3.2 |
| 0.64 |

FIG. 25G

| Antibody | hD12 | hD12 | hD12 | hD12 | Denosumab |
|---|---|---|---|---|---|
| | T289C | V442C | V282C | | |
| Payload | Vc-PBD | Vc-PBD | Vc-PBD | Vc-PBD | Vc-PBD |
| N87 | Max %kill / IC50 (uM) | 90% / --- | 90% / --- | 92% / --- | 71% / --- | 71% / --- |
| SNU-5 | Max %kill / IC50 (uM) | 94% / 5.1 | 88% / 13.5 | 93% / 4.5 | 93% / 9.8 | 72% / --- |
| DAR: | 2 | 2 | 2 | | |
| Ave DAR (HIC): | --- | --- | --- | 1.98 | 2.31 |
| DAR 0% (HIC): | --- | --- | --- | 23.25% | 5.88% |
| Free Drug (RP): | --- | --- | --- | 0.71% | 0.43% |
| Batch #: | SPADC3118.01 | SPADC3117.01 | SPADC3119.01 | SG3249.019 | SG3249.019 |

| pM |
|---|
| 50000 |
| 10000 |
| 2000 |
| 400 |
| 80 |
| 16 |
| 3.2 |
| 0.64 |

FIG. 27D

| | pM |
|---|---|
| | 50000 |
| | 10000 |
| | 2000 |
| | 400 |
| | 80 |
| | 16 |
| | 3.2 |
| | 0.64 |

FIG. 27E

| Antibody | hD12 | hD12 | hD12 | hD12 | Denosumab |
|---|---|---|---|---|---|
| | T289C | V442C | V282C | Vc-PBD | Vc-PBD |
| Payload | = | = | = | = | = |
| H1373 Max %kill / IC50 (uM) | 98% / --- | 96% / --- | 97% / 65.0 | 77% / 17.9 | 72% / --- |
| H1573 Max %kill / IC50 (uM) | 89% / --- | 88% / --- | 91% / --- | 69% / 18.3 | 53% / --- |
| H1975 Max %kill / IC50 (uM) | 98% / 23.9 | 97% / 27.8 | 98% / 41.5 | 87% / 49.2 | 78% / --- |
| DAR: | 2 | 2 | 2 | | |
| Ave DAR (HIC): | --- | --- | --- | 1.98 | 2.31 |
| DAR 0% (HIC): | --- | --- | --- | 23.25% | 5.88% |
| Free Drug (RP): | --- | --- | --- | 0.71% | 0.43% |
| Batch #: | SPADC3118.01 | SPADC3117.01 | SPADC3119.01 | SG3249.019 | SG3249.019 |

| Test article | T ½ (hours) | AUC_LAST (µg x h/ml) | CL_F_OBS (ml/h/kg) | $C_{max}$ (µg/ml) |
|---|---|---|---|---|
| hD12-V282C-II 1 mg/kg | 273.5 (11.4d) | 3777 | 0.0007 | 32.9 |
| hD12-T289C-II 1 mg/kg | 431.6 (18d) | 3152 | 0.0007 | 34.9 |
| hD12-V442C-II 1 mg/kg | 337.0 (14d) | 3712 | 0.0007 | 32.1 |

FIG. 31

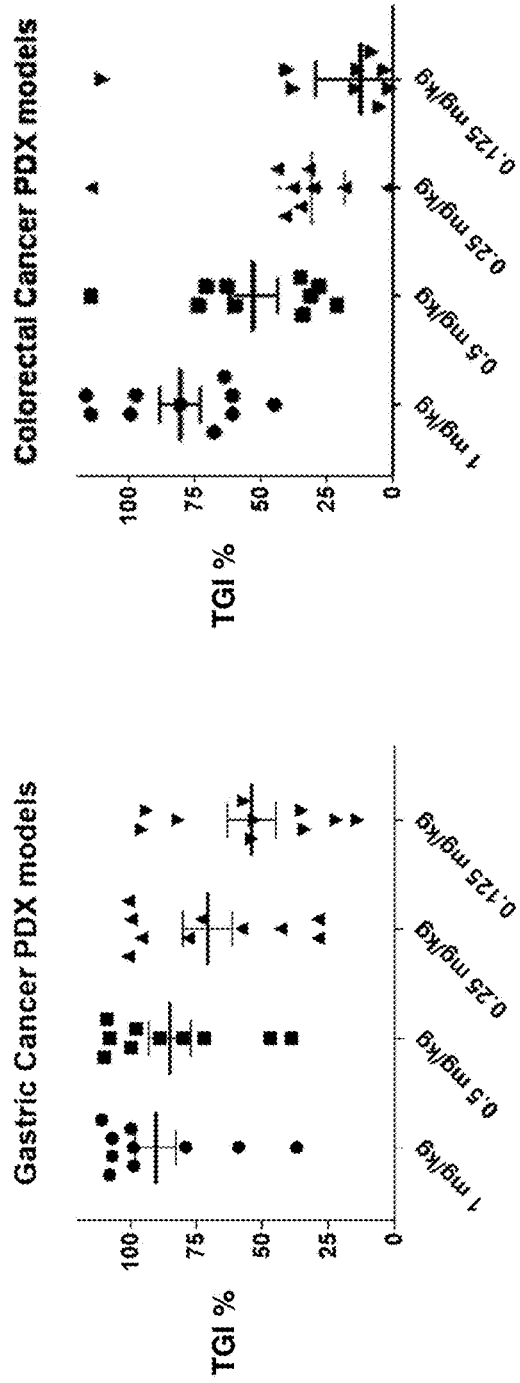
FIG. 32A
FIG. 32B
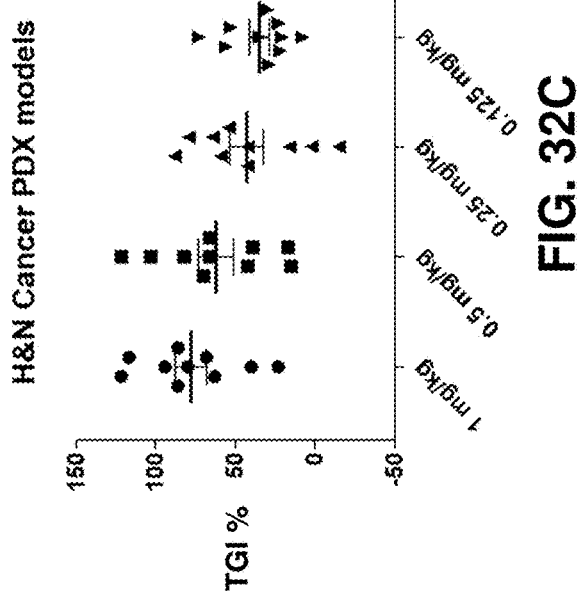
FIG. 32C

```
                            SEQUENCE LISTING

<160> NUMBER OF SEQ ID NOS: 116

<210> SEQ ID NO 1
    <211> LENGTH: 16
    <212> TYPE: PRT
    <213> ORGANISM: Mus musculus

<400> SEQUENCE: 1

Arg Ser Ser Gln Thr Ile Val His Gly Thr Gly Asn Thr Tyr Leu Glu
    1               5                   10                  15

<210> SEQ ID NO 2
    <211> LENGTH: 11
    <212> TYPE: PRT
    <213> ORGANISM: Mus musculus

<400> SEQUENCE: 2

Gln Thr Ile Val His Gly Thr Gly Asn Thr Tyr
    1               5                   10

<210> SEQ ID NO 3
    <211> LENGTH: 11
    <212> TYPE: PRT
    <213> ORGANISM: Mus musculus

<400> SEQUENCE: 3

Lys Ala Ser Glu Asn Val Gly Thr Tyr Val Ser
    1               5                   10

<210> SEQ ID NO 4
    <211> LENGTH: 6
    <212> TYPE: PRT
    <213> ORGANISM: Mus musculus

<400> SEQUENCE: 4

Glu Asn Val Gly Thr Tyr
    1               5

<210> SEQ ID NO 5
    <211> LENGTH: 17
    <212> TYPE: PRT
    <213> ORGANISM: Mus musculus

<400> SEQUENCE: 5
```

Arg Ser Ser Gln Ser Leu Leu Tyr Ser Ile Asn Gln Lys Asn Tyr Leu
1               5                   10                  15
Ala

<210> SEQ ID NO 6
<211> LENGTH: 12
<212> TYPE: PRT
<213> ORGANISM: Mus musculus

<400> SEQUENCE: 6

Gln Ser Leu Leu Tyr Ser Ile Asn Gln Lys Asn Tyr
1               5                   10

<210> SEQ ID NO 7
<211> LENGTH: 11
<212> TYPE: PRT
<213> ORGANISM: Mus musculus

<400> SEQUENCE: 7

Arg Ala Ser Glu Asn Ile Tyr Asn Thr Leu Ala
1               5                   10

<210> SEQ ID NO 8
<211> LENGTH: 6
<212> TYPE: PRT
<213> ORGANISM: Mus musculus

<400> SEQUENCE: 8

Glu Asn Ile Tyr Asn Thr
1               5

<210> SEQ ID NO 9
<211> LENGTH: 12
<212> TYPE: PRT
<213> ORGANISM: Mus musculus

<400> SEQUENCE: 9

Ser Ala Ser Ser Ser Val Thr Ser Asn Tyr Leu Tyr
1               5                   10

<210> SEQ ID NO 10
<211> LENGTH: 7
<212> TYPE: PRT
<213> ORGANISM: Mus musculus

<400> SEQUENCE: 10

Ser Ser Val Thr Ser Asn Tyr
1               5

<210> SEQ ID NO 11
<211> LENGTH: 12
<212> TYPE: PRT
<213> ORGANISM: Mus musculus

<400> SEQUENCE: 11

Ser Ala Ser Ser Ser Val Ser Ser Asn Tyr Leu Tyr
1               5                   10

<210> SEQ ID NO 12
<211> LENGTH: 7
<212> TYPE: PRT
<213> ORGANISM: Mus musculus

<400> SEQUENCE: 12

```
Ser Ser Val Ser Ser Asn Tyr
1               5

<210> SEQ ID NO 13
<211> LENGTH: 12
<212> TYPE: PRT
<213> ORGANISM: Mus musculus
<220> FEATURE:
<221> NAME/KEY: misc_feature
<222> LOCATION: (7)..(7)
<223> OTHER INFORMATION: X is S or T

<400> SEQUENCE: 13

Ser Ala Ser Ser Ser Val Xaa Ser Asn Tyr Leu Tyr
1               5                   10

<210> SEQ ID NO 14
<211> LENGTH: 7
<212> TYPE: PRT
<213> ORGANISM: Mus musculus

<400> SEQUENCE: 14

Gln Ser Val Thr Ser Asn Tyr
1               5

<210> SEQ ID NO 15
<211> LENGTH: 12
<212> TYPE: PRT
<213> ORGANISM: Mus musculus

<400> SEQUENCE: 15

Arg Ala Ser Gln Ser Val Thr Ser Asn Tyr Leu Tyr
1               5                   10

<210> SEQ ID NO 16
<211> LENGTH: 7
<212> TYPE: PRT
<213> ORGANISM: Mus musculus

<400> SEQUENCE: 16

Lys Val Ser Asn Arg Phe Ser
1               5

<210> SEQ ID NO 17
<400> SEQUENCE: 17

000

<210> SEQ ID NO 18
<211> LENGTH: 7
<212> TYPE: PRT
<213> ORGANISM: Mus musculus

<400> SEQUENCE: 18

Gly Ala Ser Asn Arg Tyr Thr
1               5

<210> SEQ ID NO 19
<400> SEQUENCE: 19

000

<210> SEQ ID NO 20
<211> LENGTH: 7
```

```
<212> TYPE: PRT
<213> ORGANISM: Mus musculus

<400> SEQUENCE: 20

Trp Ala Ser Thr Arg Glu Ser
1               5

<210> SEQ ID NO 21

<400> SEQUENCE: 21

000

<210> SEQ ID NO 22
<211> LENGTH: 7
<212> TYPE: PRT
<213> ORGANISM: Mus musculus

<400> SEQUENCE: 22

Ala Ala Thr Asn Leu Ala Asp
1               5

<210> SEQ ID NO 23

<400> SEQUENCE: 23

000

<210> SEQ ID NO 24
<211> LENGTH: 7
<212> TYPE: PRT
<213> ORGANISM: Mus musculus

<400> SEQUENCE: 24

Ser Thr Ser Asn Leu Ala Ser
1               5

<210> SEQ ID NO 25

<400> SEQUENCE: 25

000

<210> SEQ ID NO 26
<211> LENGTH: 20
<212> TYPE: PRT
<213> ORGANISM: Mus musculus

<400> SEQUENCE: 26

Phe Gln Gly Ser His Val Pro Tyr Thr Phe Gly Gly Gly Thr Lys Leu
1               5                   10                  15

Glu Ile Lys Arg
            20

<210> SEQ ID NO 27
<211> LENGTH: 9
<212> TYPE: PRT
<213> ORGANISM: Mus musculus

<400> SEQUENCE: 27

Phe Gln Gly Ser His Val Pro Tyr Thr
1               5

<210> SEQ ID NO 28
<211> LENGTH: 20
```

```
<212> TYPE: PRT
<213> ORGANISM: Mus musculus

<400> SEQUENCE: 28

Gly Gln Ser Tyr Ser Tyr Pro Leu Thr Phe Gly Ala Gly Thr Lys Leu
1               5                   10                  15

Glu Leu Lys Arg
            20

<210> SEQ ID NO 29
<211> LENGTH: 9
<212> TYPE: PRT
<213> ORGANISM: Mus musculus

<400> SEQUENCE: 29

Gly Gln Ser Tyr Ser Tyr Pro Leu Thr
1               5

<210> SEQ ID NO 30
<211> LENGTH: 19
<212> TYPE: PRT
<213> ORGANISM: Mus musculus

<400> SEQUENCE: 30

Gln Gln Tyr Tyr Thr Tyr Pro Leu Thr Phe Gly Ala Gly Thr Lys Leu
1               5                   10                  15

Glu Leu Lys

<210> SEQ ID NO 31
<211> LENGTH: 9
<212> TYPE: PRT
<213> ORGANISM: Mus musculus

<400> SEQUENCE: 31

Gln Gln Tyr Tyr Thr Tyr Pro Leu Thr
1               5

<210> SEQ ID NO 32
<211> LENGTH: 19
<212> TYPE: PRT
<213> ORGANISM: Mus musculus

<400> SEQUENCE: 32

Gln His Phe Trp Gly Thr Pro Tyr Thr Phe Gly Gly Gly Thr Lys Leu
1               5                   10                  15

Glu Ile Lys

<210> SEQ ID NO 33
<211> LENGTH: 9
<212> TYPE: PRT
<213> ORGANISM: Mus musculus

<400> SEQUENCE: 33

Gln His Phe Trp Gly Thr Pro Tyr Thr
1               5

<210> SEQ ID NO 34
<211> LENGTH: 19
<212> TYPE: PRT
<213> ORGANISM: Mus musculus

<400> SEQUENCE: 34

His Gln Trp Ser Ser Tyr Pro Pro Thr Phe Gly Ser Gly Thr Lys Leu
```

Glu Ile Lys

<210> SEQ ID NO 35
<211> LENGTH: 9
<212> TYPE: PRT
<213> ORGANISM: Mus musculus

<400> SEQUENCE: 35

His Gln Trp Ser Ser Tyr Pro Pro Thr
1               5

<210> SEQ ID NO 36
<211> LENGTH: 9
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa is His, Gln or Gly
<220> FEATURE:
<221> NAME/KEY: misc_feature
<222> LOCATION: (3)..(3)
<223> OTHER INFORMATION: Xaa is Trp, Ser or Tyr
<220> FEATURE:
<221> NAME/KEY: misc_feature
<222> LOCATION: (4)..(4)
<223> OTHER INFORMATION: Xaa is Ser or Tyr
<220> FEATURE:
<221> NAME/KEY: misc_feature
<222> LOCATION: (5)..(5)
<223> OTHER INFORMATION: Xaa is Ser or Thr
<220> FEATURE:
<221> NAME/KEY: misc_feature
<222> LOCATION: (8)..(8)
<223> OTHER INFORMATION: Xaa is Pro or Leu

<400> SEQUENCE: 36

Xaa Gln Xaa Xaa Xaa Tyr Pro Xaa Thr
1               5

<210> SEQ ID NO 37
<211> LENGTH: 113
<212> TYPE: PRT
<213> ORGANISM: Mus musculus

<400> SEQUENCE: 37

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Gly
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg

<210> SEQ ID NO 38

```
<211> LENGTH: 108
<212> TYPE: PRT
<213> ORGANISM: Mus musculus

<400> SEQUENCE: 38

Asp Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Asp Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Leu
                85                  90                  95

Thr Phe Gly Ala Gly Thr Lys Leu Glu Leu Lys Arg
            100                 105

<210> SEQ ID NO 39
<211> LENGTH: 114
<212> TYPE: PRT
<213> ORGANISM: Mus musculus

<400> SEQUENCE: 39

Asp Ile Val Met Ser Gln Ser Pro Ser Ser Leu Ala Val Ser Val Gly
1               5                   10                  15

Glu Lys Val Thr Met Ser Cys Arg Ser Ser Gln Ser Leu Leu Tyr Ser
            20                  25                  30

Ile Asn Gln Lys Asn Tyr Leu Ala Trp Tyr Gln Gln Ile Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Arg Val Lys Ala Glu Asp Leu Ala Leu Tyr Tyr Cys Gln Gln
                85                  90                  95

Tyr Tyr Thr Tyr Pro Leu Thr Phe Gly Ala Gly Thr Lys Leu Glu Leu
            100                 105                 110

Lys Arg

<210> SEQ ID NO 40
<211> LENGTH: 110
<212> TYPE: PRT
<213> ORGANISM: Mus musculus

<400> SEQUENCE: 40

Arg Cys Asp Ile Gln Met Thr Gln Ser Pro Ala Ser Leu Ser Val Ser
1               5                   10                  15

Val Gly Glu Thr Val Thr Ile Thr Cys Arg Ala Ser Glu Asn Ile Tyr
            20                  25                  30

Asn Thr Leu Ala Trp Tyr Leu Gln Lys Gln Gly Lys Ser Pro Gln Leu
        35                  40                  45

Leu Val Tyr Ala Ala Thr Asn Leu Ala Asp Gly Val Pro Ser Arg Phe
    50                  55                  60

Ser Gly Ser Gly Ser Gly Thr Gln Tyr Ser Leu Lys Ile Asn Ser Leu
```

```
                65                  70                  75                  80
Gln Ser Glu Asp Phe Gly Ser Tyr Tyr Cys Gln His Phe Trp Gly Thr
                85                  90                  95
Pro Tyr Thr Phe Gly Gly Gly Thr Lys Leu Glu Ile Lys Arg
            100                 105                 110
```

<210> SEQ ID NO 41
<211> LENGTH: 109
<212> TYPE: PRT
<213> ORGANISM: Mus musculus

<400> SEQUENCE: 41

```
Gln Ile Val Leu Thr Gln Ser Pro Ala Ile Met Ser Ala Ser Pro Gly
1               5                   10                  15
Glu Lys Val Thr Leu Thr Cys Ser Ala Ser Ser Val Thr Ser Asn
                20                  25                  30
Tyr Leu Tyr Trp Tyr Gln Gln Lys Pro Gly Ser Ser Pro Lys Leu Trp
                35                  40                  45
Ile Tyr Ser Thr Ser Asn Leu Ala Ser Gly Val Pro Ala Arg Phe Ser
            50                  55                  60
Gly Ser Gly Ser Gly Thr Ser Tyr Ser Leu Thr Ile Ser Ser Met Glu
65                  70                  75                  80
Ala Glu Asp Ala Ala Ser Tyr Phe Cys His Gln Trp Ser Ser Tyr Pro
                85                  90                  95
Pro Thr Phe Gly Ser Gly Thr Lys Leu Glu Ile Lys Arg
            100                 105
```

<210> SEQ ID NO 42
<211> LENGTH: 109
<212> TYPE: PRT
<213> ORGANISM: Mus musculus

<400> SEQUENCE: 42

```
Gln Ile Val Leu Thr Gln Ser Pro Ala Ile Met Ser Ala Ser Pro Gly
1               5                   10                  15
Glu Lys Val Thr Leu Thr Cys Ser Ala Ser Ser Ser Val Ser Ser Asn
                20                  25                  30
Tyr Leu Tyr Trp Tyr Gln Gln Lys Pro Gly Ser Ser Pro Lys Leu Trp
                35                  40                  45
Ile Tyr Ser Thr Ser Asn Leu Ala Ser Gly Val Pro Val Arg Phe Ser
            50                  55                  60
Gly Ser Gly Ser Gly Thr Ser Tyr Ser Leu Thr Ile Ser Ser Met Glu
65                  70                  75                  80
Ala Glu Asp Ala Ala Ser Tyr Phe Cys His Gln Trp Ser Ser Tyr Pro
                85                  90                  95
Pro Thr Phe Gly Ser Gly Thr Lys Leu Glu Ile Lys Arg
            100                 105
```

<210> SEQ ID NO 43
<211> LENGTH: 109
<212> TYPE: PRT
<213> ORGANISM: Mus musculus

<400> SEQUENCE: 43

```
Gln Ile Val Leu Thr Gln Ser Pro Ala Ile Met Ser Ala Ser Pro Gly
1               5                   10                  15
Glu Lys Val Thr Leu Thr Cys Ser Ala Ser Ser Ser Val Ser Ser Asn
                20                  25                  30
```

Tyr Leu Tyr Trp Tyr His Gln Lys Pro Gly Ser Ser Pro Lys Leu Trp
            35                  40                  45

Ile Tyr Ser Thr Ser Asn Leu Ala Ser Gly Val Pro Val Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Ser Tyr Phe Cys His Gln Trp Ser Ser Tyr Pro
                    85                  90                  95

Pro Thr Phe Gly Ser Gly Thr Lys Leu Glu Ile Lys Arg
                100                 105

<210> SEQ ID NO 44
<211> LENGTH: 108
<212> TYPE: PRT
<213> ORGANISM: Mus musculus
<220> FEATURE:
<221> NAME/KEY: MISC_FEATURE
<222> LOCATION: (38)..(38)
<223> OTHER INFORMATION: Xaa is His or Gln
<220> FEATURE:
<221> NAME/KEY: MISC_FEATURE
<222> LOCATION: (61)..(61)
<223> OTHER INFORMATION: Xaa is Ala or Arg

<400> SEQUENCE: 44

Gln Ile Val Leu Thr Gln Ser Pro Ala Ile Met Ser Ala Ser Pro Gly
 1               5                  10                  15

Glu Lys Val Thr Leu Thr Cys Ser Ala Ser Ser Ser Val Ser Ser Asn
                20                  25                  30

Tyr Leu Tyr Trp Tyr Xaa Gln Lys Pro Gly Ser Ser Pro Lys Leu Trp
            35                  40                  45

Ile Tyr Ser Thr Ser Asn Leu Ala Ser Gly Val Pro Xaa Phe Ser Gly
 50                  55                  60

Ser Gly Ser Gly Thr Ser Tyr Ser Leu Thr Ile Ser Ser Met Glu Ala
 65                  70                  75                  80

Glu Asp Ala Ala Ser Tyr Phe Cys His Gln Trp Ser Ser Tyr Pro Pro
                85                  90                  95

Thr Phe Gly Ser Gly Thr Lys Leu Glu Ile Lys Arg
            100                 105

<210> SEQ ID NO 45
<211> LENGTH: 109
<212> TYPE: PRT
<213> ORGANISM: Artificial Sequence
<220> FEATURE:
<223> OTHER INFORMATION: Humanized Light Chain

<400> SEQUENCE: 45

Gln Ile Val Leu Thr Gln Ser Pro Ala Ile Met Ser Ala Ser Pro Gly
 1               5                  10                  15

Glu Lys Val Thr Leu Thr Cys Ser Ala Ser Ser Ser Val Thr Ser Asn
                20                  25                  30

Tyr Leu Tyr Trp Tyr Gln Gln Lys Pro Gly Ser Ser Pro Lys Leu Trp
            35                  40                  45

Ile Tyr Ser Thr Ser Asn Leu Ala Ser Gly Val Pro Ala Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Ser Tyr Phe Cys His Gln Trp Ser Ser Tyr Pro

```
                            85                  90                  95
Pro Thr Phe Gly Ser Gly Thr Lys Leu Glu Ile Lys Arg
                100                 105

<210> SEQ ID NO 46
<211> LENGTH: 109
<212> TYPE: PRT
<213> ORGANISM: Artificial Sequence
<220> FEATURE:
<223> OTHER INFORMATION: Humanized Light Chain

<400> SEQUENCE: 46

Gln Ile Val Leu Thr Gln Ser Pro Ala Thr Met Ser Ala Ser Pro Gly
1               5                   10                  15
Glu Arg Val Thr Leu Ser Cys Ser Ala Ser Ser Ser Val Thr Ser Asn
                20                  25                  30
Tyr Leu Tyr Trp Tyr Gln Gln Lys Pro Gly Ser Ser Pro Arg Leu Trp
            35                  40                  45
Ile Tyr Ser Thr Ser Asn Leu Ala Ser Gly Val Pro Ala Arg Phe Ser
        50                  55                  60
Gly Ser Gly Ser Gly Thr Ser Tyr Thr Leu Thr Ile Ser Arg Met Glu
65                  70                  75                  80
Pro Glu Asp Ala Ala Ser Tyr Phe Cys His Gln Trp Ser Ser Tyr Pro
                85                  90                  95
Pro Thr Phe Gly Ser Gly Thr Lys Leu Glu Ile Lys Arg
                100                 105

<210> SEQ ID NO 47
<211> LENGTH: 109
<212> TYPE: PRT
<213> ORGANISM: Artificial Sequence
<220> FEATURE:
<223> OTHER INFORMATION: Humanized Light Chain

<400> SEQUENCE: 47

Gln Ile Val Leu Thr Gln Ser Pro Ala Ile Leu Ser Leu Ser Pro Gly
1               5                   10                  15
Glu Arg Ala Thr Leu Ser Cys Ser Ala Ser Ser Ser Val Thr Ser Asn
                20                  25                  30
Tyr Leu Tyr Trp Tyr Gln Gln Lys Pro Gly Ser Ser Pro Lys Leu Leu
            35                  40                  45
Ile Tyr Ser Thr Ser Asn Leu Ala Ser Gly Val Pro Ala Arg Phe Ser
        50                  55                  60
Gly Ser Gly Ser Gly Thr Ser Tyr Thr Leu Thr Ile Ser Ser Leu Glu
65                  70                  75                  80
Ala Glu Asp Ala Ala Ser Tyr Phe Cys His Gln Trp Ser Ser Tyr Pro
                85                  90                  95
Pro Thr Phe Gly Ser Gly Thr Lys Leu Glu Ile Lys Arg
                100                 105

<210> SEQ ID NO 48
<211> LENGTH: 109
<212> TYPE: PRT
<213> ORGANISM: Artificial Sequence
<220> FEATURE:
<223> OTHER INFORMATION: Humanized Light Chain

<400> SEQUENCE: 48

Gln Ile Val Leu Thr Gln Ser Pro Ala Thr Leu Ser Leu Ser Pro Gly
1               5                   10                  15
```

Glu Arg Ala Thr Leu Ser Cys Arg Ala Ser Gln Ser Val Thr Ser Asn
            20                  25                  30

Tyr Leu Tyr Trp Tyr Gln Gln Lys Pro Gly Ser Ser Pro Arg Leu Leu
        35                  40                  45

Ile Tyr Ser Thr Ser Asn Leu Ala Ser Gly Val Pro Ala Arg Phe Ser
    50                  55                  60

Gly Ser Gly Ser Gly Thr Asp Tyr Thr Leu Thr Ile Ser Arg Leu Glu
65                  70                  75                  80

Pro Glu Asp Phe Ala Ser Tyr Phe Cys His Gln Trp Ser Ser Tyr Pro
                85                  90                  95

Pro Thr Phe Gly Ser Gly Thr Lys Leu Glu Ile Lys Arg
            100                 105

<210> SEQ ID NO 49
<211> LENGTH: 109
<212> TYPE: PRT
<213> ORGANISM: Artificial Sequence
<220> FEATURE:
<223> OTHER INFORMATION: Humanized Light Chain

<400> SEQUENCE: 49

Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Thr Ser Asn
            20                  25                  30

Tyr Leu Tyr Trp Tyr Gln Gln Lys Pro Gly Ser Ser Pro Arg Leu Leu
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Thr Leu Thr Ile Ser Arg Leu Glu
65                  70                  75                  80

Pro Glu Asp Phe Ala Ser Tyr Phe Cys His Gln Trp Ser Ser Tyr Pro
                85                  90                  95

Pro Thr Phe Gly Ser Gly Thr Lys Leu Glu Ile Lys Arg
            100                 105

<210> SEQ ID NO 50
<211> LENGTH: 10
<212> TYPE: PRT
<213> ORGANISM: Mus musculus

<400> SEQUENCE: 50

Gly Phe Ser Leu Thr Asn Tyr Gly Val Asn
1               5                   10

<210> SEQ ID NO 51
<211> LENGTH: 8
<212> TYPE: PRT
<213> ORGANISM: Mus musculus

<400> SEQUENCE: 51

Gly Phe Ser Leu Thr Asn Tyr Gly
1               5

<210> SEQ ID NO 52
<211> LENGTH: 10
<212> TYPE: PRT
<213> ORGANISM: Mus musculus

<400> SEQUENCE: 52

Gly Phe Asn Ile Asn Asp Tyr Phe Met His
1               5                   10

<210> SEQ ID NO 53
<211> LENGTH: 7
<212> TYPE: PRT
<213> ORGANISM: Mus musculus

<400> SEQUENCE: 53

Phe Asn Ile Asn Asp Tyr Phe
1               5

<210> SEQ ID NO 54
<211> LENGTH: 10
<212> TYPE: PRT
<213> ORGANISM: Mus musculus

<400> SEQUENCE: 54

Gly Phe Thr Phe Thr Asp Tyr Tyr Met Ser
1               5                   10

<210> SEQ ID NO 55
<211> LENGTH: 8
<212> TYPE: PRT
<213> ORGANISM: Mus musculus

<400> SEQUENCE: 55

Gly Phe Thr Phe Thr Asp Tyr Tyr
1               5

<210> SEQ ID NO 56
<211> LENGTH: 10
<212> TYPE: PRT
<213> ORGANISM: Mus musculus

<400> SEQUENCE: 56

Gly Tyr Thr Phe Thr Asp Tyr Asn Met Asp
1               5                   10

<210> SEQ ID NO 57
<211> LENGTH: 7
<212> TYPE: PRT
<213> ORGANISM: Mus musculus

<400> SEQUENCE: 57

Tyr Thr Phe Thr Asp Tyr Asn
1               5

<210> SEQ ID NO 58
<211> LENGTH: 10
<212> TYPE: PRT
<213> ORGANISM: Mus musculus

<400> SEQUENCE: 58

Gly Tyr Thr Phe Thr Ser Tyr Trp Met His
1               5                   10

<210> SEQ ID NO 59
<211> LENGTH: 7
<212> TYPE: PRT
<213> ORGANISM: Mus musculus

<400> SEQUENCE: 59

Tyr Thr Phe Thr Ser Tyr Trp

```
<210> SEQ ID NO 60
<211> LENGTH: 8
<212> TYPE: PRT
<213> ORGANISM: Mus musculus
<220> FEATURE:
<221> NAME/KEY: MISC_FEATURE
<222> LOCATION: (6)..(6)
<223> OTHER INFORMATION: Xaa is Asp or Ser
<220> FEATURE:
<221> NAME/KEY: MISC_FEATURE
<222> LOCATION: (8)..(8)
<223> OTHER INFORMATION: Xaa is Asn or Trp

<400> SEQUENCE: 60

Gly Tyr Thr Phe Thr Xaa Tyr Xaa
1               5

<210> SEQ ID NO 61
<211> LENGTH: 10
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa is Tyr or Phe
<220> FEATURE:
<221> NAME/KEY: misc_feature
<222> LOCATION: (6)..(6)
<223> OTHER INFORMATION: Xaa is Asp or Ser
<220> FEATURE:
<221> NAME/KEY: misc_feature
<222> LOCATION: (8)..(8)
<223> OTHER INFORMATION: Xaa is Asn, Trp or Tyr
<220> FEATURE:
<221> NAME/KEY: misc_feature
<222> LOCATION: (10)..(10)
<223> OTHER INFORMATION: Xaa is His or Ser

<400> SEQUENCE: 61

Gly Xaa Thr Phe Thr Xaa Tyr Xaa Met Xaa
1               5                   10

<210> SEQ ID NO 62
<211> LENGTH: 16
<212> TYPE: PRT
<213> ORGANISM: Mus musculus

<400> SEQUENCE: 62

Leu Ile Trp Gly Gly Gly Asp Thr Asp Tyr Asn Ser Ala Leu Lys Ser
1               5                   10                  15

<210> SEQ ID NO 63
<211> LENGTH: 7
<212> TYPE: PRT
<213> ORGANISM: Mus musculus

<400> SEQUENCE: 63

Ile Trp Gly Gly Gly Asp Thr
1               5

<210> SEQ ID NO 64
<211> LENGTH: 17
<212> TYPE: PRT
<213> ORGANISM: Mus musculus

<400> SEQUENCE: 64

Trp Ile Asp Pro Glu Asn Gly Asn Thr Ile Tyr Asp Pro Lys Phe Gln
```

<210> SEQ ID NO 65
<211> LENGTH: 8
<212> TYPE: PRT
<213> ORGANISM: Mus musculus

<400> SEQUENCE: 65

Ile Asp Pro Glu Asn Gly Asn Thr
1               5

<210> SEQ ID NO 66
<211> LENGTH: 19
<212> TYPE: PRT
<213> ORGANISM: Mus musculus

<400> SEQUENCE: 66

Phe Ile Arg Asn Lys Ala Asn Gly Tyr Thr Thr Lys Tyr Ser Ala Ser
1               5                   10                  15

Val Lys Gly

<210> SEQ ID NO 67
<211> LENGTH: 10
<212> TYPE: PRT
<213> ORGANISM: Mus musculus

<400> SEQUENCE: 67

Ile Arg Asn Lys Ala Asn Gly Tyr Thr Thr
1               5                   10

<210> SEQ ID NO 68
<211> LENGTH: 17
<212> TYPE: PRT
<213> ORGANISM: Mus musculus

<400> SEQUENCE: 68

Asp Ile Asn Pro Asn Asn Gly Gly Thr Ile Tyr Asn Gln Lys Phe Lys
1               5                   10                  15

Gly

<210> SEQ ID NO 69
<211> LENGTH: 8
<212> TYPE: PRT
<213> ORGANISM: Mus musculus

<400> SEQUENCE: 69

Ile Asn Pro Asn Asn Gly Gly Thr
1               5

<210> SEQ ID NO 70
<211> LENGTH: 17
<212> TYPE: PRT
<213> ORGANISM: Mus musculus

<400> SEQUENCE: 70

Tyr Ile Lys Pro Ser Thr Asp Asn Thr Glu Tyr Asn Gln Lys Phe Lys
1               5                   10                  15

Asp

<210> SEQ ID NO 71
<211> LENGTH: 8

```
<212> TYPE: PRT
<213> ORGANISM: Mus musculus

<400> SEQUENCE: 71

Ile Lys Pro Ser Thr Asp Asn Thr
1               5

<210> SEQ ID NO 72
<211> LENGTH: 17
<212> TYPE: PRT
<213> ORGANISM: Mus musculus

<400> SEQUENCE: 72

Tyr Ile Asn Pro Ser Thr Asp Tyr Thr Glu Tyr Asn Gln Lys Phe Lys
1               5                   10                  15

Asp

<210> SEQ ID NO 73
<211> LENGTH: 8
<212> TYPE: PRT
<213> ORGANISM: Mus musculus

<400> SEQUENCE: 73

Ile Asn Pro Ser Thr Asp Tyr Thr
1               5

<210> SEQ ID NO 74
<211> LENGTH: 17
<212> TYPE: PRT
<213> ORGANISM: Mus musculus

<400> SEQUENCE: 74

Tyr Ile Asn Pro Ser Thr Asp Tyr Ile Glu Tyr Asn Gln Lys Phe Lys
1               5                   10                  15

Asp

<210> SEQ ID NO 75
<211> LENGTH: 8
<212> TYPE: PRT
<213> ORGANISM: Mus musculus

<400> SEQUENCE: 75

Ile Asn Pro Ser Thr Asp Tyr Ile
1               5

<210> SEQ ID NO 76
<211> LENGTH: 8
<212> TYPE: PRT
<213> ORGANISM: Mus musculus
<220> FEATURE:
<221> NAME/KEY: misc_feature
<222> LOCATION: (8)..(8)
<223> OTHER INFORMATION: Xaa is Ile or Thr

<400> SEQUENCE: 76

Ile Asn Pro Ser Thr Asp Tyr Xaa
1               5

<210> SEQ ID NO 77
<211> LENGTH: 17
<212> TYPE: PRT
<213> ORGANISM: Mus musculus
<220> FEATURE:
<221> NAME/KEY: misc_feature
<222> LOCATION: (1)..(1)
```

```
<223> OTHER INFORMATION: Xaa is Tyr or Asp
<220> FEATURE:
<221> NAME/KEY: misc_feature
<222> LOCATION: (3)..(3)
<223> OTHER INFORMATION: Xaa is Lys or Asn
<220> FEATURE:
<221> NAME/KEY: misc_feature
<222> LOCATION: (8)..(8)
<223> OTHER INFORMATION: Xaa is Asn or Tyr
<220> FEATURE:
<221> NAME/KEY: misc_feature
<222> LOCATION: (9)..(9)
<223> OTHER INFORMATION: Xaa is Thr or Ile
<220> FEATURE:
<221> NAME/KEY: misc_feature
<222> LOCATION: (12)..(12)
<223> OTHER INFORMATION: Xaa is Ala or Asn
<220> FEATURE:
<221> NAME/KEY: misc_feature
<222> LOCATION: (16)..(16)
<223> OTHER INFORMATION: Xaa is Gln or Lys
<220> FEATURE:
<221> NAME/KEY: misc_feature
<222> LOCATION: (17)..(17)
<223> OTHER INFORMATION: Xaa is Gly or Asp

<400> SEQUENCE: 77

Xaa Ile Xaa Pro Ser Thr Asp Xaa Xaa Glu Tyr Xaa Gln Lys Phe Xaa
1               5                   10                  15

Xaa

<210> SEQ ID NO 78
<211> LENGTH: 17
<212> TYPE: PRT
<213> ORGANISM: Mus musculus

<400> SEQUENCE: 78

Tyr Ile Lys Pro Ser Thr Asp Asn Thr Glu Tyr Ala Gln Lys Phe Gln
1               5                   10                  15

Gly

<210> SEQ ID NO 79
<211> LENGTH: 10
<212> TYPE: PRT
<213> ORGANISM: Mus musculus

<400> SEQUENCE: 79

Cys Ala Arg Asp Tyr Tyr Gly Phe Asp Tyr
1               5                   10

<210> SEQ ID NO 80
<211> LENGTH: 7
<212> TYPE: PRT
<213> ORGANISM: Mus musculus

<400> SEQUENCE: 80

Asp Tyr Tyr Gly Phe Asp Tyr
1               5

<210> SEQ ID NO 81
<211> LENGTH: 18
<212> TYPE: PRT
<213> ORGANISM: Mus musculus

<400> SEQUENCE: 81

Cys Ala Arg Gly Gly Asn Tyr Leu Arg Glu Ser Tyr Tyr Tyr Ala Met
1               5                   10                  15
```

-continued

Asp Tyr

<210> SEQ ID NO 82
<211> LENGTH: 16
<212> TYPE: PRT
<213> ORGANISM: Mus musculus

<400> SEQUENCE: 82

Arg Gly Gly Asn Tyr Leu Arg Glu Ser Tyr Tyr Tyr Ala Met Asp Tyr
1               5                   10                  15

<210> SEQ ID NO 83
<211> LENGTH: 10
<212> TYPE: PRT
<213> ORGANISM: Mus musculus

<400> SEQUENCE: 83

Cys Ser Lys Asp Arg Gly Tyr Phe Asp Tyr
1               5                   10

<210> SEQ ID NO 84
<211> LENGTH: 7
<212> TYPE: PRT
<213> ORGANISM: Mus musculus

<400> SEQUENCE: 84

Asp Arg Gly Tyr Phe Asp Tyr
1               5

<210> SEQ ID NO 85
<211> LENGTH: 18
<212> TYPE: PRT
<213> ORGANISM: Mus musculus

<400> SEQUENCE: 85

Arg Ala Arg Gly Asp Tyr Tyr Gly Ser Ser Arg Tyr Tyr Ala Met
1               5                   10                  15

Asp Tyr

<210> SEQ ID NO 86
<211> LENGTH: 16
<212> TYPE: PRT
<213> ORGANISM: Mus musculus

<400> SEQUENCE: 86

Arg Gly Asp Tyr Tyr Gly Ser Ser Arg Tyr Tyr Ala Met Asp Tyr
1               5                   10                  15

<210> SEQ ID NO 87
<211> LENGTH: 13
<212> TYPE: PRT
<213> ORGANISM: Mus musculus

<400> SEQUENCE: 87

Cys Ala Arg Ser Tyr Gly Asn Tyr Pro Leu Met Asp Tyr
1               5                   10

<210> SEQ ID NO 88
<211> LENGTH: 10
<212> TYPE: PRT
<213> ORGANISM: Mus musculus

<400> SEQUENCE: 88

Ser Tyr Gly Asn Tyr Pro Leu Met Asp Tyr

```
                      1               5                    10

<210> SEQ ID NO 89
<211> LENGTH: 13
<212> TYPE: PRT
<213> ORGANISM: Mus musculus

<400> SEQUENCE: 89

Cys Val Arg Ser Tyr Gly Asn Tyr Pro Leu Met Asp Tyr
1               5                    10

<210> SEQ ID NO 90
<211> LENGTH: 13
<212> TYPE: PRT
<213> ORGANISM: Mus musculus

<400> SEQUENCE: 90

Cys Ala Arg Ser Tyr Gly Asn Phe Pro Leu Met Asp Tyr
1               5                    10

<210> SEQ ID NO 91
<211> LENGTH: 11
<212> TYPE: PRT
<213> ORGANISM: Mus musculus

<400> SEQUENCE: 91

Arg Ser Tyr Gly Asn Phe Pro Leu Met Asp Tyr
1               5                    10

<210> SEQ ID NO 92
<211> LENGTH: 13
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa is Ala or Val
<220> FEATURE:
<221> NAME/KEY: misc_feature
<222> LOCATION: (8)..(8)
<223> OTHER INFORMATION: Xaa is Phe or Tyr

<400> SEQUENCE: 92

Cys Xaa Arg Ser Tyr Gly Asn Xaa Pro Leu Met Asp Tyr
1               5                    10

<210> SEQ ID NO 93
<211> LENGTH: 11
<212> TYPE: PRT
<213> ORGANISM: Mus musculus
<220> FEATURE:
<221> NAME/KEY: misc_feature
<222> LOCATION: (6)..(6)
<223> OTHER INFORMATION: Xaa is Phe or Tyr

<400> SEQUENCE: 93

Arg Ser Tyr Gly Asn Xaa Pro Leu Met Asp Tyr
1               5                    10

<210> SEQ ID NO 94
<211> LENGTH: 117
<212> TYPE: PRT
<213> ORGANISM: Mus musculus

<400> SEQUENCE: 94

Gln Val Gln Leu Lys Glu Ser Gly Pro Gly Leu Val Ala Pro Ser Gln
1               5                    10                  15
```

```
Ser Leu Ser Ile Thr Cys Thr Val Ser Gly Phe Ser Leu Thr Asn Tyr
            20                  25                  30

Gly Val Asn Trp Val Arg Gln Pro Gly Lys Gly Leu Glu Trp Leu
        35                  40                  45

Gly Leu Ile Trp Gly Gly Asp Thr Asp Tyr Asn Ser Ala Leu Lys
50                  55                  60

Ser Arg Leu Ser Ile Ser Lys Asp Asn Ser Lys Ser Gln Val Phe Leu
65                  70                  75                  80

Lys Met Glu Thr Asn Ser Leu Gln Thr Asp Thr Ala Arg Tyr Tyr
                85                  90                  95

Cys Ala Arg Asp Tyr Tyr Gly Phe Asp Tyr Trp Gly Gln Gly Thr Thr
                100                 105                 110

Leu Thr Val Ser Ser
        115

<210> SEQ ID NO 95
<211> LENGTH: 118
<212> TYPE: PRT
<213> ORGANISM: Mus musculus

<400> SEQUENCE: 95

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Lys Tyr Ser Ala
50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ser Lys Asp Arg Gly Tyr Phe Asp Tyr Trp Gly Gln Gly Thr
                100                 105                 110

Thr Leu Thr Val Ser Ser
        115

<210> SEQ ID NO 96
<211> LENGTH: 127
<212> TYPE: PRT
<213> ORGANISM: Mus musculus

<400> SEQUENCE: 96

Val Asn Ser Glu Val Gln Leu Gln Gln Ser Gly Ala Glu Leu Val Arg
1               5                   10                  15

Pro Gly Ala Leu Val Lys Leu Ser Cys Lys Ala Ser Gly Phe Asn Ile
            20                  25                  30

Asn Asp Tyr Phe Met His Trp Val Lys Gln Arg Pro Glu Gln Gly Leu
        35                  40                  45

Glu Trp Ile Gly Trp Ile Asp Pro Glu Asn Gly Asn Thr Ile Tyr Asp
50                  55                  60

Pro Lys Phe Gln Gly Lys Ala Ser Ile Thr Ala Asp Thr Ser Ser Asn
65                  70                  75                  80

Thr Ala Tyr Leu Gln Leu Ser Ser Leu Thr Ser Glu Asp Thr Ala Val
                85                  90                  95
```

Tyr Tyr Cys Ala Arg Gly Gly Asn Tyr Leu Arg Glu Ser Tyr Tyr Tyr
            100                 105                 110

Ala Met Asp Tyr Trp Gly Gln Gly Thr Ser Val Thr Val Ser Ser
            115                 120                 125

<210> SEQ ID NO 97
<211> LENGTH: 127
<212> TYPE: PRT
<213> ORGANISM: Mus musculus

<400> SEQUENCE: 97

Val Leu Ser Glu Val Leu Leu Gln Gln Ser Gly Pro Glu Leu Val Lys
1               5                   10                  15

Pro Gly Ala Ser Val Lys Ile Pro Cys Lys Ala Ser Gly Tyr Thr Phe
            20                  25                  30

Thr Asp Tyr Asn Met Asp Trp Val Lys Gln Ser His Gly Lys Ser Leu
        35                  40                  45

Glu Trp Ile Gly Asp Ile Asn Pro Asn Gly Gly Thr Ile Tyr Asn
    50                  55                  60

Gln Lys Phe Lys Gly Lys Ala Thr Leu Thr Val Asp Lys Ser Ser Ser
65                  70                  75                  80

Thr Ala Tyr Met Glu Leu Arg Ser Leu Thr Ser Glu Asp Thr Ala Val
                85                  90                  95

Tyr Tyr Arg Ala Arg Gly Asp Tyr Tyr Gly Ser Ser Arg Tyr Tyr Tyr
            100                 105                 110

Ala Met Asp Tyr Trp Gly Gln Gly Thr Ser Val Thr Val Ser Ser
            115                 120                 125

<210> SEQ ID NO 98
<211> LENGTH: 119
<212> TYPE: PRT
<213> ORGANISM: Mus musculus

<400> SEQUENCE: 98

Gln Val Gln Leu Gln Gln Ser Gly Ala Glu Leu Ala Lys Pro Gly Ala
1               5                   10                  15

Ser Val Lys Met Ser Cys Arg Ala Ser Gly Tyr Thr Phe Thr Ser Tyr
            20                  25                  30

Trp Met His Trp Val Lys Gln Arg Pro Gly Gln Gly Leu Asp Trp Ile
        35                  40                  45

Gly Tyr Ile Lys Pro Ser Thr Asp Asn Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Tyr Gly Asn Tyr Pro Leu Met Asp Tyr Trp Gly Gln Gly
            100                 105                 110

Thr Ser Val Thr Val Ser Ser
            115

<210> SEQ ID NO 99
<211> LENGTH: 119
<212> TYPE: PRT
<213> ORGANISM: Mus musculus

<400> SEQUENCE: 99

-continued

Gln Val Gln Leu Gln Gln Ser Gly Ala Glu Leu Ala Lys Pro Gly Ala
1               5                   10                  15

Ser Val Lys Met Ser Cys Arg Ala Ser Gly Tyr Thr Phe Thr Ser Tyr
            20                  25                  30

Trp Met His Trp Val Lys Gln Arg Pro Gly Gln Gly Leu Asp Trp Ile
        35                  40                  45

Gly Tyr Ile Lys Pro Ser Thr Asp Asn Thr Glu Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Ser Tyr Gly Asn Tyr Pro Leu Met Asp Tyr Trp Gly Gln Gly
            100                 105                 110

Thr Ser Val Thr Val Ser Ser
        115

<210> SEQ ID NO 100
<211> LENGTH: 119
<212> TYPE: PRT
<213> ORGANISM: Mus musculus

<400> SEQUENCE: 100

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Tyr Cys
            85                  90                  95

Val Arg Ser Tyr Gly Asn Tyr Pro Leu Met Asp Tyr Trp Gly Gln Gly
            100                 105                 110

Thr Ser Val Thr Val Ser Ser
        115

<210> SEQ ID NO 101
<211> LENGTH: 119
<212> TYPE: PRT
<213> ORGANISM: Mus musculus

<400> SEQUENCE: 101

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Asp Tyr Thr Glu Tyr Asn Gln Lys Phe
    50                  55                  60

Lys Asp Lys Ala Thr Leu Thr Ala Asp Lys Ser Ser Thr Thr Ala Tyr
65                  70                  75                  80

```
Met Gln Leu Ser Ser Leu Thr Ser Glu Asp Ser Ala Val Tyr Tyr Cys
                85                  90                  95

Val Arg Ser Tyr Gly Asn Tyr Pro Leu Met Asp Tyr Trp Gly Gln Gly
            100                 105                 110

Thr Ser Val Thr Val Ser Ser
        115
```

<210> SEQ ID NO 102
<211> LENGTH: 119
<212> TYPE: PRT
<213> ORGANISM: Mus musculus

<400> SEQUENCE: 102

```
Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Asp Tyr Ile Glu Tyr Asn Gln Lys Phe
    50                  55                  60

Lys Asp Lys Ala Thr Leu Thr Ala Gly Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Tyr Gly Asn Phe Pro Leu Met Asp Tyr Trp Gly Gln Gly
            100                 105                 110

Thr Ser Val Thr Val Ser Ser
        115
```

<210> SEQ ID NO 103
<211> LENGTH: 119
<212> TYPE: PRT
<213> ORGANISM: Mus musculus
<220> FEATURE:
<221> NAME/KEY: misc_feature
<222> LOCATION: (23)..(23)
<223> OTHER INFORMATION: Xaa is Lys or Arg
<220> FEATURE:
<221> NAME/KEY: misc_feature
<222> LOCATION: (46)..(46)
<223> OTHER INFORMATION: Xaa is Glu or Asp
<220> FEATURE:
<221> NAME/KEY: misc_feature
<222> LOCATION: (52)..(52)
<223> OTHER INFORMATION: Xaa is Lys or Asn
<220> FEATURE:
<221> NAME/KEY: misc_feature
<222> LOCATION: (57)..(57)
<223> OTHER INFORMATION: Xaa is Tyr or Asn
<220> FEATURE:
<221> NAME/KEY: misc_feature
<222> LOCATION: (58)..(58)
<223> OTHER INFORMATION: Xaa is Thr or Ile
<220> FEATURE:
<221> NAME/KEY: misc_feature
<222> LOCATION: (77)..(77)
<223> OTHER INFORMATION: Xaa is Ser or Thr
<220> FEATURE:
<221> NAME/KEY: misc_feature
<222> LOCATION: (97)..(97)
<223> OTHER INFORMATION: Xaa is Ala or Val
<220> FEATURE:
<221> NAME/KEY: misc_feature
<222> LOCATION: (103)..(103)
<223> OTHER INFORMATION: Xaa is Tyr or Phe

<400> SEQUENCE: 103

Gln Val Gln Leu Gln Gln Ser Gly Ala Glu Leu Ala Lys Pro Gly Ala
1               5                   10                  15

Ser Val Lys Met Ser Cys Xaa Ala Ser Gly Tyr Thr Phe Thr Ser Tyr
            20                  25                  30

Trp Met His Trp Val Lys Gln Arg Pro Gly Gln Gly Leu Xaa Trp Ile
        35                  40                  45

Gly Tyr Ile Xaa Pro Ser Thr Asp Xaa Xaa Glu Tyr Asn Gln Lys Phe
    50                  55                  60

Lys Asp Lys Ala Thr Leu Thr Ala Asp Lys Ser Ser Xaa Thr Ala Tyr
65                  70                  75                  80

Met Gln Leu Ser Ser Leu Thr Ser Glu Asp Ser Ala Val Tyr Tyr Cys
                85                  90                  95

Xaa Arg Ser Tyr Gly Asn Xaa Pro Leu Met Asp Tyr Trp Gly Gln Gly
            100                 105                 110

Thr Ser Val Thr Val Ser Ser
        115

<210> SEQ ID NO 104
<211> LENGTH: 119
<212> TYPE: PRT
<213> ORGANISM: Artificial Sequence
<220> FEATURE:
<223> OTHER INFORMATION: Humanized Heavy Chain

<400> SEQUENCE: 104

Gln Val Gln Leu Gln Gln Ser Gly Ala Glu Leu Ala Lys Pro Gly Ala
1               5                   10                  15

Ser Val Lys Met Ser Cys Arg Ala Ser Gly Tyr Thr Phe Thr Ser Tyr
            20                  25                  30

Trp Met His Trp Val Lys Gln Arg Pro Gly Gln Gly Leu Asp Trp Ile
        35                  40                  45

Gly Tyr Ile Lys Pro Ser Thr Asp Asn Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Tyr Gly Asn Tyr Pro Leu Met Asp Tyr Trp Gly Gln Gly
            100                 105                 110

Thr Ser Val Thr Val Ser Ser
        115

<210> SEQ ID NO 105
<211> LENGTH: 119
<212> TYPE: PRT
<213> ORGANISM: Artificial Sequence
<220> FEATURE:
<223> OTHER INFORMATION: Humanized Heavy Chain

<400> SEQUENCE: 105

Gln Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Asp Trp Ile
        35                  40                  45

```
Gly Tyr Ile Lys Pro Ser Thr Asp Asn Thr Glu Tyr Asn Gln Lys Phe
        50                  55                  60

Lys Asp Arg Val Thr Leu Thr Ala Asp Lys Ser Thr Ser Thr Ala Tyr
 65                  70                  75                  80

Met Gln Leu Ser Asn Leu Ile Ser Glu Asp Thr Ala Val Tyr Tyr Cys
                 85                  90                  95

Ala Arg Ser Tyr Gly Asn Tyr Pro Leu Met Asp Tyr Trp Gly Gln Gly
                100                 105                 110

Thr Ser Val Thr Val Ser Ser
            115
```

<210> SEQ ID NO 106
<211> LENGTH: 119
<212> TYPE: PRT
<213> ORGANISM: Artificial Sequence
<220> FEATURE:
<223> OTHER INFORMATION: Humanized Heavy Chain

<400> SEQUENCE: 106

```
Gln Val Gln Leu Val Gln Ser Gly Ala Glu Val Ala Lys Pro Gly Ala
 1               5                  10                  15

Ser Val Lys Met Ser Cys Lys Ala Ser Gly Tyr Thr Phe Thr Ser Tyr
                20                  25                  30

Trp Met His Trp Val Lys Gln Ala Pro Gly Gln Gly Leu Asp Trp Ile
             35                  40                  45

Gly Tyr Ile Lys Pro Ser Thr Asp Asn Thr Glu Tyr Asn Gln Lys Phe
        50                  55                  60

Lys Asp Lys Ala Thr Leu Thr Ala Asp Lys Ser Thr Ser Thr Ala Tyr
 65                  70                  75                  80

Met Gln Leu Ser Ser Leu Arg Ser Glu Asp Thr Ala Val Tyr Tyr Cys
                 85                  90                  95

Ala Arg Ser Tyr Gly Asn Tyr Pro Leu Met Asp Tyr Trp Gly Gln Gly
                100                 105                 110

Thr Thr Val Thr Val Ser Ser
            115
```

<210> SEQ ID NO 107
<211> LENGTH: 119
<212> TYPE: PRT
<213> ORGANISM: Artificial Sequence
<220> FEATURE:
<223> OTHER INFORMATION: Humanized Heavy Chain

<400> SEQUENCE: 107

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Trp Met His Trp Val Lys Gln Ala Pro Gly Gln Gly Leu Asp Trp Met
             35                  40                  45

Gly Tyr Ile Lys Pro Ser Thr Asp Asn Thr Glu Tyr Ala Gln Lys Phe
        50                  55                  60

Gln Gly Arg Val Thr Leu Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Tyr Gly Asn Tyr Pro Leu Met Asp Tyr Trp Gly Gln Gly
                100                 105                 110
```

Thr Thr Val Thr Val Ser Ser
        115

<210> SEQ ID NO 108
<211> LENGTH: 119
<212> TYPE: PRT
<213> ORGANISM: Artificial Sequence
<220> FEATURE:
<223> OTHER INFORMATION: Humanized Heavy Chain

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Lys Gln Ala Pro Gly Gln Gly Leu Asp Trp Ile
            35                  40                  45

Gly Tyr Ile Lys Pro Ser Thr Asp Asn Thr Glu Tyr Asn Gln Lys Phe
        50                  55                  60

Lys Asp Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Gly Asn Tyr Pro Leu Met Asp Tyr Trp Gly Gln Gly
            100                 105                 110

Thr Thr Val Thr Val Ser Ser
        115

<210> SEQ ID NO 109
<211> LENGTH: 1390
<212> TYPE: PRT
<213> ORGANISM: Homo sapiens

<400> SEQUENCE: 109

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Ile Leu His Glu His Ile Phe Leu
        50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
            115                 120                 125

Gln Leu Ile Ser Cys Gly Ser Val Asn Arg Gly Thr Cys Gln Arg His
        130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

```
Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
    450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
    530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
```

-continued

```
                595                 600                 605
Ser Cys Thr Leu Thr Leu Ser Glu Ser Thr Met Asn Thr Leu Lys Cys
610                 615                 620
Thr Val Gly Pro Ala Met Asn Lys His Phe Asn Met Ser Ile Ile Ile
625                 630                 635                 640
Ser Asn Gly His Gly Thr Thr Gln Tyr Ser Thr Phe Ser Tyr Val Asp
                    645                 650                 655
Pro Val Ile Thr Ser Ile Ser Pro Lys Tyr Gly Pro Met Ala Gly Gly
                    660                 665                 670
Thr Leu Leu Thr Leu Thr Gly Asn Tyr Leu Asn Ser Gly Asn Ser Arg
                    675                 680                 685
His Ile Ser Ile Gly Gly Lys Thr Cys Thr Leu Lys Ser Val Ser Asn
690                 695                 700
Ser Ile Leu Glu Cys Tyr Thr Pro Ala Gln Thr Ile Ser Thr Glu Phe
705                 710                 715                 720
Ala Val Lys Leu Lys Ile Asp Leu Ala Asn Arg Glu Thr Ser Ile Phe
                    725                 730                 735
Ser Tyr Arg Glu Asp Pro Ile Val Tyr Glu Ile His Pro Thr Lys Ser
                    740                 745                 750
Phe Ile Ser Gly Gly Ser Thr Ile Thr Gly Val Gly Lys Asn Leu Asn
                    755                 760                 765
Ser Val Ser Val Pro Arg Met Val Ile Asn Val His Glu Ala Gly Arg
770                 775                 780
Asn Phe Thr Val Ala Cys Gln His Arg Ser Asn Ser Glu Ile Ile Cys
785                 790                 795                 800
Cys Thr Thr Pro Ser Leu Gln Gln Leu Asn Leu Gln Leu Pro Leu Lys
                    805                 810                 815
Thr Lys Ala Phe Phe Met Leu Asp Gly Ile Leu Ser Lys Tyr Phe Asp
                    820                 825                 830
Leu Ile Tyr Val His Asn Pro Val Phe Lys Pro Phe Glu Lys Pro Val
                    835                 840                 845
Met Ile Ser Met Gly Asn Glu Asn Val Leu Glu Ile Lys Gly Asn Asp
850                 855                 860
Ile Asp Pro Glu Ala Val Lys Gly Glu Val Leu Lys Val Gly Asn Lys
865                 870                 875                 880
Ser Cys Glu Asn Ile His Leu His Ser Glu Ala Val Leu Cys Thr Val
                    885                 890                 895
Pro Asn Asp Leu Leu Lys Leu Asn Ser Glu Leu Asn Ile Glu Trp Lys
                    900                 905                 910
Gln Ala Ile Ser Ser Thr Val Leu Gly Lys Val Ile Val Gln Pro Asp
                    915                 920                 925
Gln Asn Phe Thr Gly Leu Ile Ala Gly Val Val Ser Ile Ser Thr Ala
                    930                 935                 940
Leu Leu Leu Leu Leu Gly Phe Phe Leu Trp Leu Lys Lys Arg Lys Gln
945                 950                 955                 960
Ile Lys Asp Leu Gly Ser Glu Leu Val Arg Tyr Asp Ala Arg Val His
                    965                 970                 975
Thr Pro His Leu Asp Arg Leu Val Ser Ala Arg Ser Val Ser Pro Thr
                    980                 985                 990
Thr Glu Met Val Ser Asn Glu Ser  Val Asp Tyr Arg Ala  Thr Phe Pro
                    995                 1000                1005
Glu Asp  Gln Phe Pro Asn Ser  Ser Gln Asn Gly Ser  Cys Arg Gln
1010                 1015                1020
```

Val Gln Tyr Pro Leu Thr Asp Met Ser Pro Ile Leu Thr Ser Gly
1025                1030                1035

Asp Ser Asp Ile Ser Ser Pro Leu Leu Gln Asn Thr Val His Ile
1040                1045                1050

Asp Leu Ser Ala Leu Asn Pro Glu Leu Val Gln Ala Val Gln His
1055                1060                1065

Val Val Ile Gly Pro Ser Ser Leu Ile Val His Phe Asn Glu Val
1070                1075                1080

Ile Gly Arg Gly His Phe Gly Cys Val Tyr His Gly Thr Leu Leu
1085                1090                1095

Asp Asn Asp Gly Lys Lys Ile His Cys Ala Val Lys Ser Leu Asn
1100                1105                1110

Arg Ile Thr Asp Ile Gly Glu Val Ser Gln Phe Leu Thr Glu Gly
1115                1120                1125

Ile Ile Met Lys Asp Phe Ser His Pro Asn Val Leu Ser Leu Leu
1130                1135                1140

Gly Ile Cys Leu Arg Ser Glu Gly Ser Pro Leu Val Val Leu Pro
1145                1150                1155

Tyr Met Lys His Gly Asp Leu Arg Asn Phe Ile Arg Asn Glu Thr
1160                1165                1170

His Asn Pro Thr Val Lys Asp Leu Ile Gly Phe Gly Leu Gln Val
1175                1180                1185

Ala Lys Gly Met Lys Tyr Leu Ala Ser Lys Lys Phe Val His Arg
1190                1195                1200

Asp Leu Ala Ala Arg Asn Cys Met Leu Asp Glu Lys Phe Thr Val
1205                1210                1215

Lys Val Ala Asp Phe Gly Leu Ala Arg Asp Met Tyr Asp Lys Glu
1220                1225                1230

Tyr Tyr Ser Val His Asn Lys Thr Gly Ala Lys Leu Pro Val Lys
1235                1240                1245

Trp Met Ala Leu Glu Ser Leu Gln Thr Gln Lys Phe Thr Thr Lys
1250                1255                1260

Ser Asp Val Trp Ser Phe Gly Val Leu Leu Trp Glu Leu Met Thr
1265                1270                1275

Arg Gly Ala Pro Pro Tyr Pro Asp Val Asn Thr Phe Asp Ile Thr
1280                1285                1290

Val Tyr Leu Leu Gln Gly Arg Arg Leu Leu Gln Pro Glu Tyr Cys
1295                1300                1305

Pro Asp Pro Leu Tyr Glu Val Met Leu Lys Cys Trp His Pro Lys
1310                1315                1320

Ala Glu Met Arg Pro Ser Phe Ser Glu Leu Val Ser Arg Ile Ser
1325                1330                1335

Ala Ile Phe Ser Thr Phe Ile Gly Glu His Tyr Val His Val Asn
1340                1345                1350

Ala Thr Tyr Val Asn Val Lys Cys Val Ala Pro Tyr Pro Ser Leu
1355                1360                1365

Leu Ser Ser Glu Asp Asn Ala Asp Asp Glu Val Asp Thr Arg Pro
1370                1375                1380

Ala Ser Phe Trp Glu Thr Ser
1385                1390

<210> SEQ ID NO 110
<211> LENGTH: 1382

-continued

<212> TYPE: PRT
<213> ORGANISM: Rattus norvegicus

<400> SEQUENCE: 110

```
Met Lys Ala Pro Thr Ala Leu Ala Pro Gly Ile Leu Leu Leu Leu
1               5                   10                  15

Thr Leu Ala Gln Arg Ser His Gly Glu Cys Lys Glu Ala Leu Val Lys
            20                  25                  30

Ser Glu Met Asn Val Asn Met Lys Tyr Gln Leu Pro Asn Phe Thr Ala
        35                  40                  45

Glu Thr Pro Ile His Asn Val Val Leu Pro Gly His Ile Tyr Leu
    50                  55                  60

Gly Ala Thr Asn Tyr Ile Tyr Val Leu Asn Asp Lys Asp Leu Gln Lys
65                  70                  75                  80

Val Ser Glu Phe Lys Thr Gly Pro Val Val Glu His Pro Asp Cys Phe
                85                  90                  95

Pro Cys Gln Asp Cys Ser Ser Lys Ala Asn Val Ser Gly Gly Val Trp
            100                 105                 110

Lys Asp Asn Val Asn Met Ala Leu Leu Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Leu Pro Pro Asp Asn Ala Ala Asp Ile Gln Ser Glu Val His Cys
145                 150                 155                 160

Met Phe Ser Pro Leu Ala Glu Glu Ser Gly Gln Cys Pro Asp Cys
                165                 170                 175

Val Val Ser Ala Leu Gly Ala Lys Val Leu Leu Ser Glu Lys Asp Arg
            180                 185                 190

Phe Ile Asn Phe Val Gly Asn Thr Ile Asn Ser Ser Tyr Pro Pro
        195                 200                 205

Asp Tyr Ser Leu His Ser Ile Ser Val Arg Arg Leu Lys Glu Thr Gln
    210                 215                 220

Asp Gly Phe Lys Phe Leu Thr Asp Gln Ser Tyr Ile Asp Val Leu Pro
225                 230                 235                 240

Glu Phe Arg Asp Ser Tyr Pro Ile Lys Tyr Ile His Ala Phe Glu Ser
                245                 250                 255

Asn His Phe Ile Tyr Phe Leu Thr Val Gln Lys Glu Thr Leu Asp Ala
            260                 265                 270

Gln Thr Phe His Thr Arg Ile Ile Arg Phe Cys Ser Val Asp Ser Gly
        275                 280                 285

Leu His Ser Tyr Met Glu Met Pro Leu Glu Cys Ile Leu Thr Glu Lys
    290                 295                 300

Arg Arg Lys Arg Ser Thr Arg Glu Glu Val Phe Asn Ile Leu Gln Ala
305                 310                 315                 320

Ala Tyr Val Ser Lys Pro Gly Ala Asn Leu Ala Lys Gln Ile Gly Ala
                325                 330                 335

Ser Pro Tyr Asp Asp Ile Leu Tyr Gly Val Phe Ala Gln Ser Lys Pro
            340                 345                 350

Asp Ser Ala Glu Pro Met Asn Arg Ser Ala Val Cys Ala Phe Pro Ile
        355                 360                 365

Lys Tyr Val Asn Asp Phe Phe Asn Lys Ile Val Asn Lys Asn Val
    370                 375                 380

Arg Cys Leu Gln His Phe Tyr Gly Pro Asn His Glu His Cys Phe Asn
385                 390                 395                 400
```

```
Arg Thr Leu Leu Arg Asn Ser Ser Gly Cys Glu Val Arg Ser Asp Glu
            405                 410                 415

Tyr Arg Thr Glu Phe Thr Thr Ala Leu Gln Arg Val Asp Leu Phe Met
            420                 425                 430

Gly Arg Leu Asn His Val Leu Leu Thr Ser Ile Ser Thr Phe Ile Lys
            435                 440                 445

Gly Asp Leu Thr Ile Ala Asn Leu Gly Thr Ser Glu Gly Arg Phe Met
            450                 455                 460

Gln Val Val Leu Ser Arg Thr Ala His Phe Thr Pro His Val Asn Phe
465                 470                 475                 480

Leu Leu Asp Ser Tyr Pro Val Ser Pro Glu Val Ile Val Glu His Pro
            485                 490                 495

Ser Asn Gln Asn Gly Tyr Thr Leu Val Val Thr Gly Lys Lys Ile Thr
            500                 505                 510

Lys Ile Pro Leu Asn Gly Leu Gly Cys Gly His Phe Gln Ser Cys Ser
            515                 520                 525

Gln Cys Leu Ser Pro Pro Tyr Phe Ile Gln Cys Gly Trp Cys His Asn
            530                 535                 540

Arg Cys Val His Ser Asn Glu Cys Pro Ser Gly Thr Trp Thr Gln Glu
545                 550                 555                 560

Ile Cys Leu Pro Ala Val Tyr Lys Val Phe Pro Thr Ser Ala Pro Leu
            565                 570                 575

Glu Gly Gly Thr Met Leu Thr Ile Cys Gly Trp Asp Phe Gly Phe Lys
            580                 585                 590

Lys Asn Asn Lys Phe Asp Leu Arg Lys Thr Lys Val Leu Leu Gly Asn
            595                 600                 605

Glu Ser Cys Thr Leu Thr Leu Ser Glu Ser Thr Thr Asn Thr Leu Lys
            610                 615                 620

Cys Thr Val Gly Pro Ala Met Ser Glu His Phe Asn Val Ser Val Ile
625                 630                 635                 640

Val Ser Asn Ser Arg Glu Thr Thr Gln Tyr Ser Ala Phe Ser Tyr Val
            645                 650                 655

Asp Pro Val Ile Thr Ser Ile Ser Pro Arg Tyr Gly Pro His Ala Gly
            660                 665                 670

Gly Thr Leu Leu Thr Leu Thr Gly Lys Tyr Leu Asn Ser Gly Asn Ser
            675                 680                 685

Arg His Ile Ser Ile Gly Gly Lys Thr Cys Thr Leu Lys Ser Val Ser
            690                 695                 700

Asp Ser Ile Leu Glu Cys Tyr Thr Pro Gly His Thr Val Ser Ala Glu
705                 710                 715                 720

Phe Pro Val Lys Leu Lys Ile Asp Leu Ala Asp Arg Val Thr Ser Ser
            725                 730                 735

Phe Ser Tyr Arg Glu Asp Pro Val Val Ser Glu Ile His Pro Thr Lys
            740                 745                 750

Ser Phe Ile Ser Gly Gly Ser Thr Ile Thr Gly Ile Gly Lys Asn Leu
            755                 760                 765

Asn Ser Val Ser Thr Pro Lys Leu Val Ile Glu Val His Asp Val Gly
            770                 775                 780

Val Asn Tyr Thr Val Ala Cys Gln His Arg Ser Ser Ser Glu Ile Ile
785                 790                 795                 800

Cys Cys Thr Thr Pro Ser Leu Arg Gln Leu Asp Leu Gln Leu Pro Leu
            805                 810                 815
```

```
Lys Thr Lys Ala Phe Phe Leu Leu Asp Gly Ile Leu Ser Lys His Phe
            820                 825                 830

Asp Leu Thr Tyr Val His Asp Pro Met Phe Lys Pro Phe Glu Lys Pro
            835                 840                 845

Val Met Ile Ser Met Gly Asn Glu Asn Val Val Glu Ile Lys Gly Asp
            850                 855                 860

Asp Ile Asp Pro Glu Ala Val Lys Gly Glu Val Leu Lys Val Gly Asn
865                 870                 875                 880

Lys Ser Cys Glu Asn Leu His Trp His Ser Glu Ala Leu Leu Cys Thr
                885                 890                 895

Val Pro Ser Asp Leu Leu Lys Leu Asn Gly Gly Glu Leu Asn Ile Glu
            900                 905                 910

Trp Lys Gln Ala Val Ser Ser Thr Val Leu Gly Lys Val Ile Val Gln
            915                 920                 925

Pro Asp Gln Asn Phe Ala Gly Leu Ile Ile Gly Ala Val Ser Ile Ser
            930                 935                 940

Val Val Val Leu Leu Val Ser Gly Leu Phe Leu Trp Leu Arg Lys Arg
945                 950                 955                 960

Lys His Lys Asp Leu Gly Ser Glu Leu Val Arg Tyr Asp Ala Arg Val
            965                 970                 975

His Thr Pro His Leu Asp Arg Leu Val Ser Ala Arg Ser Val Ser Pro
            980                 985                 990

Thr Thr Glu Met Val Ser Asn Glu  Ser Val Asp Tyr Arg  Ala Thr Phe
            995                 1000                 1005

Pro Glu  Asp Gln Phe Pro Asn  Ser Ser Gln Asn Gly  Ala Cys Arg
1010                 1015                 1020

Gln Val  Gln Tyr Leu Leu Thr  Asp Leu Ser Pro Ile  Leu Thr Ser
      1025                 1030                 1035

Gly Asp  Ser Asp Ile Ser Ser  Pro Leu Leu Gln Asn  Thr Val His
      1040                 1045                 1050

Ile Asp  Leu Ser Ala Leu Asn  Pro Glu Leu Val Gln  Ala Val Pro
      1055                 1060                 1065

His Val  Val Ile Gly Pro Ser  Ser Leu Ile Val His  Phe Asn Glu
      1070                 1075                 1080

Val Ile  Gly Arg Gly His Phe  Gly Cys Val Tyr His  Gly Thr Leu
      1085                 1090                 1095

Leu Asp  Ser Asp Gly Lys Lys  Ile His Cys Ala Val  Lys Ser Leu
      1100                 1105                 1110

Asn Arg  Ile Thr Asp Ile Glu  Glu Val Ser Gln Phe  Leu Thr Glu
      1115                 1120                 1125

Gly Ile  Ile Met Lys Asp Phe  Ser His Pro Asn Val  Leu Ser Leu
      1130                 1135                 1140

Leu Gly  Ile Cys Leu Arg Ser  Glu Gly Ser Pro Leu  Val Val Leu
      1145                 1150                 1155

Pro Tyr  Met Lys His Gly Asp  Leu Arg Asn Phe Ile  Arg Asn Glu
      1160                 1165                 1170

Thr His  Asn Pro Thr Val Lys  Asp Leu Ile Gly Phe  Gly Leu Gln
      1175                 1180                 1185

Val Ala  Lys Gly Met Lys Tyr  Leu Val Ser Lys Lys  Phe Val His
      1190                 1195                 1200

Arg Asp  Leu Ala Ala Arg Asn  Cys Met Leu Asp Glu  Lys Phe Thr
      1205                 1210                 1215

Val Lys  Val Ala Asp Phe Gly  Leu Ala Arg Asp Met  Tyr Asp Lys
```

```
                1220                1225                1230
Glu Tyr Tyr Ser Val His Asn Lys Thr Gly Ala Lys Leu Pro Val
    1235                1240                1245

Lys Trp Met Ala Leu Glu Ser Leu Gln Thr Gln Lys Phe Thr Thr
    1250                1255                1260

Lys Ser Asp Val Trp Ser Phe Gly Val Leu Leu Trp Glu Leu Met
    1265                1270                1275

Thr Arg Gly Ala Pro Pro Tyr Pro Asp Val Asn Thr Phe Asp Ile
    1280                1285                1290

Thr Ile Tyr Leu Leu Gln Gly Arg Arg Leu Leu Gln Pro Glu Tyr
    1295                1300                1305

Cys Pro Asp Ala Leu Tyr Glu Val Met Leu Lys Cys Trp His Pro
    1310                1315                1320

Lys Ala Glu Met Arg Pro Ser Val Ser Glu Leu Val Ser Arg Ile
    1325                1330                1335

Ser Ser Ile Phe Ser Thr Phe Ile Gly Glu His Tyr Val His Val
    1340                1345                1350

Asn Ala Thr Tyr Val Asn Val Lys Cys Val Ala Pro Tyr Pro Ser
    1355                1360                1365

Leu Leu Pro Ser Gln Asp Asn Ile Asp Gly Glu Ala Asn Thr
    1370                1375                1380

<210> SEQ ID NO 111
<211> LENGTH: 1379
<212> TYPE: PRT
<213> ORGANISM: Mus musculus

<400> SEQUENCE: 111

Met Lys Ala Pro Thr Val Leu Ala Pro Gly Ile Leu Val Leu Leu
1               5                   10                  15

Ser Leu Val Gln Arg Ser His Gly Glu Cys Lys Glu Ala Leu Val Lys
                20                  25                  30

Ser Glu Met Asn Val Asn Met Lys Tyr Gln Leu Pro Asn Phe Thr Ala
            35                  40                  45

Glu Thr Pro Ile Gln Asn Val Val Leu His Gly His His Ile Tyr Leu
        50                  55                  60

Gly Ala Thr Asn Tyr Ile Tyr Val Leu Asn Asp Lys Asp Leu Gln Lys
65                  70                  75                  80

Val Ser Glu Phe Lys Thr Gly Pro Val Leu Glu His Pro Asp Cys Leu
                85                  90                  95

Pro Cys Arg Asp Cys Ser Ser Lys Ala Asn Ser Ser Gly Gly Val Trp
            100                 105                 110

Lys Asp Asn Ile Asn Met Ala Leu Leu Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Leu Pro Pro Asp Asn Ser Ala Asp Ile Gln Ser Glu Val His Cys
145                 150                 155                 160

Met Phe Ser Pro Glu Glu Glu Ser Gly Gln Cys Pro Asp Cys Val Val
                165                 170                 175

Ser Ala Leu Gly Ala Lys Val Leu Leu Ser Glu Lys Asp Arg Phe Ile
            180                 185                 190

Asn Phe Phe Val Gly Asn Thr Ile Asn Ser Ser Tyr Pro Pro Gly Tyr
        195                 200                 205
```

```
Ser Leu His Ser Ile Ser Val Arg Arg Leu Lys Glu Thr Gln Asp Gly
    210                 215                 220
Phe Lys Phe Leu Thr Asp Gln Ser Tyr Ile Asp Val Leu Pro Glu Phe
225                 230                 235                 240
Leu Asp Ser Tyr Pro Ile Lys Tyr Ile His Ala Phe Glu Ser Asn His
                245                 250                 255
Phe Ile Tyr Phe Leu Thr Val Gln Lys Glu Thr Leu Asp Ala Gln Thr
            260                 265                 270
Phe His Thr Arg Ile Ile Arg Phe Cys Ser Val Asp Ser Gly Leu His
            275                 280                 285
Ser Tyr Met Glu Met Pro Leu Glu Cys Ile Leu Thr Glu Lys Arg Arg
    290                 295                 300
Lys Arg Ser Thr Arg Glu Glu Val Phe Asn Ile Leu Gln Ala Ala Tyr
305                 310                 315                 320
Val Ser Lys Pro Gly Ala Asn Leu Ala Lys Gln Ile Gly Ala Ser Pro
                325                 330                 335
Ser Asp Asp Ile Leu Phe Gly Val Phe Ala Gln Ser Lys Pro Asp Ser
            340                 345                 350
Ala Glu Pro Val Asn Arg Ser Ala Val Cys Ala Phe Pro Ile Lys Tyr
            355                 360                 365
Val Asn Asp Phe Phe Asn Lys Ile Val Asn Lys Asn Val Arg Cys
370                 375                 380
Leu Gln His Phe Tyr Gly Pro Asn His Glu His Cys Phe Asn Arg Thr
385                 390                 395                 400
Leu Leu Arg Asn Ser Ser Gly Cys Glu Ala Arg Ser Asp Glu Tyr Arg
                405                 410                 415
Thr Glu Phe Thr Thr Ala Leu Gln Arg Val Asp Leu Phe Met Gly Arg
            420                 425                 430
Leu Asn Gln Val Leu Leu Thr Ser Ile Ser Thr Phe Ile Lys Gly Asp
            435                 440                 445
Leu Thr Ile Ala Asn Leu Gly Thr Ser Glu Gly Arg Phe Met Gln Val
    450                 455                 460
Val Leu Ser Arg Thr Ala His Leu Thr Pro His Val Asn Phe Leu Leu
465                 470                 475                 480
Asp Ser His Pro Val Ser Pro Glu Val Ile Val Glu His Pro Ser Asn
                485                 490                 495
Gln Asn Gly Tyr Thr Leu Val Val Thr Gly Lys Lys Ile Thr Lys Ile
            500                 505                 510
Pro Leu Asn Gly Leu Gly Cys Gly His Phe Gln Ser Cys Ser Gln Cys
            515                 520                 525
Leu Ser Ala Pro Tyr Phe Ile Gln Cys Gly Trp Cys His Asn Gln Cys
    530                 535                 540
Val Arg Phe Asp Glu Cys Pro Ser Gly Thr Trp Thr Gln Glu Ile Cys
545                 550                 555                 560
Leu Pro Ala Val Tyr Lys Val Phe Pro Thr Ser Ala Pro Leu Glu Gly
                565                 570                 575
Gly Thr Val Leu Thr Ile Cys Gly Trp Asp Phe Gly Phe Arg Lys Asn
            580                 585                 590
Asn Lys Phe Asp Leu Arg Lys Thr Lys Val Leu Leu Gly Asn Glu Ser
            595                 600                 605
Cys Thr Leu Thr Leu Ser Glu Ser Thr Thr Asn Thr Leu Lys Cys Thr
    610                 615                 620
Val Gly Pro Ala Met Ser Glu His Phe Asn Val Ser Val Ile Ile Ser
```

```
              625                 630                 635                 640
Asn Ser Arg Glu Thr Thr Gln Tyr Ser Ala Phe Ser Tyr Val Asp Pro
                    645                 650                 655
Val Ile Thr Ser Ile Ser Pro Arg Tyr Gly Pro Gln Ala Gly Gly Thr
                660                 665                 670
Leu Leu Thr Leu Thr Gly Lys Tyr Leu Asn Ser Gly Asn Ser Arg His
                675                 680                 685
Ile Ser Ile Gly Gly Lys Thr Cys Thr Leu Lys Ser Val Ser Asp Ser
    690                 695                 700
Ile Leu Glu Cys Tyr Thr Pro Ala Gln Thr Thr Ser Asp Glu Phe Pro
705                 710                 715                 720
Val Lys Leu Lys Ile Asp Leu Ala Asn Arg Glu Thr Ser Ser Phe Ser
                725                 730                 735
Tyr Arg Glu Asp Pro Val Val Tyr Glu Ile His Pro Thr Lys Ser Phe
                740                 745                 750
Ile Ser Gly Gly Ser Thr Ile Thr Gly Ile Gly Lys Thr Leu Asn Ser
            755                 760                 765
Val Ser Leu Pro Lys Leu Val Ile Asp Val His Glu Val Gly Val Asn
    770                 775                 780
Tyr Thr Val Ala Cys Gln His Arg Ser Asn Ser Glu Ile Ile Cys Cys
785                 790                 795                 800
Thr Thr Pro Ser Leu Lys Gln Leu Gly Leu Gln Leu Pro Leu Lys Thr
                805                 810                 815
Lys Ala Phe Phe Leu Leu Asp Gly Ile Leu Ser Lys His Phe Asp Leu
                820                 825                 830
Thr Tyr Val His Asn Pro Val Phe Glu Pro Phe Glu Lys Pro Val Met
                835                 840                 845
Ile Ser Met Gly Asn Glu Asn Val Val Glu Ile Lys Gly Asn Asn Ile
    850                 855                 860
Asp Pro Glu Ala Val Lys Gly Glu Val Leu Lys Val Gly Asn Gln Ser
865                 870                 875                 880
Cys Glu Ser Leu His Trp His Ser Gly Ala Val Leu Cys Thr Val Pro
                885                 890                 895
Ser Asp Leu Leu Lys Leu Asn Ser Glu Leu Asn Ile Glu Trp Lys Gln
                900                 905                 910
Ala Val Ser Ser Thr Val Leu Gly Lys Val Ile Val Gln Pro Asp Gln
            915                 920                 925
Asn Phe Ala Gly Leu Ile Ile Gly Ala Val Ser Ile Ser Val Val Val
    930                 935                 940
Leu Leu Leu Ser Gly Leu Phe Leu Trp Met Arg Lys Arg Lys His Lys
945                 950                 955                 960
Asp Leu Gly Ser Glu Leu Val Arg Tyr Asp Ala Arg Val His Thr Pro
                965                 970                 975
His Leu Asp Arg Leu Val Ser Ala Arg Ser Val Ser Pro Thr Thr Glu
                980                 985                 990
Met Val Ser Asn Glu Ser Val Asp Tyr Arg Ala Thr Phe Pro Glu Asp
            995                 1000                1005
Gln Phe Pro Asn Ser Ser Gln Asn Gly Ala Cys Arg Gln Val Gln
    1010                1015                1020
Tyr Pro Leu Thr Asp Leu Ser Pro Ile Leu Thr Ser Gly Asp Ser
    1025                1030                1035
Asp Ile Ser Ser Pro Leu Leu Gln Asn Thr Val His Ile Asp Leu
    1040                1045                1050
```

Ser Ala Leu Asn Pro Glu Leu Val Gln Ala Val Gln His Val Val
    1055                1060                1065

Ile Gly Pro Ser Ser Leu Ile Val His Phe Asn Glu Val Ile Gly
    1070                1075                1080

Arg Gly His Phe Gly Cys Val Tyr His Gly Thr Leu Leu Asp Asn
    1085                1090                1095

Asp Gly Lys Lys Ile His Cys Ala Val Lys Ser Leu Asn Arg Ile
    1100                1105                1110

Thr Asp Ile Glu Glu Val Ser Gln Phe Leu Thr Glu Gly Ile Ile
    1115                1120                1125

Met Lys Asp Phe Ser His Pro Asn Val Leu Ser Leu Leu Gly Ile
    1130                1135                1140

Cys Leu Arg Ser Glu Gly Ser Pro Leu Val Val Leu Pro Tyr Met
    1145                1150                1155

Lys His Gly Asp Leu Arg Asn Phe Ile Arg Asn Glu Thr His Asn
    1160                1165                1170

Pro Thr Val Lys Asp Leu Ile Gly Phe Gly Leu Gln Val Ala Lys
    1175                1180                1185

Gly Met Lys Tyr Leu Ala Ser Lys Lys Phe Val His Arg Asp Leu
    1190                1195                1200

Ala Ala Arg Asn Cys Met Leu Asp Glu Lys Phe Thr Val Lys Val
    1205                1210                1215

Ala Asp Phe Gly Leu Ala Arg Asp Met Tyr Asp Lys Glu Tyr Tyr
    1220                1225                1230

Ser Val His Asn Lys Thr Gly Ala Lys Leu Pro Val Lys Trp Met
    1235                1240                1245

Ala Leu Glu Ser Leu Gln Thr Gln Lys Phe Thr Thr Lys Ser Asp
    1250                1255                1260

Val Trp Ser Phe Gly Val Leu Leu Trp Glu Leu Met Thr Arg Gly
    1265                1270                1275

Ala Pro Pro Tyr Pro Asp Val Asn Thr Phe Asp Ile Thr Ile Tyr
    1280                1285                1290

Leu Leu Gln Gly Arg Arg Leu Leu Gln Pro Glu Tyr Cys Pro Asp
    1295                1300                1305

Ala Leu Tyr Glu Val Met Leu Lys Cys Trp His Pro Lys Ala Glu
    1310                1315                1320

Met Arg Pro Ser Phe Ser Glu Leu Val Ser Arg Ile Ser Ser Ile
    1325                1330                1335

Phe Ser Thr Phe Ile Gly Glu His Tyr Val His Val Asn Ala Thr
    1340                1345                1350

Tyr Val Asn Val Lys Cys Val Ala Pro Tyr Pro Ser Leu Leu Pro
    1355                1360                1365

Ser Gln Asp Asn Ile Asp Gly Glu Gly Asn Thr
    1370                1375

<210> SEQ ID NO 112
<211> LENGTH: 1382
<212> TYPE: PRT
<213> ORGANISM: Canis lupus

<400> SEQUENCE: 112

Met Lys Ala Pro Ala Val Leu Ala Pro Gly Ile Leu Val Leu Leu Phe
1               5                   10                  15

Thr Leu Val Gln Lys Ser Tyr Gly Glu Cys Lys Glu Ala Leu Val Lys

-continued

```
                20                  25                  30
    Ser Glu Met Asn Val Asn Met Lys Tyr Gln Leu Pro Asn Phe Thr Ala
            35                  40                  45

Glu Thr Pro Ile Gln Asn Val Val Leu His Lys His Ile Tyr Leu
        50                  55                  60

Gly Ala Val Asn Tyr Ile Tyr Val Leu Asn Lys Asp Leu Gln Lys
    65                  70                  75                  80

Val Ala Glu Tyr Lys Thr Gly Pro Val Leu Glu His Pro Asp Cys Ser
                    85                  90                  95

Pro Cys Gln Asp Cys Ser His Lys Ala Asn Leu Ser Gly Gly Val Trp
                    100                 105                 110

Glu Asp Asn Ile Asn Met Ala Leu Leu Val Asp Thr Tyr Tyr Asp Asp
                    115                 120                 125

Gln Leu Ile Ser Cys Gly Ser Val His Arg Gly Thr Cys Gln Arg His
                    130                 135                 140

Ile Leu Pro Pro Ser Asn Ile Ala Asp Ile Gln Ser Glu Val His Cys
    145                 150                 155                 160

Met Tyr Ser Ser Gln Ala Asp Glu Pro Ser Gln Cys Pro Asp Cys
                    165                 170                 175

Val Val Ser Ala Leu Gly Thr Lys Val Leu Ile Ser Glu Lys Asp Arg
                    180                 185                 190

Phe Ile Asn Phe Phe Val Gly Asn Thr Ile Asn Ser Ser Asp His Pro
                    195                 200                 205

Asp His Ser Leu His Ser Ile Ser Val Arg Arg Leu Lys Glu Thr Gln
                    210                 215                 220

Asp Gly Phe Lys Phe Leu Thr Asp Gln Ser Tyr Ile Asp Val Leu Pro
    225                 230                 235                 240

Glu Phe Arg Asp Ser Tyr Pro Ile Lys Tyr Val His Ala Phe Glu Ser
                    245                 250                 255

Asn His Phe Ile Tyr Phe Leu Thr Val Gln Arg Glu Thr Leu Asp Ala
                    260                 265                 270

Gln Thr Phe His Thr Arg Ile Ile Arg Phe Cys Ser Val Asp Ser Gly
                    275                 280                 285

Leu His Ser Tyr Met Glu Met Pro Leu Glu Cys Ile Leu Thr Glu Lys
                    290                 295                 300

Arg Arg Lys Arg Ser Thr Arg Glu Glu Val Phe Asn Ile Leu Gln Ala
    305                 310                 315                 320

Ala Tyr Val Ser Lys Pro Gly Ala His Leu Ala Lys Gln Ile Gly Ala
                    325                 330                 335

Asn Leu Asn Asp Asp Ile Leu Tyr Gly Val Phe Ala Gln Ser Lys Pro
                    340                 345                 350

Asp Ser Ala Glu Pro Met Asn Arg Ser Ala Val Cys Ala Phe Pro Ile
                    355                 360                 365

Lys Tyr Val Asn Glu Phe Phe Asn Lys Ile Val Asn Lys Asn Val
                    370                 375                 380

Arg Cys Leu Gln His Phe Tyr Gly Pro Asn His Glu His Cys Phe Asn
    385                 390                 395                 400

Arg Thr Leu Leu Arg Asn Ser Ser Gly Cys Glu Ala Arg Asn Asp Glu
                    405                 410                 415

Tyr Arg Thr Glu Phe Thr Thr Ala Leu Gln Arg Val Asp Leu Phe Met
                    420                 425                 430

Gly Gln Phe Asn Gln Val Leu Leu Thr Ser Ile Ser Thr Phe Ile Lys
                    435                 440                 445
```

```
Gly Asp Leu Thr Ile Ala Asn Leu Gly Thr Ser Glu Gly Arg Phe Met
    450                 455                 460

Gln Val Val Val Ser Arg Ser Gly Leu Ser Thr Pro His Val Asn Phe
465                 470                 475                 480

Arg Leu Asp Ser His Pro Val Ser Pro Glu Ala Ile Val Glu His Pro
                485                 490                 495

Leu Asn Gln Asn Gly Tyr Thr Leu Val Val Thr Gly Lys Lys Ile Thr
            500                 505                 510

Arg Ile Pro Leu Asn Gly Leu Gly Cys Glu His Phe Gln Ser Cys Ser
        515                 520                 525

Gln Cys Leu Ser Ala Pro Pro Phe Val Gln Cys Gly Trp Cys His Asp
    530                 535                 540

Arg Cys Val His Leu Glu Glu Cys Pro Thr Gly Ala Trp Thr Gln Glu
545                 550                 555                 560

Val Cys Leu Pro Ala Ile Tyr Glu Val Phe Pro Thr Ser Ala Pro Leu
                565                 570                 575

Glu Gly Gly Thr Val Leu Thr Val Cys Gly Trp Asp Phe Gly Phe Arg
            580                 585                 590

Arg Asn Asn Lys Phe Asp Leu Lys Lys Thr Lys Val Phe Leu Gly Asn
        595                 600                 605

Glu Ser Cys Thr Leu Thr Leu Ser Glu Ser Thr Thr Asn Met Leu Lys
    610                 615                 620

Cys Thr Val Gly Pro Ala Val Asn Glu His Phe Asn Ile Ser Ile Ile
625                 630                 635                 640

Ile Ser Asn Gly Arg Gly Thr Ala Gln Tyr Ser Thr Phe Ser Tyr Val
                645                 650                 655

Asp Pro Ile Ile Thr Ser Ile Ser Pro Ser Tyr Gly Pro Lys Asn Gly
            660                 665                 670

Gly Thr Leu Leu Thr Leu Thr Gly Lys Tyr Leu Asn Ser Gly Asn Ser
        675                 680                 685

Arg His Ile Ser Met Gly Gly Lys Thr Cys Thr Leu Lys Ser Val Ser
    690                 695                 700

Asp Ser Ile Leu Glu Cys Tyr Thr Pro Ala Gln Ala Thr Ala Thr Glu
705                 710                 715                 720

Phe Pro Ile Lys Leu Lys Ile Asp Leu Ala Asn Arg Glu Met Asn Ser
                725                 730                 735

Phe Ser Tyr Gln Glu Asp Pro Ile Val Tyr Ala Ile His Pro Thr Lys
            740                 745                 750

Ser Phe Ile Ser Gly Gly Ser Thr Ile Thr Ala Val Gly Lys Asn Leu
        755                 760                 765

Asn Ser Val Ser Val Leu Arg Met Val Ile Asp Val His Glu Thr Arg
    770                 775                 780

Arg Asn Phe Thr Val Ala Cys Gln His Arg Ser Asn Ser Glu Ile Ile
785                 790                 795                 800

Cys Cys Thr Thr Pro Ser Leu Gln Gln Leu Asn Leu Gln Leu Pro Leu
                805                 810                 815

Lys Thr Lys Ala Phe Phe Met Leu Asp Gly Ile His Ser Lys Tyr Phe
            820                 825                 830

Asp Leu Ile Tyr Val His Asn Pro Val Phe Lys Pro Phe Glu Lys Pro
        835                 840                 845

Val Met Ile Ser Ile Gly Asn Glu Asn Val Leu Glu Ile Lys Gly Asn
    850                 855                 860
```

```
Asp Ile Asp Pro Glu Ala Val Lys Gly Glu Val Leu Lys Val Gly Asn
865                 870                 875                 880

Lys Ser Cys Glu Thr Ile Tyr Ser Asp Ser Lys Ala Val Leu Cys Lys
            885                 890                 895

Val Pro Asn Asp Leu Leu Lys Leu Asn Asn Glu Leu Asn Ile Glu Trp
        900                 905                 910

Lys Gln Ala Val Ser Ser Thr Val Leu Gly Lys Val Ile Val Gln Pro
    915                 920                 925

Asp Gln Asn Phe Thr Gly Leu Ile Ala Gly Val Ile Ser Ile Ser Thr
930                 935                 940

Ile Val Leu Leu Leu Leu Gly Leu Phe Leu Trp Leu Lys Arg Lys Lys
945                 950                 955                 960

Gln Ile Lys Asp Leu Gly Ser Glu Leu Val Arg Tyr Asp Ala Arg Val
            965                 970                 975

His Thr Pro His Leu Asp Arg Leu Val Ser Ala Arg Ser Val Ser Pro
        980                 985                 990

Thr Thr Glu Met Val Ser Asn Glu  Ser Val Asp Tyr Arg  Ala Thr Phe
            995                  1000                 1005

Pro Glu  Asp Gln Phe Pro Asn  Ser Ser Gln Asn Gly  Ser Cys Arg
1010                 1015                 1020

Gln Val  Gln Tyr Pro Leu Thr  Asp Leu Ser Pro Met  Leu Thr Ser
1025                 1030                 1035

Gly Asp  Ser Asp Ile Ser Ser  Pro Leu Leu Gln Asn  Thr Val His
1040                 1045                 1050

Ile Asp  Leu Ser Ala Leu Asn  Pro Glu Leu Val Gln  Ala Val Gln
1055                 1060                 1065

His Val  Val Ile Gly Pro Ser  Ser Leu Ile Val His  Phe Asn Glu
1070                 1075                 1080

Val Ile  Gly Arg Gly His Phe  Gly Cys Val Tyr His  Gly Thr Leu
1085                 1090                 1095

Leu Asp  Asn Asp Asp Lys Lys  Ile His Cys Ala Val  Lys Ser Leu
1100                 1105                 1110

Asn Arg  Ile Thr Asp Ile Gly  Glu Val Ser Gln Phe  Leu Thr Glu
1115                 1120                 1125

Gly Ile  Ile Met Lys Asp Phe  Ser His Pro Asn Val  Leu Ser Leu
1130                 1135                 1140

Leu Gly  Ile Cys Leu Arg Ser  Glu Gly Ser Pro Leu  Val Val Leu
1145                 1150                 1155

Pro Tyr  Met Lys His Gly Asp  Leu Arg Asn Phe Ile  Arg Asn Glu
1160                 1165                 1170

Thr His  Asn Pro Thr Val Lys  Asp Leu Ile Gly Phe  Gly Leu Gln
1175                 1180                 1185

Val Ala  Lys Gly Met Lys Tyr  Leu Ala Ser Lys Lys  Phe Val His
1190                 1195                 1200

Arg Asp  Leu Ala Ala Arg Asn  Cys Met Leu Asp Glu  Lys Phe Thr
1205                 1210                 1215

Val Lys  Val Ala Asp Phe Gly  Leu Ala Arg Asp Met  Tyr Asp Lys
1220                 1225                 1230

Glu Tyr  Tyr Ser Val His Asn  Lys Thr Gly Ala Lys  Leu Pro Val
1235                 1240                 1245

Lys Trp  Met Ala Leu Glu Ser  Leu Gln Thr Gln Lys  Phe Thr Thr
1250                 1255                 1260

Lys Ser  Asp Val Trp Ser Phe  Gly Val Leu Leu Trp  Glu Leu Met
```

-continued

```
              1265                1270                1275
Thr Arg Gly Ala Pro Pro Tyr Pro Asp Val Asn Thr Phe Asp Ile
            1280                1285                1290

Thr Val Tyr Leu Leu Gln Gly Arg Arg Leu Leu Gln Pro Glu Tyr
            1295                1300                1305

Cys Pro Asp Pro Leu Tyr Glu Val Met Leu Lys Cys Trp His Pro
            1310                1315                1320

Arg Ala Glu Leu Arg Pro Ser Phe Ser Glu Leu Val Ser Arg Ile
            1325                1330                1335

Ser Ala Ile Phe Ser Thr Phe Ile Gly Glu His Tyr Val His Val
            1340                1345                1350

Asn Ala Thr Tyr Val Asn Val Lys Cys Val Ala Pro Tyr Pro Ser
            1355                1360                1365

Leu Leu Ser Ser Gln Asp Asn Ile Asp Gly Glu Gly Asp Thr
            1370                1375                1380

<210> SEQ ID NO 113
<211> LENGTH: 1381
<212> TYPE: PRT
<213> ORGANISM: Macaca mulatta

<400> SEQUENCE: 113

Met Lys Ala Pro Ala Val Leu Val Pro Gly Ile Leu Val Leu Leu Phe
1               5                   10                  15

Thr Leu Val Gln Arg Ser Asn Gly Glu Cys Lys Glu Ala Leu Ala Lys
                20                  25                  30

Ser Glu Met Asn Val Asn Met Lys Tyr Gln Leu Pro Asn Phe Thr Ala
            35                  40                  45

Glu Thr Ala Ile Gln Asn Val Ile Leu His Glu His His Ile Phe Leu
        50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Asn Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro His
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Ile His Ala Phe Glu Ser Asn
                245                 250                 255
```

```
Asn Phe Ile Tyr Phe Leu Thr Val Gln Arg Glu Thr Leu Asn Ala Gln
                260                 265                 270

Thr Phe His Thr Arg Ile Ile Arg Phe Cys Ser Leu Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
        340                 345                 350

Ser Ala Glu Pro Met Asp Arg Ser Ala Met Cys Ala Phe Pro Ile Lys
    355                 360                 365

Tyr Val Asn Asp Phe Phe Asn Lys Ile Val Asn Lys Asn Asn Val Arg
370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Ala Glu Phe Thr Thr Ala Leu Gln Arg Val Asp Leu Phe Met Gly
        420                 425                 430

Gln Phe Ser Glu Val Leu Leu Thr Ser Ile Ser Thr Phe Val Lys Gly
    435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Pro Leu
                485                 490                 495

Asn Gln Asn Gly Tyr Thr Leu Val Val Thr Gly Lys Lys Ile Thr Lys
        500                 505                 510

Ile Pro Leu Asn Gly Leu Gly Cys Arg His Phe Gln Ser Cys Ser Gln
    515                 520                 525

Cys Leu Ser Ala Pro Pro Phe Val Gln Cys Gly Trp Cys His Asp Lys
530                 535                 540

Cys Val Arg Ser Glu Glu Cys Pro Ser Gly Thr Trp Thr Gln Gln Ile
545                 550                 555                 560

Cys Leu Pro Ala Ile Tyr Lys Val Phe Pro Thr Ser Ala Pro Leu Glu
                565                 570                 575

Gly Gly Thr Arg Leu Thr Ile Cys Gly Trp Asp Phe Gly Phe Arg Arg
        580                 585                 590

Asn Asn Lys Phe Asp Leu Lys Lys Thr Arg Val Leu Leu Gly Asn Glu
    595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Ile Ile Thr Ser Ile Ser Pro Lys Tyr Gly Pro Met Ala Gly Gly
        660                 665                 670

Thr Leu Leu Thr Leu Thr Gly Asn Tyr Leu Asn Ser Gly Asn Ser Arg
```

```
            675                 680                 685
His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Gly Gly Ser Thr Ile Thr Gly Val Gly Lys Asn Leu His
        755                 760                 765

Ser Val Ser Val Pro Arg Met Val Ile Asn Val His Glu Ala Gly Arg
    770                 775                 780

Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
                805                 810                 815

Thr Lys Ala Phe Phe Met Leu Asp Gly Ile Leu Ser Lys Tyr Phe Asp
            820                 825                 830

Leu Ile Tyr Val His Asn Pro Val Phe Lys Pro Phe Glu Lys Pro Val
        835                 840                 845

Met Ile Ser Met Gly Asn Glu Asn Val Leu Glu Ile Lys Gly Asn Asp
    850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Ile Ala
    930                 935                 940

Leu Leu Leu Leu Leu Gly Leu Phe Leu Trp Leu Lys Lys Arg Lys Gln
945                 950                 955                 960

Ile Lys Asp Leu Gly Ser Glu Leu Val Arg Tyr Asp Ala Arg Val His
                965                 970                 975

Thr Pro His Leu Asp Arg Leu Val Ser Ala Arg Ser Val Ser Pro Thr
            980                 985                 990

Thr Glu Met Val Ser Asn Glu Ser  Val Asp Tyr Arg Ala  Thr Phe Pro
        995                 1000                1005

Glu Asp  Gln Phe Pro Asn Ser  Ser Gln Asn Gly Ser  Cys Arg Gln
    1010                1015                1020

Val Gln  Tyr Pro Leu Thr Asp  Met Ser Pro Ile Leu  Thr Ser Gly
    1025                1030                1035

Asp Ser  Asp Ile Ser Ser Pro  Leu Leu Gln Asn Thr  Val His Ile
    1040                1045                1050

Asp Leu  Ser Ala Leu Asn Pro  Glu Leu Val Gln Ala  Val Gln His
    1055                1060                1065

Val Val  Ile Gly Pro Ser Ser  Leu Ile Val His Phe  Asn Glu Val
    1070                1075                1080

Ile Gly  Arg Gly His Phe Gly  Cys Val Tyr His Gly  Thr Leu Leu
    1085                1090                1095
```

Asp Asn Asp Gly Lys Lys Ile His Cys Ala Val Lys Ser Leu Asn
1100                1105                1110

Arg Ile Thr Asp Ile Gly Glu Val Ser Gln Phe Leu Thr Glu Gly
     1115                1120                1125

Ile Ile Met Lys Asp Phe Ser His Pro Asn Val Leu Ser Leu Leu
         1130                1135                1140

Gly Ile Cys Leu Arg Ser Glu Gly Ser Pro Leu Val Val Leu Pro
     1145                1150                1155

Tyr Met Lys His Gly Asp Leu Arg Asn Phe Ile Arg Asn Glu Thr
         1160                1165                1170

His Asn Pro Thr Val Lys Asp Leu Ile Gly Phe Gly Leu Gln Val
     1175                1180                1185

Ala Lys Gly Met Lys Tyr Leu Ala Ser Lys Lys Phe Val His Arg
         1190                1195                1200

Asp Leu Ala Ala Arg Asn Cys Met Leu Asp Glu Lys Phe Thr Val
     1205                1210                1215

Lys Val Ala Asp Phe Gly Leu Ala Arg Asp Met Tyr Asp Lys Glu
         1220                1225                1230

Tyr Tyr Ser Val His Asn Lys Thr Gly Ala Lys Leu Pro Val Lys
     1235                1240                1245

Trp Met Ala Leu Glu Ser Leu Gln Thr Gln Lys Phe Thr Thr Lys
         1250                1255                1260

Ser Asp Val Trp Ser Phe Gly Val Leu Leu Trp Glu Leu Met Thr
     1265                1270                1275

Arg Gly Ala Pro Pro Tyr Pro Asp Val Asn Thr Phe Asp Ile Thr
         1280                1285                1290

Val Tyr Leu Leu Gln Gly Arg Arg Leu Leu Gln Pro Glu Tyr Cys
     1295                1300                1305

Pro Asp Pro Leu Tyr Glu Val Met Leu Lys Cys Trp His Pro Lys
         1310                1315                1320

Ala Glu Met Arg Pro Ser Phe Ser Glu Leu Val Ser Arg Ile Ser
     1325                1330                1335

Ala Ile Phe Ser Thr Phe Ile Gly Glu His Tyr Val His Val Asn
         1340                1345                1350

Ala Thr Tyr Val Asn Val Lys Cys Val Ala Pro Tyr Pro Ser Leu
     1355                1360                1365

Leu Ser Ser Glu Asp Asn Ala Asp Asp Glu Val Asp Thr
         1370                1375                1380

<210> SEQ ID NO 114
<211> LENGTH: 445
<212> TYPE: PRT
<213> ORGANISM: Artificial Sequence
<220> FEATURE:
<223> OTHER INFORMATION: Heavy Chain Sequence of hD12

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Asp Trp Ile
        35                  40                  45

Gly Tyr Ile Lys Pro Ser Thr Asp Asn Thr Glu Tyr Asn Gln Lys Phe
    50                  55                  60

-continued

Lys Asp Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Gly Asn Tyr Pro Leu Met Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 115
<211> LENGTH: 215
<212> TYPE: PRT
<213> ORGANISM: Artificial Sequence
<220> FEATURE:

<223> OTHER INFORMATION: Light Chain sequence of hD12

<400> SEQUENCE: 115

Gln Ile Val Leu Thr Gln Ser Pro Ala Ile Leu Ser Leu Ser Pro Gly
1               5                   10                  15

Glu Arg Ala Thr Leu Ser Cys Ser Ala Ser Ser Val Thr Ser Asn
            20                  25                  30

Tyr Leu Tyr Trp Tyr Gln Gln Lys Pro Gly Ser Ser Pro Lys Leu Leu
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Thr Leu Thr Ile Ser Ser Leu Glu
65                  70                  75                  80

Ala Glu Asp Ala Ala Ser Tyr Phe Cys His Gln Trp Ser Ser Tyr Pro
                85                  90                  95

Pro Thr Phe Gly Ser Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 116
<211> LENGTH: 445
<212> TYPE: PRT
<213> ORGANISM: Artificial Sequence
<220> FEATURE:
<223> OTHER INFORMATION: Heavy Chain sequence of hD12 T289C

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Ala Pro Gly Gln Gly Leu Asp Trp Ile
        35                  40                  45

Gly Tyr Ile Lys Pro Ser Thr Asp Asn Thr Glu Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Gly Asn Tyr Pro Leu Met Asp Tyr Trp Gly Gln Gly
            100                 105                 110

Thr Thr Val Thr Val Ser Ser Ala Ser Thr Lys Gly Pro Ser Val Phe
            115                 120                 125

-continued

```
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Asn Phe Gly Thr Gln Thr Tyr Thr Cys Asn Val Asp His Lys Pro
        195                 200                 205
Ser Asn Thr Lys Val Asp Lys Thr Val Glu Arg Lys Cys Cys Val Glu
        210                 215                 220
Cys Pro Pro Cys Pro Ala Pro Pro Val Ala Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Gln
                260                 265                 270
Phe Asn Trp Tyr Val Asp Gly Val Glu Val His Asn Ala Lys Cys Lys
                275                 280                 285
Pro Arg Glu Glu Gln Phe Asn Ser Thr Phe Arg Val Val Ser Val Leu
        290                 295                 300
Thr Val Val His Gln Asp Trp Leu Asn Gly Lys Glu Tyr Lys Cys Lys
305                 310                 315                 320
Val Ser Asn Lys Gly Leu Pro Ala Pro Ile Glu Lys Thr Ile Ser Lys
                325                 330                 335
Thr Lys Gly Gln Pro Arg Glu Pro Gln Val Tyr Thr Leu Pro Pro Ser
                340                 345                 350
Arg Glu Glu Met Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Met Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
                420                 425                 430
His Tyr Thr Gln Lys Ser Leu Ser Leu Ser Pro Gly Lys
            435                 440                 445
```

DRUG CONJUGATES OF CMET MONOCLONAL BINDING AGENTS, AND USES THEREOF

RELATED APPLICATIONS

This patent application is a national phase filing of, and claims the benefit of, International Patent Application No. based on PCT/JP2019/013345 filed on Mar. 27, 2019, entitled DRUG CONJUGATES OF cMET MONOCLONAL BINDING AGENTS, AND USES THEREOF, and naming Julia Coronella, Marco Gymnopoulos, Vincent Blot, Ryo Fujita and Roland Newman as an inventors, which claims the benefit of U.S. Provisional Patent Application No. 62/649,078 filed on Mar. 28, 2018, entitled DRUG CONJUGATES OF cMET MONOCLONAL BINDING AGENTS, AND USES THEREOF, naming Julia Coronella, Marco Gymnopoulos, Vincent Blot, Ryo Fujita and Roland Newman as inventors. The entire content of the foregoing patent application is incorporated herein by reference, including all text, tables and drawings.

SEQUENCE LISTING

The present application is being filed with a Sequence Listing. The Sequence Listing is submitted electronically in ASCII format via EFS-Web in the form of a text file. Said ASCII copy, created on Aug. 12, 2020, is named 674112_sequence.txt and is 112 KB in size, the contents of which are incorporated herein by reference in their entirety.

FIELD OF THE INVENTION

Embodiments of the invention relate to cMET binding agents that are conjugated to pyrrolobenzodiazepine toxins, composition thereof and uses thereof.

BACKGROUND

The protein cMET, sometimes called MET or hepatocyte growth factor receptor (HGFR), is a protein that in humans is encoded by the MET gene (MET proto-oncogene, receptor tyrosine kinase). cMET is a single-pass cell surface receptor that possesses tyrosine kinase activity. The primary single chain precursor protein of the MET translation product is post-translationally cleaved to produce an alpha and a beta subunit, which are disulfide linked to form a mature cell surface cMET receptor. cMET is expressed on cells of epithelial origin, as well as stem cells, progenitor cells and other cell types (e.g., various cancer cell types). Hepatocyte growth factor/Scatter Factor (HGF/SF) and its splicing isoforms (NK1, NK2) have been identified as ligands of cMET.

cMET is thought to be essential for normal embryonic development, organogenesis and wound healing. Abnormal cMET expression and/or activity is associated with certain neoplastic disorders and cancers (e.g., cancers of kidney, liver, stomach, breast, and brain) where cMET is implicated in tumor growth, angiogenesis, and metastasis. The overexpression of cMET as well as its autocrine activation by co-expression of its ligand are also implicated in oncogenesis.

Presented herein are novel anti-cMET binding agents (e.g., a monoclonal antibody) that are conjugated to a cytotoxic payload, pharmaceutical compositions thereof and methods of using the same.

SUMMARY OF THE INVENTION

In some aspects, presented herein is a binding agent-drug conjugate comprising a binding agent and a payload, where the payload comprises a pyrrolobenzodiazepine toxin and the binding agent specifically binds to mesenchymal epithelial transition factor (cMET). In some embodiments, a payload comprises a linking group where the pyrrolobenzodiazepine toxin is covalently linked to the linking group, and the linking group is covalently linked to the binding agent. In some embodiments, a binding agent is a monoclonal antibody, or antigen binding portion thereof.

In some aspects, presented herein is a binding agent-drug conjugate comprising a binding agent and a payload, wherein the binding agent comprises: (i) two or more of a CDR-L1, a CDR-L2 and a CDR-L3 which are polypeptide sequences of a light chain complementarity determining region (CDR-L), wherein the CDR-L1 is selected from the amino acid sequences of SEQ ID NOs: 1-15, the CDR-L2 is selected from the amino acid sequences of SEQ ID NOs: 16-25, and the CDR-L3 is selected from the amino acid sequences of SEQ ID NOs: 26-36, and (ii) two or more of a CDR-H1, a CDR-H2 and a CDR-H3 which are polypeptide sequences of a heavy chain complementarity determining region (CDR-H), wherein the CDR-H1 is selected from the amino acid sequences of SEQ ID NOs: 50-61, the CDR-H2 is selected from the amino acid sequences of SEQ ID NOs: 62-78, and the CDR-H3 is selected from the amino acid sequences of SEQ ID NOs: 79-93; and the payload comprises a pyrrolobenzodiazepine toxin and a linking group; wherein the pyrrolobenzodiazepine toxin is covalently linked to the linking group, the linking group is covalently linked to the binding agent, and the binding agent specifically binds to an extracellular domain of mesenchymal epithelial transition factor (cMET).

In certain embodiments, a pyrrolobenzodiazepine toxin comprises the structure of chemical formula I:

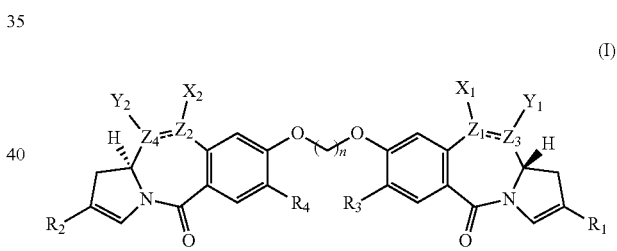

(I)

wherein
$Z_1$ and $Z_2$ are both N;
$Z_3$ and $Z_4$ are both C;
the double-dash lines ===== represent a single bond or a double bond;
n is 1 to 12;
each of $R_3$ and $R_4$ are independently H, or a $C_{1-4}$ alkoxyl; and
each of $R_1$ and $R_2$ are independently selected from the group consisting of H, $C_{1-5}$ alkyl, $C_{3-6}$ cycloalkyl, $C_{2-5}$ alkenyl, and a phenyl optionally substituted with $R_5$, wherein
$R_5$ is selected from the group consisting of —$NH_2$, —$NHR_6$, and a piperazinyl substituted with $R_7$ having the structure

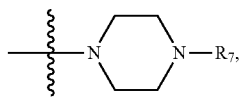

$R_6$ comprises the linking group, and
$R_7$ is H, or a $C_{1-5}$ alkyl;
$X_1$ is null, a protecting group, or comprises the linking group;
$X_2$ is null, a protecting group, or comprises the linking group;
only one of $X_1$, $X_2$, $R_1$, and $R_2$ comprises the linking group; and
each of $Y_1$ and $Y_2$ are independently either null, OH, or $SO_3H$;
provided that:
(i) when $X_1$ comprises the linking group, $Z_1 \text{=====} Z_3$ is N—C,
(ii) when $X_2$ comprises the linking group. $Z_2 \text{=====} Z_4$ is N—C,
(iii) when X comprises the protecting group, $Z_1 \text{=====} Z_3$ is N—C, and
(iv) when $X_2$ comprises the protecting group, $Z_2 \text{=====} Z_4$ is N—C,
wherein null indicates the absence of the moiety or the presence of one or more hydrogens to complete a required valency.

In some embodiments of the pyrrolobenzodiazepine toxin of the structure of chemical formula I, n is 3 or 5. In some embodiments of the pyrrolobenzodiazepine toxin of the structure of chemical formula I, $R_3$ and $R_4$ are both —O—$CH_3$. In certain embodiments of the pyrrolobenzodiazepine toxin of the structure of chemical formula I, $R_1$ and $R_2$ are both methyl or $R_1$ and $R_2$ are both —CH=CH—$CH_3$. In some embodiment of the pyrrolobenzodiazepine toxin of the structure of chemical formula I, $R_2$ is a cyclopropyl. In certain embodiments of the pyrrolobenzodiazepine toxin of the structure of chemical formula I, $R_2$ is phenyl substituted with 4-methylpiperazin-1-yl or phenyl substituted with $R_5$, where $R_5$ is —$NHR_6$ and $R_6$ comprises the linking group. In certain embodiments of the pyrrolobenzodiazepine toxin of the structure of chemical formula I, the linking group is attached to the pyrrolobenzodiazepine toxin by a carbamate group or an amide group.

In some embodiments of the pyrrolobenzodiazepine toxin of the structure of chemical formula I, $X_1$ is null, $Y_1$ is null, $Z_1 \text{=====} Z_3$ is N—C, $X_2$ is null, $Y_2$ is null and $Z_2 \text{=====} Z_4$ is N—C. In certain embodiments of the pyrrolobenzodiazepine toxin of the structure of chemical formula I, $X_1$ comprises the linking group, $Y_1$ is a OH, $Z_2 \text{=====} Z_4$ is N—C, $X_2$ is null, and $Y_2$ is null. In certain embodiments of the pyrrolobenzodiazepine toxin of the structure of chemical formula I, $X_1$ comprises the linking group, $Y_1$ is OH, $Z_2 \text{=====} Z_4$ is N—C, $X_2$ is a protecting group, and $Y_2$ is OH.

In certain embodiments, a linking group comprises the structure of chemical formula A:

wherein the asterisk indicates the point of attachment to a pyrrolobenzodiazepine toxin; the wavy line indicates the point of attachment to the binding agent; m is 1 to 20; q is 1 to 10; and E is a connecting group. In certain embodiments of the linking group of chemical formula A, m is 4 or 8 and q is 0, 1 or 2. In some embodiments, m is 8 and q is 2.

In certain embodiments, a linking group comprises the structure of chemical formula B:

(B)

wherein the asterisk indicates the point of attachment to the pyrrolobenzodiazepine toxin; the wavy line indicates the point of attachment to the binding agent; E comprises a connecting group; v is 0 to 10; and u is 0 or 1; wherein when u is 1, t is 1 to 10. In certain embodiments of the linking group of chemical formula B, v is 1. In certain embodiments of the linking group of chemical formula B, u is 1, and t is 8. In certain embodiments of the linking group of chemical formula B, u is 0, and v is 4.

In certain embodiments of the linking group of chemical formulas A and B, a binding agent is connected to E by a thioether bond formed between a cysteine thiol residue of the binding agent and E. In some embodiments, E comprises the structure of chemical formula C:

(C)

wherein the wavy line indicates the point of attachment to a binding agent and the double asterisk indicates a point of attachment to the linking group.

In some embodiments of the pyrrolobenzodiazepine toxin of the structure of chemical formula I, the protecting group has the following structure (D):

(A)

(D)

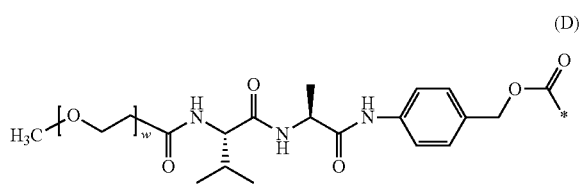

wherein the asterisk indicates a point of attachment to a pyrrolobenzodiazepine toxin; and w is 1 to 5. In some embodiments, w is 2. In some embodiments, a protecting group is a cleavable protecting group.

In certain aspects, presented herein is a binding agent-drug conjugate comprising a binding agent and a payload, where the binding agent specifically binds to an extracellular domain of mesenchymal epithelial transition factor (cMET), the payload is covalently linked to the binding agent, and the payload comprises a structure selected from the group consisting of chemical formulas II, III, V, VI and VII, where chemical formula II comprises the structure:

(II)

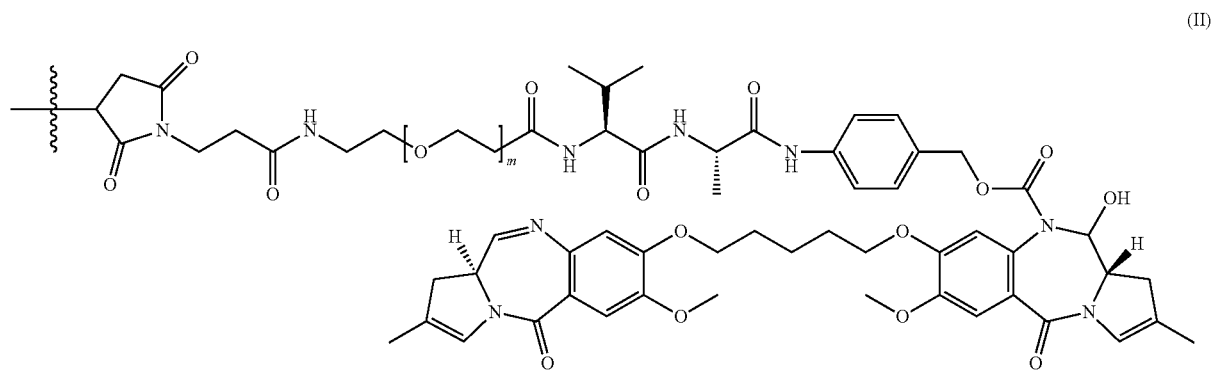

wherein m is 8 and the wavy line indicates the point of attachment to a binding agent;
chemical formula III comprises the structure:

(III)

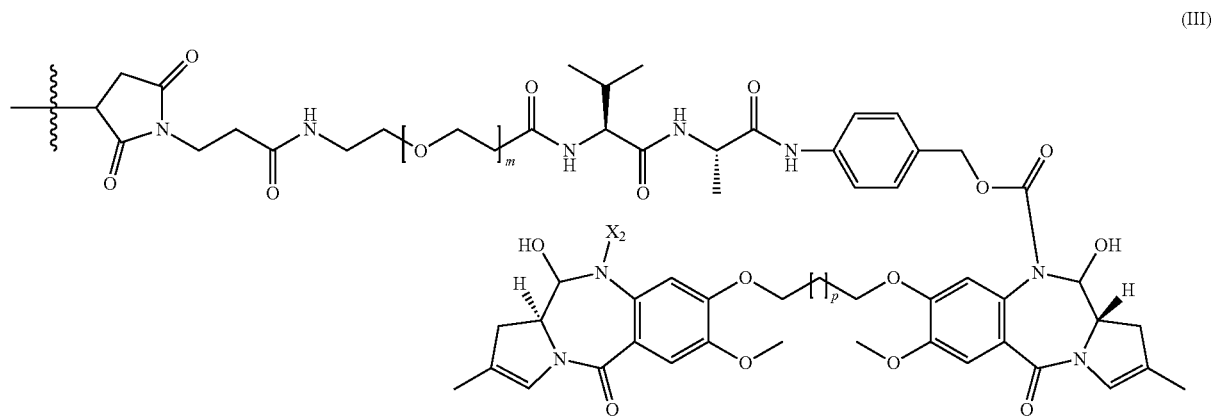

wherein m is 8, p is 2 or 3, $X_2$ is a protecting group and the wavy line indicates the point of attachment to a binding agent;
chemical formula V comprises the structure:

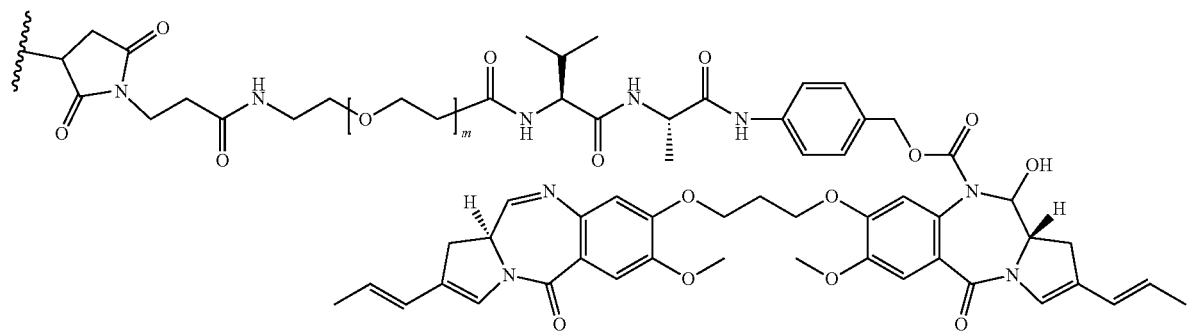

(V)

wherein m is 8, and the wavy line indicates a point of attachment to a binding agent;
chemical formula VI comprises the structure:

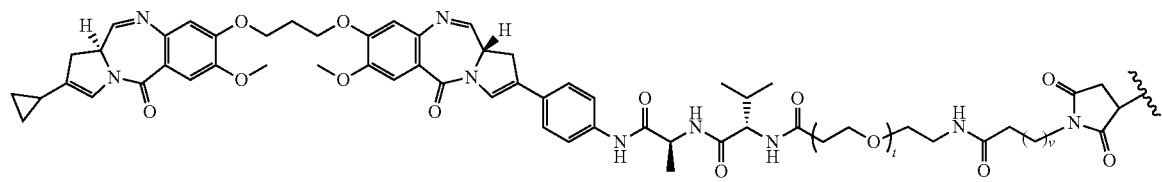

(VI)

wherein t is 8, v is 1 and the wavy line indicates a point of attachment to a binding agent;
and chemical formula VII comprises the structure:

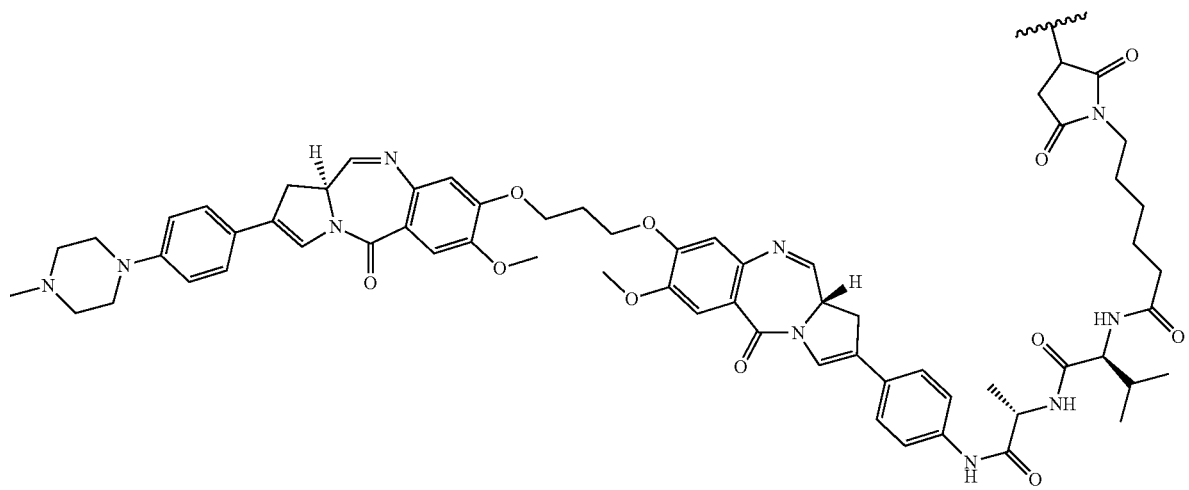

(VII)

wherein the wavy line indicates the point of attachment to a binding agent.

In certain embodiments, the protecting group of $X_2$ has the following structure (D):

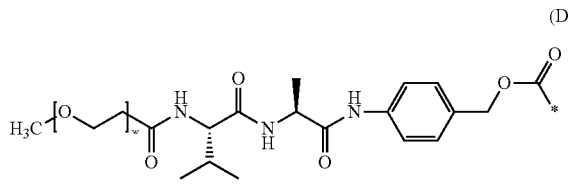

wherein the asterisk indicates the point of attachment to the payload; and w is 1 to 5.

In certain aspects presented herein is a binding agent-drug conjugate comprising a monoclonal antibody, or antigen binding portion thereof, and a payload, wherein the monoclonal antibody, or antigen binding portion thereof, comprises a CDR-L1 selected from the amino acid sequences of SEQ ID NOs: 2, 4, 6, 8, 10, 12 and 14, a CDR-L2 selected from the amino acid sequences of SEQ ID NOs: 17, 19, 21, 23 and 25, a CDR-L3 selected from the amino acid sequences of SEQ ID NOs: 27, 29, 31, 33 and 35, a CDR-H1 selected from the amino acid sequences of SEQ ID NOs: 51, 53, 55, 57 and 59, a CDR-H2 is selected from the amino acid sequences of SEQ ID NOs: 63, 65, 67, 69, 73 and 75, and a CDR-H3 selected from the amino acid sequences of SEQ ID NOs: 80, 82, 84, 86, 88, 91 and 93.

In certain embodiments, a binding agent of a binding agent-drug conjugate described herein comprises a CDR-L1 comprising the amino acid sequence of SEQ ID NO: 10 or 14; a CDR-L2 comprising the amino acid sequence of SEQ ID NO: 25; a CDR-L3 comprising the amino acid sequence of SEQ ID NO: 35; a CDR-H1 comprising the amino acid sequence of SEQ ID NO: 59; a CDR-H2 comprising the amino acid sequence of SEQ ID NO: 71; and a CDR-H3 comprising the amino acid sequence of SEQ ID NO: 88.

In certain embodiments, a binding agent of a binding agent-drug conjugate described herein comprises a CDR-L1 comprising the amino acid sequence of SEQ ID NO: 9 or 15; a CDR-L2 comprising the amino acid sequence of SEQ ID NO: 24; a CDR-L3 comprising the amino acid sequence of SEQ ID NO: 34; a CDR-H1 comprising the amino acid sequence of SEQ ID NO: 58; a CDR-H2 comprising the amino acid sequence of SEQ ID NO: 70 or 78; and a CDR-H3 comprising the amino acid sequence of SEQ ID NO: 87.

In some embodiments, a binding agent comprises a variable light chain region comprising an amino acid sequence selected from the amino acid sequences of SEQ ID NOs: 37-44. In some embodiments, a binding agent comprises a variable light chain sequence having at least 90% sequence identity, or 100% sequence identity to any one of the amino acid sequences of SEQ ID NOs: 45-49. In some embodiments, a binding agent comprises a variable light chain sequence having at least 90% sequence identity to any one or SEQ ID NOs: 37-49, wherein the variable light chain sequence has one to ten, or one to five amino acid modifications selected from an amino acid addition, an amino acid deletion and an amino acid substitution.

In some embodiments, a binding agent comprises a variable heavy chain region comprising an amino acid sequence selected from the amino acid sequences of SEQ ID NOs: 94-103. In some embodiments, a binding agent comprises a variable heavy chain region having at least 90% sequence identity, or 100% sequence identity to any one of the amino acid sequences of SEQ ID NOs: 104-108. In some embodiments, a binding agent comprises a variable heavy chain region having at least 90% sequence identity to any one of the amino acid sequences of SEQ ID NOs: 94-108, wherein the variable heavy chain sequence has one to ten, or one to five amino acid modifications selected from an amino acid addition, an amino acid deletion and an amino acid substitution.

In certain embodiments, a binding agent comprises a variable light chain sequence having at least 90% sequence identity to any one or SEQ ID NOs: 37-49, and a variable heavy chain sequence having at least 90% sequence identity to any one of the amino acid sequences of SEQ ID NOs: 94-108.

In certain embodiments, a binding agent, monoclonal antibody, or antigen binding portion thereof, is chimeric or humanized. For example, in some embodiments, a binding agent comprises one or more humanized or human framework region and/or one or more mouse framework regions.

In certain embodiments, a binding agent, monoclonal antibody, or antigen binding portion thereof comprises: a heavy chain and light chain each having CDRs that are the same as respective CDRs of heavy chain and light chain of an antibody produced by hybridoma cell line F6B1P3D12 deposited with ATCC on Mar. 20, 2019.

A binding agent-drug conjugate comprising a binding agent and a payload, wherein the binding agent comprises: a heavy chain and light chain each having CDRs that are the same as respective CDRs of heavy chain and light chain of an antibody produced by hybridoma cell line F6B1P3D12 deposited with ATCC on Mar. 20, 2019, and the payload comprises a pyrrolobenzodiazepine toxin and a linking group; wherein the pyrrolobenzodiazepine toxin is covalently linked to the linking group, the linking group is covalently linked to the binding agent, and the binding agent specifically binds to an extracellular domain of mesenchymal epithelial factor (cMET).

In some embodiments, a binding agent that specifically binds to cMET, or a portion thereof, comprises an antigen binding portion of an antibody or a single chain antibody. For example, in certain embodiments, a binding agent of a binding agent-drug conjugate comprises a Fab, Fab', F(ab')2, Fv or scFV fragment of an antibody.

In certain embodiments, a binding agent binds specifically to a mammalian cMET. In certain embodiments, a binding agent binds specifically to a human cMET, monkey cMET and/or rat cMET. In some embodiments, a binding agent specifically binds to the extracellular domain of a wild type or variant cMET. In some embodiments, a binding agent that specifically binds to cMET is a binding agent that induces internalization and/or degradation of cMET on a human cancer cell. In some embodiments, a binding agent that specifically binds to cMET is a binding agent that is not a cMET agonist. Accordingly, a cMET binding agent that is not a cMET agonist is a binding agent, that upon binding to a cell-surface cMET, does not substantially induce signaling through the cell-surface cMET.

In certain aspects, presented herein is a pharmaceutical composition comprising the binding agent-drug conjugate described herein and a pharmaceutically acceptable excipient, diluent, additive or carrier.

In certain aspects, presented herein is a method of treating a subject having a neoplastic disorder or cancer, the method comprising administering a therapeutically effective amount of the binding agent-drug conjugate described herein to a subject having, or suspected of having, a neoplastic disorder or cancer. In certain embodiments, a binding agent-drug conjugate blocks, inhibits, ameliorates, abrogates, or suppresses growth, viability or metastasis of the cancer. In certain embodiments, a binding agent-drug conjugate induces death, necrosis or apoptosis of some or all of the cancer. In certain embodiments, a neoplastic disorder or cancer comprises a carcinoma, sarcoma, neuroblastoma, glioblastoma, myeloma, lymphoma, melanoma or a solid or soft tissue tumor. In certain embodiments, a neoplastic disorder or cancer comprises a bladder cancer, breast cancer, colorectal cancer, gastric cancer, pancreatic cancer (e.g., exocrine pancreatic cancer and pancreatic neuroendocrine cancer), esophageal cancer, liver cancer, hepatocellular cancer, hypopharynx cancer, lung cancer, adenocarcinoma, ovarian cancer or renal cancer. In certain embodiments, a neoplastic disorder or cancer comprises a pancreatic adenocarcinoma, colorectal adenocarcinoma, small intestinal malignancy, cholangiocarcinoma, non-small cell lung cancer (NSCLC), thyroid carcinoma, esophageal or esophagogastric junction (EGJ) cancer, gastric adenocarcinoma, liver hepatocellular carcinoma, head and neck squamous carcinoma, female genital tract malignancy, breast carcinoma, lung small cell carcinoma, ovarian surface epithelial carcinoma, retroperitoneal or peritoneal sarcoma, prostatic adenocarcinoma, neuroendocrine tumor, gastrointestinal stromal tumor, glioblastoma or non-epithelial ovarian cancer. In certain embodiments, a cancer that can be treated by a method described herein is a cancer comprising a cell (e.g., a malignant or neoplastic cell) that expresses a cMET polypeptide (e.g., cMET, e.g., expressed on the cell surface).

Certain aspects of the technology are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 4 shows characterization results from an exemplary fusion (FUSION 6B1, plate 3). Anti-cMET hybridomas were selected, in part, for the presence of specific binding to cMET as assayed by ELISA (see column labeled "MET Binding ELISA $OD_{450}$ nm") and for ability to induce internalization of cMET on human cancer cell lines as measured by flow cytometry (see column labeled "FACS Geom. Mean"). A FACS Geom. Mean value lower than a negative control indicates internalization of cMET. The arrow indicates a lead hybridoma F6B1P3D12.

Figures 8A, 8B:
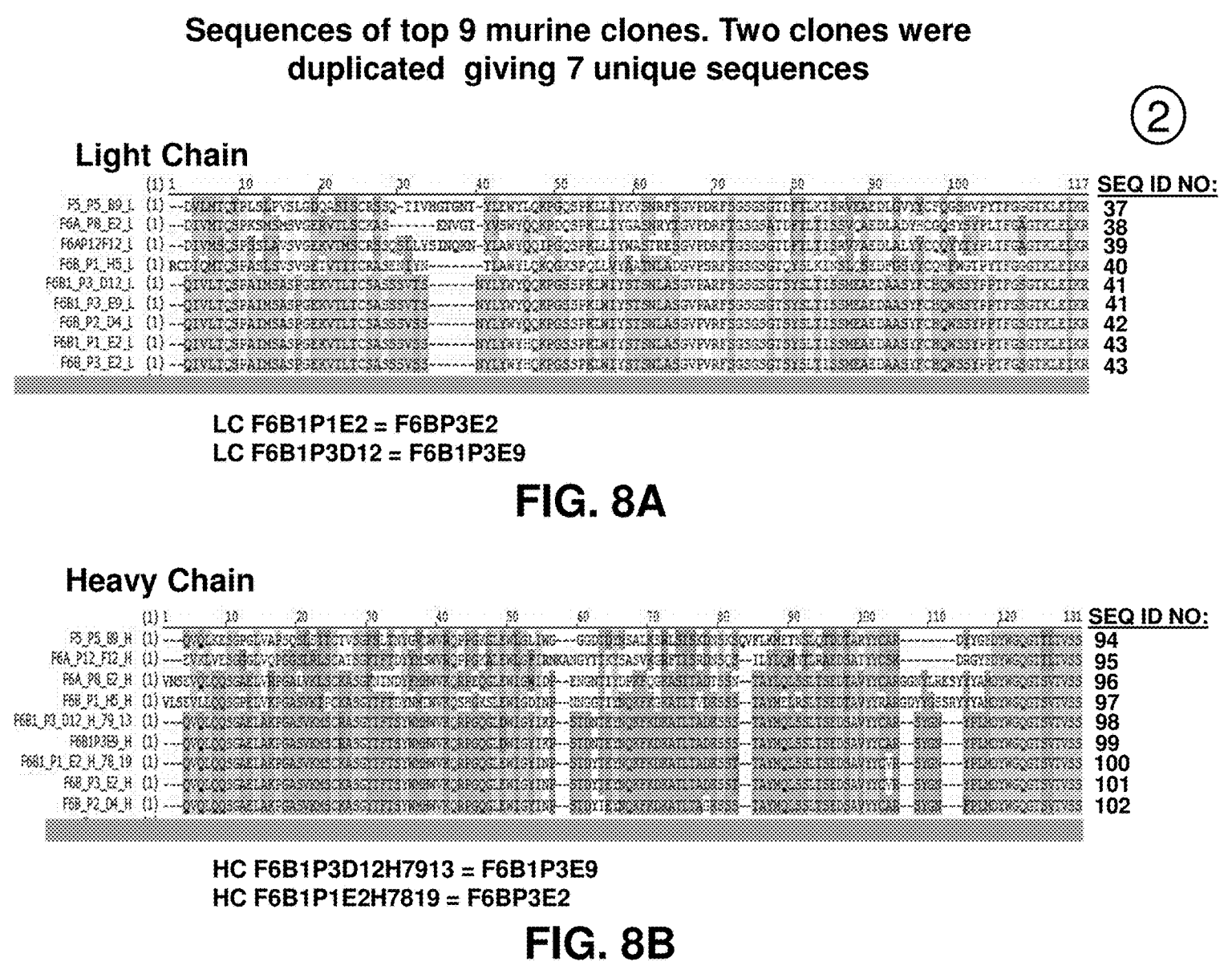

FIG. 8A shows an alignment of the amino acid sequences of the light chain variable regions of nine mouse monoclonal anti-cMET antibodies, the names of which are indicated to the left of each sequence. SEQ ID NOs: are indicated to the right of each sequence. Amino acid sequences of the light chain variable regions of LC F6B1P1E2 and F6BP3E2 are 100% identical. Also, amino acid sequences of the light chain variable regions of LC F6B1P3D12 and F6B1P3E9 are 100% identical.

FIG. 8B shows an alignment of the amino acid sequences of the heavy chain variable regions of nine mouse monoclonal anti-cMET antibodies, the names of which are indicated to the left of each sequence. SEQ ID NOs: are indicated to the right of each sequence. Amino acid sequences of the heavy chain variable regions of F6B1P3D12H7913 and F6B1P3E9 are 100% identical. Also, amino acid sequences of the heavy chain variable regions of F6B1P1E2H7819 and F6BP3E2 are 100% identical.

FIGS. 9A and 9B show the results of an in vivo xenograft mouse model evaluating the efficacy of the indicated anti-cMET antibody drug conjugates (ADC) using the MKN45 tumor model (a cMET+ gastric cancer model) in nude mice. Animals were treated once with ADCs at 2.5 mg/kg (9A) or 5.0 mg/kg (9B). The efficacy of each drug conjugated anti-cMET binding agent is compared to PBS or an unrelated non-targeting monoclonal antibody (IgG-ADC). Tumor volume (y-axis) was measured at various time points after inoculation (y-axis, Days (post inoculation)). Inhibition of tumor growth indicates positive efficacy. Anti-cMET binding agents and the non-targeting control monoclonal antibody (IgG) were conjugated to monomethyl auristatin F (MMAF).

FIG. 13 shows an alignment of five humanized light chain variable regions of humanized versions of the murine anti-cMET clone P3D12, the names and SEQ ID NOs: of which are indicated to the left of each sequence. Five independent methods were used to humanize the murine anti-cMET mAbs. Two of the methods gave the same result, therefore there are four different light chains shown.

FIG. 14 shows an alignment of five humanized heavy chain variable regions of humanized versions of the murine clone P3D12, the names and SEQ ID NOs: of which are indicated to the left of each sequence. Five independent methods were used to humanize the murine anti-cMET mAb. Two of the methods gave the same result, therefore there are four different light chains (see FIG. 13) and four different heavy chains which can make a combination of 16 different binding agents.

FIG. 24 shows the results of an ELISA-based cMET binding assay showing the relative affinity of hD12 and four variants of hD12 (hD12-T289C, hD12-V442C and hD12-V282C) that are covalently linked to the payload II, for plate-bound human cMET. hD12-II was stochastically linked to the payload at random sulfhydryl groups. hD12-T289C-II, hD12-V442C-II and hD12-V282C-II were site-specially linked to the payload at the position of the variant cysteine residue (i.e., T289C, V442C and V282C, respectively). The antibody drug conjugates were tested at increasing concentrations (x-axis, concentration of antibody-drug conjugate (μg/ml)) for their ability to bind plate-bound human cMET. Relative binding strength is indicated by luminescence (y-axis). A negative control antibody (Denosumab-II) was tested as a negative control. FIG. 24B shows $IC_{50}$ values for each of the antibodies tested in FIG. 24A.

FIG. 31 shows a table summarizing the pharmacokinetic data obtained from the experiment of FIG. 30.

FIG. 32 shows the results of an in vivo patient-derived xenograft (PDX) study using human primary gastric cancer tissue (FIG. 32A), human primary colorectal cancer tissue (FIG. 32B) and human head & neck cancer tissue (FIG. 32C). Percentage of tumor growth inhibition (TGI %) is shown on the y-axis and the concentration of the antibody conjugate (hD12-T289C-II) administered is shown on the x-axis. TGI % was calculated as described in Example 12.

DETAILED DESCRIPTION

Figure 1:
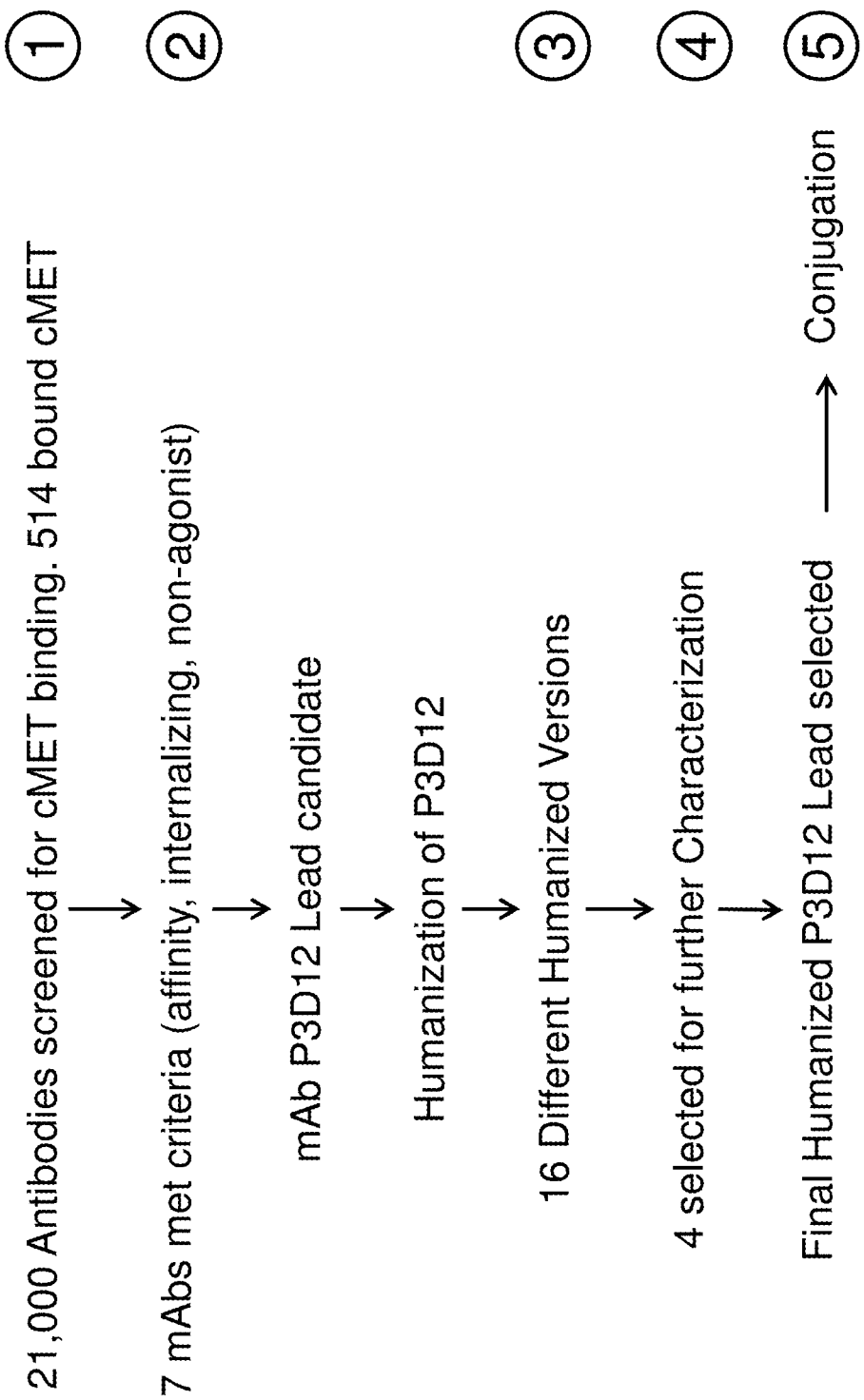
FIG. 1 shows a summary of the work flow used for generation of monoclonal antibodies (exemplary binding agents) that bind specifically to cMET. The lead monoclonal Ab P3D12 was generated from a mouse immunized with recombinant intact extracellular domain of cMET fused to human Fc.

Presented herein, in some embodiments, are binding agent-drug conjugates comprising a binding agent (e.g., a monoclonal antibody, or antigen binding portion thereof) and a payload (e.g., a cytotoxic payload). In some embodiments, a binding agent is a novel monoclonal antibody, or an antigen binding portion thereof, that binds specifically to cMET. In some embodiments, a payload comprises a pyrrolobenzodiazepine (PBD) toxin and a specific linking group. The novel binding agent-drug conjugates presented herein are useful for treating cancer and/or neoplastic disorders.

The binding agents disclosed herein are novel, not only in the amino acid sequences of their antigen binding regions (e.g., heavy and light chain variable regions), but also in their functional characteristics. For example, the anti-cMET binding agents described herein possess a combination of distinct characteristics not found in other cMET antibodies. First, the anti-cMET binding agents described herein do not induce significant signaling (e.g., receptor tyrosine kinase activity) from a cMET receptor upon binding. Accordingly, upon binding, the cMET binding agents described herein do not induce undesirable oncogenic activity upon binding (e.g., growth, proliferation, metastasis or angiogenesis). Second, anti-cMET binding agents described herein can induce cMET degradation and are internalized after binding. The benefit to this characteristic is that any toxic payload attached to the anti-cMET binding agent is brought into the interior of a target cell thereby reducing off-target, non-specific toxicity of the payload. This feature also allows for the activity of a toxic payload to be controlled or regulated. For example, in some embodiments, a toxic payload described herein is substantially inactive until contacted with an intracellular protease. Third, certain anti-cMET binding agents described herein cross-react with non-human primates, rat and/or mouse which allows for the antibody drug conjugates to be tested and optimized using non-human animal models. Four, the anti-cMET binding agents described herein are soluble, display pro-longed half-life in vivo and are stable upon storage.

A number of cytotoxic payloads are known which can be attached to an antibody using a known linker to generate an antibody drug conjugate (ADC)(e.g., see US 2014/0120118, US 2014/0127239, US 2016/0250344, US 2016/0250345 and Tiberghien, et al., (2016) *ACS Medicinal Chemistry Letters* 7 (11):983-987). However, the biochemical functionalities of an antibody binding agent often changes after conjugation to a payload. Similarly, the biochemical characteristics of a payload after conjugation to an antibody are not always predictable. For example, the in vivo activity of a known payload may differ significantly, ranging from lethal to no therapeutic effect, depending on the type of linker used and where the linker is attached to the antibody. Therefore, generating an antibody drug conjugate by combining a specific cMET binding agent with an ideal linker, a selected toxic payload and an optimal conjugation site of linker to antibody to provide for optimal delivery of the toxin, while substantially limiting adverse events (e.g., off-target toxicity), and maintaining the desirable bio-functional properties of the binding agent, is extremely challenging, time consuming and requires a substantial inventive effort. The ADCs presented herein provide for a unique combination of toxins, linkers and novel cMET binding agents that result in highly effective ADCs that provide for optimal therapeutic effects while substantially reducing or eliminating off-target toxicity.

cMET

MET is used synonymously herein with the term "cMET". cMET is also known as hepatocyte growth factor receptor (HGFR). Human cMET (e.g., SEQ ID NO:109) comprises an immature polypeptide sequence of 1390 amino acids and includes an N-terminal single sequence from amino acids 1-24, an extracellular domain of human cMET from about amino acid 24-932, a transmembrane domain from about amino acid 933 to 955 and a cytoplasmic domain at about amino acid 956 to 1390, numbered from the N-terminus to the C-terminus. Methods of identifying leader sequences, extracellular domains, transmembrane domains, and cytoplasmic domains of a cMET receptor are known and any suitable method can be used to identify such domains or regions within a cMET polypeptide sequence derived from a suitable mammalian species. A human cMET polypeptide may comprise several known variants (e.g., see www<dot>uniprot<dot>org/uniprot/P08581, as accessed on May 5, 2016, which cMET variants and alternative sequences disclosed therein are incorporated herein by reference). Non-limiting examples of naturally occurring variants of a human cMET include amino acid substitutions at 143, 150, 156, 168, 238, 316, 320, 375, 385, 773, 970, 991, and/or 992 of human cMET (SEQ ID NO: 109). In some embodiments cMET or a cMET extracellular domain comprises an E to D substitution at position 168 of human cMET, referred to herein as E168D. In some embodiments cMET or a cMET extracellular domain comprises an N to S substitution at position 375 of human cMET, referred to herein as N375S.

In some embodiments cMET is a mammalian cMET. In some embodiments cMET is a primate cMET. In some embodiments cMET is a human cMET. In some embodiments cMET is a monkey cMET. In some embodiments cMET is a rodent cMET (e.g., rat and/or mouse). In some embodiments cMET is a canine cMET (e.g., a dog cMET). Non-limiting examples of a mammalian cMET are provided in Example 5 and/or in a sequence listing of this application. In certain embodiments, an extracellular domain of cMET comprises an N-terminal portion of a cMET polypeptide that is typically expressed on the cell surface of an intact mammalian cell. An extracellular domain of cMET may comprise two or more polypeptide chains derived from a MET translation product. In certain embodiments an extracellular domain of cMET can be expressed in a soluble and/or a non-membrane bound form that lacks a cytoplasmic and/or transmembrane domain. In certain embodiments an extracellular domain of cMET is expressed, isolated and/or purified as a fusion protein. For example, the extracellular domain of a mammalian cMET can be engineered and expressed as a fusion protein comprising an Fc portion of an immunoglobulin (e.g., cMET-Fc). In certain embodiments cMET and/or the extracellular domain of cMET comprises one or more amino acid additions, deletions or substitutions. A cMET polypeptide may be at least 80%, at least 85%, at least 90% or at least 95% to a cMET polypeptide disclosed herein. In certain embodiments, a cMET polypeptide comprises a portion of (e.g., a sub-sequence of) a cMET protein. In some embodiments a portion of a cMET comprises an extracellular domain of cMET, or a portion thereof.

Binding Agents

In certain embodiments, a binding agent comprises or consists of one or more polypeptides or one or more proteins that bind specifically to cMET or a portion thereof. In some embodiments, a binding agent comprises or consists of a protein that binds specifically to cMET or a portion thereof. A binding agent often comprises at least one antigen binding portion (i.e. a binding portion). An antigen binding portion of a binding agent is that portion that binds specifically to an antigen. In certain embodiments a binding portion of a binding agent comprises or consists of a single polypeptide (e.g., single chain antibody). In some embodiments a binding portion of a binding agent comprises or consists of two polypeptides. In some embodiments a binding portion of a binding agent comprises or consists of 2, 3, 4 or more polypeptides. In some embodiments a binding agent comprises one or more structural portions (e.g., scaffolds, structural polypeptides, constant regions and/or framework regions). In some embodiments a binding agent, or binding portion thereof is attached to a substrate (e.g., a polymer, a non-organic material, silicon, a bead, and the like).

A binding agent may comprise one antigen binding portion or multiple antigen binding portions. For example, a binding agent that comprises one binding portion is sometimes referred to as monovalent. A binding agent that comprises two binding portions is sometimes referred as divalent. In some embodiments a binding agent comprises 1, 2, 3, 4, 5, 6, 7, 8, 9, or 10 or more binding portions. In certain embodiments, all of the binding portions of a multivalent binding agent bind to the same antigen. In certain embodiments, all of the binding portions of a multivalent binding agent comprise one or more polypeptide sequences that are at least 90%, at least 95%, at least 99% or 100% identical.

In certain embodiments, two or more binding portions of a binding agent bind to different antigens. Such binding agents are sometimes referred to as bi-specific or multi-specific binding agents (e.g., antibodies). Thus, in certain embodiments a binding agent comprises a first antigen binding portion that specifically binds cMET, or a portion thereof, and a second antigen binding portion that specifically binds another antigen (e.g., a polypeptide that is not cMET, or a portion thereof). A binding agent that specifically binds cMET, in some embodiments, is covalently or non-covalently attached to another binding agent that does not bind specifically to cMET, or a portion thereof. In certain embodiments, a binding agent that specifically binds cMET comprises a second binding agent the specifically binds to another antigen.

In some embodiments a binding agent comprises an antibody, or a portion thereof (e.g., a binding portion thereof). In certain embodiments, a binding agent comprises or consists of a suitable antibody, or antigen binding portion of an antibody. In some embodiments a binding agent is an antibody (e.g., a monoclonal antibody and/or a recombinant antibody). A binding agent or antibody can be generated, manufactured or produced by a suitable method. In some embodiments a binding agent is monoclonal. In some embodiments a binding agent is a monoclonal antibody derived from a suitable species. Certain non-limiting examples of a binding agent include monoclonal antibodies, chimeric antibodies, antibody binding fragments (e.g., an antigen binding portion of an antibody), a CDR-grafted antibody, a humanized antibody, a human antibody, or portions thereof. Human antibodies can be obtained by any suitable method. For example, human antibodies can be obtained from trans-chromosomal animals engineered to produce fully human antibodies. In certain embodiments, a binding agent is not polyclonal, is not a polyclonal antibody and the term "binding agent" does not refer to polyclonal antibodies.

In some embodiments a binding agent is derived, produced, obtained, isolated, and/or purified from a suitable species. In some embodiments a binding agent is derived, produced, obtained, isolated, and/or purified from a rabbit, goat, horse, cow, rat, mouse, fish, bird, or llama, for example. In some embodiments a binding agent is derived, produced, obtained, isolated, and/or purified from a bird (e.g., a chicken, or a bird egg). In some embodiments a binding agent is derived, produced, obtained, isolated, and/or purified from a plant (e.g., a recombinant binding agent produced by a genetically engineered plant). In some embodiments a binding agent is derived, produced, obtained, isolated, and/or purified from a suitable mammal. In certain embodiments a suitable mammal is a genetically altered mammal (e.g., a trans-chromosomal or transgenic mammal) engineered to produce antibodies comprising human heavy chains and/or human light chains or portions thereof. In some embodiments a binding agent is produced, obtained, isolated, or purified from a prokaryotic or eukaryotic cell (e.g., a recombinant binding agent produced by a genetically engineered cell). In some embodiments a binding agent is produced, obtained, isolated, or purified from a virus (e.g., a recombinant binding agent produced by a genetically engineered virus). A binding agent can be expressed, isolated from and/or purified from a suitable expression system non-limiting examples of which include a suitable bacteria, phage, insect, virus, plant or mammalian expression system. For example, a nucleic acid encoding a binding agent can be introduced into a suitable mammalian cell line that expresses and secretes the binding agent into the cell culture media.

In certain embodiments, a binding agent is not found in nature and is not naturally occurring. For example, in certain embodiments, a binding agent is generated artificially in an animal by administering an emulsified cocktail that includes a foreign recombinant antigen, a powerful adjuvant, and often a mineral oil and/or a detergent, thereby inducing an artificial immune response to the foreign recombinant antigen (e.g., cMET, cMET-Fc).

In certain embodiments, a monoclonal antibody or a monoclonal binding agent is a substantially homogeneous population of binding agents, or binding fragments thereof, where each individual binding agent in the population is substantially identical and/or binds to the same epitope, with the exception of possible variants that may arise during production of a monoclonal binding agent. In some embodiments such variants generally are absent or may be present in minor amounts. In contrast to polyclonal antibody preparations which typically include a population of different antibodies directed against different determinants (epitopes), each binding agent of a population of monoclonal binding agents often binds to a single determinant of an antigen. Monoclonal binding agents are often not contaminated by other immunoglobulins. One or more different monoclonal binding agents may be purposely added to a composition to form a mixture.

The modifier "monoclonal" is not to be construed as requiring production of a binding agent by any particular method. A monoclonal binding agent can be produced by any suitable method. For example, in certain embodiments, a monoclonal antibody is made by a hybridoma method described by Kohler et al. (1975) *Nature*, 256:495, or a variation thereof. In some embodiments a monoclonal binding agent is made by a suitable recombinant DNA method. For example, monoclonal antibodies can be made or altered by a method, or variation thereof, described in U.S. Pat. No. 5,225,539 and/or Daugherty et al. (1991) *Nucleic Acids Research* 19(9):2471-2476. A monoclonal binding agent can be made by screening a recombinant library using a suitable expression system (e.g., a phage display expression system), for example. In some embodiments a monoclonal binding agent is isolated from a phage library of binding agents, for example by using a technique described in Clackson et al. (1991) *Nature* 352:624-628 and/or Marks et al. (1991) *J. Mol Biol*, 222:581-597, or a variation thereof.

In certain embodiments, a binding agent comprises one or more structural or backbone portions, sometimes referred to as scaffolds. A binding agent may comprise a scaffold, non-limiting examples of which include a scaffold derived from an antibody, a Z domain of Protein A, gamma-B crystalline, ubiquitin, cystatin, Sac7d, a triple helix coiled coil, a lipocalin, an ankyrin repeat motif, an SH3 domain of Fyn, a Kunitz domain of a suitable protease inhibitor, a fibronectin domain, a nucleic acid polymer, the like, portions thereof or combinations thereof. In some embodiments a binding agent does not comprise a scaffold. In certain embodiments, a binding agent comprises one or more structural portions of a mammalian antibody.

In certain embodiments a binding agent comprises one or more constant regions (e.g., constant regions derived from an antibody, e.g., a mammalian antibody). In certain embodiments a binding agent comprises a constant region of an antibody light chain and/or a constant region of an antibody heavy chain. In a mammalian antibody at least two types of immunoglobulin light chains exist which are referred to as lambda (λ) and kappa (κ). A binding agent may comprise any suitable constant region of an antibody, or one or more portions thereof. In some embodiments a binding agent comprises a lambda light chain constant region or a portion thereof. In some embodiments a binding agent comprises a kappa light chain constant region or a portion thereof. In some embodiments a binding agent comprises a polypeptide that is at least 75%, at least 80%, at least 85%, at least 90%, at least 95% or at least 99% identical to a polypeptide sequence of a constant region, or portion thereof, of a light chain of a mammalian antibody. In some embodiments a binding agent comprises a polypeptide that is at least 75%, at least 80%, at least 85%, at least 90%, at least 95% or at least 99% identical to a polypeptide sequence of a constant region of an antibody light chain of a human antibody. In some embodiments a binding agent does not include a light chain constant region.

In certain embodiments a binding agent comprises a constant region of an antibody heavy chain. In mammals, an antibody can have at least five types/classes of Ig heavy chains denoted as IgA, IgD, IgE, IgG, and IgM, which are determined by the presence of distinct heavy chain constant regions, or portion thereof (e.g., CH1, CL, CH2, CH3 domains). A binding agent can include any suitable heavy chain constant region, or portion thereof. In some embodiments a binding agent comprises a heavy chain constant region of an IgG1, IgG2, IgG3 or IgG4, or one or more portions thereof. In some embodiments a binding agent comprises one or more heavy chain constant regions of an IgM, IgD, IgA, or IgE isotype, or a portion thereof.

Unless otherwise specified herein, numbering of amino acid residues in the constant region of an antibody is according to the EU numbering system as described in Edelman, G. M. et al., Proc. Natl. Acad. USA, 63, 78-85 (1969). PMID: 5257969.

In some embodiments a binding agent comprises a polypeptide that is at least 75%, at least 80%, at least 85%, at least 90%, at least 95%, at least 99% identical, or 100% identical to a polypeptide sequence of a constant region, or portion thereof, of a heavy chain of a mammalian antibody. In some embodiments a binding agent comprises a polypeptide that is at least 75%, at least 80%, at least 85%, at least 90%, at least 95%, at least 99% identical or 100% identical to a polypeptide sequence of a constant region of an antibody heavy chain of a human antibody. In some embodiments a binding agent comprises one or more additions, deletions and/or modification to a constant region. A binding agent is sometimes modified to change the antibody class, or isotype of a binding agent. In some embodiments a binding agent comprises one or more additions, deletions and/or modification (one or more amino acid substitutions, deletions or additions) to modify one or more functions of a binding agent, for example to abolish, enhance or decrease serum half-life, Fc receptor binding, complement binding (e.g., C1q binding), glycosylation, sialylation, cellular toxicity, antibody-dependent cell-mediated phagocytosis (ADCP), antibody dependent cellular cytotoxicity (ADCC), and the like. In some embodiments a binding agent does not include one or more portions of a heavy chain constant region or light chain constant region. In some embodiments a binding agent does not include a heavy chain constant region.

In some embodiments a binding agent comprises or consists of one or more variable regions of an antibody, or a portion thereof. In some embodiments a binding agent comprises one or more light chain variable regions, or a portion thereof. In some embodiments a binding agent comprises one or more heavy chain variable regions, or a portion thereof. In certain embodiments a binding agent comprises at least one light chain variable region and at least one heavy chain variable region. A light chain variable region and heavy chain variable region can be on the same or different polypeptides. In certain embodiments, an antigen binding portion of a binding agent consists of one or more heavy chain variable regions. In certain embodiments, an antigen binding portion of a binding agent consists of one or more light chain variable regions. In certain embodiments, an antigen binding portion of a binding agent consists of one or more light chain variable regions and one or more heavy chain variable regions.

In some embodiments a binding agent comprises or consists of a Fab, Fab', F(ab')2, Fv fragment, single chain Fv (scFv), diabody (Dab), synbody, the like and/or a combination or portion thereof. In some embodiments a binding agent is a Fab, Fab', F(ab')2, Fv fragment, single chain Fv (scFv), diabody (Dab), synbody, the like and/or a combination, or portion thereof (see, e.g., U.S. Pat. Nos. 6,099,842 and 5,990,296). In some embodiments a binding agent comprises a single chain polypeptide comprising one or more antigen binding portions. For example, a single chain binding agent can be constructed by joining a heavy chain variable region, or antigen binding portion thereof, with a light chain variable region, or antigen binding portion thereof, with a linker (e.g., an amino acid, a polypeptide linker) using recombinant molecular biology processes. Such single chain binding agents often exhibit specificities and affinities for an antigen similar to a parent two-chain monoclonal binding agent. Binding agents often comprise engineered regions such as CDR-grafted or humanized portions. In certain embodiments a binding agent is an intact two-chain immunoglobulin, and in other embodiments a binding agent is a Fab monomer or a Fab dimer.

Nucleic acids, or portions thereof, that encode a polypeptide of a binding agent may be cloned, subcloned, rearranged or modified for recombinant expression by a suitable cloning procedure and subsequently expressed using a suitable expression system by a method known to those skilled in the art (e.g., see Maniatis et al. (1982) Molecular Cloning: A Laboratory Manual, Cold Spring Harbor Laboratory Press; Sambrook et al. (1989), Molecular Cloning: A Laboratory Manual, Second Edition, Cold Spring Harbor Laboratory Press; Sambrook et al. (2001) Molecular Cloning: A Laboratory Manual, Cold Spring Harbor Laboratory Press, Cold Spring Harbor, N.Y.; Ausubel et al., Current Protocols in Molecular Biology, John Wiley & Sons (1987 and annual updates); Methods in molecular biology, edited by Benny K. C. Lo, Springer Science & Business Media, 2004; Antibody Engineering, Vol. 1, Roland E. Kontermann, Stefan Dübel, Edition 2, Publisher Springer Science & Business Media, 2010; Antibody Phage Display: Methods and Protocols, Biomed Protocols, Vol. 178 of Methods in molecular biology, Editors Philippa M. O'Brien, Robert Aitken, Springer Science & Business Media, 2004).

In mammals, the heavy chain variable region and light chain variable region of an antibody each contribute three CDRs (complementarity-determining regions) commonly referred to as CDR1, CDR2 and CDR3, that are separated and/or flanked by framework regions (e.g., FR1, FR2, FR3 and FR4). The term "CDR" as used herein refers to an amino acid sequence of a polypeptide identified as a complementarity-determining region. In certain embodiments, definitive delineation of a CDR polypeptide sequence and identification of residues comprising the binding site of a binding agent is accomplished by solving the structure of a binding agent and/or solving the structure of a binding agent-antigen complex. In certain embodiments, this can be accomplished by any suitable method, such as X-ray crystallography and/or computer modeling. In certain embodiments, various methods of analysis can be employed to identify or approximate the CDR sequences of a binding agent or antibody. For example, the amino acid sequence and/or location of CDRs in a polypeptide sequence of a binding agent, an antibody, a binding portion thereof or variable region thereof, can be identified using a suitable method, non-limiting examples of which include the Kabat system (e.g., see Kabat, E. A., et al. (1991) *Sequences of Proteins of Immunological Interest*, Fifth Edition, NIH Publication No. 91-3242, as well as Johnson, G. and Wu, T. T. (2000) *Nucleic Acids Research* 28(1):214-8 and/or the Chothia Numbering Scheme (e.g., Chothia & Lesk, (1987) *J. Mol. Biol,* 196:901-917; Chothia et al. (1989) *Nature* 342:878-883; and Al-Lazikani et al. (1997) *JMB* 273,927-948). In some embodiments the amino sequence and/or location of CDRs of an antibody can be identified using the AbM method and/or contact method. The "AbM" definition uses an integrated suite of computer programs produced by Oxford Molecular Group that model antibody structure (see e.g., Martin et al. (1989) *Proc. Natl. Acad. Sci.* (USA) 86:9268-9272; "AbM™, A Computer Program for Modeling Variable Regions of Antibodies," Oxford, UK; Oxford Molecular, Ltd.). The AbM definition models the tertiary structure of an antibody from primary sequence using a combination of knowledge databases and ab initio methods, such as those described by Samudrala et al. (1999) *Proteins, Structure, Function and Genetics*, Suppl, 3:194-198 and Xia Y, et al. (2000) *J Mol Biol.* 300(1):171-85. In certain embodiments, a contact definition is based on an analysis of the available complex crystal structures (see e.g., MacCallum et al. (1996) *J. Mol. Biol* 5:732-45).

In some embodiments a binding agent and/or an antigen binding portion of a binding agent comprises at least 2, at least 3, at least 4, at least 5 or at least 6 CDRs. In some embodiments a binding agent comprises 3 to 60 CDRs (e.g., for binding agents having multiple antigen binding portions). In some embodiments a binding agent comprises 3 to 12 CDRs. In some embodiments an antigen binding portion of a binding agent comprises 1 to 6 CDR polypeptide sequences.

In certain embodiments, a binding agent and/or an antigen binding portion of a binding agent comprises one, two or three CDRs of a light chain variable region. In some embodiments a light chain variable region of a binding agent comprises one or more CDRs (e.g., one, two, three, or more CDRs). The amino acid sequences representing a CDR in a light chain variable region of an antibody or binding agent is referred to as CDR-L1, CDR-L2, and CDR-L3 which are numbered sequentially (i.e., L1, L2 and L3) in the direction from the amino terminus (N-terminus) to the carboxy terminus (C-terminus) of a light chain variable region. For example, in a polypeptide representing a light chain variable region of a binding agent, CDR-L1, when present, is the most N-terminal light chain CDR; CDR-L3, when present, is the most C-terminal light chain CDR; and CDR-L2, when present, is located (i) between CDR-L1 and CDR-L3, (ii) on the N-terminal side of CDR-L3 or (iii) on the C-terminal side of CDR-L1, of a light chain variable region or binding portion of a binding agent. The terms "CDR-L1", "CDR-L2" and "CDR-L3" refer to, in part, an amino acid sequence of a polypeptide identified as, or disclosed herein as, a complementarity-determining region of a binding agent (e.g., a CDR of a light chain variable region). Non-limiting examples of amino acid sequences of a CDR-L1, CDR-L2 and CDR-L3 are provided in Tables 1-3, respectively. A light chain variable region or antigen binding portion of a binding agent described herein may comprise any combination of a CDR-L1, a CDR-L2, and a CDR-L3 disclosed herein, wherein the binding agent retains specific binding to cMET, or a portion thereof. In certain embodiments, a light chain variable region or antigen binding portion of a binding agent described herein comprises a single light chain CDR comprising an amino acid sequence at least 70% identical to a CDR-L3 selected from Table 3.

In certain embodiments, a light chain variable region or antigen binding portion of a binding agent described herein comprises an amino acid sequence at least 70% identical to a CDR-L3 selected from Table 3, and any other suitable CDR-L2 and/or CDR-L1 polypeptide sequence, where the binding agent retains specific binding to cMET, or a portion thereof. In certain embodiments, the light chain CDRs of a light chain variable region or antigen binding portion of a binding agent consists of a CDR-L3 and a CDR-L2, where the CDR-L3 comprises an amino acid sequence at least 70% identical to a CDR-L3 selected from Table 3 and the CDR-L2 comprises an amino acid sequence at least 70% identical to a CDR-L2 selected from Table 2. In certain embodiments, a light chain variable region or antigen binding portion of a binding agent described herein comprises an amino acid sequence at least 70% identical to a CDR-L3 selected from Table 3 and an amino acid sequence at least 70% identical to a CDR-L2 selected from Table 2, and any other suitable CDR-L1 polypeptide sequence, where the binding agent retains specific binding to cMET, or a portion thereof. In certain embodiments, a light chain variable region or antigen binding portion of a binding agent described herein comprises three light chain CDRs consisting of an amino acid sequence at least 70% identical to a CDR-L3 selected from Table 3, an amino acid sequence at least 70% identical to a CDR-L2 selected from Table 2 and an amino acid sequence selected at least 70% identical to a CDR-L1 of Table 1. In certain embodiments, a light chain variable region or antigen binding portion of a binding agent described herein comprises an amino acid sequence at least 70% identical to a CDR-L3 selected from Table 3, an amino acid sequence at least 70% identical to a CDR-L2 selected from Table 2 and an amino acid sequence at least 70% identical to a CDR-L1 selected from Table 1, where the binding agent retains specific binding to cMET, or a portion thereof.

In some embodiments a binding agent comprises one or more light chain CDRs that are at least 70%, 75%, 85%, 86%, 87%, 88%, 89%, 90%, 91%, 92%, 93%, 94%, 95%, 96%, 97%, 98%, or at least 99% identical to any one of the CDR sequences listed in Tables 1, 2 or 3. In some embodiments a binding agent or the antigen binding portion of a binding agent comprises a CDR-L1 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 1. In some embodiments a binding agent or the antigen binding portion of a binding agent comprises a CDR-L1 of any one of the sequences shown in Table 1.

TABLE 1

CDR-L1 Sequences

| ID | Clone | Amino Acid Sequence |
|---|---|---|
| SEQ ID NO: 1 | F5_P5_B9_L | RSSQTIVHGTGNTYLE |
| SEQ ID NO: 2 | F5_P5_B9_L | QTIVHGTGNTY |
| SEQ ID NO: 3 | F6A_P8_E2_L | KASENVGTYVS |
| SEQ ID NO: 4 | F6A_P8_E2_L | ENVGTY |
| SEQ ID NO: 5 | F6AP12F12_L | RSSQSLLYSINQKNYLA |
| SEQ ID NO: 6 | F6AP12F12_L | QSLLYSINQKNY |
| SEQ ID NO: 7 | F6B_P1_H5_L | RASENIYNTLA |
| SEQ ID NO: 8 | F6B_P1_H5_L | ENIYNT |
| SEQ ID NO: 9 | F6B1_P3_D12_L/ F6B1_P3_E9_L | SASSSVTSNYLY |
| SEQ ID NO: 10 | F6B1_P3_D12_L/ F6B1_P3_E9_L | SSVTSNY |
| SEQ ID NO: 11 | F6B_P2_D4_L/ F6B1_P1_E2_L/ F6B_P3_E2_L | SASSSVSSNYLY |
| SEQ ID NO: 12 | F6B_P2_D4_L/ F6B1_P1_E2_L/ F6B_P3_E2_L | SSVSSNY |
| SEQ ID NO: 13 | Consensus | SASSSV(S/T)SNYLY |
| SEQ ID NO: 14 | P3D12 VL-abb/sdr | QSVTSNY |
| SEQ ID NO: 15 | P3D12 VL-abb/sdr | RASQSVTSNYLY |

Clone names referenced in Tables 1-10 indicate the Fusion number (F), Plate number (P) and well number (A1 to H12) of a 96-well plate from which the clone was derived. Accordingly, clone F6AP12F12 was derived from Fusion 6A, Plate 12, Well F12, for example. Fusion numbers of each clone correspond to the Fusions indicated in FIG. 2.

In some embodiments a binding agent or the antigen binding portion of a binding agent comprises a CDR-L2 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 2. In some embodiments a binding agent or the antigen binding portion of a binding agent comprises a CDR-L2 of any one of the sequences shown in Table 2.

TABLE 2

CDR-L2 Sequences

| ID | Clone | Amino Acid Sequence |
|---|---|---|
| SEQ ID NO: 16 | F5_P5_B9_L | KVSNRFS |
| SEQ ID NO: 17 | F5_P5_B9_L | KVS |

TABLE 2-continued

CDR-L2 Sequences

| ID | Clone | Amino Acid Sequence |
|---|---|---|
| SEQ ID NO: 18 | F6A_P8_E2_L | GASNRYT |
| SEQ ID NO: 19 | F6A_P8_E2_L | GAS |
| SEQ ID NO: 20 | F6AP12F12_L | WASTRES |
| SEQ ID NO: 21 | F6AP12F12_L | WAS |
| SEQ ID NO: 22 | F6B_P1_H5_L | AATNLAD |
| SEQ ID NO: 23 | F6B_P1_H5_L | AAT |
| SEQ ID NO: 24 | F6B1_P3_D12_L/ F6B1_P3_E9_L/ F6B_P2_D4_L/ F6B1_P1_E2_L/ F6B_P3_E2_L | STSNLAS |
| SEQ ID NO: 25 | F6B1_P3_D12_L/ F6B1_P3_E9_L/ F6B_P2_D4_L/ F6B1_P1_E2_L/ F6B_P3_E2_L | STS |

In some embodiments a binding agent or the antigen binding portion of a binding agent comprises a CDR-L3 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 3. In some embodiments a binding agent or the antigen binding portion of a binding agent comprises a CDR-L3 of any one of the sequences shown in Table 3.

TABLE 3

CDR-L3 Sequences

| ID | Clone | Amino Acid Sequence |
|---|---|---|
| SEQ ID NO: 26 | F5_P5_B9_L | FQGSHVPYTFGGGTKLEIKR |
| SEQ ID NO: 27 | F5_P5_B9_L | FQGSHVPYT |
| SEQ ID NO: 28 | F6A_P8_E2_L | GQSYSYPLTFGAGTKLELKR |
| SEQ ID NO: 29 | F6A_P8_E2_L | GQSYSYPLT |
| SEQ ID NO: 30 | F6AP12F12_L | QQYYTYPLTFGAGTKLELK |
| SEQ ID NO: 31 | F6AP12F12_L | QQYYTYPLT |
| SEQ ID NO: 32 | F6B_P1_H5_L/ | QHFWGTPYTFGGGTKLEIK |
| SEQ ID NO: 33 | F6B_P1_H5_L/ | QHFWGTPYT |
| SEQ ID NO: 34 | F6B1_P3_D12_L/ F6B1_P3_E9_L/ F6B_P2_D4_L/ F6B1_P1_E2_L/ F6B_P3_E2_L | HQWSSYPPTFGSGTKLEIK |
| SEQ ID NO: 35 | F6B1_P3_D12_L/ F6B1_P3_E9_L/ F6B_P2_D4_L/ F6B1_P1_E2_L/ F6B_P3_E2_L | HQWSSYPPT |

TABLE 3-continued

CDR-L3 Sequences

| ID | Clone | Amino Acid Sequence |
|---|---|---|
| SEQ ID NO: 36 | Consensus | $(X_1)Q(X_2)(X_3)(X_4)YP(X_5)T$ where $X_1$ is H, Q, or G; $X_2$ is W, S or Y; $X_3$ is S or Y; $X_4$ is S or T; and $X_5$ is P or L. |

In some embodiments a binding agent or the antigen binding portion of a binding agent comprises a light chain variable region having at least 70%, 75%, 85%, 86%, 87%, 88%, 89%, 90%, 91%, 92%, 93%, 94%, 95%, 96%, 97%, 98%, or at least 99% identity to an amino acid sequence of Table 4. In some embodiments a binding agent or the antigen binding portion of a binding agent comprises a light chain variable region sequence of Table 4.

TABLE 4

VARIABLE LIGHT CHAIN SEQUENCES

| ID | Clone | Amino Acid Sequence |
|---|---|---|
| SEQ ID NO: 37 | F5_P5_B9_L | DVLMTQTPLSLPVSLGDQASISCRSSQTIVHGTGNTYLEWYLQKPGQSPKLLIYKVSNRFSGVPDRFSGSGSGTDFTLKISRVEAEDLGVYYCFQGSHVPYTFGGGTKLEIKR |
| SEQ ID NO: 38 | F6A_P8_E2_L | DIVMTQSPKSMSMSVGERVTLSCKASENVGTYVSWYQQKPDQSPKLLIYGASNRYTGVPDRFTGSGSATDFTLTISSVQAEDLADYHCGQSYSYPLTFGAGTKLELKR |
| SEQ ID NO: 39 | F6AP12F12_L | DIVMSQSPSSLAVSVGEKVTMSCRSSQSLLYSINQKNYLAWYQQIPGQSPKLLIYWASTRESGVPDRFTGSGSGTDFTLTISRVKAEDLALYYCQQYYTYPLTFGAGTKLELKR |
| SEQ ID NO: 40 | F6B_P1_H5_L | RCDIQMTQSPASLSVSVGETVTITCRASENIYNTLAWYLQKQGKSPQLLVYAATNLADGVPSRFSGSGSGTQYSLKINSLQSEDFGSYYCQHFWGTPYTFGGGTKLEIKR |
| SEQ ID NO: 41 | F6B1_P3_D12_L & F6B1_P3_E9_L | QIVLTQSPAIMSASPGEKVTLTCSASSSVTSNYLYWYQQKPGSSPKLWIYSTSNLASGVPARFSGSGSGTSYSLTISSMEAEDAASYFCHQWSSYPPTFGSGTKLEIKR |
| SEQ ID NO: 42 | F6B1_P2_D4_L | QIVLTQSPAIMSASPGEKVTLTCSASSSVSSNYLYWYQQKPGSSPKLWIYSTSNLASGVPVRFSGSGSGTSYSLTISSMEAEDAASYFCHQWSSYPPTFGSGTKLEIKR |
| SEQ ID NO: 43 | F6B1_P1_E2_L & F6B_P3_E2_L | QIVLTQSPAIMSASPGEKVTLTCSASSSVSSNYLYWYHQKPGSSPKLWIYSTSNLASGVPVRFSGSGSGTSYSLTISSMEAEDAASYFCHQWSSYPPTFGSGTKLEIKR |
| SEQ ID NO: 44 | Consensus | QIVLTQSPAIMSASPGEKVTLTCSASSSVSSNYLYWY(H/Q)QKPGSSPKLWIYSTSNLASGVP(A/R)FSGSGSGTSYSLTISSMEAEDAASYFCHQWSSYPPTFGSGTKLEIKR |

TABLE 5

Humanized P3D12 Light Chains

| ID | Clone | Amino Acid Sequence |
|---|---|---|
| SEQ ID NO: 45 | P3D12 VL | QIVLTQSPAIMSASPGEKVTLTCSASSSVTSNYLYWYQQKPGSSPKLWIYSTSNLASGVPARFSGSGSGTSYSLTISSMEAEDAASYFCHQWSSYPPTFGSGTKLEIKR |
| SEQ ID NO: 46 | P3D12 VL-ven | QIVLTQSPATMSASPGERVTLSCSASSSVTSNYLYWYQQKPGSSPRLWIYSTSNLASGVPARFSGSGSGTSYTLTISRMEPEDAASYFCHQWSSYPPTFGSGTKLEIKR |
| SEQ ID NO: 47 | P3D12 VL-fra | QIVLTQSPAILSLSPGERATLSCSASSSVTSNYLYWYQQKPGSSPKLLIYSTSNLASGVPARFSGSGSGTSYTLTISSLEAEDAASYFCHQWSSYPPTFGSGTKLEIKR |
| SEQ ID NO: 48 | P3D12 VL-abb/sdr | QIVLTQSPATLSLSPGERATLSCRASQSVTSNYLYWYQQKPGSSPRLLIYSTSNLASGVPARFSGSGSGTDYTLTISRLEPEDFASYFCHQWSSYPPTFGSGTKLEIKR |
| SEQ ID NO: 49 | P3D12 VL-cdr | QIVLTQSPATLSLSPGERATLSCSASSSVTSNYLYWYQQKPGSSPRLLIYSTSNLASGVPARFSGSGSGTSYTLTISRLEPEDFASYFCHQWSSYPPTFGSGTKLEIKR |

In some embodiments a binding agent or the antigen binding portion of a binding agent comprises a humanized light chain variable region having at least 70%, 75%, 85%, 86%, 87%, 88%, 89%, 90%, 91%, 92%, 93%, 94%, 95%, 96%, 97%, 98%, or at least 99% identity to a sequence of Table 5. In some embodiments a binding agent or the antigen binding portion of a binding agent comprises a humanized light chain variable region sequence of Table 5.

In certain embodiments, a binding agent and/or an antigen binding portion of a binding agent comprises one, two or three CDRs of a heavy chain variable region. In some embodiments a heavy chain variable region comprises one or more CDRs (e.g., one, two, three, or more CDRs). The amino acid sequences representing a CDR in a heavy chain variable region of an antibody or binding agent is referred to as CDR-H1, CDR-H2, and CDR-H3, which are numbered sequentially (i.e., H1, H2 and H3) in the direction from the amino terminus (N-terminus) to the carboxy terminus (C-terminus) of a heavy chain variable region. For example, in a polypeptide representing a heavy chain variable region of a binding agent, CDR-H1, when present, is the most N-terminal CDR; CDR-H3, when present, is the most C-terminal CDR; and CDR-H2, when present, is located (i) between CDR-H1 and CDR-H3, (ii) on the N-terminal side of CDR-H3 or (iii) on the C-terminal side of CDR-H, of a heavy chain variable region. The terms "CDR-H1", "CDR-H2" and "CDR-H3" refer to, in part, an amino acid sequence of a polypeptide identified as, or disclosed herein as, a complementarity-determining region of a binding agent (e.g., a CDR of a heavy chain variable region of a binding agent). Non-limiting examples of amino acid sequences of a CDR-H1, CDR-H2 and CDR-H3 are provided in Tables 6-8, respectively. A heavy chain variable region or antigen binding portion of a binding agent described herein may comprise any combination of a CDR-H1, a CDR-H2, and a CDR-H3 disclosed herein where the binding agent retains specific binding to cMET, or a portion thereof. In certain embodiments, a heavy chain variable region or antigen binding portion of a binding agent described herein comprises a single heavy chain CDR consisting of an amino acid sequence at least 70% identical to a CDR-H3 selected from Table 8. In certain embodiments, a heavy chain variable region or antigen binding portion of a binding agent described herein comprises an amino acid sequence at least 70% identical to a CDR-H3 selected from Table 8, and any other suitable CDR-H2 and/or CDR-H1 polypeptide sequence, where the binding agent retains specific binding to cMET, or a portion thereof. In certain embodiments, the heavy chain CDRs of a heavy chain variable region or antigen binding portion of a binding agent consists of a CDR-H3 and a CDR-H2, where the CDR-H3 comprises an amino acid sequence at least 70% identical to a CDR-H3 selected from Table 8 and the CDR-H2 comprises an amino acid sequence at least 70% identical to a CDR-H2 selected from Table 7. In certain embodiments, a heavy chain variable region or antigen binding portion of a binding agent described herein comprises an amino acid sequence at least 70% identical to a CDR-H3 selected from Table 8 and an amino acid sequence at least 70% identical to a CDR-H2 selected from Table 7, and any other suitable CDR-H1 polypeptide sequence, where the binding agent retains specific binding to cMET or a portion thereof. In certain embodiments, a heavy chain variable region or antigen binding portion of a binding agent described herein comprises three heavy chain CDRs consisting of an amino acid sequence at least 70% identical to a CDR-H3 selected from Table 8, an amino acid sequence at least 70% identical to a CDR-H2 selected from Table 7 and an amino acid sequence at least 70% identical to a CDR-H1 of Table 6. In certain embodiments, a heavy chain variable region or antigen binding portion of a binding agent described herein comprises an amino acid sequence at least 70% identical to a CDR-H3 selected from Table 8, an amino acid sequence at least 70% identical to a CDR-H2 selected from Table 7 and an amino acid sequence at least 70% identical to a CDR-H1 selected from Table 6, where the binding agent retains specific binding to cMET, or a portion thereof.

In some embodiments a binding agent comprises one or more heavy chain CDRs with at least 70%, 75%, 85%, 86%, 87%, 88%, 89%, 90%, 91%, 92%, 93%, 94%, 95%, 96%, 97%, 98%, or at least 99% identity to any one of the CDRs of Tables 6, 7 or 8. In some embodiments a binding agent or the antigen binding portion of a binding agent comprises a CDR-H1 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 6. In some embodiments a binding agent or the antigen binding portion of a binding agent comprises a CDR-H1 of any one of the sequences shown in Table 6.

TABLE 6

CDR-H1 Sequences

| ID | Clone | Amino Acid Sequence |
|---|---|---|
| SEQ ID NO: 50 | F5_P5_B9_H | GFSLTNYGVN |
| SEQ ID NO: 51 | F5_P5_B9_H | GFSLTNYG |
| SEQ ID NO: 52 | F6A_P8_E2_H | GFNINDYFMH |
| SEQ ID NO: 53 | F6A_P8_E2_H | FNINDYF |
| SEQ ID NO: 54 | F6A_P12_F12_H | GFTFTDYYMS |
| SEQ ID NO: 55 | F6A_P12_F12_H | GFTFTDYY |
| SEQ ID NO: 56 | F6B_P1_H5_H | GYTFTDYNMD |
| SEQ ID NO: 57 | F6B_P1_H5_H | YTFTDYN |
| SEQ ID NO: 58 | F6B1_P3_D12_H/ F6B1P3E9_H/ F6_B1_P1_E2_H/ F6B_P3_E2_H/ F6B_P2_D4_H | GYTFTSYWMH |
| SEQ ID NO: 59 | F6B1_P3_D12_H/ F6B1P3E9_H/ F6_B1_P1_E2_H/ F6B_P3_E2_H/ F6B_P2_D4_H | YTFTSYW |
| SEQ ID NO: 60 | Consensus | GYTFT(D/S)Y(N/W) |
| SEQ ID NO: 61 | Consensus | G(Y/F)TFT(D/S)Y(N/W/Y)M(H/S) |

In some embodiments a binding agent or the antigen binding portion of a binding agent comprises a CDR-H2 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 7. In some embodiments a binding agent or the antigen binding portion of a binding agent comprises a CDR-H2 of any one of the sequences shown in Table 7.

TABLE 7

CDR-H2 Sequences

| ID | Clone | Amino Acid Sequence |
|---|---|---|
| SEQ ID NO: 62 | F5_P5_B9_H | LIWGGGDTDYNSALKS |
| SEQ ID NO: 63 | F5_P5_B9_H | IWGGGDT |
| SEQ ID NO: 64 | F6A_P8_E2_H | WIDPENGNTIYDPKFQG |

TABLE 7-continued

CDR-H2 Sequences

| ID | Clone | Amino Acid Sequence |
|---|---|---|
| SEQ ID NO: 65 | F6A_P8_E2_H | IDPENGT |
| SEQ ID NO: 66 | F6A_P12_F12_H | FIRNKANGYTTKYSASVKG |
| SEQ ID NO: 67 | F6A_P12_F12_H | IRNKANGYTT |
| SEQ ID NO: 68 | F6B_P1_H5_H | DINPNNGGTIYNQKFKG |
| SEQ ID NO: 69 | F6B_P1_H5_H | INPNNGGT |
| SEQ ID NO: 70 | F6B1_P3_D12_H/ F6B1P3E9_H | YIKPSTDNTEYNQKFKD |
| SEQ ID NO: 71 | F6B1_P3_D12_H/ F6B1P3E9_H | IKPSTDNT |
| SEQ ID NO: 72 | F6_B1_P1_E2_H/ F6B_P3_E2_H | YINPSTDYTEYNQKFKD |
| SEQ ID NO: 73 | F6_B1_P1_E2_H/ F6B_P3_E2_H | INPSTDYT |
| SEQ ID NO: 74 | F6B_P2_D4_H | YINPSTDYIEYNQKFKD |
| SEQ ID NO: 75 | F6B_P2_D4_H | INPSTDYI |
| SEQ ID NO: 76 | Consensus | INPSTDY(I/T) |
| SEQ ID NO: 77 | Consensus | (Y/D)I(K/N)PSTD(N/Y)(T/I)EY(A/N)QKF(Q/K)(G/D) |
| SEQ ID NO: 78 | P3D12 VH-abb/sdr | YIKPSTDNTEYAQKFQG |

In some embodiments a binding agent or the antigen binding portion of a binding agent comprises a CDR-H3 that is at least 70%, 75%, 85%, 86%, 87%, 88%, 89%, 90%, 91%, 92%, 93%, 94%, 95%, 96%, 97%, 98%, or at least 99% identical to any one of the sequences shown in Table 8. In some embodiments a binding agent or the antigen binding portion of a binding agent comprises a CDR-H3 of any one of the sequences shown in Table 8.

TABLE 8

CDR-H3 Sequences

| ID | Clone | Amino Acid Sequence |
|---|---|---|
| SEQ ID NO: 79 | F5_P5_B9_H | CARDYYGFDY |
| SEQ ID NO: 80 | F5_P5_B9_H | DYYGFDY |
| SEQ ID NO: 81 | F6A_P8_E2_H | CARGGNYLRESYYYAMDY |
| SEQ ID NO: 82 | F6A_P8_E2_H | RGGNYLRESYYYAMDY |
| SEQ ID NO: 83 | F6A_P12_F12_H | CSKDRGYFDY |
| SEQ ID NO: 84 | F6A_P12_F12_H | DRGYFDY |
| SEQ ID NO: 85 | F6B_P1_H5_H | RARGDYYGSSRYYYAMDY |
| SEQ ID NO: 86 | F6B_P1_H5_H | RGDYYGSSRYYYAMDY |

TABLE 8-continued

CDR-H3 Sequences

| ID | Clone | Amino Acid Sequence |
|---|---|---|
| SEQ ID NO: 87 | F6B1_P3_D12_H/ F6B1P3E9_H | CARSYGNYPLMDY |
| SEQ ID NO: 88 | F6B1_P3_D12_H/ F6B1P3E9_H & F6_B1_P1_E2_H/ F6B_P3_E2_H | SYGNYPLMDY |
| SEQ ID NO: 89 | F6_B1_P1_E2_H/ F6B_P3_E2_H | CVRSYGNYPLMDY |
| SEQ ID NO: 90 | F6B_P2_D4_H | CARSYGNFPLMDY |
| SEQ ID NO: 91 | F6B_P2_D4_H | RSYGNFPLMDY |
| SEQ ID NO: 92 | Consensus | C(A/V)RSYGN(F/Y)PLMDY |
| SEQ ID NO: 93 | Consensus | RSYGN(F/Y)PLMDY |

In some embodiments a binding agent or the antigen binding portion of a binding agent comprises a heavy chain variable region having at least 70%, 75%, 85%, 86%, 87%, 88%, 89%, 90%, 91%, 92%, 93%, 94%, 95%, 96%, 97%, 98%, or at least 99% identity to a sequence of Table 9. In some embodiments a binding agent or the antigen binding portion of a binding agent comprises a heavy chain variable region sequence of Table 9.

TABLE 9

VARIABLE HEAVY CHAIN SEQUENCES

| ID | Clone | Amino Acid Sequence |
|---|---|---|
| SEQ ID NO: 94 | F5_P5_B9_H | QVQLKESGPGLVAPSQSLSITCTVSGFSLTNYGVNWVRQPPGKGLEWLGLIWGGGDTDYNSALKSRLSISKDNSKSQVFLKMETNSLQTDDTARYYCARDYYGFDYWGQGTTLTVSS |
| SEQ ID NO: 95 | F6A_P12_F12_H | EVKLVESGGGLVQPGGSLRLSCATSGFTFTDYYMSWVRQPPGKALEWLGFIRNKANGYTTKYSASVKGRFTISRDNSQSILYLQMNTLRAEDSATYYCSKDRGYFDYWGQGTTLTVSS |
| SEQ ID NO: 96 | F6A_P8E2_H | VNSEVQLQQSGAELVRPGALVKLSCKASGFNINDYFMHWVKQRPEQGLEWIGWIDPENGNTIYDPKFQGKASITADTSSNTAYLQLSSLTSEDTAVYYCARGGNYLRESYYYAMDYWGQGTSVTVSS |
| SEQ ID NO: 97 | F6B_P1_H5_H | VLSEVLLQQSGPELVKPGASVKIPCKASGYTFTDYNMDWVKQSHGKSLEWIGDINPNNGGTIYNQKFKGKATLTVDKSSSTAYMELRSLTSEDTAVYYRARGDYYGSSRYYYAMDYWGQGTSVTVSS |
| SEQ ID NO: 98 | F6B1_P3_D12_H | QVQLQQSGAELAKPGASVKMSCRASGYTFTSYWMHWVKQRPGQGLDWIGYIKPSTDNTEYNQKFKDKATLTADKSSSTAYMQLSSLTSEDSAVYYCARSYGNYPLMDYWGQGTSVTVSS |
| SEQ ID NO: 99 | F6B1P3E9_H | QVQLQQSGAELAKPGASVKMSCRASGYTFTSYWMHWVKQRPGQGLDWIGYIKPSTDNTEYNQKFKDKATLTADKSSSTAYMQLSSLTSEDSAVYYCARSYGNYPLMDYWGQGTSVTVSS |
| SEQ ID NO: 100 | F6B1_P1_E2_H | QVQLQQSGAELAKPGASVKMSCKASGYTFTSYWMHWVKQRPGQGLEWIGYINPS |

TABLE 9-continued

VARIABLE HEAVY CHAIN SEQUENCES

| ID | Clone | Amino Acid Sequence |
|---|---|---|
|  |  | TDYTEYNQKFKDKATLTADKSSTTAYM<br>QLSSLTSEDSAVYYCVRSYGNYPLMDY<br>WGQGTSVTVSS |
| SEQ ID<br>NO: 101 | F6B_P3_E2_H | QVQLQQSGAELAKPGASVKMSCKASGY<br>TFTSYWMHWVKQRPGQGLEWIGYINPS<br>TDYTEYNQKFKDKATLTADKSSTTAYM<br>QLSSLTSEDSAVYYCVRSYGNYPLMDY<br>WGQGTSVTVSS |
| SEQ ID<br>NO: 102 | F6B_P2_D4_H | QVQLQQSGAELAKPGASVKMSCKASGY<br>TFTSYWMHWVKQRPGQGLEWIGYINPS<br>TDYIEYNQKFKDKATLTAGKSSSTAYM<br>QLSSLTSEDSAVYYCARSYGNFPLMDY<br>WGQGTSVTVSS |
| SEQ ID<br>NO: 103 | Consensus | QVQLQQSGAELAKPGASVKMSC(K/R)<br>ASGYTFTSYWMHWVKQRPGQGL(E/D)<br>WIGYI(K/N)PSTD(Y/N)(T/I)EYN<br>QKFKDKATLTADKSS(S/T)TAYMQLS<br>SLTSEDSAVYYC(A/V)RSYGN(Y/F)<br>PLMDYWGQGTSVTVSS |

In some embodiments a binding agent or the antigen binding portion of a binding agent comprises a humanized heavy chain variable region having at least 70%, 75%, 85%, 86%, 87%, 88%, 89%, 90%, 91%, 92%, 93%, 94%, 95%, 96%, 97%, 98%, or at least 99% identity to a sequence of Table 10. In some embodiments a binding agent or the antigen binding portion of a binding agent comprises a humanized heavy chain variable region sequence of Table 10.

TABLE 10

Humanized P3D12 Heavy Chains

| ID | Clone | Amino Acid Sequence |
|---|---|---|
| SEQ ID<br>NO: 104 | P3D12 VH | QVQLQQSGAELAKPGASVKMSCRASGYTFTSY<br>WMHWVKQRPGQGLDWIGYIKPSTDNTEYNQKF<br>KDKATLTADKSSSTAYMQLSSLTSEDSAVYYC<br>ARSYGNYPLMDYWGQGTSVTVSS |
| SEQ ID<br>NO: 105 | P3D12 VH-<br>fra | QVQLQQSGAEVKKPGASVKVSCKASGYTFTSY<br>WMHWVKQRPGQGLDWIGYIKPSTDNTEYNQKF<br>KDRVTLTADKSTSTAYMQLSNLISEDTAVYYC<br>ARSYGNYPLMDYWGQGTSVTVSS |
| SEQ ID<br>NO: 106 | P3D12 VH-<br>ven | QVQLVQSGAEVAKPGASVKMSCKASGYTFTSY<br>WMHWVKQAPGQGLDWIGYIKPSTDNTEYNQKF<br>KDKATLTADKSTSTAYMQLSSLRSEDTAVYYC<br>ARSYGNYPLMDYWGQGTTVTVSS |
| SEQ ID<br>NO: 107 | P3D12 VH-<br>abb/sdr | QVQLVQSGAEVKKPGASVKVSCKASGYTFTSY<br>WMHWVKQAPGQGLDWMGYIKPSTDNTEYAQKF<br>QGRVTLTADKSTSTAYMELSSLRSEDTAVYYC<br>ARSYGNYPLMDYWGQGTTVTVSS |
| SEQ ID<br>NO: 108 | P3D12 VH-<br>cdr | QVQLVQSGAEVKKPGASVKVSCKASGYTFTSY<br>WMHWVKQAPGQGLDWIGYIKPSTDNTEYNQKF<br>KDKATLTADKSTSTAYMELSSLRSEDTAVYYC<br>ARSYGNYPLMDYWGQGTTVTVSS |

In some embodiments a binding agent, or an antigen binding portion of a binding agent, comprises a CDR-L3 comprising an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of the amino acid sequences of SEQ ID NOs: 26 to 36 (e.g., a CDR-L3 sequence selected from Table 3) and a CDR-H3 comprising an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of the amino acid sequences of SEQ ID NOs: 79 to 93 (e.g., a CDR-H3 sequence selected from Table 8). In some embodiments a binding agent, or an antigen binding portion of a binding agent, comprises a CDR-L3 comprising an amino acid sequence at least 70%, at least 90%, at least 95%, at least 98%, at least 99% or 100% identical to the amino acid sequence of SEQ ID NO: 34 or 35, and a CDR-H3 comprising an amino acid sequence at least 70%, at least 90%, at least 95%, at least 98%, at least 99% or 100% identical to the amino acid sequence of SEQ ID NO: 87, 88, 92 or 93.

In some embodiments a binding agent, or an antigen binding portion of a binding agent, comprises a CDR-L3 comprising an amino acid sequence at least 70%, at least 90%, or 100% identical to any one of the amino acid sequences of SEQ ID NOs: 26 to 36 (e.g., a CDR-L3 sequence selected from Table 3), a CDR-L2 comprising an amino acid sequence at least 70%, at least 90%, or 100% identical to any one of the amino acid sequences of SEQ ID NOs: 16 to 25 (e.g., a CDR-L2 sequence selected from Table 2), a CDR-H3 comprising an amino acid sequence at least 70%, at least 90%, or 100% identical to any one of the amino acid sequences of SEQ ID NOs: 79 to 93 (e.g., a CDR-H3 sequence selected from Table 8) and a CDR-H2 comprising an amino acid sequence at least 70%, at least 90%, or 100% identical to any one of the amino acid sequences of SEQ ID NOs: 62 to 78 (e.g., a CDR-H2 sequence selected from Table 7). In some embodiments a binding agent, or an antigen binding portion of a binding agent, comprises a CDR-L3 comprising an amino acid sequence at least 70%, at least 90%, or 100% identical to the amino acid sequence of SEQ ID NO: 34 or 35, a CDR-L2 comprising an amino acid sequence at least 70%, at least 90%, or 100% identical to the amino acid sequence of SEQ ID NO: 24 or 25, a CDR-H3 comprising an amino acid sequence at least 70%, at least 90%, or 100% identical to the amino acid sequence of SEQ ID NO: 87, 88, 92 or 93 and a CDR-H2 comprising an amino acid sequence at least 70%, at least 90%, or 100% identical to the amino acid sequence of SEQ ID NO: 70, 71 or 78.

In some embodiments a binding agent, or an antigen binding portion of a binding agent, comprises a CDR-L3 comprising an amino acid sequence at least 70%, at least 90%, or 100% identical to any one of the amino acid sequences of SEQ ID NOs: 26 to 36 (e.g., a CDR-L3 sequence selected from Table 3), a CDR-L2 comprising an amino acid sequence at least 70%, at least 90%, or 100% identical to any one of the amino acid sequences of SEQ ID NOs: 16 to 25 (e.g., a CDR-L2 sequence selected from Table 2), a CDR-L1 comprising an amino acid sequence at least 70%, at least 90%, or 100% identical to any one of the amino acid sequences of SEQ ID NOs: 1 to 15 (e.g., a CDR-L1 sequence selected from Table 1), a CDR-H3 comprising an amino acid sequence at least 70%, at least 90%, or 100% identical to any one of the amino acid sequences of SEQ ID NOs: 79 to 93 (e.g., a CDR-H3 sequence selected from Table 8), a CDR-H2 comprising an amino acid sequence at least 70%, at least 90%, or 100% identical to any one of the amino acid sequences of SEQ ID NOs: 62 to 78 (e.g., a CDR-H2 sequence selected from Table 7), and a CDR-H1 comprising an amino acid sequence at least 70%, at least 90%, or 100% identical to the amino acid sequences of SEQ ID NOs: 50 to 61 (e.g., a CDR-H1 sequence selected from Table 6). In some embodiments a binding agent, or an antigen binding portion of a binding agent, comprises a CDR-L3 comprising an amino acid sequence at least 70%, at least 90%, or 100% identical to the amino acid sequence of SEQ ID NOs: 34 or 35, a CDR-L2 comprising an amino acid sequence at least 70%, at least 90%, or 100% identical to the amino acid sequence of SEQ ID NO: 24 or 25, a CDR-L1 comprising an amino acid sequence at least 70%, at least 90%, or 100% identical to the amino acid sequence of SEQ ID NO: 9, 10 or 15, a CDR-H3 comprising an amino acid sequence at least 70%, at least 90%, or 100% identical to the amino acid sequence of SEQ ID NO: 87 or 88, a CDR-H2 comprising an amino acid sequence at least 70%, at least 90%, or 100% identical to the amino acid sequence of SEQ ID NO: 70, 71 or 78, and a CDR-H1 comprising an amino acid sequence at least 70%, at least 90%, or 100% identical to the amino acid sequence of SEQ ID NO: 58 or 59.

In some embodiments a binding agent, or an antigen binding portion of a binding agent, comprises a heavy chain variable region comprising an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of the amino acid sequences of SEQ ID NOs: 94 to 108 (e.g., a heavy chain variable region selected from Tables 9 and 10), and a light chain variable region comprising an amino acid sequence at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any one of the amino acid sequences of SEQ ID NOs: 37 to 49 (e.g., a light chain variable region selected from Tables 4 and 5). In some embodiments a binding agent, or an antigen binding portion of a binding agent, comprises a heavy chain variable region comprising an amino acid sequence at least 90% identical to any one of the amino acid sequences of SEQ ID NOs: 104 to 108 (e.g., a heavy chain variable region selected from Table 10), and a light chain variable region comprising an amino acid sequence at least 90% identical to any one of the amino acid sequences of SEQ ID NOs: 45 to 49 (e.g., a light chain variable region selected from Table 5).

The abbreviations of "abb", "sdr", "fra", "ven." and "cdr" as used herein are explained below. The abbreviation "cdr" or "CDR" refer to a Complementarity-Determining Region. The abbreviation "abb" refers to an abbreviated CDR, for example as described in Padlan et al. (1995) *FASEB J* 9:133-139. In some embodiments, abbreviated CDRs are residues 27D-34, 50-55, and 89-96 in the light chain, and 31-35B, 50-58, and 95-101 in the heavy chain, which are grafted onto an appropriate human scaffold. Critical framework residues are often preserved. The abbreviation "sdr" refers to "specificity determining residues", for example as described in Padlan et al. (1995) which are residues thought to be involved in antigen binding. The abbreviation "fra" refers to a "Frankenstein approach", for example as described in Wu and Kabat (1992) *Mol Immunol* 29:1141-1146. The abbreviation "ven" refers to "Veneering", for example as described in Padlan (1991), *Mol Immunol* 28:489-498.

The term "percent identical" or "percent identity" refers to sequence identity between two amino acid sequences. Identity can be determined by comparing a position in each sequence which may be aligned for purposes of comparison. When an equivalent position in the compared sequences is occupied by the same amino acid, then the molecules are identical at that position. When the equivalent site is occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, Vol. 266: Computer Methods for Macromolecular Sequence Analysis (1996), ed. Doolittle, Academic Press, Inc., a division of Harcourt Brace & Co., San Diego, Calif., USA. In some embodiments an alignment program that permits gaps in the sequence is utilized to align the sequences. The Smith-Waterman is one type of algorithm that permits gaps in sequence alignments. See Meth. Mol. Biol. 70:173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

In some embodiments a binding agent, or antigen binding portion of a binding agent comprises one or more CDRs selected from a light chain variable region of Tables 4 and 5. In some embodiments a binding agent, or antigen binding portion of a binding agent comprises one or more CDRs selected from a heavy chain variable region of Tables 9 and 10. In some embodiments a binding agent, or antigen binding portion of a binding agent comprises one or more CDRs selected from a light chain variable region of Tables 4 and 5 and one or more CDRs selected from a heavy chain variable region of Tables 9 and 10. In certain embodiments, a binding agent, or antigen binding portion of a binding agent, comprises a CDR-L1, a CDR-L2, and a CDR-L3, each selected from any one of the light chain variable regions of Tables 4 and 5, and a CDR-H1, a CDR-H2, and a CDR-H3, each selected from any one of the heavy chain variable regions of Tables 9 and 10. An amino acid sequence of a CDR (e.g., a CDR-L1, CDR-L2, CDR-L3, CDR-H1, CDR-H2, and CDR-H3) can be identified within a heavy chain or light chain variable region disclosed herein by any suitable method described herein or known to those skilled in the art.

In certain embodiments, a binding agent that specifically binds to cMET comprises (i) a CDR-L1, a CDR-L2 and a CDR-L3 which are polypeptide sequences of a light chain complementarity determining region (CDR-L), where the CDR-L1 is selected from the amino acid sequences of SEQ ID NOs: 1-15, the CDR-L2 is selected from the amino acid sequences of SEQ ID NOs: 16-25, and the CDR-L3 is selected from the amino acid sequences of SEQ ID NOs: 26-36, and (ii) a CDR-H1, a CDR-H2 and a CDR-H3 which are polypeptide sequences of a heavy chain complementarity determining region (CDR-H), where the CDR-H1 is selected from the amino acid sequences of SEQ ID NOs: 50-61, the CDR-H2 is selected from the amino acid sequences of SEQ ID NOs: 62-78, and the CDR-H3 is selected from the amino acid sequences of SEQ ID NOs: 79-93.

In some embodiments a binding agent comprises one or more suitable sequences selected from Tables 1-10 wherein the selected polypeptide sequence comprises 0 to 5, 1 to 5, 0 to 10, 1 to 10, 0 to 15, or 1 to 15 amino acid modifications where an amino acid modification can be an amino acid addition, an amino acid deletion and/or an amino acid substitution. In some embodiments a binding agent comprises one or more suitable sequences selected from Tables 4, 5, 9 or 10, wherein the selected polypeptide sequence comprises 0 to 5, 1 to 5, 0 to 10, 1 to 10, 0 to 15, or 1 to 15 amino acid modifications in a framework regions or a constant region, where an amino acid modification can be an amino acid addition, an amino acid deletion and/or an amino acid substitution. In some embodiments an amino acid modification is a conservative amino acid substitution. In some embodiments, a binding agent disclosed herein comprises one or more amino acid analogues, non-native amino acids or amino acid derivatives.

In certain embodiments, a binding agent, or antigen binding portion of a binding agent comprises one or more framework regions (FR). Framework regions are often located between CDRs and/or flank CDR sequences of a heavy or light chain variable region of an antibody or binding agent. In mammals, a heavy chain variable region often comprises four framework regions and a light chain variable region often comprises four framework regions. Any suitable method can be used to identify one or more framework regions in an antibody, in a variable region of an antibody or in a binding agent. A binding agent may comprise synthetic or naturally occurring framework regions which are unmodified or modified (e.g., optimized) as discussed below.

In some embodiments a binding agent, or antigen binding portion thereof is chimeric, grafted and/or humanized. Chimeric, grafted and or humanized binding agents often comprise modified or substituted constant regions and/or framework regions while maintaining binding specificity to cMET, or a portion thereof. In some embodiments a binding agent, or antigen binding portion thereof, comprises constant regions, framework regions, or portions thereof, derived from a human antibody. In some embodiments a binding agent, or antigen binding portion thereof, comprises fully synthetic portions, one or more amino acids, or sequences of amino acids that are not found in native antibody molecules.

Naturally occurring framework regions, or portions thereof may be obtained from any suitable species. In certain embodiments the complementarity determining regions (CDRs) of the light and heavy chain variable regions of a binding agent, or an antigen binding portion thereof, is grafted into framework regions from the same, or another, species. For example, one or more framework regions of a binding agent may be derived from a rodent species (e.g., a mouse or rat) or a primate species (e.g., a human).

In certain embodiments, the CDRs of the light and/or heavy chain variable regions of a binding agent, or an antigen binding portion thereof, can be grafted to consensus human framework regions. To create consensus human framework regions, in certain embodiments, framework regions from several human heavy chain or light chain amino acid sequences can be aligned to identify a consensus sequence. In certain embodiments, the heavy chain or light chain framework regions of an antibody or binding agent are replaced with one or more framework regions, or portions thereof, from a different heavy chain or light chain variable region. In some embodiments a binding agent, or antigen binding portion thereof, comprises one or more human framework regions. In certain embodiments a binding agent, or antigen binding portion thereof, comprises at least 1, 2, 3, 4, 5, 6, 7, 8, 9 or 10 human framework regions. In some embodiments a binding agent, or antigen binding portion thereof, comprises one or more mouse framework regions. In certain embodiments a binding agent, or antigen binding portion thereof, comprises at least 1, 2, 3, 4, 5, 6, 7, 8, 9 or 10 mouse framework regions. In certain embodiments a binding agent, or antigen binding portion thereof, comprises one or more human framework regions and one or more mouse framework regions.

Methods of generating chimeric, humanized and/or optimized antibodies or binding agents, for example by modifying, substituting or deleting framework regions, or portions thereof, are known. Non-limiting examples of CDR grafting are described, e.g., in U.S. Pat. Nos. 6,180,370; 6,054,297; 5,693,762; 5,859,205; 5,693,761; 5,565,332; 5,585,089; and 5,530,101, and in Jones et al. (1986) *Nature* 321:522-525; Verhoeyen et al. (1988) Science 239:1534-1536, and Winter (1998) *FEBS Letts.* 430:92-94. Additional non-limiting examples of generating chimeric, grafted and/or humanized binding agents include U.S. Pat. Nos. 5,530, 101; 5,707,622; 5,994,524; 6,245,894; Queen et al. (1988) *PNAS* 86:10029-10033; Riechmann et al. (1988) *Nature* 332:323-327; Antibody Engineering: Methods and Protocols, Vol. 248 of Methods in molecular biology, edited by Benny K. C. Lo, Springer Science & Business Media, (2004); and Antibody Engineering, Vol. 1, Roland E. Kontermann, Stefan Dübel, Edition 2, Publisher Springer Science & Business Media, (2010). In some embodiments a binding agent can be humanized by exchanging one or more framework regions, or portions thereof (e.g., one or more amino acids), with one or more framework regions, or portions thereof from a human antibody. In certain embodiments, an antibody or binding agent can be humanized or grafted by transferring one or more CDRs (e.g., 1, 2, 3, 4, 5 or all 6 CDRs) from a donor binding agent (e.g., a mouse monoclonal antibody) to an acceptor binding agent (e.g., a human antibody) while retaining the binding specificity of the donor binding agent. In certain embodiments, the process of making a chimeric, grafted or humanized binding agent comprises making one or more amino acid substitutions, additions or deletions in a constant region or framework region of a binding agent. In certain embodiments, techniques such as "reshaping", "hyperchimerization," or "veneering/resurfacing" can be used to produce humanized binding agents. (e.g., see Vaswami et al. (1998) *Annals of Allergy, Asthma, & Immunol.* 81:105; Roguska et al. (1996) *Prot. Engin.* 9:895-904; and U.S. Pat. No. 6,072,035). In some aspects, a binding agent is modified by a method discussed above, or by another suitable method, to reduce immunogenicity (e.g., see Gilliland et al. (1999) *J. Immunol.* 62(6):3663-71).

In certain embodiments, an amino acid sequence of a binding agent is modified to optimize binding affinity for a target (e.g., cMET), species cross-reactivity, solubility and/or function (e.g., agonist activity, or lack thereof). In some embodiments a specific combination of CDRs disclosed herein can be optimized for binding to cMET, and/or to optimize a function or characteristic of a binding agent disclosed herein. For example, a characterized light chain variable region disclosed herein (e.g., a light chain variable region of SEQ ID NO:48) can be co-expressed, using a suitable expression system, with a library of heavy chain variable regions comprising a CDR-H1 and CDR-H2 of a characterized heavy chain variable region (e.g., a heavy chain variable region of SEQ ID NO:107), where the CDR-H3 is replaced with a library of CDR-H3 sequences, which may include one or more CDR-H3 regions of Table 8, for example. The resulting light chain/heavy chain binding agents can be screened for binding to cMET and/or for a specific function. Optimized binding agents can be identified and the amino acid sequence of the CDR-H3 can be identified by a suitable method. The above screening method can be used to identify binding agents comprising specific combinations of CDRs, or specific optimized CDR sequences (e.g., CDR sequences comprising amino acid substitutions, additions or deletions) that provide a binding agent with improved binding specificity, binding affinity and/or function. Such methods of screening and optimizing binding agents are known (e.g., see Portolano et al. (1993) Journal of Immunology 150:880-887; and Clarkson et al. (1991) Nature 352:624-628). Such references teach methods of producing antibodies that bind a specific antigen by using known variable light chain, known variable heavy chains, or portion thereof (e.g., CDRs thereof) by screening a library of complementary variable regions.

In certain embodiments, a binding agent is modified to eliminate or add glycosylation sites in order to optimize affinity and/or function of a binding agent (e.g., see Co et al. (1993) Mol. Immunol. 30:1361-1367). In some embodiments the number and/or type of glycosylation sites in a binding agent is modified or altered. An N-linked glycosylation site is often characterized by the sequence Asn-X-Ser or Asn-X-Thr, where the amino acid residue designated as X can be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided in certain embodiments is a rearrangement of N-linked carbohydrate chains where one or more N-linked glycosylation sites (typically those that are naturally occurring) are eliminated and one or more new N-linked sites are created. In some embodiments a binding agent is modified by deleting one or more cysteine residues or substituting one or more cysteine residues for another amino acid (e.g., serine) as compared to an unmodified binding agent. In certain embodiments cysteine variants can be useful for optimizing expression, secretion, and/or solubility.

In certain embodiments a binding agent is modified to include certain amino acid additions, substitutions, or deletions designed or intended, for example, to reduce susceptibility of a binding agent to proteolysis, reduce susceptibility of a binding agent to oxidation, increase serum half-life and/or confer or modify other physicochemical, pharmacokinetic or functional properties of a binding agent.

In some embodiments a binding agent specifically binds to a mammalian cMET, or portion thereof. In some embodiments a binding agent specifically binds to an extracellular domain or extracellular regions of a mammalian cMET, or a portion thereof. In certain aspects, a binding agent specifically binds to a wild-type cMET produced by a cell of an unaltered (non-genetically modified) mammal found in nature. In certain aspects a binding agent specifically binds to a naturally occurring cMET variant. In certain aspects a binding agent specifically binds to a cMET comprising one or more amino acid substitutions, additions or deletions. In certain embodiments a binding agent specifically binds to a cMET produced and/or expressed on the surface of a cell of a human, non-human primate, dog, cat, or rodent (e.g., a mouse or rat). In certain embodiments, a binding agent specifically binds to one or more cMET polypeptides, or a portion thereof, having an amino acid sequence of any one of SEQ ID NOs: 109 to 113. In certain embodiments, a binding agent specifically binds to a human cMET. In certain embodiments, a binding agent specifically binds to an extracellular domain of human cMET. In certain embodiments, a binding agent specifically binds to a human cMET, and/or an extracellular domain thereof, wherein the human cMET comprises an E168 to D168 substitution (i.e., an E168D variant of cMET). In certain embodiments, a binding agent specifically binds to a human cMET, and/or an extracellular domain thereof, wherein the human cMET comprises an N375 to S375 substitution (i.e., an N375S variant of human cMET).

The term "specifically binds" refers to a binding agent that binds a target peptide in preference to binding other molecules or other peptides as determined by, for example, as determined by a suitable in vitro assay (e.g., an Elisa, Immunoblot, Flow cytometry, and the like). A specific binding interaction discriminates over non-specific binding interactions by about 2-fold or more, often about 10-fold or more, and sometimes about 100-fold or more, 1000-fold or more, 10,000-fold or more, 100,000-fold or more, or 1,000,000-fold or more.

In some embodiments a binding agent that specifically binds to cMET, or a portion thereof, is a binding agent that binds cMET, or a portion thereof (e.g., an extracellular domain of cMET), with a binding affinity constant (KD) equal to or less than 100 nM, equal to or less than 50 nM, equal to or less than 25 nM, equal to or less than 10 nM, equal to or less than 5 nM, equal to or less than 1 nM, equal to or less than 900 pM, equal to or less than 800 pM, equal to or less than 750 pM, equal to or less than 700 pM, equal to or less than 600 pM, equal to or less than 500 pM, equal to or less than 400 pM, equal to or less than 300 pM, equal to or less than 200 pM, or equal to or less than 100 pM. In some embodiments a binding agent that specifically binds to cMET, or a portion thereof, is a binding agent that binds human cMET, or a portion thereof (e.g., an extracellular domain of human cMET), with a binding affinity constant (KD) equal to or less than 100 nM, equal to or less than 50 nM, equal to or less than 25 nM, equal to or less than 10 nM, equal to or less than 5 nM, equal to or less than 1 nM, equal to or less than 900 pM, equal to or less than 800 pM, equal to or less than 750 pM, equal to or less than 700 pM, equal to or less than 600 pM, equal to or less than 500 pM, equal to or less than 400 pM, equal to or less than 300 pM, equal to or less than 200 pM, or equal to or less than 100 pM. In some embodiments a binding agent that specifically binds to cMET, or a portion thereof, is a binding agent that binds specifically to cMET, or a portion thereof, derived from a non-human species (e.g., a non-human primate, or rodent; e.g., a mouse or rat), with a binding affinity constant (KD) equal to or less than 100 nM, equal to or less than 50 nM, equal to or less than 25 nM, equal to or less than 10 nM, equal to or less than 5 nM, equal to or less than 1 nM, equal to or less than 900 pM, equal to or less than 800 pM, equal to or less than 750 pM, equal to or less than 700 pM, equal to or less than 600 pM, equal to or less than 500 pM, equal to or less than 400 pM, equal to or less than 300 pM, equal to or less than 200 pM, or equal to or less than 100 pM. In certain embodiments, a binding agent disclosed herein specifically binds human cMET, or a portion thereof, and specifically binds to cMET, or a portion thereof, derived from a non-human primate. In certain embodiments, a binding agent disclosed herein specifically binds human cMET, or a portion thereof, and specifically binds to cMET, or a portion thereof, derived from a rodent (e.g., a mouse or rat). In certain embodiments, a binding agent (i) specifically binds to a human cMET, or portion thereof (e.g., an extracellular domain of human cMET) with a KD of 10 nM or less, or 1 nM or less, and (ii) specifically binds to a rat or mouse cMET, or portion thereof (e.g., an extracellular domain of rat or mouse cMET) with a KD of 100 nM or less, 90 nM or less, 80 nM or less, 70 nM or less, 60 nM or less, 50 nM or less, 40 nM or less, 30 nM or less, 20 nM or less or 10 nM or less.

In certain embodiments, a binding agent comprises one or more functional characteristics. Accordingly, a binding agent can be described structurally and functionally (e.g., by what it does, or by what it is capable of doing). Binding agents disclosed herein can bind specifically to an extracellular portion of cMET, for example, an extracellular portion of cMET present on the surface of a cell. In some embodiments a cell is a human cancer cell or human neoplastic cell that expresses cMET. In certain embodiments, binding agents disclosed herein, upon binding cMET on the surface of a cell, induce internalization of cMET. The ability of a cMET binding agent to induce internalization and/or degradation of cMET provides an advantage over other cMET binding agents that lack this ability. A cMET binding agent-drug conjugate that induces internalization and/or degradation of cMET after binding provides for localized intracellular delivery of a cytotoxic drug. Further, in some embodiments, a binding agent-drug conjugate is configured to release a PBD toxin from the binding agent only after internalization, for example by means of a lysosomal enzyme cleavage site integrated into a linking group. Accordingly, binding agent-drug conjugates described herein can deliver a toxin specifically to the inside of a cancer cell that expresses cMET while minimizing non-specific cytotoxicity to healthy cells in a subject. Consequently, the anti-cMET binding agent-drug conjugates described herein provide for higher efficacy (e.g., target-specific cytotoxicity) and less adverse side effects (e.g., less non-specific cytotoxicity). Accordingly, in certain embodiments, a binding agent-drug conjugate comprises a binding agent that specifically binds cMET on a cell surface of a cell and induces internalization of cMET after binding. In some embodiments, a binding agent binds specifically to cMET, or a portion thereof, and induces degradation of cMET. Accordingly, in certain embodiments, a binding agent-drug conjugate comprises a binding agent that specifically binds cMET on a cell surface of a cell and induces internalization and/or degradation of cMET after binding. Internalization and/or degradation of a cell surface-bound receptor induced by binding of a ligand or binding agent is a known biological process that can be detected, measured, and/or quantitated using a suitable assay known in the art. Accordingly, the ability of a binding agent to induce cMET internalization and/or degradation can be determined, without undue experimentation, by use of a suitable experimental assay. Accordingly, in some embodiments, a binding agent described herein is a binding agent that binds specifically to cMET, or a portion thereof, on a cell surface and induces internalization and/or degradation of cMET.

Activation of cMET by binding of its cognate ligands is implicated in tumor growth, angiogenesis, and metastasis. Agonist anti-cMET antibodies often mimic ligand binding by cross-linking cMET receptors and inducing cMET activation. Accordingly, a binding agent that binds cell-surface cMET without activating the cMET receptor is better suited for anti-cancer therapy applications. In some embodiments, a binding agent of a binding agent-drug conjugate binds specifically to cMET, or a portion thereof, on a cell surface and does not detectably induce or promote signaling (e.g., tyrosine kinase activity). In some embodiments, a binding agent of a binding agent-drug conjugate binds specifically to cMET, or a portion thereof, on a cell surface and does not substantially activate cMET (e.g., tyrosine kinase activity). In certain embodiments, an anti-cMET binding agent disclosed herein does not have detectable cMET agonist activity. In certain embodiments, an anti-cMET binding agent lacks agonistic activity upon binding cMET on a cell surface and/or fails to induce or promote detectable tyrosine kinase activity upon binding to cMET on a cell surface. In some embodiments, an anti-cMET binding agent is a cMET antagonist. In certain embodiments, an anti-cMET binding agent decreases, inhibits, reduces, blocks or prevents signaling through a cMET receptor and/or decreases, inhibits, reduces, blocks or prevents a cMET receptor from inducing or promoting detectable tyrosine kinase activity. In some embodiments, an anti-cMET binding agent disclosed herein decreases, inhibits, reduces, prevents or blocks cMET from binding to its native cognate ligand (e.g., hepatocyte growth factor, or an isoform thereof).

In some embodiments a binding agent comprises a label. As used herein, the terms "label" or "labeled" refers to incorporation of a detectable marker, e.g., by incorporation of a labeled amino acid or attachment to a polypeptide of biotin moieties that can be detected by labeled avidin (e.g., streptavidin containing a fluorescent marker or enzymatic activity that can be detected by optical or colorimetric methods). In certain embodiments, a label or marker can be attached to a binding agent to generate a therapeutic or diagnostic agent. A binding agent can be attached covalently or non-covalently to any suitable label or marker. Various methods of labeling polypeptides and glycoproteins are known to those skilled in the art and can be used. Non-limiting examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{125}$I, $^{131}$I), fluorescent labels, enzymatic labels (e.g., horseradish peroxidase, β-galactosidase, luciferase, alkaline phosphatase), chemiluminescent labels, a metallic label, a chromophore, an electrochemiluminescent label, a phosphorescent label, a quencher (e.g., a fluorophore quencher), a fluorescence resonance energy transfer (FRET) pair (e.g., donor and acceptor), a dye, an enzyme substrate, a small molecule, a mass tag, quantum dots, nanoparticles, biotinyl groups, predetermined polypeptide epitopes recognized by a secondary reporter (e.g., leucine zipper pair sequences, binding sites for secondary antibodies, metal binding domains, epitope tags), the like or combinations thereof.

In some embodiments a binding agent comprises a suitable carrier. A binding agent can be attached covalently or non-covalently to a suitable carrier. In certain embodiments, a carrier is an agent or molecule that alters or extends the in vivo half-life of a binding agent, or improves its pharmacokinetic characteristics. Non-limiting examples of a carrier include polyethylene glycol, glycogen (e.g., by glycosylation of a binding agent), dextran, and a carrier or vehicle described in U.S. Pat. No. 6,660,843, the like or combinations thereof.

Payloads

PBD Toxins

In certain embodiments, a binding agent-drug conjugate comprises a binding agent described herein (e.g., a binding agent that specifically binds to cMET) and a payload (e.g., a cytotoxic payload). A payload of a binding agent-drug conjugate is often covalently linked to a binding agent. In some embodiments, a payload comprises a pyrrolobenzodiazepine (PBD) toxin. In some embodiments, a payload comprises a linking group or a suitable linker. In some embodiments, a payload comprises a pyrrolobenzodiazepine (PBD) toxin and a linking group. In certain embodiments a payload comprises a pyrrolobenzodiazepine (PBD) toxin and a linking group, where the pyrrolobenzodiazepine toxin is covalently linked to a linking group, and the linking group is covalently linked to a binding agent described herein.

Non-limiting examples of PBD toxins and methods of making PBD toxins are described in the following patent application publications: US 2011/0256157, WO/2015/052322, US 2016/0106861, US 2007/0072846, US 2011/0201803, US 2010/0113425, US 2008/0167293, US 2014/0127239, US 2015/0158869, US 2015/0344482, US 2015/0111880, US 2015/0315196, US 2016/0015828, US 2014/0088089, US 2013/0035484, US 2011/0196148, US 2013/0028919, US 2013/0059800, US 2014/0274907, US 2014/0275522, US 2014/0234346, US 2013/0266595, US 2014/0302066, US 2014/0286970, US 2014/0294868, US 2016/0144052, US 2016/0031887, US 2014/0120118, US 2016/0250344, WO/2017/137553, WO/2017/137555 and WO/2017/186894, the entire contents of which are incorporated herein by reference in their entirety.

In some embodiments, a pyrrolobenzodiazepine toxin comprises the structure of chemical formula I:

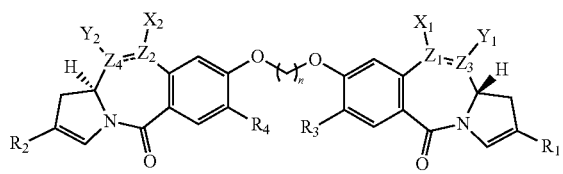

(I)

where $Z_1$ and $Z_2$ are both N; $Z_3$ and $Z_4$ are both C; the double-dash lines ===== represent a single bond or a double bond; n is 1 to 12; each of $R_3$ and $R_4$ are independently H, or a $C_{1-4}$ alkoxyl; and each of $R_1$ and $R_2$ are independently selected from the group consisting of H, $C_{1-5}$ alkyl, $C_{3-6}$ cycloalkyl, $C_{2-5}$ alkenyl, and a phenyl optionally substituted with $R_5$, where $R_5$ is selected from the group consisting of —$NH_2$, —$NHR_6$, and a piperazinyl substituted with $R_7$ having the structure

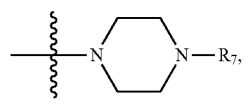

where $R_6$ comprises a linking group, and $R_7$ is null, or a $C_{1-5}$ alkyl; $X_1$ is null, a protecting group, or comprises a linking group; $X_2$ is null, a protecting group, or comprises a linking group; only one of $X_1$, $X_2$, $R_1$, and $R_2$ comprises a linking group; and each of $Y_1$ and $Y_2$ are independently either null, OH, or $SO_3$; provided that: (i) when $X_1$ comprises a linking group, $Z_1$ ===== $Z_3$ is N—C, (ii) when $X_2$ comprises a linking group, $Z_2$ ===== $Z_4$ is N—C, (iii) when $X_1$ comprises the protecting group, $Z_1$ ===== $Z_3$ is N—C, and (iv) when $X_2$ comprises the protecting group, $Z_2$ ===== $Z_4$ is N—C.

In certain embodiments, a PBD toxin comprises only one linking group. For example, in chemical formula I, only one of $X_1$, $X_2$, $R_1$, and $R_2$ may comprise a linking group. For example, where $X_1$ comprises a linking group, $X_2$, $R_1$, and $R_2$ do not comprise a linking group.

In certain embodiments of the PBD toxin of chemical formula I, n is 1-12. In certain embodiments of the PBD toxin of chemical formula I, n is 1-10, 1-9, 1-7, 1-5, or 1-3. In certain embodiments of the PBD toxin of chemical formula I, n is 1, 2, 3, 4, 5, 6, 7, 8, 9, 10, 11 or 12. In some embodiments, n is 1, 3 or 5. In some embodiments, n is 3 or 5.

In certain embodiments of the PBD toxin of chemical formula I, $R_3$ and $R_4$ are independently $C_{1-4}$ alkoxyl. In certain embodiments of the PBD toxin of chemical formula I, $R_3$ and $R_4$ are independently selected from —O—$CH_2CH_3$ or —O—$CH_3$. In certain embodiments of the PBD toxin of chemical formula I, $R_3$ and $R_4$ are both —O—$CH_3$.

In certain embodiments of the PBD toxin of chemical formula I, $R_1$ and $R_2$ are independently selected from the group consisting of H, $C_{1-5}$ alkyl, $C_3$-$C_6$ cycloalkyl, and $C_{2-5}$ alkenyl. $R_1$ and $R_2$ can be the same or different. In some embodiments, $R_1$ and $R_2$ are independently selected from a $C_1$-$C_3$ alkyl and a $C_2$-$C_3$ alkenyl. In certain embodiments, $R_1$ and $R_2$ are independently selected from —$CH_2CH_2CH_3$ and —$CH_3$. In certain embodiments, both $R_1$ and $R_2$ are —$CH_2CH_2CH_3$ or —$CH_3$.

In certain embodiments of the PBD toxin of chemical formula I, $R_1$ and $R_2$ are independently selected from a $C_3$-$C_6$ cycloalkyl, and a phenyl optionally substituted with $R_5$, where $R_5$ is selected from the group consisting of —$NH_2$, —$NHR_6$, and a piperazinyl substituted with $R_7$ having the structure

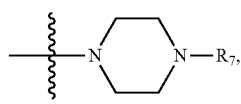

where $R_6$ comprises a linking group, and $R_7$ is null, or a $C_{1-5}$ alkyl. In certain embodiments, $R_1$ and $R_2$ are different and independently selected from a (i) a $C_3$-$C_6$ cycloalkyl, and (ii) a phenyl optionally substituted with $R_5$, where $R_5$ is selected from —$NH_2$, and —$NHR_6$, where $R_6$ comprises a linking group. In certain embodiments, $R_1$ and $R_2$ are different and independently selected from a (i) a $C_3$ cycloalkyl, and (ii) a phenyl substituted with —$NH_2$, or —$NHR_6$, where $R_6$ comprises a linking group. In certain embodiments, $R_1$ and $R_2$ are different and independently selected from a (i) a phenyl optionally substituted with $R_5$, where $R_5$ is selected from —$NH_2$, and —$NHR_6$, where $R_6$ comprises a linking group and (ii) a piperazinyl substituted with $R_7$ having the structure

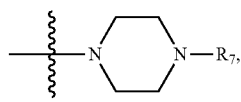

where $R_7$ is null, or a $C_1$-$C_2$ alkyl. In certain embodiments, $R_1$ and $R_2$ are different and independently selected from a (i) a phenyl substituted with $R_5$, where $R_5$ is —$NH_2$, and —$NHR_6$, where $R_6$ comprises a linking group and (ii) a piperazinyl substituted with $R_7$ having the structure

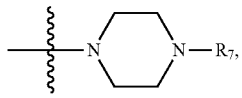

where $R_7$ is —$CH_3$. In certain embodiments, $R_2$ is phenyl substituted with 4-methylpiperazin-1-yl.

In certain embodiments of the PBD toxin of chemical formula I, $X_1$ is null, $Y_1$ is null, $Z_1$ ----- $Z_3$ is N=C, $X_2$ is null, $Y_2$ is null and $Z_2$ ----- $Z_4$ is N=C. In certain embodiments of the PBD toxin of chemical formula I, $X_1$ comprises the linking group, $Y_1$ is a OH, $Z_2$ ----- $Z_4$ is N=C, $X_2$ is null, and $Y_2$ is null. In certain embodiments of the PBD toxin of chemical formula I, $X_1$ comprises the linking group, $Y_1$ is a OH, $Z_2$ ----- $Z_4$ is N—C, $X_2$ is a protecting group, and $Y_2$ is OH.

In some embodiments, a PBD toxin comprises the structure of chemical formula VII shown below:

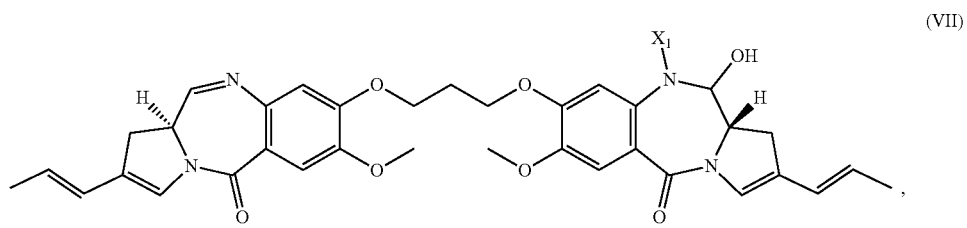

(VII)

where $X_1$ comprises the linking group.

In some embodiments, a PBD toxin comprises the structure of chemical formula VIII shown below:

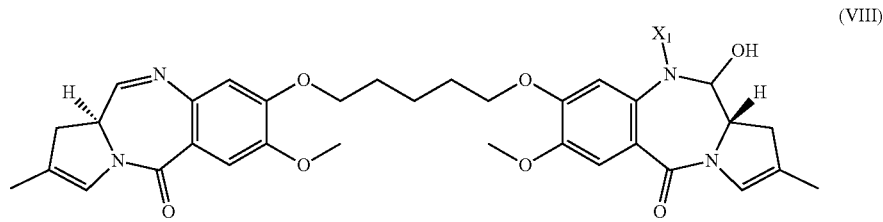

(VIII)

where $X_1$ comprises the linking group.

In some embodiments, a PBD toxin comprises the structure of chemical formula IX shown below:

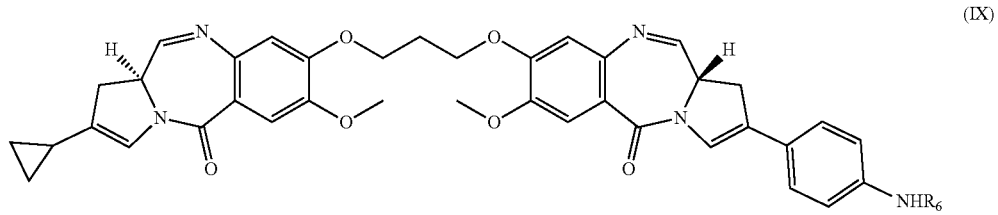

(IX)

where $R_6$ comprises the linking group.

In some embodiments, a PBD toxin comprises the structure of chemical formula X shown below:

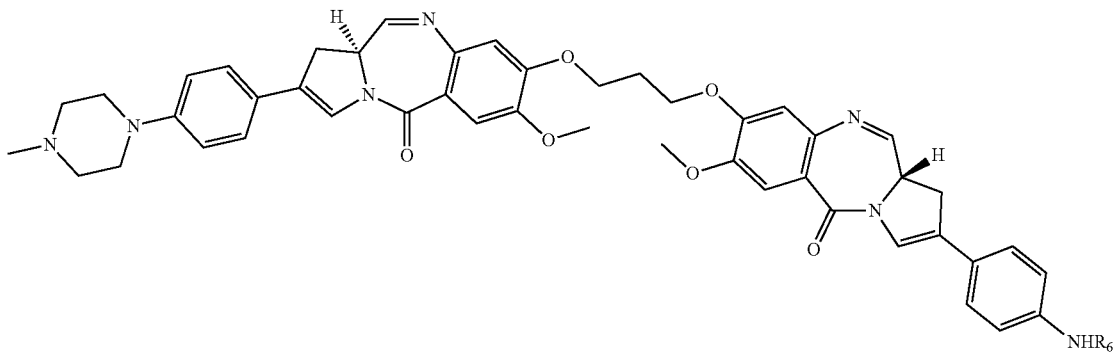

(X)

where $R_6$ comprises the linking group.

In some embodiments, a PBD toxin is attached (e.g., covalently linked) to a linking group by a suitable bond, moiety or group. In some embodiments, a PBD toxin is attached (e.g., covalently linked) to a linking group by a carbonyl linkage or an amide linkage. In some embodiments, a PBD toxin is attached (e.g., covalently linked) to a linking group by a carbamate group. In some embodiments, a PBD toxin is attached (e.g., covalently linked) to a linking group by an amide group. Non-limiting examples of attaching PBD toxin to a linking group are described in US 2017/0002096, US 2016/0331842, US 2015/0250896, US 2017/0080103, US 2016/0136300, US 2017/0152274, US 2015/0209444, US 2013/0274091, US 2017/0095570, US 2017/0157264, US 2015/0125474, US 2011/0256157, WO/2015/052322, US 2016/0106861, US 2007/0072846, US 2011/0201803, US 2010/0113425, US 2008/0167293, US 2014/0127239, US 2015/0158869, US 2015/0344482, US 2015/0111880, US 2015/0315196, US 2016/0015828, US 2014/0088089, US 2013/0035484, US 2011/0196148, US 2013/0028919, US 2013/0059800, US 2014/0274907, US 2014/0275522, US 2014/0234346, US 2013/0266595, US 2014/0302066, US 2014/0286970, US 2014/0294868, US 2016/0144052, US 2016/0031887, US 2014/0120118, US 2016/0250344, WO/2017/137553, WO/2017/137555 and WO/2017/186894, the entire contents of which are incorporated herein by reference in their entirety.

The term "null" as used herein means that an indicated moiety is absent from a structure, however, the indicated moiety may be replaced or occupied by one or more hydrogen atoms to complete a required valency. Further, in reference to any structure shown herein, one or more hydrogens may be present to complete a required valency of a carbon, nitrogen or oxygen atom shown in a structure. Accordingly, where not explicitly indicated, one or more hydrogen atoms may be present.

Linking Groups

In some embodiments, a payload comprises a linking group that, in part, facilitates a linkage between a binding agent and a PBD toxin. In certain embodiments, any suitable linking group can be used to link a PBD toxin to a binding agent. Non-limiting examples of linking groups and methods a making linking groups are described in WO/2015/052322, US 2015/0158869, US 2015/0344482, US 2014/0127239, US 2017/0002096, US 2016/0331842, US 2015/0250896, US 2017/0080103, US 2016/0136300, US 2017/0152274, US 2015/0209444, US 2013/0274091, US 2017/0095570, US 2017/0157264 and US 2015/0125474, which are incorporated herein by reference in their entirety. In some embodiments, a linking group comprises a C1-C20 alkyl, a C1-C20 alkenyl, a C1-C20 alkoxyl, one or more amino acids or amino acid derivatives, a peptide comprising 1 to 20 amino acids, a phenyl group, a suitable polymer (e.g., polyethylene glycol), or a combination thereof.

In some embodiments, a linking group comprises the structure of chemical formula A:

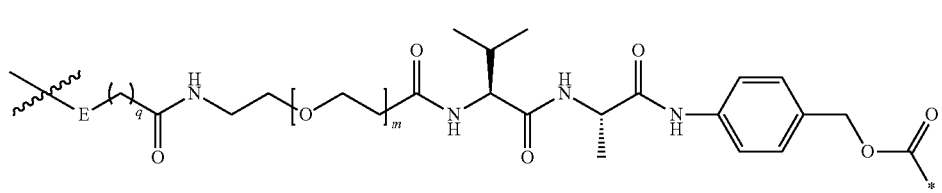

(A)

wherein the asterisk indicates the point of attachment of the linking group to a pyrrolobenzodiazepine toxin, the wavy line indicates the point of attachment of the linking group to a binding agent, m is 0 to 20, q is 0 to 10 and E is a connecting group. In some embodiments of the linking group of chemical formula A, m is 1 to 20, 1 to 10, 1 to 8, 1 to 6, 1 to 4, 2 to 8 or 4 or 8. In some embodiments of the linking group of chemical formula A, m is selected from 1, 2, 3, 4, 5, 6, 7, 8, 9 or 10. In some embodiments of the linking group of chemical formula A, q is 1 to 10, 1 to 8, 1 to 6, or 1 to 4. In some embodiments of the linking group of chemical formula A, q is selected from 0, 1, 2, 3, 4, 5, 6, 7, 8, 9 or 10. In some embodiments of the linking group of chemical formula A, q is 0, 1 or 2. 18. In some embodiments of the linking group of chemical formula A, m is 8 and q is 2.

In some embodiments, a linking group comprises the structure of chemical formula B:

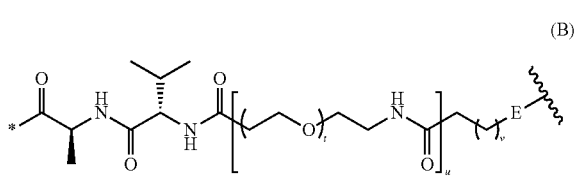

(B)

wherein the asterisk indicates the point of attachment of the linking group to a pyrrolobenzodiazepine toxin, the wavy line indicates the point of attachment of the linking group to a binding agent, v is 0 to 10, and u is 0 or 1, wherein when u is 1, t is 1 to 10, and E is a connecting group. In some embodiments of the linking group of chemical formula B, v is 1 to 10, 1 to 8, 1 to 4, or 0 to 4. 21. In some embodiments of the linking group of chemical formula B, v is selected from 0, 1, 2, 3, 4, 5, 6, 7 or 8. In some embodiments of the linking group of chemical formula B, when u is 1, t is 1 to 8, 1 to 5, 1 to 4, or 2 to 5. In some embodiments of the linking group of chemical formula B, when u is 1, t is selected from 0, 1, 2, 3, 4, 5, 6, 7, 8, 9 or 10. In some embodiments of the linking group of chemical formula B, t is 8, u is 1, and v is 2. In some embodiments of the linking group of chemical formula B, u is 0, and v is 4.

The connecting group E of chemical formulas A and B can comprise any suitable bond, linker or moiety non-limiting examples of which include a disulfide bond, a thioether bond, a thioester bond, an amide bond, an amine, a ketone, a carboxylate ether, a carbamate, an ester, a thioester, the like, or a combination thereof. In certain embodiments, E comprises a covalent linkage between the linking group and the binding agent. In some embodiments, E comprises a covalent bond. In some embodiments, E comprises a reacted moiety that remains after a suitable conjugation reaction is conducted. A multitude of conjugation reactions are known in the art, any one of which can be used to covalently link a linking group disclosed herein to a binding agent disclosed herein. Any suitable conjugation chemistry can be used to covalently attach a linking group to a binding agent, either stochastically or site-specifically, non-limiting examples of which include a conjugation reaction described in Shan S. Wong (Published Jun. 18, 1991) Chemistry of Protein Conjugation and Cross-Linking, CRC Press; Greg T. Hermanson (Copyright 2013) Bioconjugate Techniques, Third Edition, Elsevier Inc.; and Thiol-X Chemistries in Polymer and Materials Science, RSC Polymer Chemistry Series No. 6 (2013) Edited by Andrew B. Lowe and Christopher N. Bowman, RCS Publishing, WO/2015/052322, US 2015/0158869, US 2015/0344482, US 2014/0127239, US 2017/0002096, US 2016/0331842, US 2015/0250896, US 2017/0080103, US 2016/0136300, US 2017/0152274, US 2015/0209444, US 2013/0274091, US 2017/0095570, US 2017/0157264 and US 2015/0125474, the entire contents of which are incorporated herein by reference in their entirety. Other non-limiting examples of conjugating a payload or linking group to a binding agent include reacting an amine or amino group with an N-hydroxysuccinimide (NHS) ester, succinimidyl succinate, succinimidyl succinamide, succinimidyl propionate, succinimidyl carbonate, oxycarbonylimidazole, nitrophenyl carbonates, trichlorophenyl carbonate, tresylate, maleic anhydride, methylmaleic anhydride, an imidoester, a pentafluorophenyl (PFP) ester, a hydroxymethyl phosphine, an oxirane or any other carbonyl moiety; reacting a carboxyl moiety with a carbodiimide; reacting a sulfhydryl moiety with a maleimide, a haloacetyl, a pyridyldisulfide, orthopyridyldisulfide and/or a vinyl sulfone; reacting an aldehyde moiety with a hydrazine or hydrazide; reacting any non-selective group with diazirine and/or aryl azide; reacting a hydroxyl moiety with isocyanate; reacting a hydroxylamine moiety with a carbonyl moiety; the like and combinations thereof.

Accordingly, E is often defined by a chemistry used to conjugate a linking group to a binding agent. In some embodiments, E comprises a suitable moiety configured to attach a linking group to a binding agent. In some embodiments, a linking group is covalently linked to a binding agent by means of a suitable sulfhydryl-sulfhydryl reaction, for example by use of a maleimide or pyridyldithiol reactive group that reacts with a reduced cysteine to form stable thioether bond. Additional non-limiting examples of reactive sulfhydryl reactive moieties include a haloacetyls, aziridines, acryloyls, arylating agents, vinylsulfones, a pyridyl disulfide, and TNB-thiol. In certain embodiments, a binding agent is connected to E by a thioether bond formed between a cysteine thiol residue (e.g., a thiol) of the binding agent and E. Accordingly, in certain embodiments, E comprises a disulfide bond or thioether bond. In some embodiments, for example where a maleimide reaction is used to covalently link a binding agent to a linking group, E comprises the structure of chemical formula C:

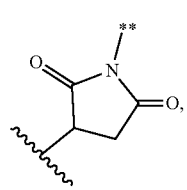

(C)

wherein the wavy line indicates the point of attachment to the binding agent and the double asterisk (**) indicates the point of attachment to the linking group. In certain embodiments the double asterisk of chemical formula C represents a thioether bond.

A payload, linking group or connecting group can be conjugated stochastically or site-specifically to any suitable amino acid of a binding agent. In some embodiments, a payload, linking group or connecting group is conjugated to one or more suitable cysteines of a binding agent. In some embodiments, a payload, linking group or connecting group is conjugated to one or more suitable lysine residues of a binding agent. In certain embodiments, one or more amino acids of a binding agent are substituted with an amino acid that is suitable for conjugation to a payload, linking group or connecting group. Non-limiting examples of amino acids that can be substituted with a thiol containing amino acid residue or a lysine residue include A118, S119, S239, V282, T289, N361, and V422 of an IgG2, S115, S252, V289, T306, and N384 of an IgG1, or a corresponding position in an IgG1, IgG2, IgG3 or IgG4. Incorporation of cysteines into antibodies by mutagenesis allows for direct conjugation of a payload, linking group or connecting group to specific sites on the antibody, for example via a disulfide bond or thioether bond. For example, one or more amino acids of a binding agent can be substituted with a cysteine, where the cysteine can be used for site-specific conjugation of a payload, linking group or connecting group using a suitable chemical reaction. Any suitable amino acid of a constant region of an antibody can be mutated to a cysteine or lysine for site-specific conjugation to a payload, linking group or connecting group. The stability of an antibody drug conjugate resulting from a site-specific conjugation can be assessed by methods known in the art.

In some embodiments, a linking group comprises a suitable enzyme cleavage site. In certain embodiments, an enzyme cleavage site comprises an enzyme recognition site of a mammalian protease. Accordingly, in some embodiments, a linking group, or portion thereof, is cleavable by a mammalian protease. A linking group may be cleaved by an enzyme present at or near a target site (e.g., at or near a cMET protein). An enzyme present at or near a target site may be intracellular, membrane bound, membrane associated or extracellular (e.g., secreted). For example a linking group may be configured to be cleaved by a cell surface protease, a secreted protease, or an intracellular protease (e.g., a lysosomal protease). Non-limiting examples of enzyme cleavage sites include a protease recognition site of a lysosomal cysteine protease and/or a lysosomal aspartic protease. Non-limiting examples of lysosomal proteases include cathepsin B, C, H, I, J, K, L, M, N, O, P, S, T and X, and cathepsin D, E, F, G, and/or cathepsin A (carboxypeptidase A).

Protecting Groups

In some embodiments, a PBD toxin comprises a suitable protecting group. Non-limiting examples of protecting groups and method of making protecting groups are described in the following patent application publications: US 2011/0256157, WO/2015/052322, US2011/0201803, US2008/0167293, US2014/0127239, US2015/0158869, US2015/0344482, US2015/0315196, US2015/0315196, US2014/0302066, US2006/0264622 and US2015/0133435, the entire contents of which are incorporated herein by reference in their entirety.

In some embodiments, a protecting group comprises the structure of chemical formula D below:

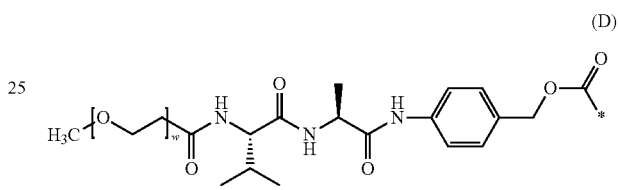

(D)

wherein the asterisk indicates a point of attachment to a pyrrolobenzodiazepine toxin; and w is 0 to 10. In some embodiments, w is 0 to 8, 0 to 6, 0 to 4, 1 to 10, 1 to 8, 1 to 5, or 1 to 4. In certain embodiments, w is selected from 0, 1, 2, 3, 4, 5, 6, 7, 8, 9 and 10. In some embodiments, w is 2.

In some embodiments, a protecting group is removable. In certain embodiments, a protecting group is cleavable using a suitable chemistry.

In some embodiments, a payload comprises a structure of chemical formula II:

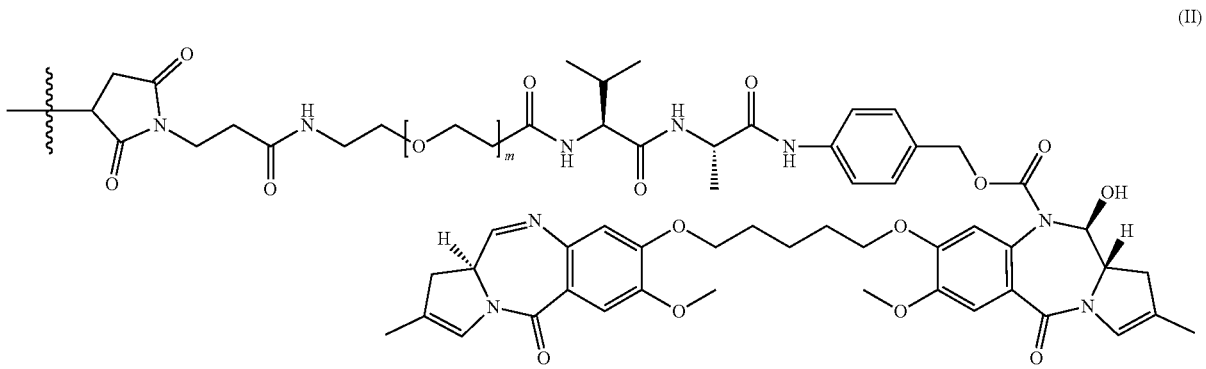

(II)

wherein m is 8 and the wavy line indicates the point of attachment to the binding agent.

In some embodiments, a payload comprises a structure of chemical formula I:
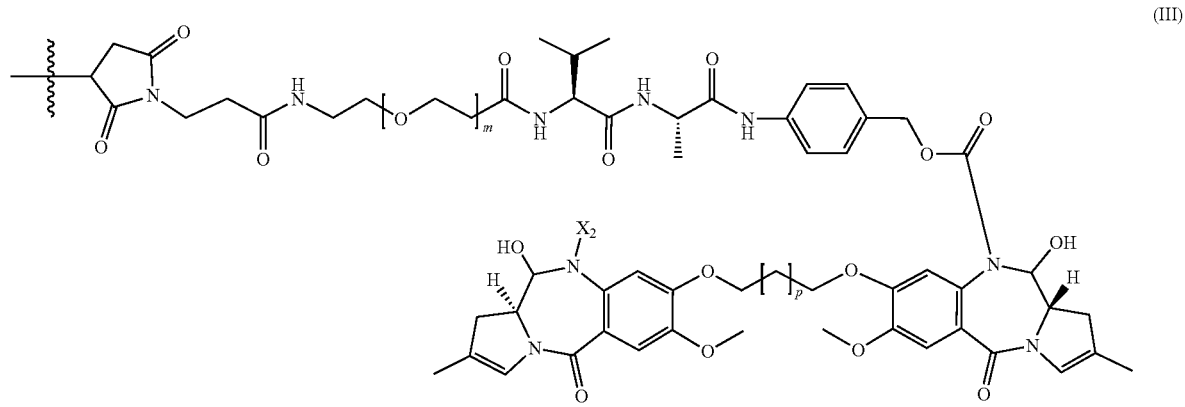
wherein m is 8, p is 1 or 3, $X_2$ is null, or is a protecting group and the wavy line indicates the point of attachment to the binding agent. In certain embodiments, a payload comprises a structure of chemical formula IV:
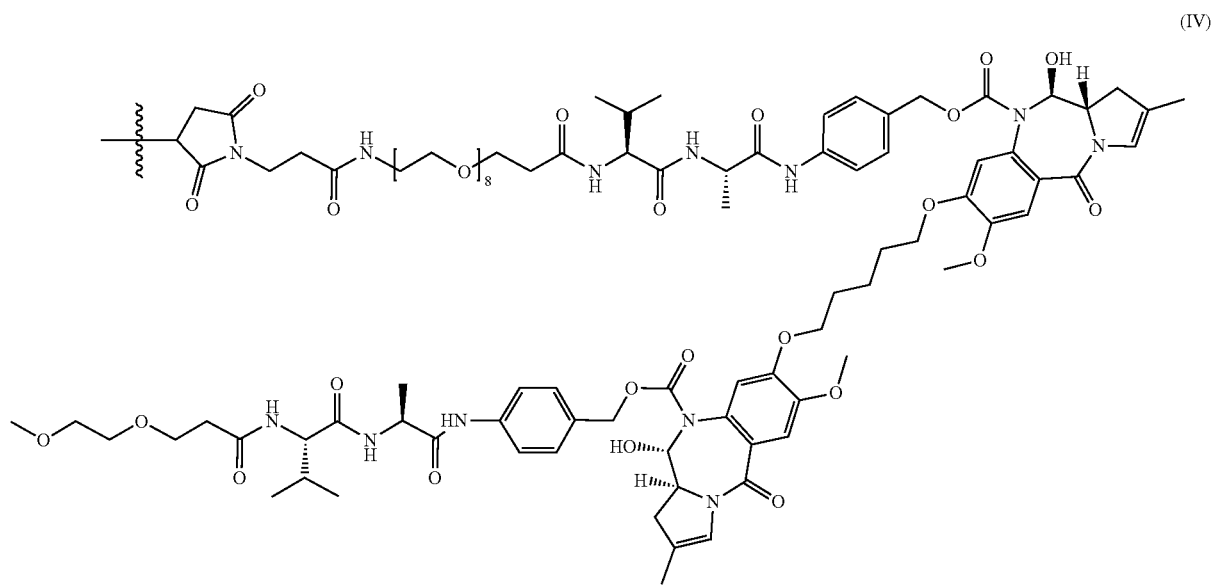
where the wavy line indicates the point of attachment to the binding agent.

In some embodiments, a payload comprises a structure of chemical formula V:

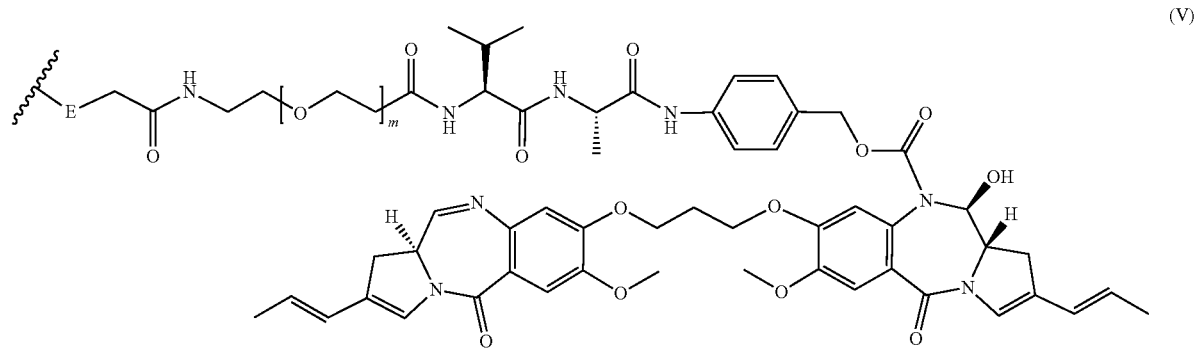

(V)

wherein m is 8, E is a suitable connecting group and the wavy line indicates the point of attachment to the binding agent. In some embodiments, E comprises a succinamide moiety of the structure C:

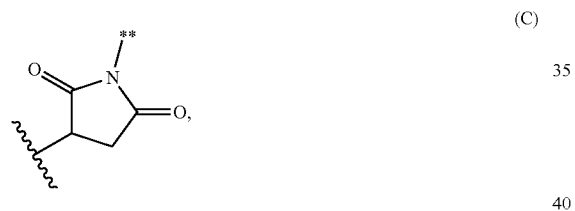

(C)

wherein the wavy line indicates the point of attachment to the binding agent and the double asterisk indicates the point of attachment to the payload of chemical formula V. The payload of chemical formula V comprising the connecting group of structure C is sometimes referred to herein as chemical formula XI.

In some embodiments, a payload comprises a structure of chemical formula VI:

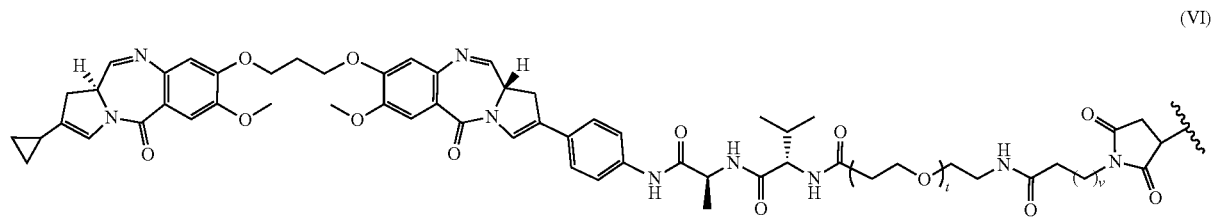

(VI)

wherein t is 8, v is 1 and the wavy line indicates the point of attachment to the binding agent.

In some embodiments, a payload comprises a structure of chemical formula VII:

(VII)

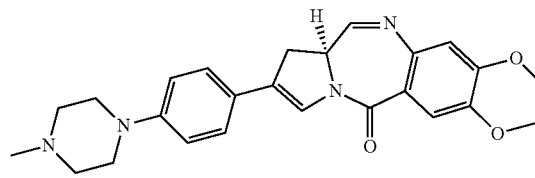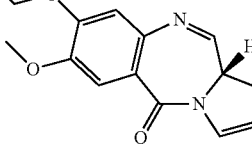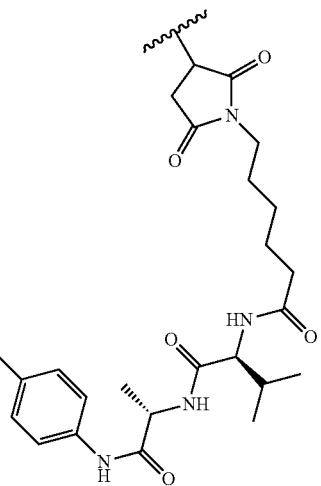

wherein the wavy line indicates the point of attachment to the binding agent.

In some embodiments, a binding agent-drug conjugate comprises a payload comprising a structure selected from any one of chemical formulas II, III, IV, V, VI, VII and XI, and a binding agent comprising a CDR-L1 selected from the amino acid sequences of SEQ ID NOs: 2, 4, 6, 8, 10, 12 and 14, a CDR-L2 selected from the amino acid sequences of SEQ ID NOs: 17, 19, 21, 23 and 25, a CDR-L3 selected from the amino acid sequences of SEQ ID NOs: 27, 29, 31, 33 and 35, a CDR-H1 selected from the amino acid sequences of SEQ ID NOs: 51, 53, 55, 57 and 59, a CDR-H2 selected from the amino acid sequences of SEQ ID NOs: 63, 65, 67, 69, 71, 73 and 75, and a CDR-H3 selected from the amino acid sequences of SEQ ID NOs: 80, 82, 84, 86, 88, 91 and 93.

In some embodiments, a binding agent-drug conjugate comprises a payload comprising a structure selected from any one of chemical formulas II, III, IV, V, VI, VII and XI, and a binding agent comprising a CDR-L1 comprising the amino acid sequence of SEQ ID NO: 10 or 14, a CDR-L2 comprising the amino acid sequence of SEQ ID NO: 21, a CDR-L3 comprising the amino acid sequence of SEQ ID NO: 35, a CDR-H1 comprising the amino acid sequences of SEQ ID NO: 59, a CDR-H2 comprising the amino acid sequence of SEQ ID NO: 71, and a CDR-H3 comprising the amino acid sequence of SEQ ID NO: 88.

In some embodiments, a binding agent-drug conjugate comprises a payload comprising a structure selected from any one of chemical formulas II, III, IV, V, VI, VII and XI, and a binding agent comprising a CDR-L1 comprising the amino acid sequence of SEQ ID NO: 9, a CDR-L2 comprising the amino acid sequence of SEQ ID NO: 24, a CDR-L3 comprising the amino acid sequence of SEQ ID NO: 34, a CDR-H1 comprising the amino acid sequences of SEQ ID NO: 58, a CDR-H2 comprising the amino acid sequence of SEQ ID NO: 70, and a CDR-H3 comprising the amino acid sequence of SEQ ID NO: 87.

In some embodiments, a binding agent-drug conjugate comprises a payload comprising a structure selected from any one of chemical formulas II, III, IV, V, VI, VII and XI, and a binding agent comprising a variable light chain region having at least 90% sequence identity to an amino acid sequence selected from the amino acid sequences of SEQ ID NOs: 37-44, and a variable heavy chain region having at least 90% sequence identity to an amino acid sequence selected from the amino acid sequences of SEQ ID NOs: 94-103.

In some embodiments, a binding agent-drug conjugate comprises a payload comprising a structure selected from any one of chemical formulas II, III, IV, V, VI, VII and XI, and a binding agent comprising a variable light chain region having an amino acid sequence selected from the amino acid sequences of SEQ ID NOs: 37-44, and a variable heavy chain region having an amino acid sequence selected from the amino acid sequences of SEQ ID NOs: 94-103.

In some embodiments, a binding agent-drug conjugate comprises a payload comprising a structure selected from any one of chemical formulas II, III, IV, V, VI, VII and XI, and a binding agent comprising a variable light chain region having at least 90% sequence identity to an amino acid sequence selected from the amino acid sequences of SEQ ID NOs: 45-49, and a variable heavy chain region having at least 90% sequence identity to an amino acid sequence selected from the amino acid sequences of SEQ ID NOs: 104-108.

In some embodiments, a binding agent-drug conjugate comprises a payload comprising a structure selected from any one of chemical formulas II, III, IV, V, VI, VII and XI, and a binding agent comprising a variable light chain region comprising an amino acid sequence selected from the amino acid sequences of SEQ ID NOs: 45-49, and a variable heavy chain region comprising an amino acid sequence selected from the amino acid sequences of SEQ ID NOs: 104-108.

Pharmaceutical Compositions

In some embodiments, a composition or pharmaceutical composition comprises a binding agent-drug conjugate described herein. In some embodiments, a pharmaceutical composition comprises a binding agent-drug conjugate and a pharmaceutically acceptable excipient, diluent, additive or carrier.

A pharmaceutical composition can be formulated for a suitable route of administration. In some embodiments a pharmaceutical composition is formulated for subcutaneous (s.c.), intradermal, intramuscular, intraperitoneal and/or intravenous (i.v.) administration. In certain embodiments, a pharmaceutical composition can contain formulation materials for modifying, maintaining, or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates (e.g., phosphate buffered saline) or suitable organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); solvents (such as glycerin, propylene glycol or polyethylene glycol); diluents; excipients and/or pharmaceutical adjuvants. In particular, pharmaceutical compositions can comprise any suitable carrier, formulation, or ingredient, the like or combinations thereof as listed in "Remington: The Science And Practice Of Pharmacy" Mack Publishing Co., Easton, PA, 19$^{th}$ Edition, (1995)(hereafter, Remington '95), or "Remington: The Science And Practice Of Pharmacy", Pharmaceutical Press, Easton, PA, 22$^{nd}$ Edition, (2013)(hereafter, Remington 2013), the contents of which are incorporated herein by reference in their entirety. The various materials listed herein, alone or in combination, can be incorporated into or used with the materials described in Remington '95 or Remington 2013. Any suitable techniques, carriers, and excipients can be used, including those understood in the art; e.g., as described in Remington '95 or Remington 2013.

In certain embodiments, a pharmaceutical composition comprises a suitable excipient, non-limiting examples of which include anti-adherents (e.g., magnesium stearate), a binder, fillers, monosaccharides, disaccharides, other carbohydrates (e.g., glucose, mannose or dextrin), sugar alcohols (e.g., mannitol or sorbitol), coatings (e.g., cellulose, hydroxypropyl methylcellulose (HPMC), microcrystalline cellulose, synthetic polymers, shellac, gelatin, corn protein zein, enterics or other polysaccharides), starch (e.g., potato, maize or wheat starch), silica, colors, disintegrants, flavors, lubricants, preservatives, sorbents, sweeteners, vehicles, suspending agents, surfactants and/or wetting agents (such as pluronics, PEG, sorbitan esters, polysorbates such as polysorbate 20, polysorbate 80, triton, tromethamine, lecithin, cholesterol, tyloxapal), stability enhancing agents (such as sucrose or sorbitol), and tonicity enhancing agents (such as alkali metal halides, sodium or potassium chloride, mannitol, sorbitol), and/or any excipient disclosed in Remington '95 or Remington 2013. The term "binder" as used herein refers to a compound or ingredient that helps keeps a pharmaceutical mixture combined. Suitable binders for making pharmaceutical formulations and are often used in the preparation of pharmaceutical tablets, capsules and granules are known to those skilled in the art. For clarification, the term "binding agent" as used herein does not refer to a "binder" that is used in certain pharmaceutical formulations. Although a pharmaceutical composition, in certain embodiments, may comprise a binding agent that specifically binds cMET as well as a binder.

In some embodiments a pharmaceutical composition comprises a suitable pharmaceutically acceptable additive and/or carrier. Non-limiting examples of suitable additives include a suitable pH adjuster, a soothing agent, a buffer, a sulfur-containing reducing agent, an antioxidant and the like. Non-limiting examples of a sulfur-containing reducing agent include those having a sulfhydryl group (e.g., a thiol) such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a C1-C7 thioalkanoic acid. Non-limiting examples of an antioxidant include erythorbic acid, dibutylhydroxytoluene, butylhydroxyanisole, alpha-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as disodium ethylenediaminetetraacetate (EDTA), sodium pyrophosphate and sodium metaphosphate. Furthermore, diluents, additives and excipients may comprise other commonly used ingredients, for example, inorganic salts such as sodium chloride, potassium chloride, calcium chloride, sodium phosphate, potassium phosphate and sodium bicarbonate, as well as organic salts such as sodium citrate, potassium citrate and sodium acetate.

The pharmaceutical compositions used herein can be stable over an extended period of time, for example on the order of months or years. In some embodiments a pharmaceutical composition comprises one or more suitable preservatives. Non-limiting examples of preservatives include benzalkonium chloride, benzoic acid, salicylic acid, thimerosal, phenethyl alcohol, methylparaben, propylparaben, chlorhexidine, sorbic acid, hydrogen peroxide, the like and/or combinations thereof. A preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). A preservative can comprise an alkyl-mercury salt of thiosalicylic acid, such as thimerosal, phenylmercuric nitrate, phenylmercuric acetate or phenylmercuric borate. A preservative can comprise a paraben, such as methylparaben or propylparaben. A preservative can comprise an alcohol, such as chlorobutanol, benzyl alcohol or phenyl ethyl alcohol. A preservative can comprise a biguanide derivative, such as chlorohexidine or polyhexamethylene biguanide. A preservative can comprise sodium perborate, imidazolidinyl urea, and/or sorbic acid. A preservative can comprise stabilized oxychloro complexes, such as known and commercially available under the trade name PURITE®. A preservative can comprise polyglycol-polyamine condensation resins, such as known and commercially available under the trade name POLYQUART® from Henkel KGaA. A preservative can comprise stabilized hydrogen peroxide. A preservative can be benzalkonium chloride. In some embodiments a pharmaceutical composition is free of preservatives.

In some embodiments a composition, pharmaceutical composition or binding agent-drug conjugate is substantially free of contaminants (e.g., blood cells, platelets, polypeptides, minerals, blood-borne compounds or chemicals, virus, bacteria, other pathogens, toxin, and the like). In some embodiments a composition, pharmaceutical composition or binding agent-drug conjugate is substantially free of serum and serum contaminants (e.g., serum proteins, serum lipids, serum carbohydrates, serum antigens and the like). In some embodiments a composition, pharmaceutical composition or binding agent-drug conjugate is substantially free of a pathogen (e.g., a virus, parasite or bacteria). In some embodiments a composition, pharmaceutical composition or binding agent-drug conjugate is substantially free of endotoxin. In some embodiments a composition, pharmaceutical composition or binding agent-drug conjugate is sterile. In certain embodiments, a composition or pharmaceutical composition comprises a binding agent-drug conjugate that specifically binds an extracellular domain of cMET and a suitable diluent (e.g., phosphate buffered saline).

The pharmaceutical compositions described herein may be configured for administration to a subject in any suitable form and/or amount according to the therapy in which they are employed. For example, a pharmaceutical composition configured for parenteral administration (e.g., by injection or infusion), may take the form of a suspension, solution or emulsion in an oily or aqueous vehicle and it may contain formulation agents, excipients, additives and/or diluents such as aqueous or non-aqueous solvents, co-solvents, suspending solutions, preservatives, stabilizing agents and or dispersing agents. In some embodiments a pharmaceutical composition suitable for parenteral administration may contain one or more excipients. In some embodiments a pharmaceutical composition is lyophilized to a dry powder form. In some embodiments a pharmaceutical composition is lyophilized to a dry powder form, which is suitable for reconstitution with a suitable pharmaceutical solvent (e.g., water, saline, an isotonic buffer solution (e.g., PBS), and the like). In certain embodiments, reconstituted forms of a lyophilized pharmaceutical composition are suitable for parenteral administration (e.g., intravenous administration) to a mammal.

In certain embodiments, a pharmaceutical composition is configured for oral administration and may be formulated as a tablet, microtablet, minitablets, micropellets, powders granules, capsules (e.g., capsules filled with microtablets, micropellets, powders or granules), emulsions or solutions. Pharmaceutical compositions configured for oral administration may comprise suitable coatings to delay or sustain release of the active ingredient (e.g., a binding agent), non-limiting examples of which include enteric coatings such as fatty acids, waxes, shellac, plastics, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, cellulose acetate trimellitate, sodium alginate, zein, plant fibers, the like and combinations thereof.

In some embodiments a pharmaceutical compositions described herein may be configured for topical administration and may include one or more of a binding and/or lubricating agent, polymeric glycols, gelatins, cocoa-butter or other suitable waxes or fats. In some embodiments a pharmaceutical composition described herein is incorporated into a topical formulation containing a topical carrier that is generally suited to topical drug administration and comprising any suitable material known to those skilled in the art. In certain embodiments, a topical formulation of a pharmaceutical composition is formulated for administration of a binding agent from a topical patch.

In certain embodiments, an optimal pharmaceutical composition will be determined by one skilled in the art depending upon, for example, the intended route of administration, delivery format and desired dosage (see e.g., Remington '95 or Remington 2013, supra). In certain embodiments, such compositions may influence the physical state, stability, rate of in vivo release and rate of in vivo clearance of the antibody drug conjugates of the invention. A pharmaceutical composition can be manufactured by any suitable manner, including, e.g., by means of conventional mixing, dissolving, granulating, dragee-making, levigating, emulsifying, encapsulating, entrapping or tableting processes (e.g., see methods described in Remington '95 or Remington 2013).

Second Medical Use

In some embodiments, presented herein is a composition or pharmaceutical composition for use as a medicament for the treatment of cancer or a neoplastic disorder in a subject, wherein the composition or pharmaceutical composition comprises a binding agent-drug conjugate described herein. In some embodiments, presented herein is a composition or pharmaceutical composition comprising a binding agent-drug conjugate described herein for use in the treatment of cancer or a neoplastic disorder.

Methods of Treatment

In some embodiments a composition, pharmaceutical composition or binding agent-drug conjugate described herein is used to treat a subject having or suspected of having a neoplastic disorder or cancer. In certain embodiments, a binding agent-drug conjugate or pharmaceutical composition described herein is used in treating a neoplastic disorder or cancer in a subject, wherein the binding agent-drug conjugate specifically binds to an extracellular domain of human cMET. In some embodiments, presented herein is a method of treating a subject having or suspected of having a neoplastic disorder or cancer. In certain embodiments, a method of treating a subject having or suspected of having a neoplastic disorder or cancer comprises administering a therapeutically effective amount of a composition, pharmaceutical composition or binding agent-drug conjugate described herein to the subject. In certain embodiments, a method comprises contacting a cell (e.g., one or more cells) of a subject with a therapeutically effective amount of a composition, pharmaceutical composition or binding agent-drug conjugate described herein. In certain embodiments, a method comprises contacting a cancer cell or neoplastic cell of a subject with a therapeutically effective amount of a composition, pharmaceutical composition or binding agent-drug conjugate described herein. In certain embodiments, a method comprises contacting a cell (e.g., one or more cells) of a subject with a therapeutically effective amount of a binding agent-drug conjugate that specifically binds to an extracellular portion of human cMET, or variant thereof. In certain embodiments, a method comprises contacting a cancer cell or neoplastic cell with a therapeutically effective amount of a binding agent-drug conjugate that specifically binds to an extracellular portion of human cMET, or variant thereof, wherein the cell expresses cMET on its cell surface. The cell of a subject is often a cell that expresses an extracellular portion of cMET. A cell that is contacted with a binding agent-drug conjugate may be found inside a subject (e.g., in vivo) or outside a subject (e.g., in vitro or ex vivo).

In certain embodiments, a binding agent-drug conjugate blocks, inhibits, ameliorates, abrogates, or suppresses growth, viability or metastasis of a cancer or cancer cell. In certain embodiments, a binding agent-drug conjugate induces death, necrosis or apoptosis of a cancer or cancer cell. In certain embodiments, contacting a cell of a subject with a binding agent-drug conjugate disclosed herein induces or promotes death, necrosis or apoptosis of the cell. In certain embodiments, contacting a cell of a subject with a binding agent-drug conjugate disclosed herein induces or promotes death of a cell by an ADCC, ADCP or complement-dependent cellular cytotoxicity (CDCC) process. In certain embodiments, contacting a cell of a subject with a binding agent-drug conjugate disclosed herein decreases, inhibits, or reduces mitosis of the cell. In certain embodiments, contacting a cancer or cancer cell of a subject with a binding agent-drug conjugate disclosed herein decreases, inhibits, or reduces metastasis of the cancer or cancer cell.

Subjects

The term "subject" refers to a mammal. Any suitable mammal can be treated by a method or composition described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female.

In some embodiments a subject is in need of a treatment or composition described herein. In certain embodiments a subject has or is suspected of having a neoplastic disorder or a cancer. In some embodiments a subject in need of a treatment or composition described herein has or is suspected of having a neoplastic disorder or a cancer. In certain embodiments a binding agent-drug conjugate or composition described herein is used to treat a subject having, or suspected of having, a neoplastic disorder or cancer.

Cancer Types

A composition, pharmaceutical composition or binding agent-drug conjugate disclosed herein can be used to treat a neoplastic order or cancer non-limiting examples of which include a carcinoma, sarcoma, neuro neoplasia, lymphoma, myeloma, leukemia, melanoma, mesothelioma, solid or soft tissue tumors, and secondary cancers (e.g., derived from a primary site)). Non-limiting examples of a carcinoma include respiratory system carcinomas, gastrointestinal system carcinomas, genitourinary system carcinomas, testicular carcinomas, prostatic carcinomas, endocrine system carcinomas, basal cell carcinoma of the skin, carcinoma of unknown primary, cholangiocarcinoma, ductal carcinoma in situ (DCIS), Merkel cell carcinoma, lung carcinoma, thymoma and thymic carcinoma, midline tract carcinoma, lung small cell carcinoma, thyroid carcinoma, liver hepatocellular carcinoma, squamous cell carcinoma, head and neck squamous carcinoma, breast carcinoma, epithelial carcinoma, adrenocortical carcinoma, ovarian surface epithelial carcinoma, and the like, further including carcinomas of the uterus, cervix, colon, pancreas, kidney, esophagus, stomach and ovary. Non-limiting examples of a sarcoma include Ewing sarcoma, lymphosarcoma, liposarcoma, osteosarcoma, breast sarcoma, soft tissue sarcoma, Kaposi sarcoma, rhabdomyosarcoma, uterine sarcoma, chondrosarcoma, leiomyosarcoma, fibrosarcoma and the like. Non-limiting examples of a neuro neoplasia include glioma, glioblastoma, meningioma, neuroblastoma, retinoblastoma, astrocytoma, oligodendrocytoma and the like. Non-limiting examples of lymphomas, myelomas, and leukemia include acute and chronic lymphoblastic leukemia, myeloblastic leukemia, multiple myeloma, poorly differentiated acute leukemias (e.g., erythroblastic leukemia and acute megakaryoblastic leukemia), acute promyeloid leukemia (APML), acute myelogenous leukemia (AML), chronic myelogenous leukemia (CML), acute lymphoblastic leukemia (ALL), which includes B-lineage ALL and T-lineage ALL, chronic lymphocytic leukemia (CLL), prolymphocytic leukemia (PLL), hairy cell leukemia (HLL), Waldenstrom's macroglobulinemia (WM), non-Hodgkin lymphoma and variants, peripheral T-cell lymphomas, adult T-cell leukemia/lymphoma (ATL), cutaneous T-cell lymphoma (CTCL), large granular lymphocytic leukemia (LGF), Hodgkin's disease and Reed-Sternberg disease. Non-limiting examples of soft or solid tissue tumors include visceral tumors, seminomas, hepatomas, and other tumors of the breast, liver, lung, pancreas, uterus, ovary, testicle, head, neck, eye, brain, mouth, pharynx, vocal cord, ear, nose, esophagus, stomach, intestine, colon, adrenal gland, kidney, bone, bladder, urethra, carcinomas, lung, muscle, skin, feet, hands, and soft tissue. In some embodiments, a neoplastic disorder or cancer that can be treated by a pharmaceutical composition or binding agent-drug conjugate disclosed herein is selected from a bladder cancer, breast cancer, colorectal cancer, cervical cancer, gastric cancer, liver cancer, hepatocellular cancer, hypopharynx cancer, lung cancer, adenocarcinoma, ovarian cancer and renal cancer. In some embodiments, a neoplastic disorder or cancer that can be treated by a pharmaceutical composition or binding agent-drug conjugate disclosed herein is selected from a pancreatic cancer (e.g., a pancreatic adenocarcinoma, exocrine pancreatic cancer or pancreatic neuroendocrine cancer), a colorectal cancer (e.g., a colorectal adenocarcinoma), small intestinal malignancy, cholangiocarcinoma, non-small cell lung cancer (NSCLC), thyroid carcinoma, esophageal or esophagogastric junction (EGJ) cancer, gastric adenocarcinoma, liver hepatocellular carcinoma, head and neck squamous carcinoma, female genital tract malignancy, breast carcinoma, lung small cell carcinoma, ovarian surface epithelial carcinoma, retroperitoneal or peritoneal sarcoma, prostatic adenocarcinoma, neuroendocrine tumor, gastrointestinal stromal tumor, glioblastoma or non-epithelial ovarian cancer. In some embodiments, a neoplastic disorder or cancer that can be treated by a pharmaceutical composition or binding agent-drug conjugate disclosed herein is a breast cancer, non-limiting examples of which include ductal carcinoma in situ (DCIS), invasive ductal carcinoma (IDC)(e.g., tubular carcinoma of the breast, medullary carcinoma of the breast, mucinous carcinoma of the breast, papillary carcinoma of the breast, and cribriform carcinoma of the breast), invasive lobular carcinoma (ILC), inflammatory breast cancer, lobular carcinoma in situ (LCIS), male breast cancer, molecular subtypes of breast cancer (e.g., Luminal B breast cancer or hormone-receptor positive breast cancer, Triple-negative breast cancer, HER2-enriched breast cancer, and normal-like breast cancer), Paget's disease of the nipple, phyllodes tumors of the breast, and metastatic breast cancer. In some embodiments a neoplastic disorder or cancer that can be treated by a pharmaceutical composition or binding agent-drug conjugate disclosed herein is a triple negative breast cancer.

In some embodiments, the effectiveness of a treatment described herein can be determined or predicted, in part, by an amount of cMET that a cancer or neoplasia expresses. Many cancer and tumor types are known to express cMET, non-limiting examples of which include certain bladder cancers, breast cancers, colorectal cancers, gastric cancers, hepatocellular cancers, HNSCC, hypopharynx cancers, lung cancers, adenocarcinomas, ovarian cancers and renal cancers (e.g., see Ariyawutyakorn et al. (2016) *Journal of Cancer* 7(6):633-649) and the amounts of cMET expressed by many cancer types are known (e.g., see Arguello et al. (2013) *Annual Meeting of Association for Molecular Pathology* (AMP) Abstract No. 294319). In addition, a neoplastic cell or cancer cell can be quickly assayed for expression of cMET using a suitable anti-cMET binding agent (e.g., antibody) using a suitable method (e.g., whole-cell ELISA, FACs, any suitable immunoassay, and the like). Accordingly, in some embodiments, a method of treating a subject having or suspected of having a cancer comprises administering a therapeutically effective amount of a binding agent-drug conjugate described herein, or a pharmaceutical composition comprising a binding agent-drug conjugate described herein, to the subject, wherein the cancer expresses detectable levels of cMET. In certain embodiments, a cancer that expresses detectable levels of cMET can be a cancer that is known or reported to express cMET, or is suspected of expressing cMET (e.g., by having a similar genotype or phenotype to another cancer that is known to express cMET). In some embodiments, a cancer that expresses cMET, or a cancer that is suspected of expressing cMET is a cancer that expresses an RNA transcript that encodes cMET, or a portion thereof. In some embodiments, a cancer that expresses cMET or a cancer that is suspected of expressing cMET is a cancer that expresses cMET on its cell surface.

Route of Administration

Any suitable method of administering a composition, pharmaceutical composition or binding agent-drug conjugate to a subject can be used. The exact formulation and route of administration for a composition for use according to the methods of the invention described herein can be chosen by a medical professional (e.g., a physician) in view of a patient's condition. (e.g., see Fingl et al. 1975, in "The Pharmacological Basis of Therapeutics", which is incorporated herein by reference in its entirety). Any suitable route of administration can be used for administration of a pharmaceutical composition or a binding agent-drug conjugate described herein. Non-limiting examples of routes of administration include topical or local (e.g., transdermally or cutaneously, (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranial, intra-articular, into a joint space, intracardiac (into the heart), intracavernous injection, intralesional (into a skin lesion), intraosseous infusion (into the bone marrow), intrathecal (into the spinal canal), intrauterine, intravaginal, intravesical infusion, intravitreal), the like or combinations thereof.

In some embodiments a composition herein is provided to a subject. A composition that is provided to a subject is sometimes provided to a subject for self-administration or for administration to a subject by another (e.g., a non-medical professional). For example a composition described herein can be provided as an instruction written by a medical practitioner that authorizes a patient to be provided a composition or treatment described herein (e.g., a prescription). In another example, a composition can be provided to a subject where the subject self-administers a composition orally, intravenously or by way of an inhaler, for example.

Alternately, one can administer compositions for use according to the methods of the invention in a local rather than systemic manner, for example, via direct application to the skin, mucous membrane or region of interest for treating, including using a depot or sustained release formulation.

In some embodiments a pharmaceutical composition comprising a binding agent-drug conjugate can be administered alone (e.g., as a single active ingredient (AI or e.g., as a single active pharmaceutical ingredient (API)). In other embodiments, a pharmaceutical composition comprising a binding agent-drug conjugate can be administered in combination with one or more additional AIs/APIs, for example, as two separate compositions or as a single composition where the one or more additional AIs/APIs are mixed or formulated together with the binding agent-drug conjugate in a pharmaceutical composition.

In certain embodiments, a cMET binding agent-drug conjugate is delivered to a cell (e.g., a mammalian cell). A cMET binding agent-drug conjugate can be delivered to a cell using any suitable method. In certain embodiments, delivering a cMET binding agent-drug conjugate to a cell comprises contacting a mammalian cell, in vitro or in vivo, with a composition comprising a cMET binding agent-drug conjugate under conditions that allow the binding agent-drug conjugate to bind to the cell.

Dose and Therapeutically Effective Amount

In some embodiments, an amount of a binding agent-drug conjugate in a composition is a therapeutically effective amount. In some embodiments, a therapeutically effective amount of a binding agent-drug conjugate is administered to a subject. In some embodiments, an therapeutically effective amount of a binding agent-drug conjugate in a composition is an amount needed to obtain an effective therapeutic outcome. In certain embodiments, the amount of a binding agent-drug conjugate in a composition (e.g., a pharmaceutical composition) is an amount sufficient to prevent, treat, reduce the severity of, delay the onset of, and/or alleviate a symptom of a neoplastic disorder or cancer, as contemplated herein.

A "therapeutically effective amount" means an amount sufficient to obtain an effective therapeutic outcome and/or an amount sufficient to prevent, treat, reduce the severity of, delay the onset of, and/or alleviate a symptom of a neoplastic disorder or cancer. In certain embodiments, a "therapeutically effective amount" means an amount sufficient to terminate the growth of, and/or slow the growth of a neoplasm or cancer. In certain embodiments, a "therapeutically effective amount" means an amount sufficient to inhibit the replication of, and/or induce the death of one or more neoplastic or cancer cells. Determination of a therapeutically effective amount is well within the capability of those skilled in the art, especially in light of the detailed disclosure provided herein.

In certain embodiments, a therapeutically effective amount is an amount high enough to provide an effective therapeutic effect and an amount low enough to minimize unwanted adverse reactions. Accordingly, in certain embodiments, a therapeutically effective amount of a binding agent-drug conjugate may vary from subject to subject, often depending on age, weight, general health condition of a subject, severity of a condition being treated, and a particular combination of drugs administered. Thus, in some embodiments, a therapeutically effective amount is determined empirically. Accordingly, a therapeutically effective amount of a binding agent-drug conjugate used to treat a subject can be determined by one of ordinary skill in the art based on amounts found effective in animal or clinical studies, a physician's experience, and suggested dose ranges or dosing guidelines, for example.

In certain embodiments, a binding agent-drug conjugate (e.g., a binding agent-drug conjugate in a pharmaceutical composition) is administered at a suitable therapeutically effective amount or dose (e.g., at a suitable volume and concentration, which sometimes depends, in part, on a particular route of administration). In certain embodiments, a therapeutically effective amount of a binding agent-drug conjugate is selected from one or more doses of about 0.01 mg/kg (e.g., per kg body weight of a subject) to 500 mg/kg, 0.1 mg/kg to 500 mg/kg, 0.1 mg/kg to 400 mg/kg, 0.01 mg/kg to 300 mg/kg, 0.1 mg/kg to 300 mg/kg, 0.1 mg/kg to 200 mg/kg, 0.1 mg/kg to 150 mg/kg, 0.1 mg/kg to 100 mg/kg, 0.1 mg/kg to 75 mg/kg, 0.1 mg/kg to 50 mg/kg, 0.1 mg/kg to 25 mg/kg, 0.1 mg/kg to 10 mg/kg, 0.1 mg/kg to 5 mg/kg, 0.1 mg/kg to 1 mg/kg, intervening amounts and combinations thereof. In some aspects the therapeutically effective amount of a binding agent-drug conjugate comprises one or more doses of about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, and 0.1 mg/kg, intervening amounts and combinations thereof. In some embodiments a therapeutically effective amount of a binding agent-drug conjugate is between about 0.1 mg/kg to 100 mg/kg, or between about 1 mg/kg and about 50 mg/kg.

In some embodiments administering a therapeutically effective amount of a binding agent-drug conjugate or a pharmaceutical composition comprising a binding agent-drug conjugate comprises administering a suitable dose at a frequency or interval as needed to obtain an effective therapeutic outcome. In some embodiments administering a therapeutically effective amount of a binding agent-drug conjugate or a pharmaceutical composition comprising a binding agent-drug conjugate comprises administering a suitable dose hourly, every two hours, every 4 hours, every 6 hours, three times a day, twice a day, once a day, six times a week, five times a week, four times a week, three times a week, twice a week, weekly, at combinations thereof, and/or at regular or irregular intervals thereof, and/or simply at a frequency or interval as needed or recommended by a medical professional. An effective therapeutic outcome can be determined, in certain embodiments, by monitoring the number, size, viability, growth, mitosis, or metastasis of a cancer, neoplastic growth or cancerous cells in a subject. Accordingly, in certain embodiments, a decrease or reduction in the number, viability, size, growth, mitosis, or metastasis of neoplastic or cancerous cells in a subject is considered an effective therapeutic outcome.

Kits

A pharmaceutical composition comprising an amount or dose of a binding agent-drug conjugate can, if desired, be provided in a kit, pack or dispensing device, which can contain one or more doses of a binding agent. In some embodiments, a kit comprises a pack and/or dispensing device. Non-limiting examples of a pack include a metal, glass, or plastic container, or blister pack that comprises a binding agent-drug conjugate or composition described herein. In certain embodiments, a kit comprises a dispensing device such as a syringe or inhaler. A pack and/or dispenser device can be accompanied by instructions for administration. The pack or dispenser can also be accompanied with a notice associated with the container in a form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert.

In some embodiments a kit or pack comprises an amount of a binding agent-drug conjugate sufficient to treat a patient for 1 day to 1 year, 1 day to 180 days, 1 day to 120 days, 1 day to 90 days, 1 day to 60 days, 1 day to 30 days, 1-24 hours, 1-12 hours, 1-4 hours, or amount of time there between.

A kit optionally includes a product label and/or one or more packaging inserts, that provide a description of the components or instructions for use in vitro, in vivo, or ex vivo, of the components therein. Exemplary instructions include instructions for a diagnostic method, treatment protocol or therapeutic regimen. In certain embodiments, a kit comprises packaging material, which refers to a physical structure housing components of the kit. The packaging material can maintain the components sterilely, and can be made of material commonly used for such purposes (e.g., paper, corrugated fiber, glass, plastic, foil, ampules, vials, tubes, etc.). Product labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, optical disk such as CD- or DVD-ROM/RAM, DVD, MP3, magnetic tape, or an electrical storage media such as RAM and ROM or hybrids of these such as magnetic/optical storage media, FLASH media or memory-type cards. Product labels or inserts can include identifying information of one or more components therein, dose amounts, clinical pharmacology of the active ingredient(s) including mechanism of action, pharmacokinetics (PK) and pharmacodynamics (PD). Product labels or inserts can include information identifying manufacturer information, lot numbers, manufacturer location, date, information on an indicated condition, disorder, disease or symptom for which a kit component may be used. Product labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Kits of the invention therefore can additionally include labels or instructions for practicing any of the methods and uses of the invention described herein. Product labels or inserts can include information on potential adverse side effects and/or warnings.

EXAMPLES

Example 1—Antibody Generation

Figure 2:
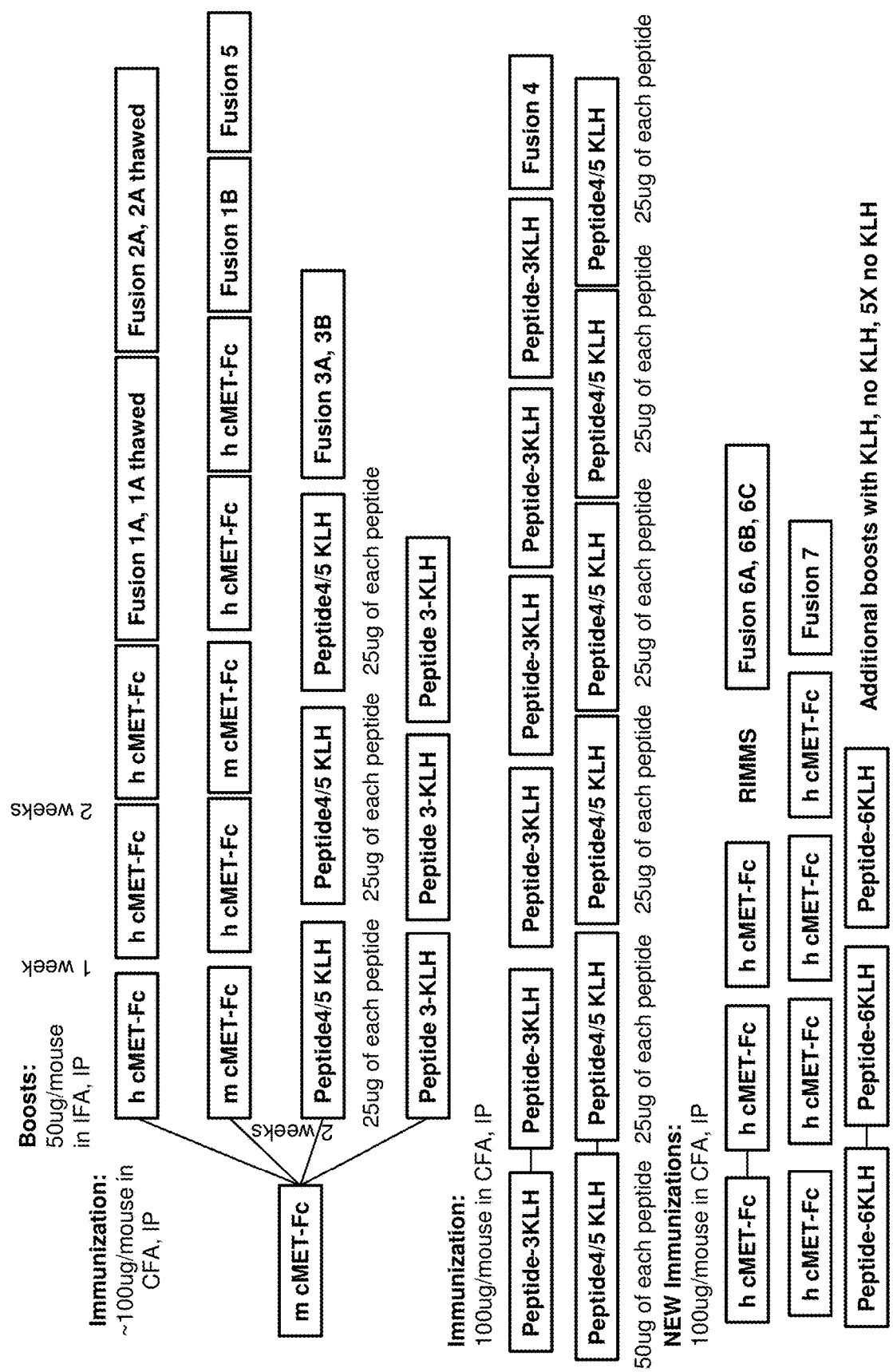
FIG. 2 shows an immunization scheme used to generate monoclonal antibodies (exemplary binding agents) that bind specifically to cMET. Mice were initially immunized by intraperitoneal injection (i.p.) with 100 μg of a human cMET-Fc fusion protein (cMET-Fc), or 50 to 100 μg of a KLH conjugated cMET peptide in Freund's Complete Adjuvant (CFA) as indicated. cMET-Fc comprises the extracellular domain of human cMET fused to an Fc portion of an antibody. cMET peptides were strategically selected from a portion of the cMET extracellular domain. Immunized mice received one or more booster immunization comprising 25 or 50 μg of cMET-Fc or peptide in Incomplete Freund's adjuvant (IFA) as indicated. Some mice received repetitive immunizations at multiple sites (RIMMS). Immunizations included Met-Fc fusions, peptides, traditional and RIMMS. Spleens of immunized mice were obtained and fused to a suitable fusion partner. Over 20,000 hybridoma clones were obtained and screened.
Figure 3:
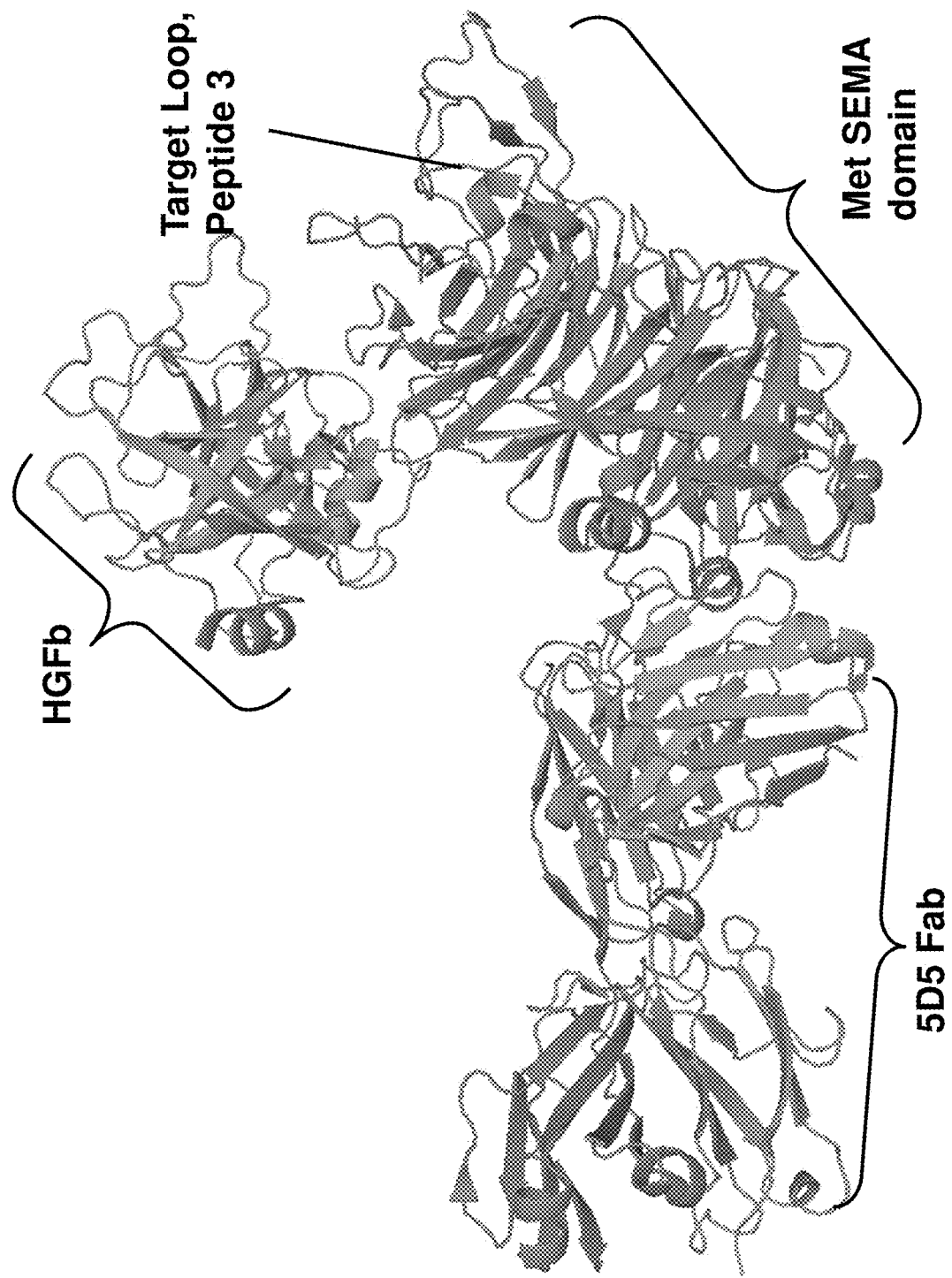
FIG. 3 shows a 3D structure of the MET SEMA domain bound with a Fab of an agonist Met-mAb antibody (5D5 Fab) and HGF beta subunit (HGFβ or HGFb). The bottom arrow indicates the position of a portion of cMET used to design peptide 3.
Figure 5:
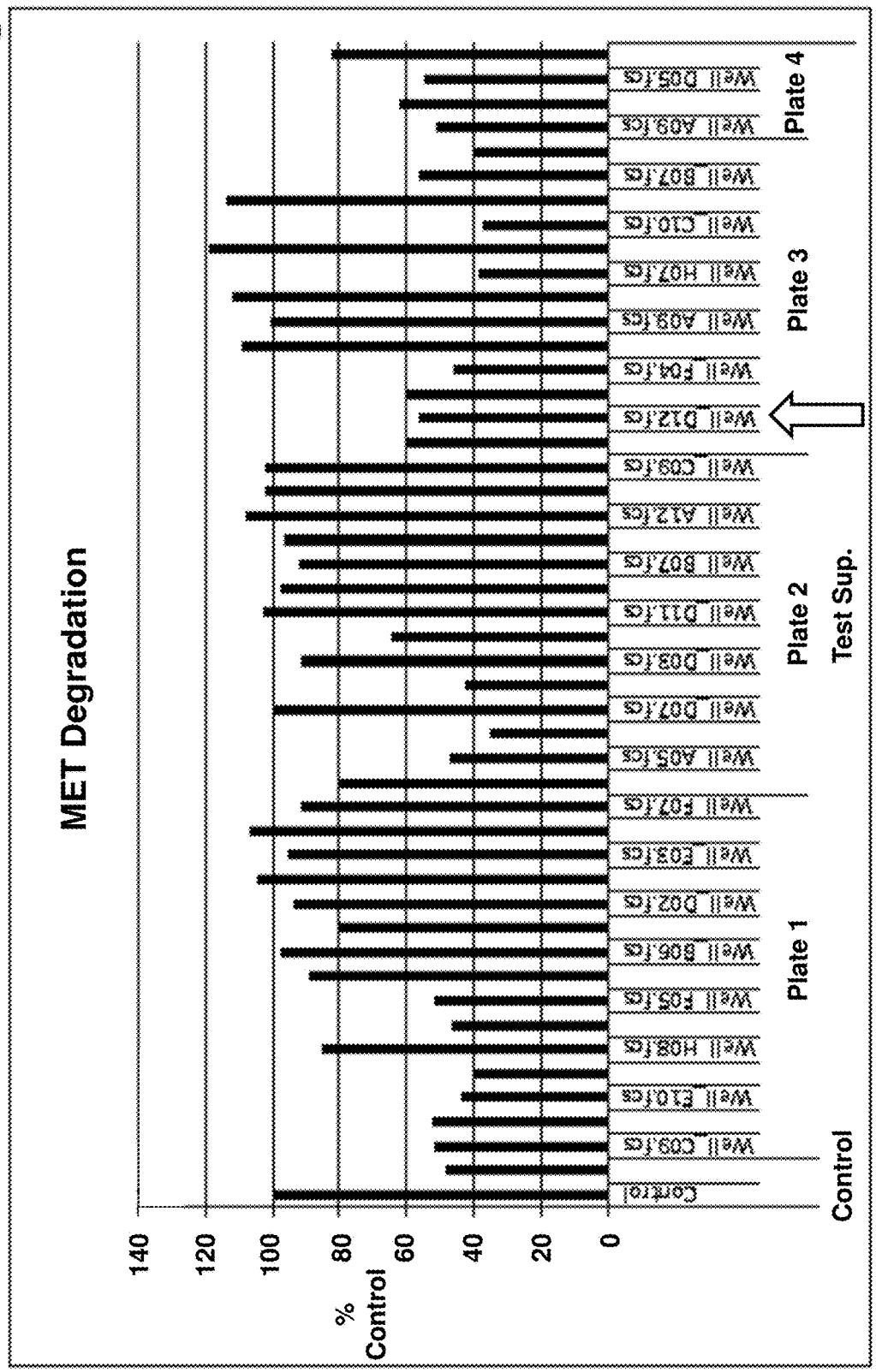
FIG. 5 shows the results of a MET degradation assay. Anti-cMET antibodies isolated from the indicated wells (x-axis) were tested and selected for their ability to induce degradation of cMET on human cancer cell lines as measured by Mesoscale (MSD) cMET protein quantification. Relative values of Met degradation are indicated on the y-axis as % control (percent of control). Values lower than 100% control (negative control level) indicate internalization and degradation of cMET. Degradation indicates not just internalization but lysosomal trafficking, an important property for an antibody drug conjugate. The arrow indicates the results for a lead hybridoma F6B1P3D12.
Figure 6:
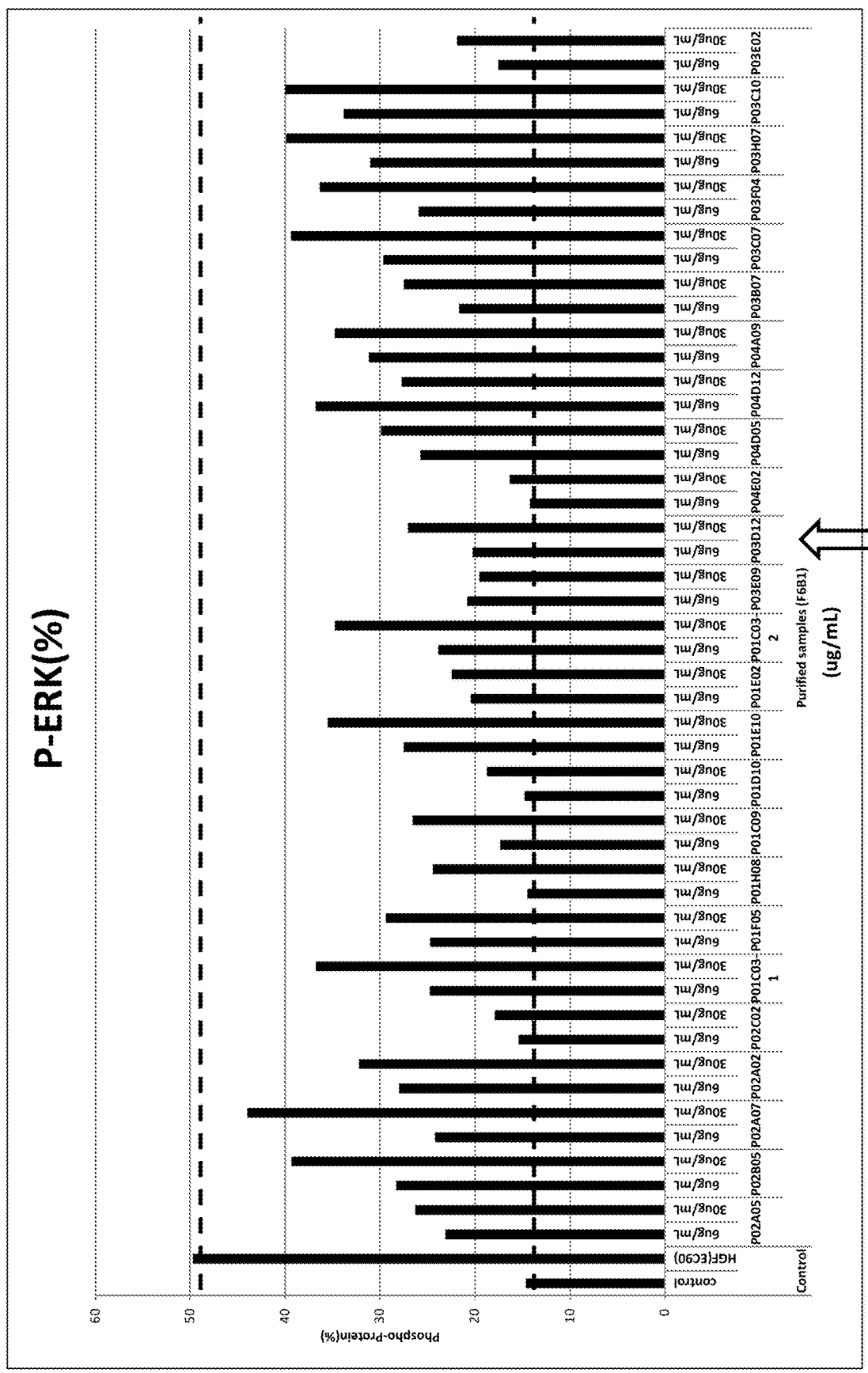
FIG. 6 shows the results of a phospho-ERK assay (P-ERK assay) that measures agonist activity of anti-cMET antibodies by indirectly measuring the phosphorylation of ERK induced by binding of an anti-cMET antibody to cMET on a cell surface. The amount of phosphorylated ERK (shown as % of control, y-axis) detected in cell lysates after treatment of viable cells with an anti-cMET antibody is shown. Anti-cMET antibodies produced from various anti-cMET hybridomas (x-axis) were tested at 6 μg/ml or 30 μg/ml (as indicated on x-axis), and selected according to their inability to induce significant phosphorylation of ERK (i.e., their ability not to induce proliferation, i.e., absence of agonist activity). A lead monoclonal antibody (mAb) P3D12 is indicated by the arrow.

To induce an antibody response against cMET, mice were immunized with cMET-Fc or cMET peptide as described in FIGS. 1 and 2. In some embodiments peptide derived from strategic regions were selected for immunization. FIG. 3 illustrates an example of a structural loop on MET that inspired the design of peptide 3. Spleens from immunized mice were obtained and splenocytes were fused to a suitable fusion partner to produce hybridomas using a standard protocol. Hybridoma clones were isolated and hybridoma media was tested for binding to MET and/or for the ability to induce internalization of cMET on human cancer cell lines as measured by flow cytometry (FIG. 4). Selected hybridoma antibodies were selected for their ability to induce MET degradation (FIG. 5) or inability to induce phosphorylation of ERK (FIG. 6). The lead hybridoma F6B1P3D12 has been deposited with American Type Culture Collection, Patent Depository of 10801 University Boulevard Manassas, Virginia 20110-2209 USA on Mar. 20, 2019. The deposit was made under the provisions of the Budapest Treaty on the International Recognition of the Deposit of Microorganisms for the Purpose of Patent Procedure and the Regulations thereunder (Budapest Treaty). An ATCC number has not been assigned yet.

Figure 7:
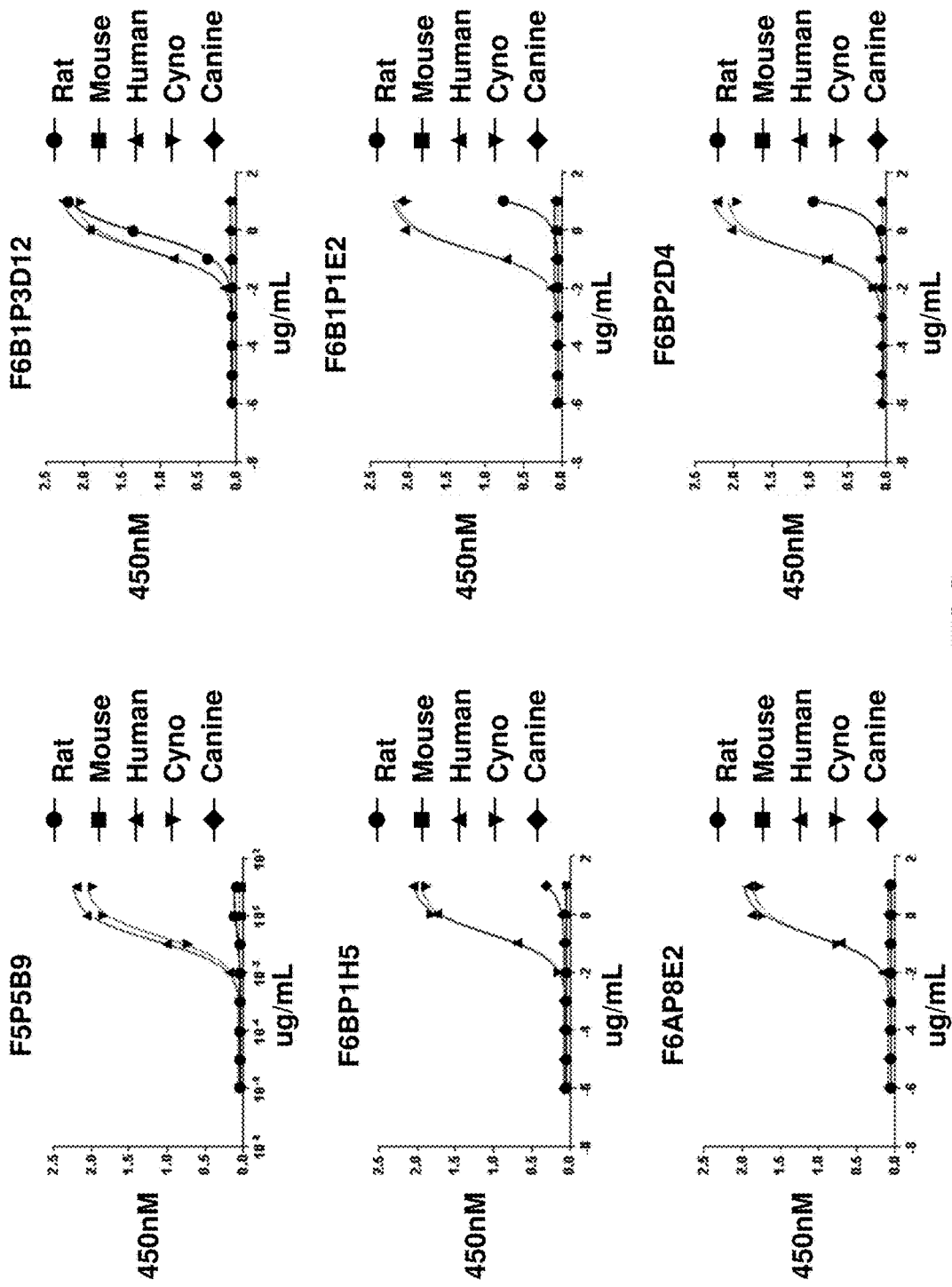
FIG. 7 shows results of six cMET monoclonal antibodies (mAbs) that were assayed by ELISA for binding to human, monkey (Cynomolgus Macaque, "Cyno"), canine, rat, and mouse cMET. All monoclonal antibodies bound human and monkey cMET. P3D12 demonstrated significant cross-reactivity with rat cMET. Various concentrations of each antibody are indicated on the x-axis. Relative amounts bound are indicated on the y-axis (OD450 nm).
Figure 10:
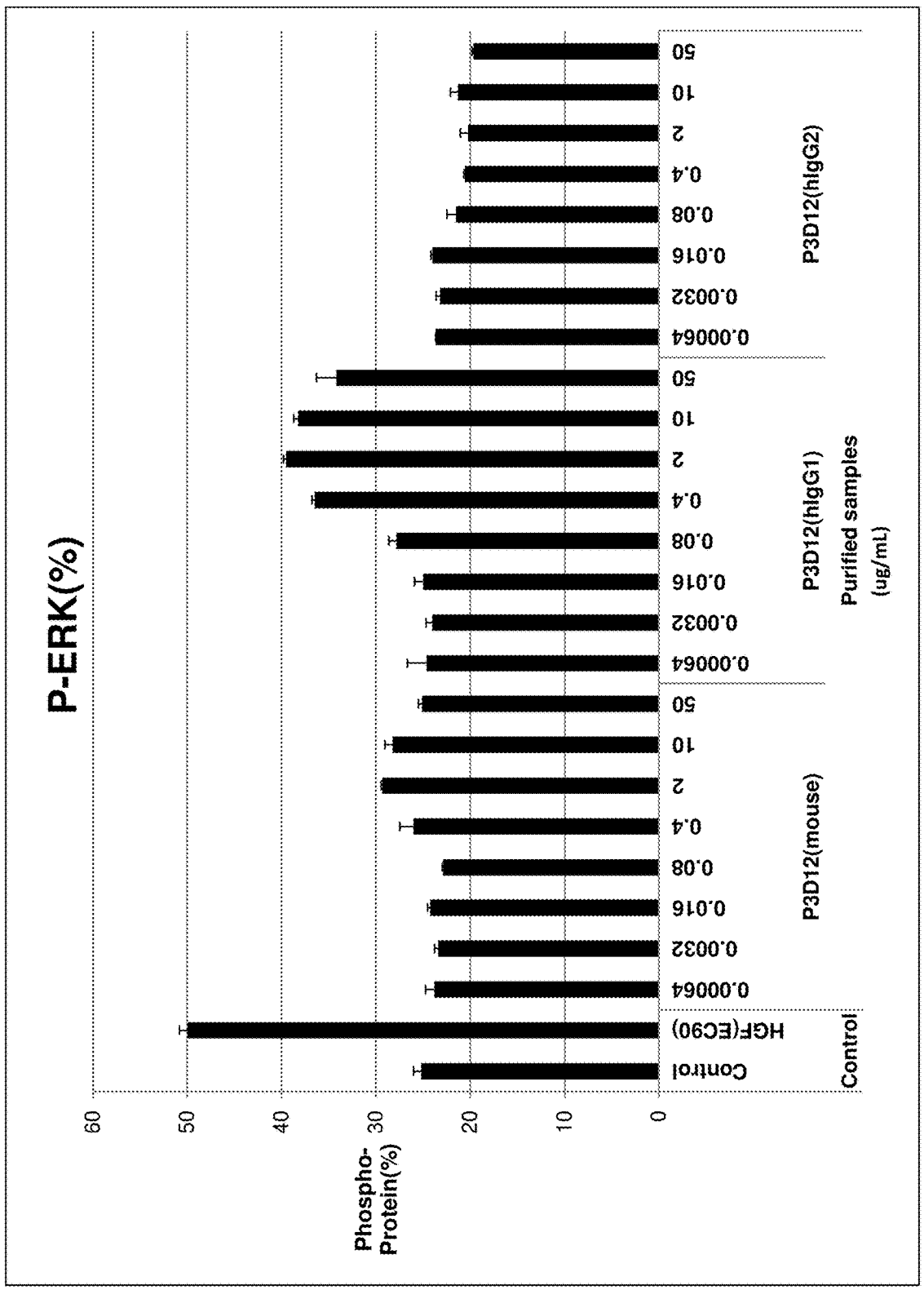
FIG. 10 shows the results of a phospho-ERK assay (P-ERK assay) that measures agonist activity of anti-cMET antibodies by indirectly measuring the phosphorylation of ERK induced by binding of an anti-cMET antibody to cMET on a cell surface. The amount of phosphorylated ERK (shown as % of control, y-axis) detected in cell lysates after treatment of viable cells with an anti-cMET antibody is shown. The constant regions of the heavy and light chains of an isolated mouse monoclonal antibody designated as P3D12 were replaced with antibody constant regions of a human IgG1 (P3D12(hIgG1)), or a human IgG2 (P3D12(hIgG2)) as indicated on the x-axis. Each antibody was tested at 0.00064 µg/ml, 0.0032 µg/ml, 0.016 µg/ml, 0.08 µg/ml, 0.4 µg/ml, 2 µg/ml, 10 µg/ml and 50 µg/ml as indicated on the x-axis. "Control" indicates an untreated negative control. HGF(EC90) is a positive control and indicates cells treated with Hepatocyte Growth Factor (HGF), the natural ligand of cMET receptor. This data indicates that the human IgG2 isotype does not display detectable agonist activity.
Figure 11:
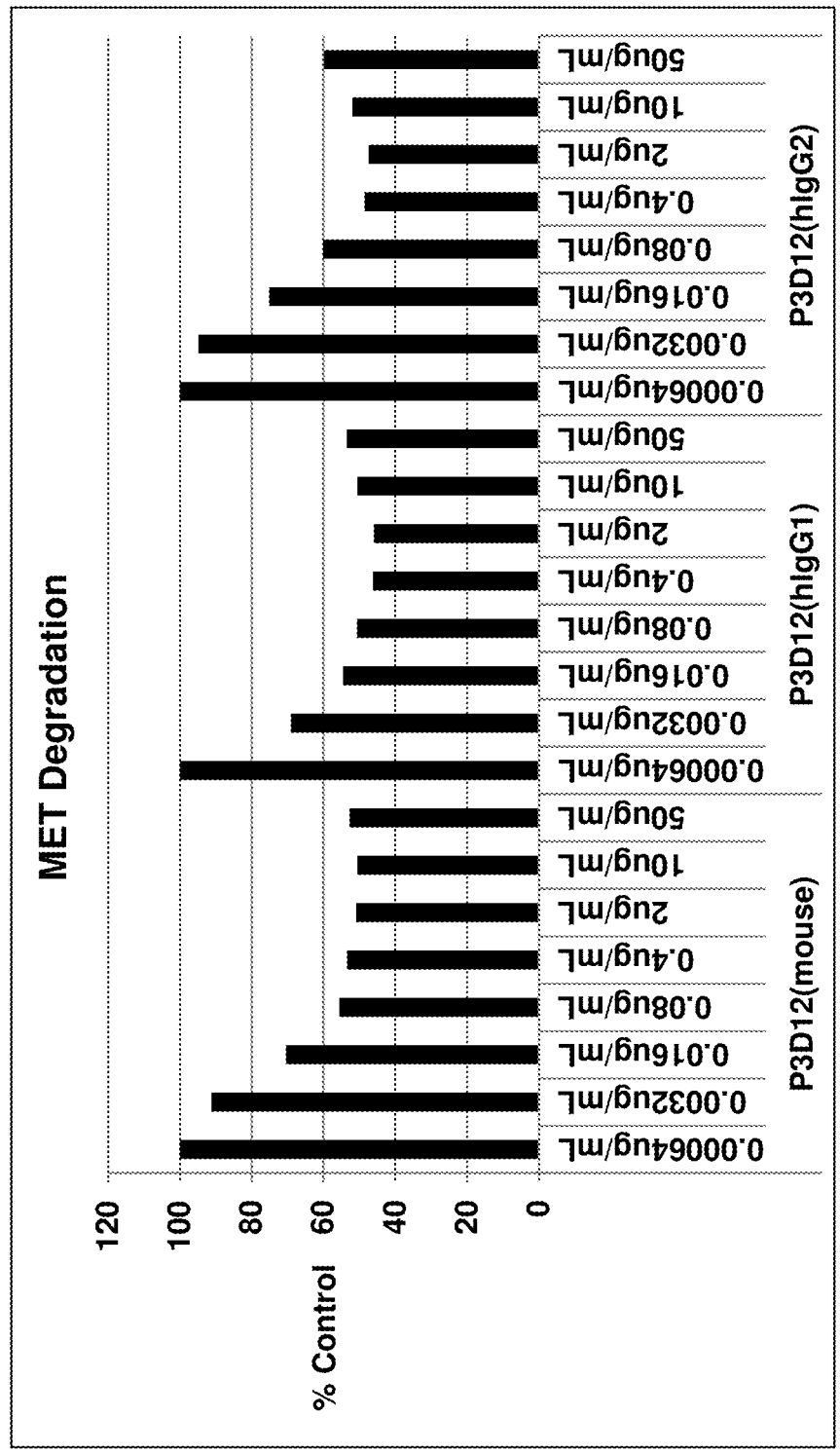
FIG. 11 shows the results of a MET degradation assay. Degradation is a measure of internalization of the cMET receptor upon antibody binding. Chimeric anti-cMET antibodies were tested for their ability to induce degradation of cMET on human cancer cell lines as measured by Mesoscale (MSD) cMET protein quantification. Relative values of Met degradation are indicated on the y-axis as % control (percent of control). Values lower than 100% control indicate internalization and degradation of cMET. Chimeric antibodies were generated by replacing the constant regions of the heavy and light chains of an isolated mouse monoclonal antibody designated as P3D12 (P3D12(mouse)) with antibody constant regions of a human IgG1 (P3D12(hIgG1)), or a human IgG2 (P3D12(hIgG2)) as indicated on the x-axis. Each antibody was tested at 0.00064 µg/ml, 0.0032 µg/ml, 0.016 µg/ml, 0.08 µg/ml, 0.4 µg/ml, 2 µg/ml, 10 µg/ml and 50 µg/ml as indicated on the x-axis. Chimeric cMET antibodies of P3D12 showed similar internalization/degradation activity as the parent mouse P3D12 antibody.
Figure 12:
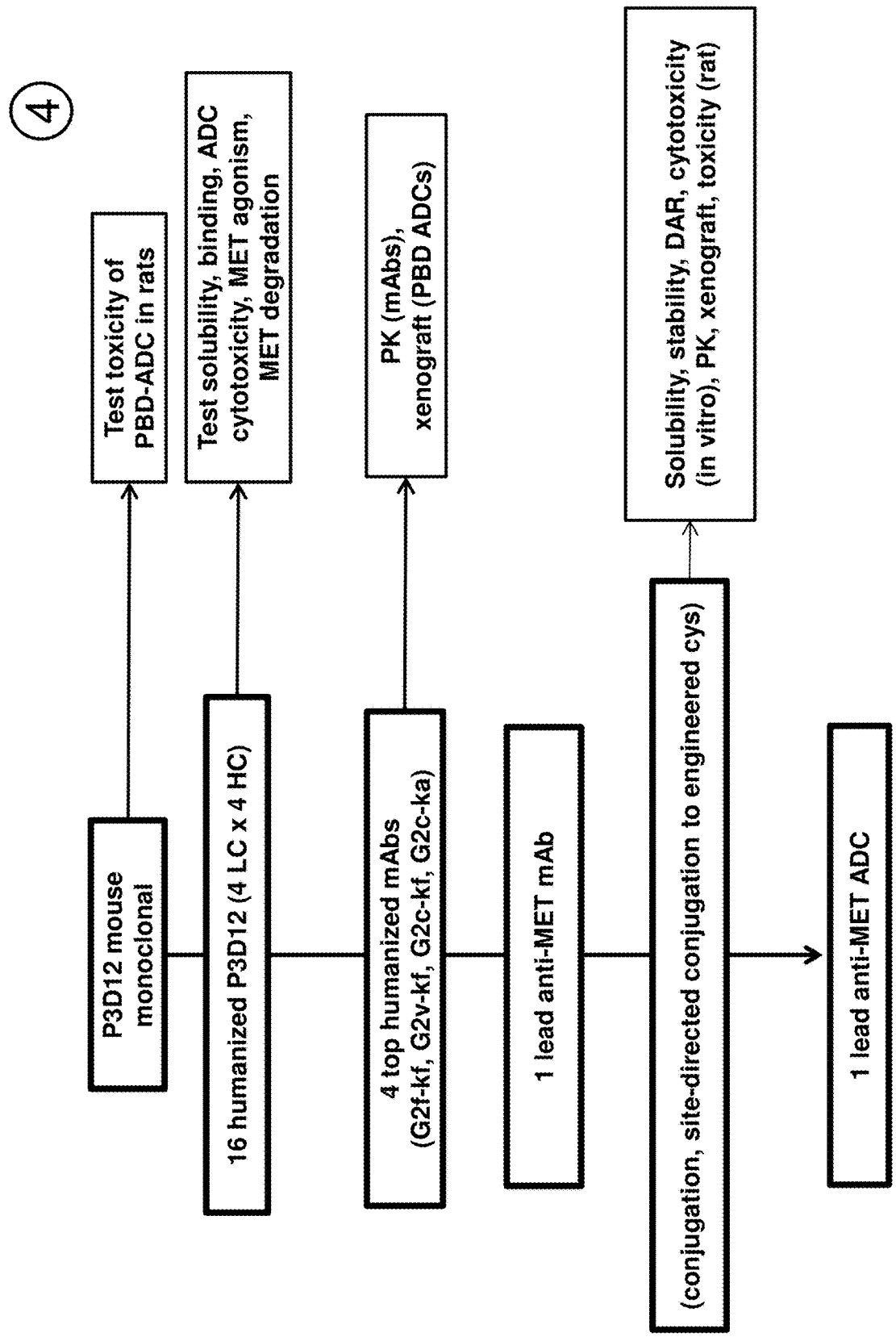
FIG. 12 shows a flow chart of process development for testing and selection of lead anti-cMET monoclonal binding agents.
Figure 15:
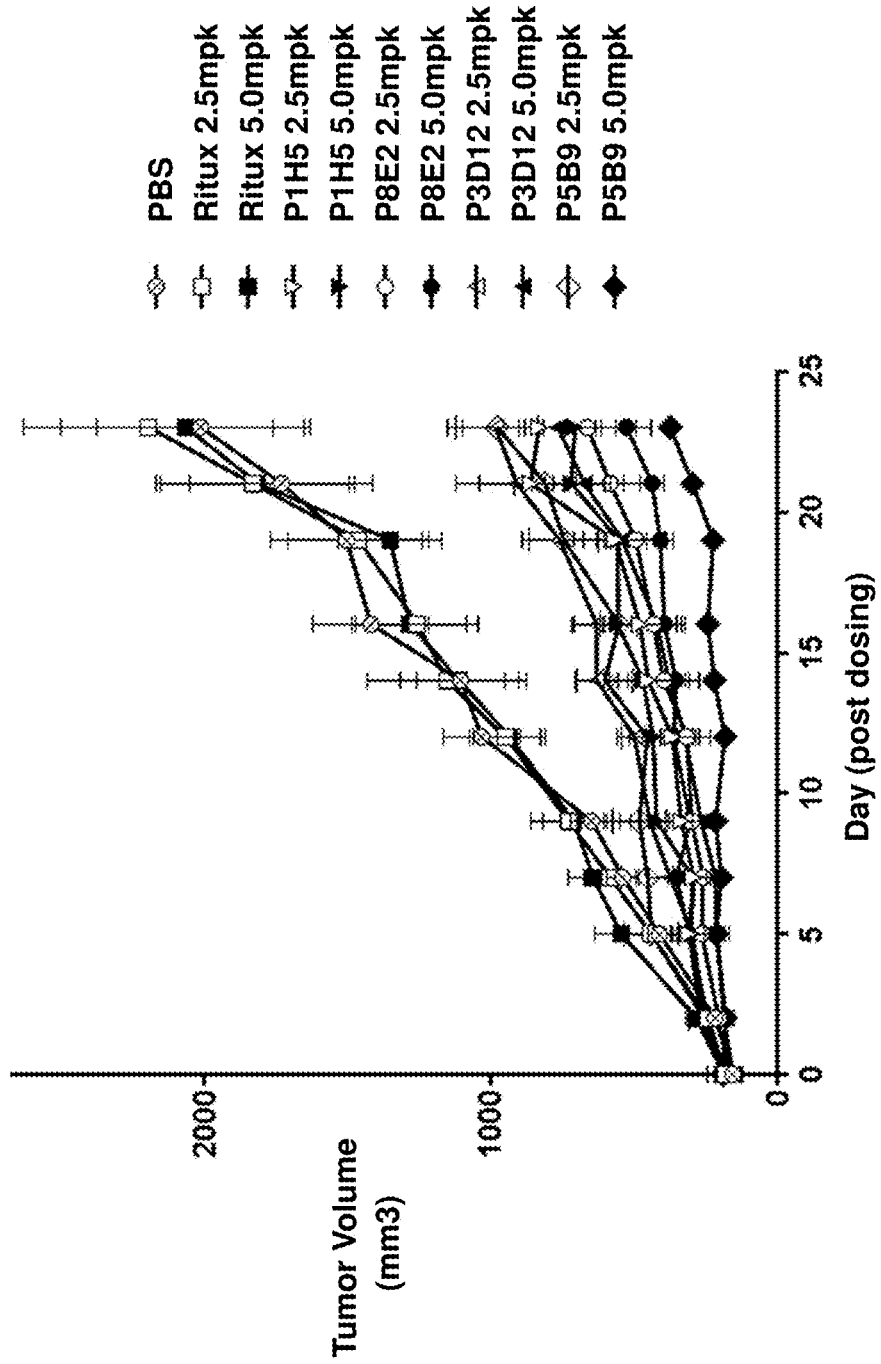
FIG. 15 shows the results of an in vivo xenograft mouse model testing the efficacy of the indicated humanized anti-cMET antibody drug conjugates (ADC) at 2.5 mg/kg (2.5 mpk), or at 5 mg/kg (5 mpk) as demonstrated using an MKN45 tumor model (a cMET+ gastric cancer model). Animals were treated once with the indicated ADCs at 2.5 or 5.0 mg/kg. The efficacy of each anti-cMET binding agent is compared to PBS or the non-targeting monoclonal antibody Rituximab (Retux), which is an anti-cancer monoclonal antibody that targets CD20, which is primarily found on the surface of immune system B cells. Tumor volume (y-axis) was measured at various time points (y-axis) after inoculation. Inhibition of tumor growth indicates positive efficacy. Anti-cMET binding agents were conjugated to monomethyl auristatin F (MMAF).
Figure 16:
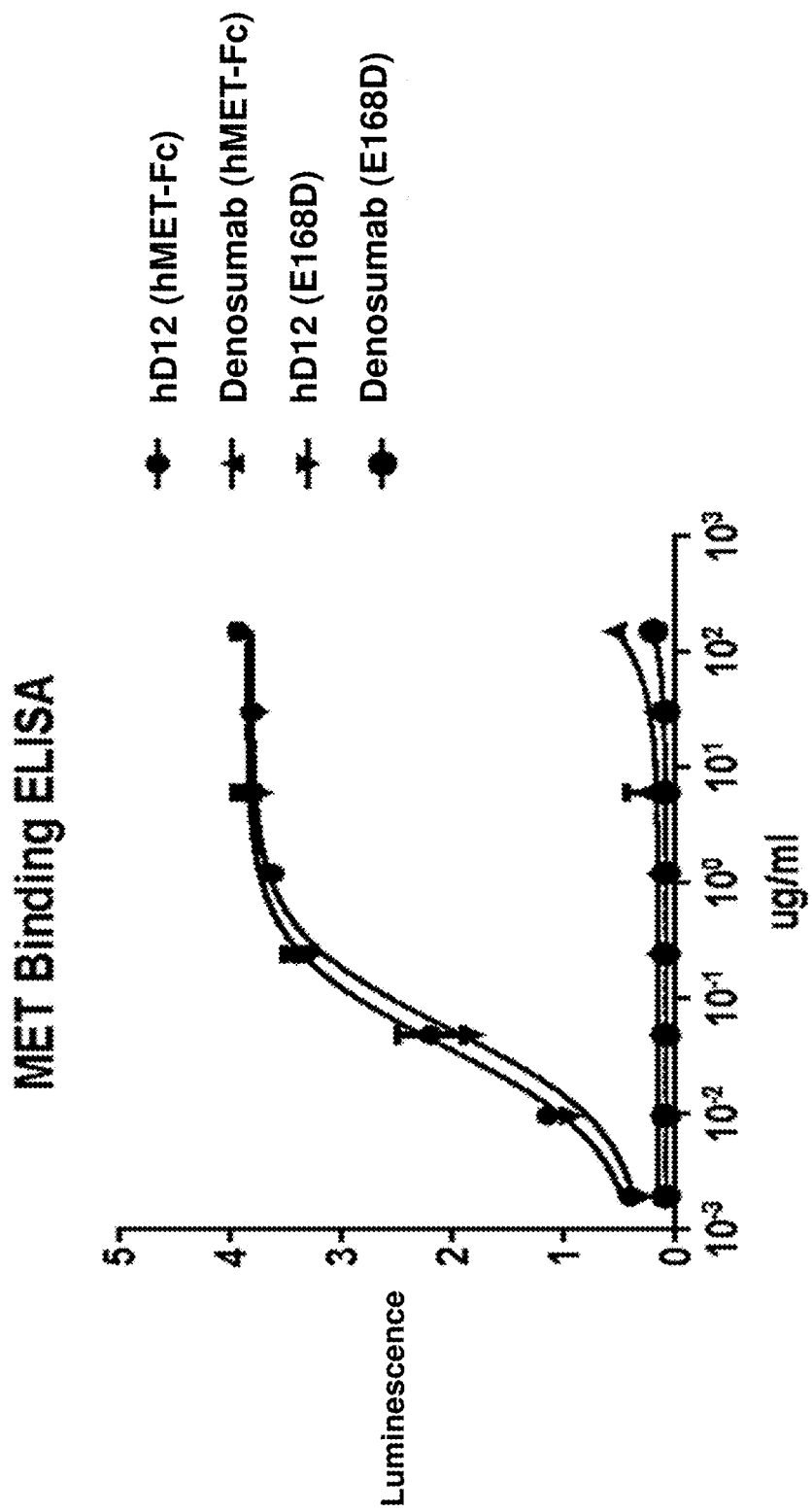
FIG. 16 shows binding of anti-cMET monoclonal binding agent hD12 comprising heavy and light chain variable regions of SEQ ID NO:108 and 47, respectively, and a human IgG2 constant regions, and a negative control antibody (Denosumab), that does not bind to cMET-Fc (hMET-Fc) or mutant cMET (E168D) Fc recombinant fusion proteins. The E168D mutation is a somatic mutation found in small cell lung cancer (SCLC). The mutation is located in the Sema domain and leads to constitutive activation of the cMET receptor. Abundance of somatic mutations of cMET are very low. E168D occurs in 0.8% to 3% of SCLC patients. A binding ELISA was performed with human cMET or E168D cMET extracellular domains fused to human IgG1 Fc. cMET proteins were coated on a plate overnight and the samples titrated and detected with a goat anti-human IgG (H+L)-HRP. $EC_{50}$s were determined using sigmoidal dose response fit.

Additional assays were performed to select ideal anti-cMET antibody candidates. For example, anti-cMET antibodies were tested for species cross-reactivity by determining the ability of an antibody to bind to human cMET, monkey cMET (e.g., *Macaca fascicularis*, i.e., Cynomolgus Macaque), rat cMET and mouse cMET as measured by ELISA (FIG. 7 & Table 11). In vivo half-life and other pharmacokinetic characteristics were also evaluated (data not shown). Potency and specificity of antibody drug conjugates (ADC) was also determined on high, medium and negative cMET expressing cell lines using anti-cMET antibodies that were conjugated to MMAF)(FIGS. 9 and 15, Tables 11 and 12). ADCs were tested for efficacy in vivo using an MKN45 Xenograft model.

TABLE 11

| In vitro Ranking | Antibody | Avg. Cytotoxicity EC50, pM SNU16 cells (Met medium) | Avg. Cytotoxicity EC50, pM SNU20 cells (Met high) | Met Binding KD (pM) SPR w/hMet-Fc | Met Degradation (pM) MSD | Cell Proliferation (Agonism) ERK Phospho Assay | Cross-reactivity | | |
|---|---|---|---|---|---|---|---|---|---|
| | | | | | | | NHP | Rat | Mouse |
| | 5D5 | | | 800 | | Yes/Strong | Yes | No | No |
| | ABF46 | 450 | 67 | 700 | 10,000 | NO | Yes | No | No |
| 1 | F6B1P3D12 | 25 | 60 | 750 | 140 | NO | Yes | Yes | No |
| 2 | F6BP2D4 | 60 | 33 | 480 | 3,000 | NO | Yes | No | No |
| 2 | F6B1P1E2 | 70 | 55 | 890 | 1,920 | Very low | Yes | Low | No |
| 3 | F6AP12F12 | 180 | 97 | 110 | 450 | NO | Not tested | Not tested | Not tested |
| 3 | F5P5B9 | 20 | 3 | 80 | 255 | Very low | Yes | No | No |
| 3 | F6AP8E2 | 351 | 102 | 160 | 7,000 | Very low at high concentrations | Yes | No | No |
| 3 | F6BP1H5/H6 | 80 | 63 | 340 | 3,000 | Maybe at high concentrations | Yes | No | No |

*SPR = Surface Plasmon Resonance
**MSD = Meso Scale Discovery Platform
***NHP-Non-human Primate (i.e., Cynomolgus Macaque)
5D5 = agonist positive control
ABF46 = MET ADC, positive control Example 2—Summary of Characteristics of Selected Humanized Monoclonal Binding Agents Humanized and isotype switched monoclonal binding agents were generated which comprise the heavy chain CDRs and light chain CDRs of the mouse monoclonal antibody P3D12. Sixteen different heavy chain (HC) and light chain (LC) combinations were tested for solubility in PBS, binding to human cMET, binding to rat cMET, binding affinity to human and rat cMET as determined by surface plasmon resonance (SPR), the presence of agonistic activity and cMET degradation reported as Meso Scale Discovery platform (MSD). The results are summarized in Table 12 below.

TABLE 12

| Rank | HC | SEQ ID NO: | LC | SEQ ID NO: | Clone | Solubility in PBS | ELISA hMET vs parental | ELISA rMET vs parental | vc-MMAF ADC IC50, pM, SNU-16 (n=1) | SPR kD, nM, hMET-Fc | SPR kD, nM, rMET-Fc | pERK (MET agonism, MSD) | MET degradation equal to parental? (MSD) |
|---|---|---|---|---|---|---|---|---|---|---|---|---|---|
|  | VH-abb/sdr | 107 | VL-abb/sdr | 48 | G2aka |  | 0.9 | 1.1 | 352 | 0.9 | 26 | negative | yes |
|  |  |  | VL-fra | 47 | G2akf | insoluble | 1.0 | 0.5 | 368 | 0.6 | 23 | negative | yes |
|  |  |  | VL-ven | 46 | G2akv |  | 1.6 | 1.3 |  |  |  | negative | yes |
|  |  |  | VL-cdr | 49 | G2akc |  | 1.3 | 0.7 | 382 | 0.7 | 38 | negative | yes |
| 3 | VH-fra | 105 | VL-abb/sdr | 48 | G2fka |  | 1.8 | 3.8 |  |  |  | negative | yes |
|  |  |  | VL-fra | 47 | G2fkf | insoluble | 1.7 | 1.4 | 266 | 0.4 | 30 | negative | yes |
|  |  |  | VL-ven | 46 | G2fkv |  | 1.7 | 1.2 |  |  |  | negative | yes |
|  |  |  | VL-cdr | 49 | G2fkc |  | 1.7 | 2.3 |  |  |  | negative | yes |
| 2 | VH-ven | 106 | VL-abb/sdr | 48 | G2vka |  | 0.9 | 2.7 |  |  |  | negative | yes |
|  |  |  | VL-fra | 47 | G2vkf | insoluble | 1.1 | 1.0 | 380 | 0.3 | 8 | negative | yes |
|  |  |  | VL-ven | 46 | G2vkv |  | 1.6 | 1.6 |  |  |  | negative | yes |
|  |  |  | VL-cdr | 49 | G2vkc |  | 1.1 | 1.9 |  |  |  | negative | yes |
| 4 | VH-cdr | 108 | VL-abb/sdr | 48 | G2cka |  | 1.3 | 2.7 | 238 | 0.4 | 29 | negative | yes |
| 1 |  |  | VL-fra | 47 | G2ckf | insoluble | 0.7 | 0.9 | 302 | 0.3 | 7 | negative | yes |
|  |  |  | VL-ven | 46 | G2ckv |  | 1.1 | 1.0 | 169 | 0.9 | 31 | negative | yes |
|  |  |  | VL-cdr | 49 | G2ckc |  | 1.0 | 2.0 | 249 | 0.7 | 30 | negative | yes |
|  | Chimeric P3D12 | 104 |  | 45 |  |  |  |  | 42 | 0.9 | 16 | negative | yes |
|  | Mouse P3D12 | 98 |  | 41 |  |  |  |  |  |  |  |  |  |

Monoclonal humanized antibody of IgG2 isotype comprising a humanized light chain variable region of SEQ ID NO: 47 and a humanized heavy chain variable region of SEQ ID NO: 108 was selected as a representative humanized anti-cMET antibody, named hD12 and used as the antibody in the following examples.

Example 3—Binding Assays

A representative humanized anti-cMET antibody, hD12 comprising the humanized heavy chain of SEQ ID NO: 105 and the humanized light chain sequences of SEQ ID NO: 47 was stochastically conjugated to five representative payloads (i.e., payloads of chemical formulas II, IV, VI, VII and XI), each payload comprising a pyrrolobenzodiazepine toxin and a linking group. In this example, the linking groups of the payload were stochastically linked to the hD12 antibody using disulfide chemistry. Briefly, the hD12 antibody was first subjected to reduction with glutathione (GSH), unreacted GSH was removed, and the linking group, which comprises a reactive maleimide group, is reacted with one or more free sulfhydryl groups (i.e., thiol groups) on the antibody. Using this approach, one or more payloads are covalently linked to the hD12 antibody at random positions occupied by a cysteine residue. Accordingly, this method is referred to a stochastic conjugation.

Figures 17A, 17B:
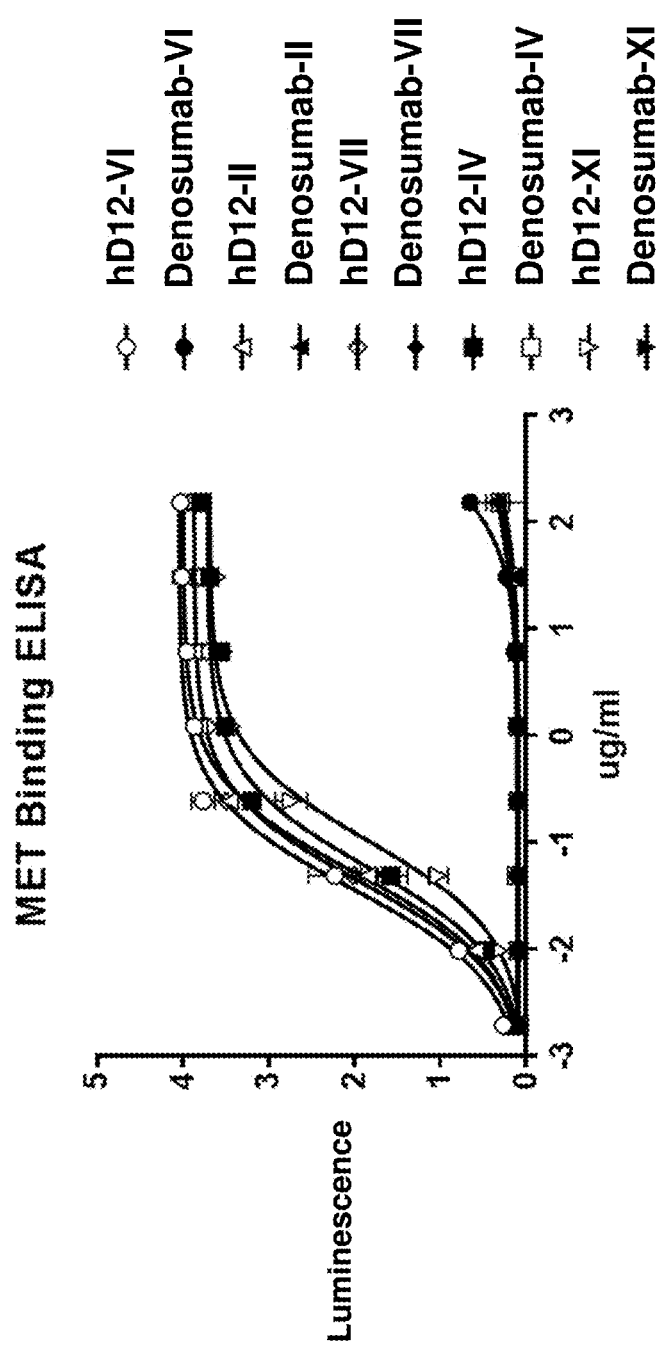
FIG. 17A shows the results of an ELISA-based cMET binding assay. Briefly, five representative antibody-drug conjugates (i.e., hD12-VI, hD12-II, hD12-VII, hD12-IV and hD12-XI (see antibody nomenclature explained in Example 3)) were tested at increasing concentrations (x-axis, concentration of antibody-drug conjugate (µg/ml)) for their ability to bind plate-bound human cMET. Relative binding strength is indicated by luminescence (y-axis). A negative control antibody (Denosumab), that does not bind cMET, was conjugated to each of the five different payloads (i.e., payloads of chemical formula VI, II, IV, VII and XI, indicated as Denosumab-VI, Denosumab-II, Denosumab-IV, Denosumab-VII, and Denosumab-XI, respectively) and tested as a negative control.
FIG. 17B shows $IC_{50}$ values for each of the antibodies tested in FIG. 17A.
Figure 18A:
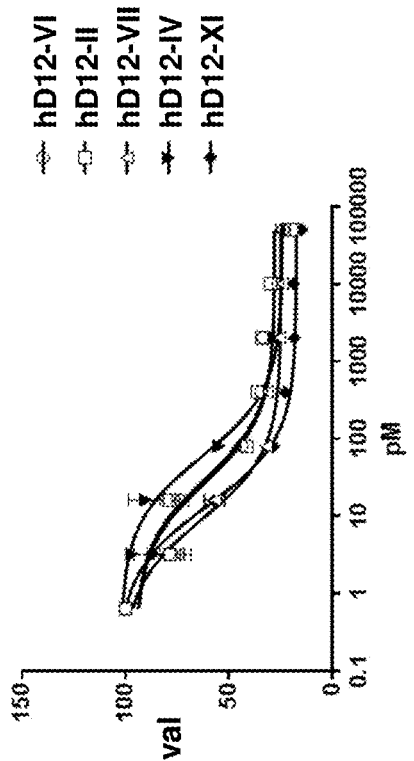
FIG. 18A-18D show the results of a cytotoxicity assay for five representative antibody-drug conjugates (hD12-VI, hD12-II, hD12-VII, hD12-IV and hD12-XI) on four cell lines that express different amounts of cMET on their cell surface (SNU-1, no expression of cMET (FIG. 18A), SNU-16, medium expression of cMET (FIG. 18B), SNU-620, high expression of cMET (FIG. 18C) and MKN-45, high expression of cMET (FIG. 18D)). Percent survival is indicated on the y-axis and the amount of antibody drug conjugate added is indicated on the x-axis (pM). The results are summarized in FIG. 18E which shows comparative $IC_{50}$ values.
Figure 18B:
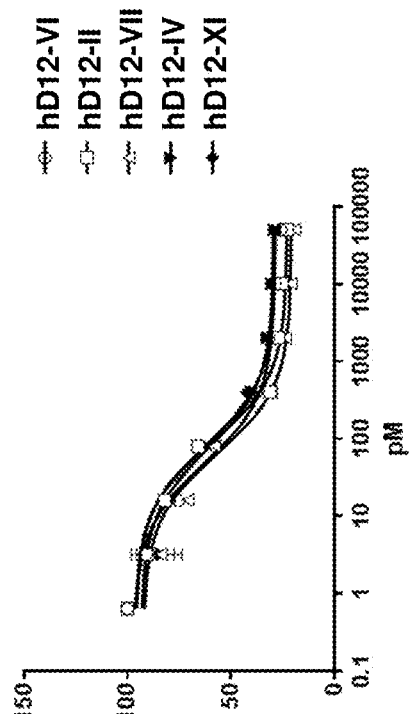
Figure 18C:
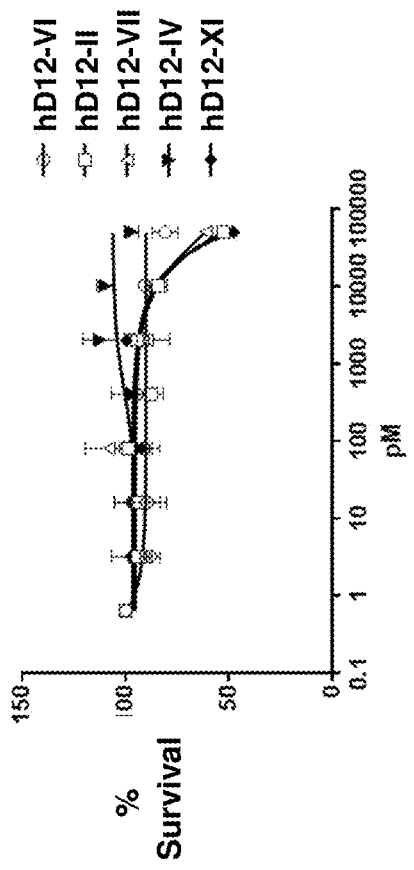
Figure 18D:
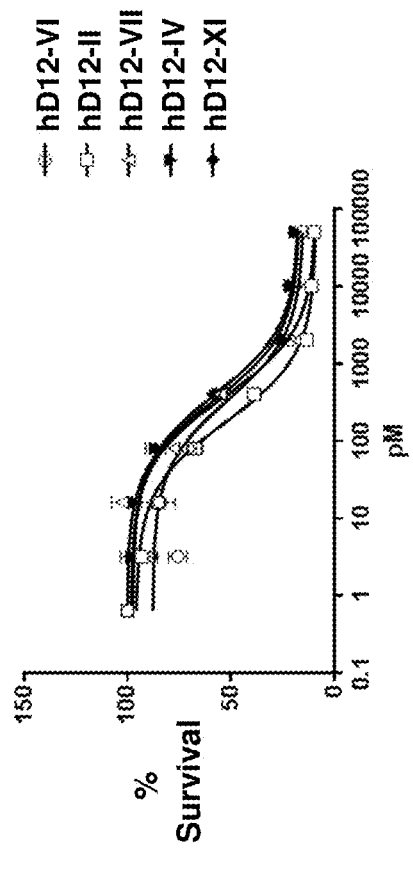
Figure 19A:
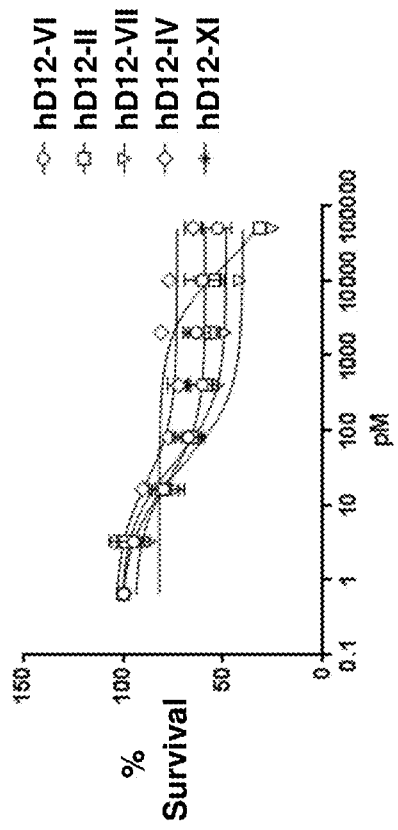
FIG. 19A-19E show the results of a cytotoxicity assay for five representative antibody-drug conjugates (hD12-VI, hD12-II, hD12-VII, hD12-IV and hD12-XI) on five cell lines that express different amount of cMET on their cell surface (H441, medium expression of cMET (FIG. 19A), H1373, medium expression of cMET (FIG. 19B), H1975, medium expression of cMET (FIG. 19C), SNU-5, high expression of cMET (FIG. 19D), and H1573, medium expression of cMET (FIG. 19E)). Percent survival is indicated on the y-axis and the amount of antibody drug conjugate added is indicated on the x-axis (pM). The results are summarized in FIG. 19F, which shows comparative $IC_{50}$ values.
Figure 19B:
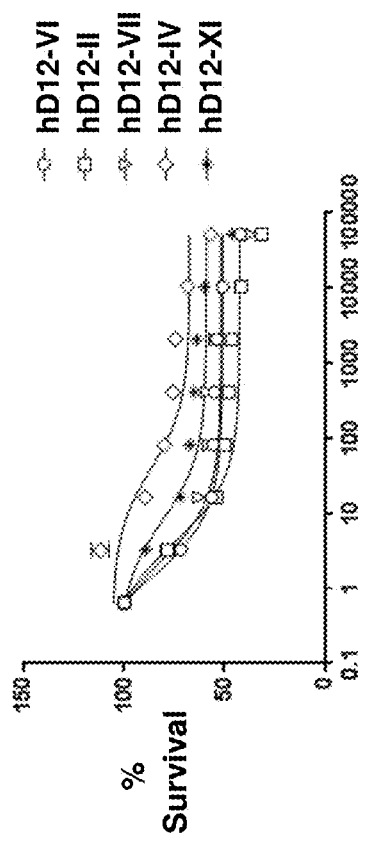
Figure 19C:
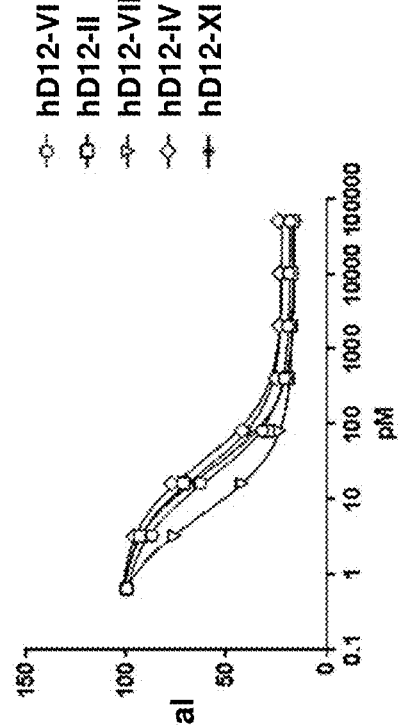
Figure 19D:
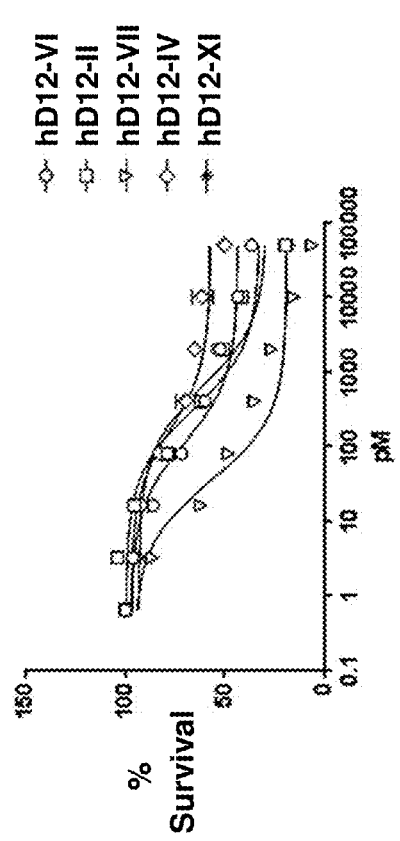
Figures 19E, 19F:
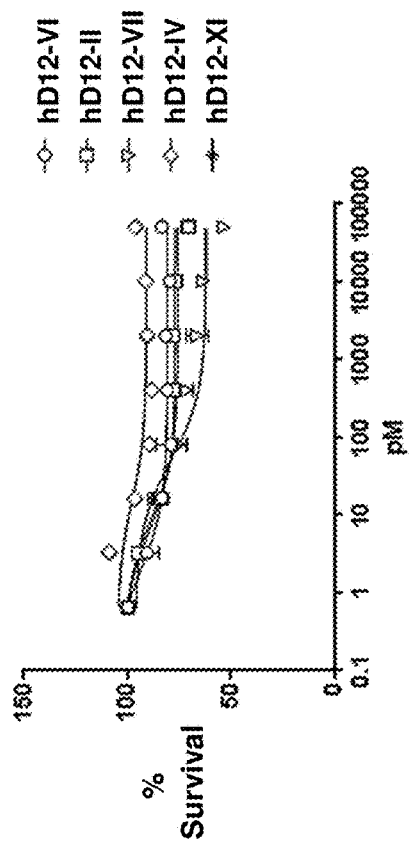

The resulting hD12 antibody drug conjugates (i.e., hD12-II (Antibody hD12 attached to the payload of chemical formula II); hD12-IV (Antibody hD12 attached to the payload of chemical formula IV); hD12-VI (Antibody hD12 attached to the payload of chemical formula VI); hD12-VII (Antibody hD12 attached to the payload of chemical formula VII); and hD12-XI (Antibody hD12 attached to the payload of chemical formula XI)) were assayed for binding to plate-bound cMET by ELISA. Denosumab conjugated to each of the five payloads was used as a negative control, as the monoclonal antibody Denosumab specifically binds to RANK ligand (RANKL) and does not bind to cMET. The results of the ELISA binding study are shown in FIGS. 17A and 17B. There were no significant differences in binding between the 5 different hD12 drug conjugates to cMET. The isotype control conjugates of Denosumab did not bind to cMET as expected.

Materials: High binding 384 well plates (Thermo Fisher #: 8755), Blocking buffer (SkyTek Lab #AAA500), Recombinant Human c-Met-10× His (1.04 mg/ml, in-house, Lot #140924TA), Anti-human Kappa Light chain HRP conjugated (1 mg/ml, Brthyl #AP80-219P), 1×KPL wash buffer in water (20×, 200 ml, KPL #50-63-01), TMB (100 ml, KPL #53-00-00), and Stop solution (Cell Signaling #7002L).

Example 4—Cytotoxicity Assays

The cytotoxicity of the five hD12 antibody drug conjugates of Example 3 were tested against cells expressing different levels of surface cMET. Denosumab conjugated to each of the five representative payloads was used as a negative control (Data not shown). Denosumab conjugates had little or no effect on cell killing in cMET expressing cell lines.

The results of the cytotoxicity assay are shown in FIGS. 18A-18E and FIGS. 19A-19F. The cell lines tested were SNU-1 (ATCC, no expression of cMET, FIG. 18A), SNU-16 (ATCC, medium expression of cMET, FIG. 18B), SNU-620 (KCLB, high expression of cMET, FIG. 18C), MKN-45 (DSMZ, high expression of cMET, FIG. 18D), H441 (ATCC, medium expression of cMET, FIG. 19A), H1573 (ATCC, medium expression of cMET, FIG. 19B), H1975 (ATCC, medium expression of cMET, FIG. 19C), SNU-5 (ATCC, high expression of cMET, FIG. 19D), and H1573 (ATCC, medium expression of cMET, FIG. 19E). hD12-II and hD12-VII showed slightly higher potency in some medium and high cMET-expressing cell lines.

Example 5—Xenograft Studies

Figure 21C:
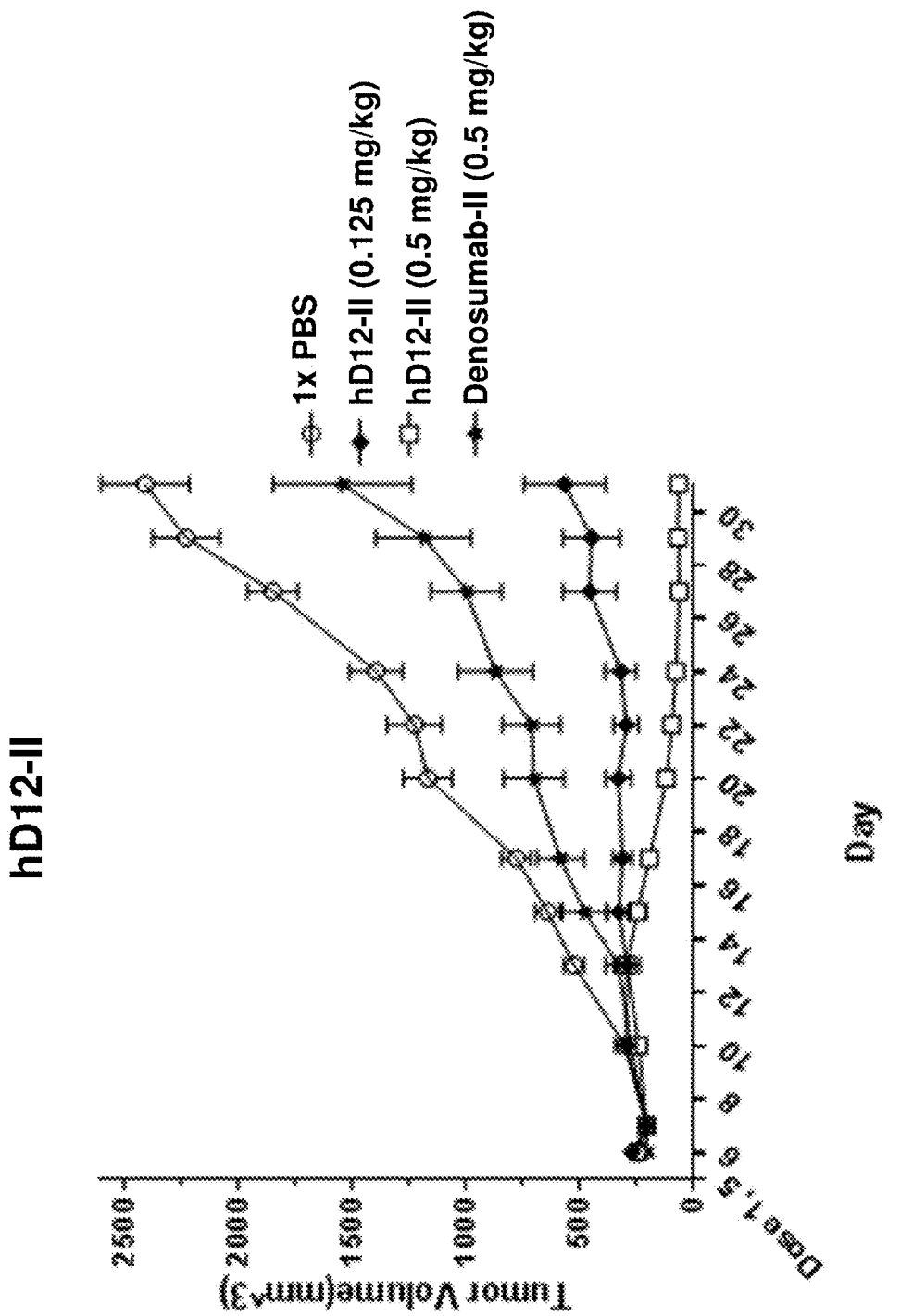
FIG. 21 shows the results of an in vivo xenograft study. Mice were injected with H1373 tumor cells (medium expression of cMET) and treated with either hD12-XI (FIG. 21A), hD12-VI (FIG. 21B), hD12-II (FIG. 21C), hD12-VII (FIG. 21D), and hD12-IV (FIG. 21E) and tumor volume (y-axis) was determined over time (i.e., days, x-axis). A negative control antibody (Denosumab) conjugated to II was tested as a negative control.
Figure 21D:
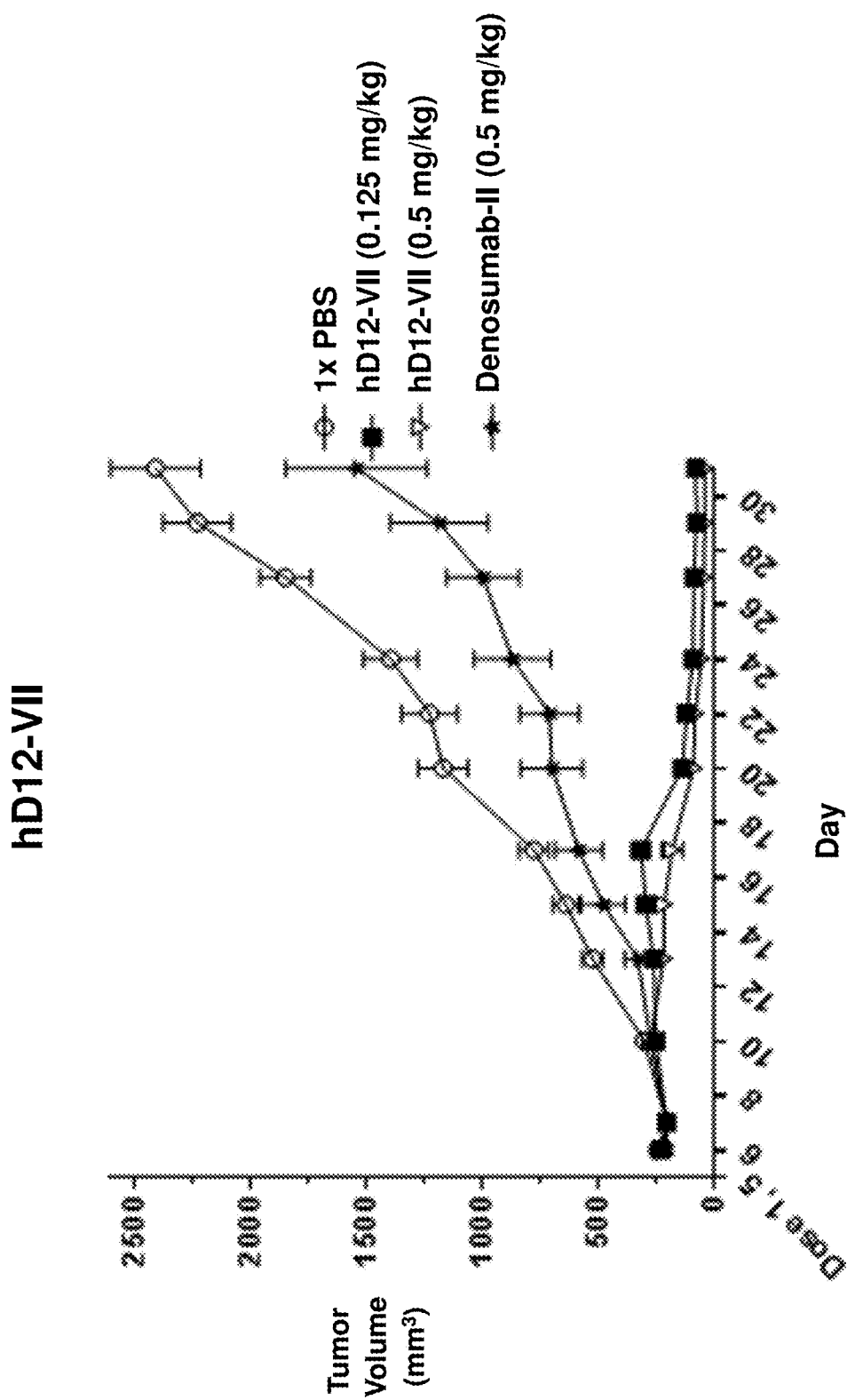
Figure 21E:
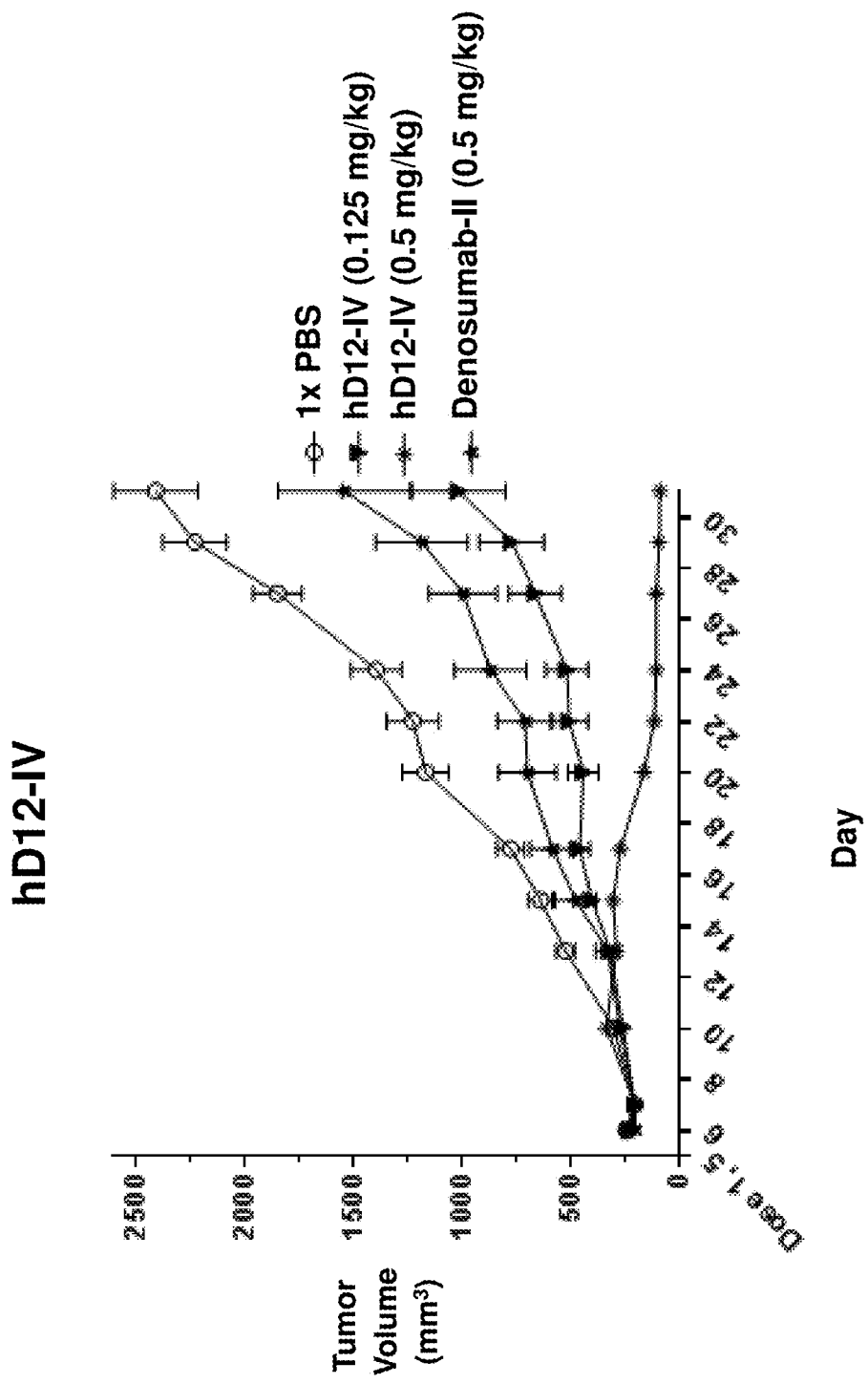
Figure 22:
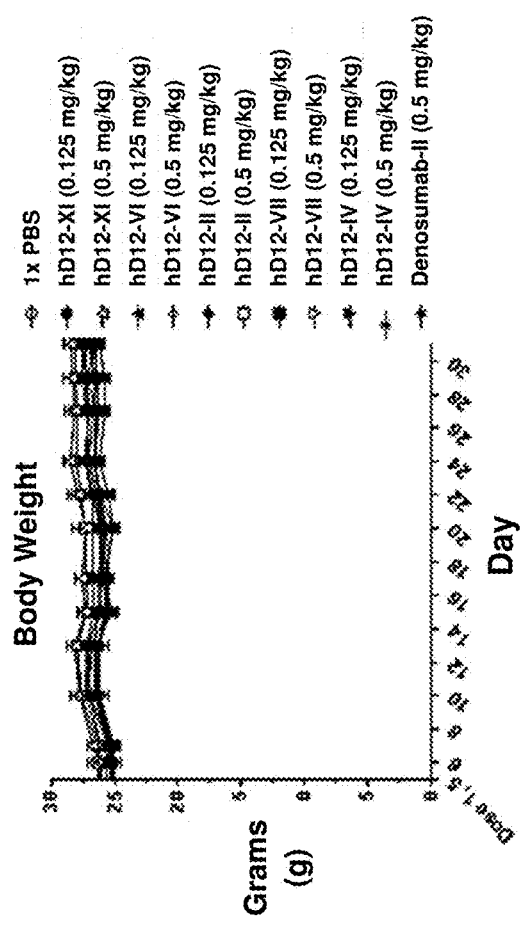
FIG. 22 shows the body weight (y-axis) of the mice treated in FIG. 21 over time (x-axis).

Two in vivo xenograft studies were conducted to assess the efficacy of the five hD12 antibody drug conjugates of Example 3 (i.e., hD12-VI, hD12-II, hD12-VII and hD12-XI). Note that the terms hD12-vc-XI, hD12-vc-VI, hD12-vc-II, hD12-vc-VII and hD12-vc-IV as shown in FIGS. 20-22 are used synonymously with the terms hD12-XI, hD12-VI, hD12-II, hD12-VII and hD12-IV, respectively. Also, Denosumab-* (e.g., Denosumab-II) is used synonymously with the terms Denosumab-vc-* (e.g., Denosumab-vc-II) as shown in the figures. The "vc" designation does not confer any significant meaning. The term "Denosumab-II" refers to the monoclonal antibody "Denosumab" attached to the payload of chemical formula II.

The first H1975 in vivo xenograft study was set up with ten mice (Nu/nu: (Charles River)) in each group. Each mouse was inoculated with H1975 cells followed by treatment with one of the indicated antibody drug conjugates, or with PBS. Antibody drug conjugates were administered as a single administration by i.v. tail vein injection on day 1. Two different doses (0.5 mg/kg and 0.125 mg/kg) of each antibody drug conjugate was tested. Denosumab-II was used as a negative control. Tumor volume and weight were measured 3 times a week. Results of the H1975 in vivo xenograft study are shown in FIGS. 20A-20G.

Figure 20A:
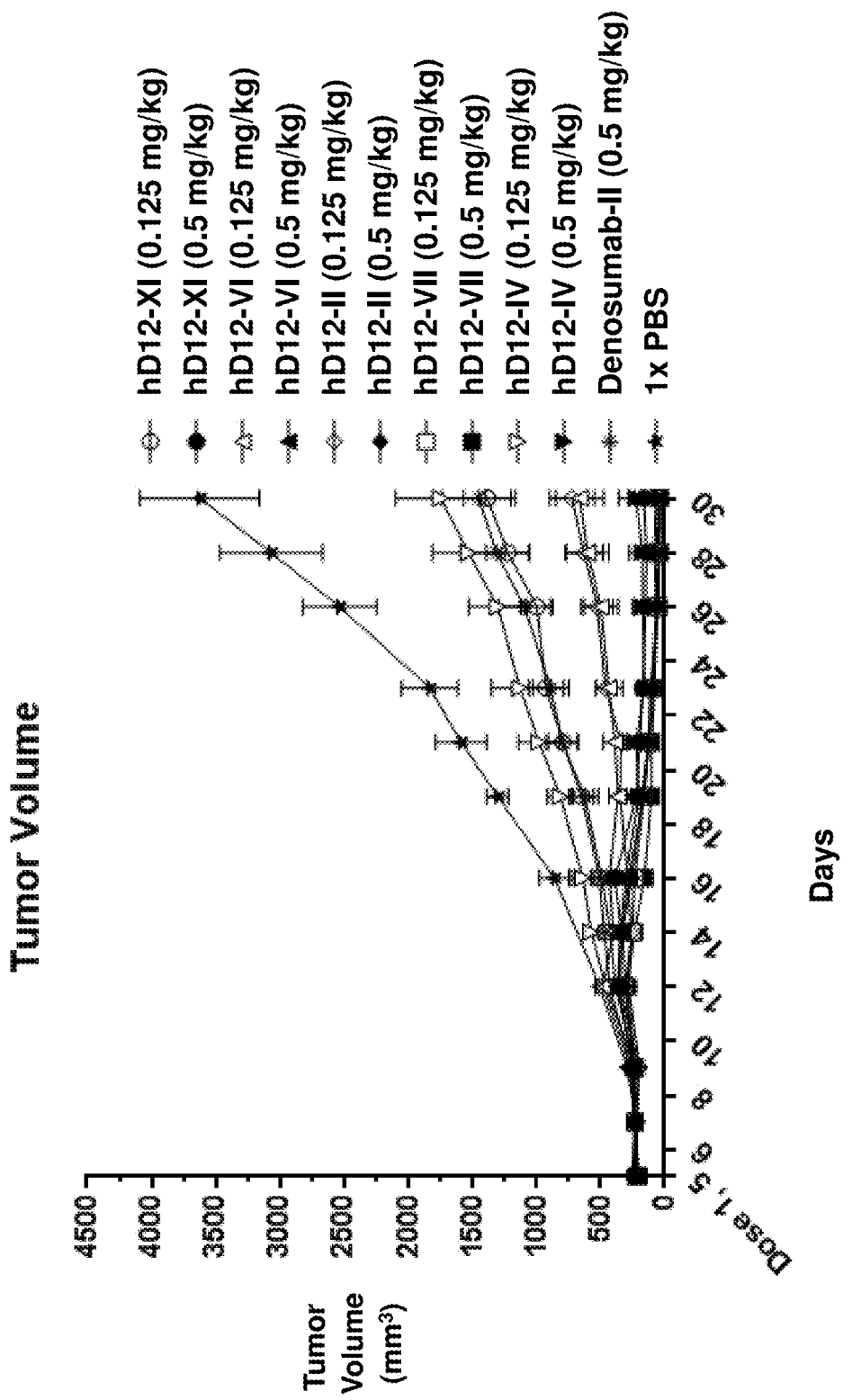
FIG. 20 shows the results of an in vivo xenograft study. Mice were injected with H1975 tumor cells (medium expression of cMET) and treated with either hD12-XI (FIGS. 20A, 20B and 20C), hD12-VI (FIGS. 20A, 20B and 20D), hD12-II (FIGS. 20A, 20B and 20E), hD12-VII (FIGS. 20A, 20B and 20F), and hD12-IV (FIGS. 20A, 20B and 20G), and tumor volume (y-axis, FIGS. 20A, and 20C-20G) or body weight (FIG. 20B) was determined over time (i.e., days, x-axis). A negative control antibody (Denosumab) conjugated to each of the five different payloads (i.e., VI, II, IV, VII and XI) was tested as a negative control.
Figure 20B:
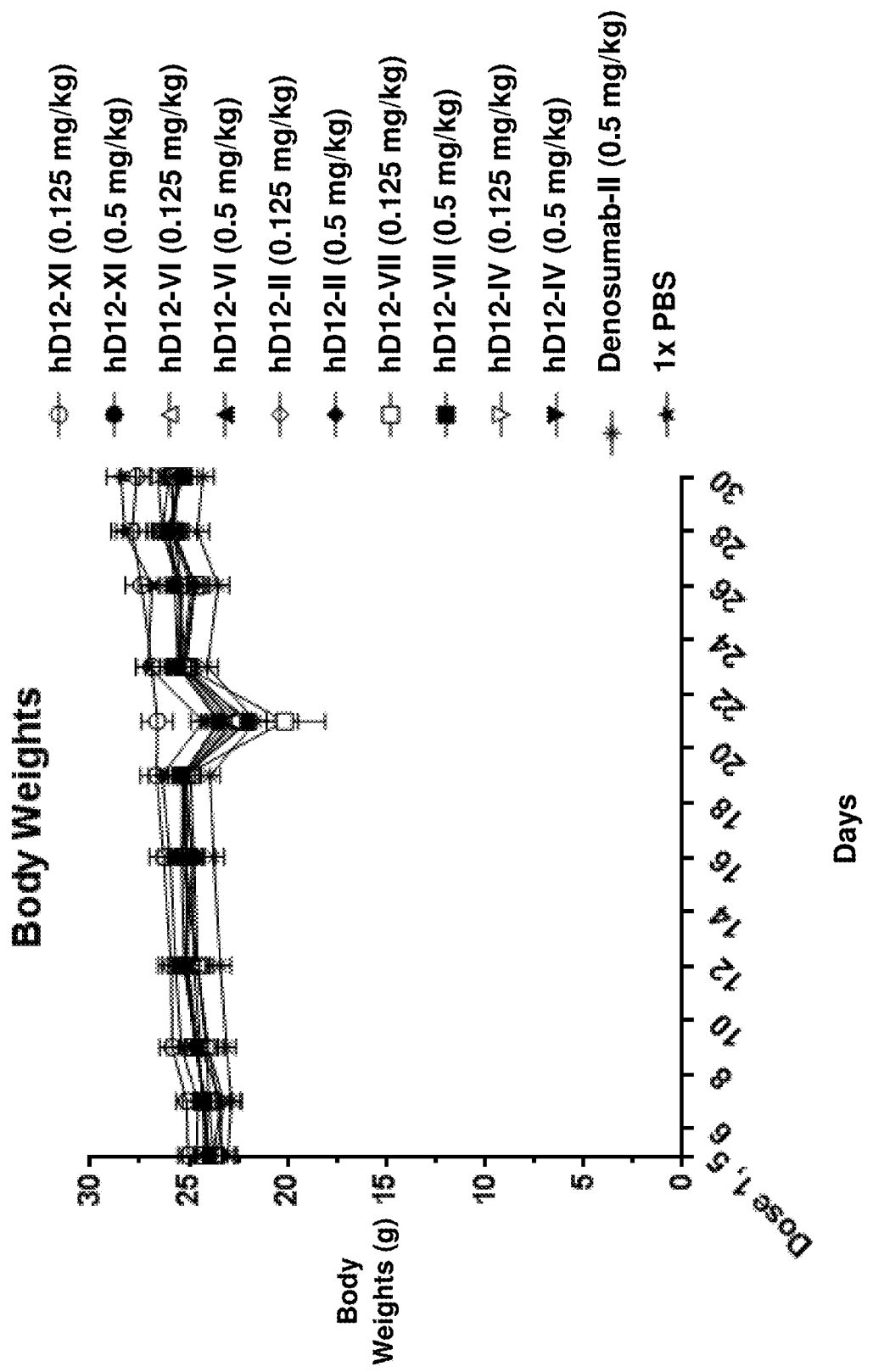
Figure 20C:
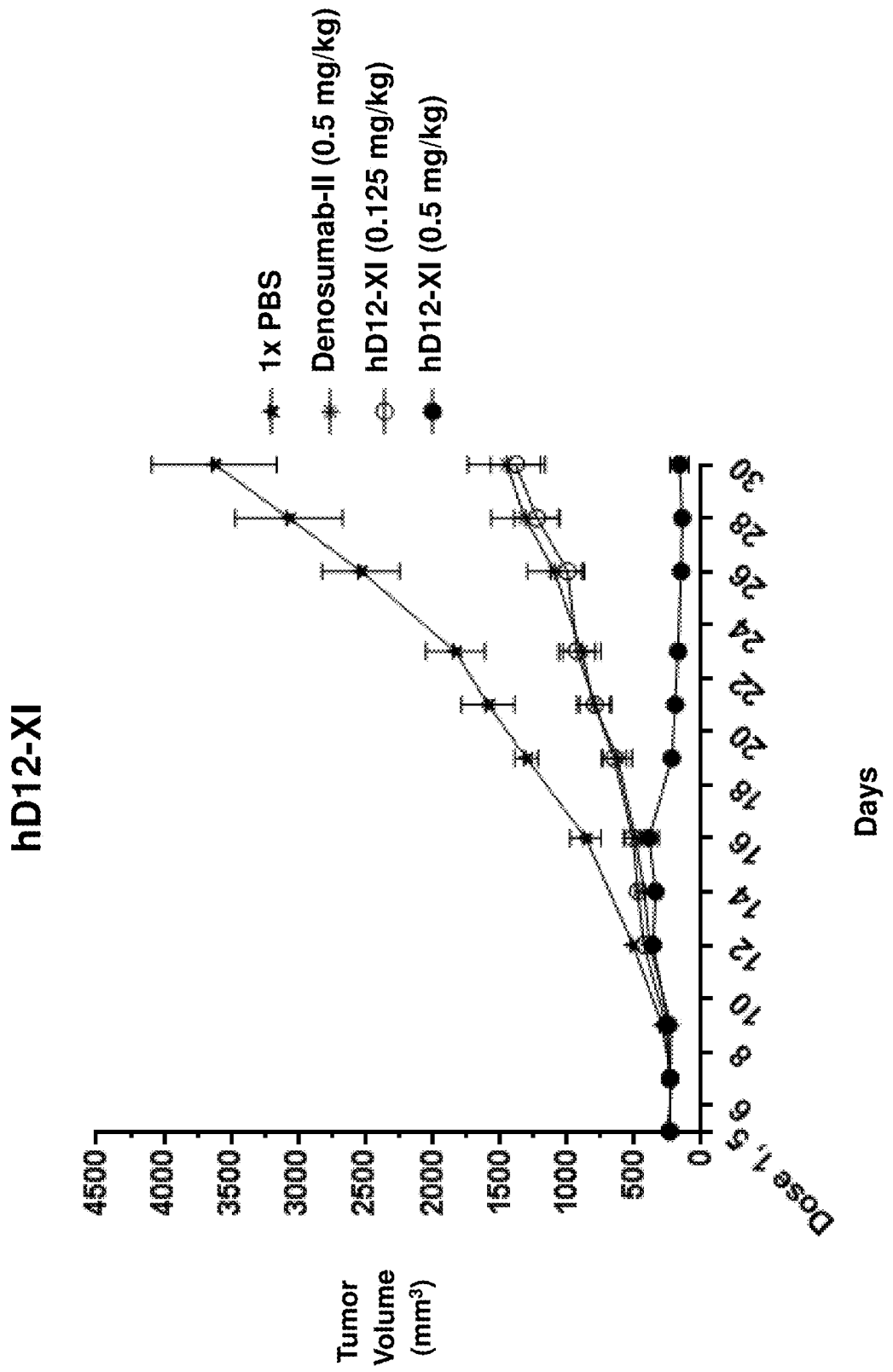
Figure 20D:
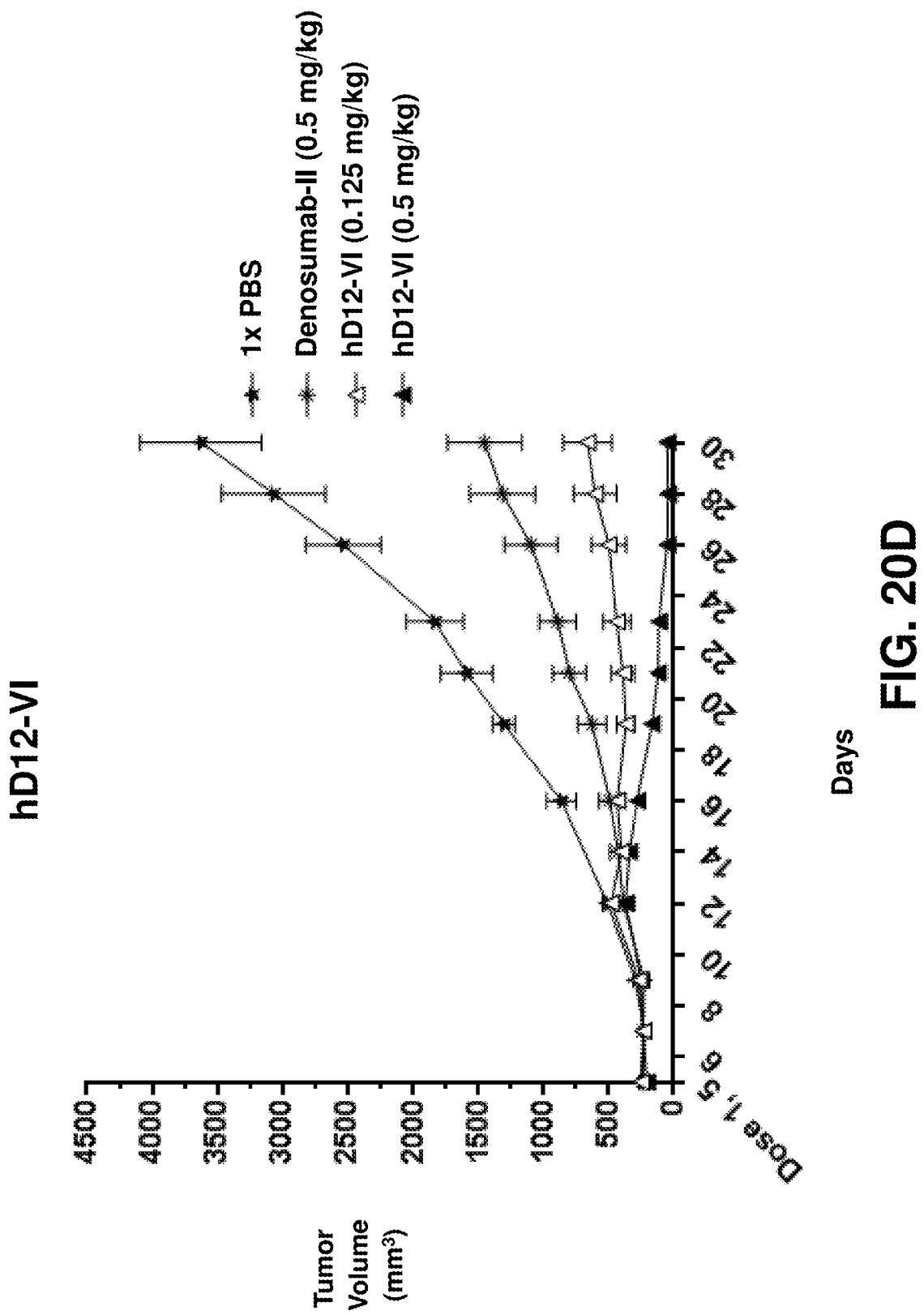
Figure 20E:
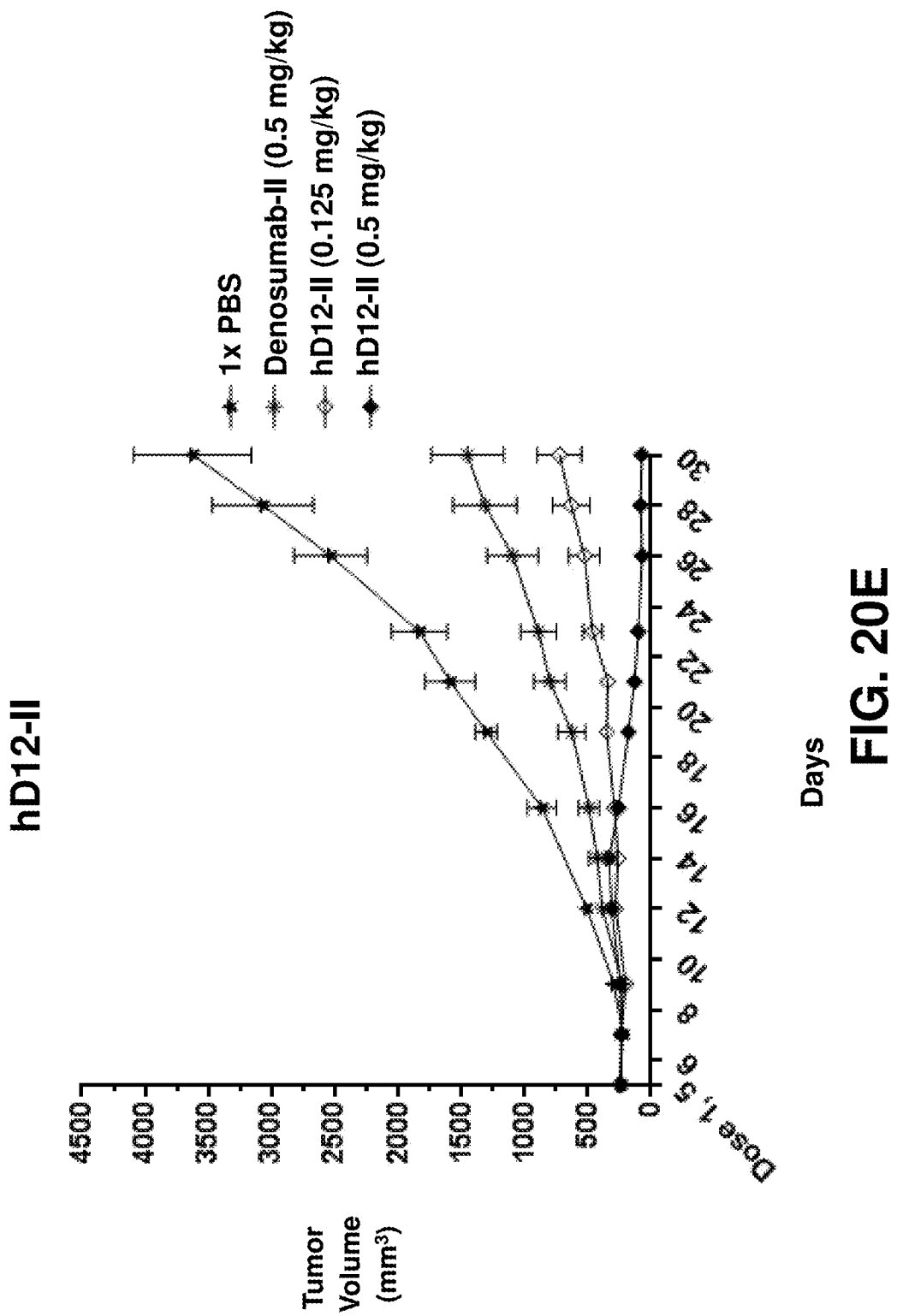
Figure 20F:
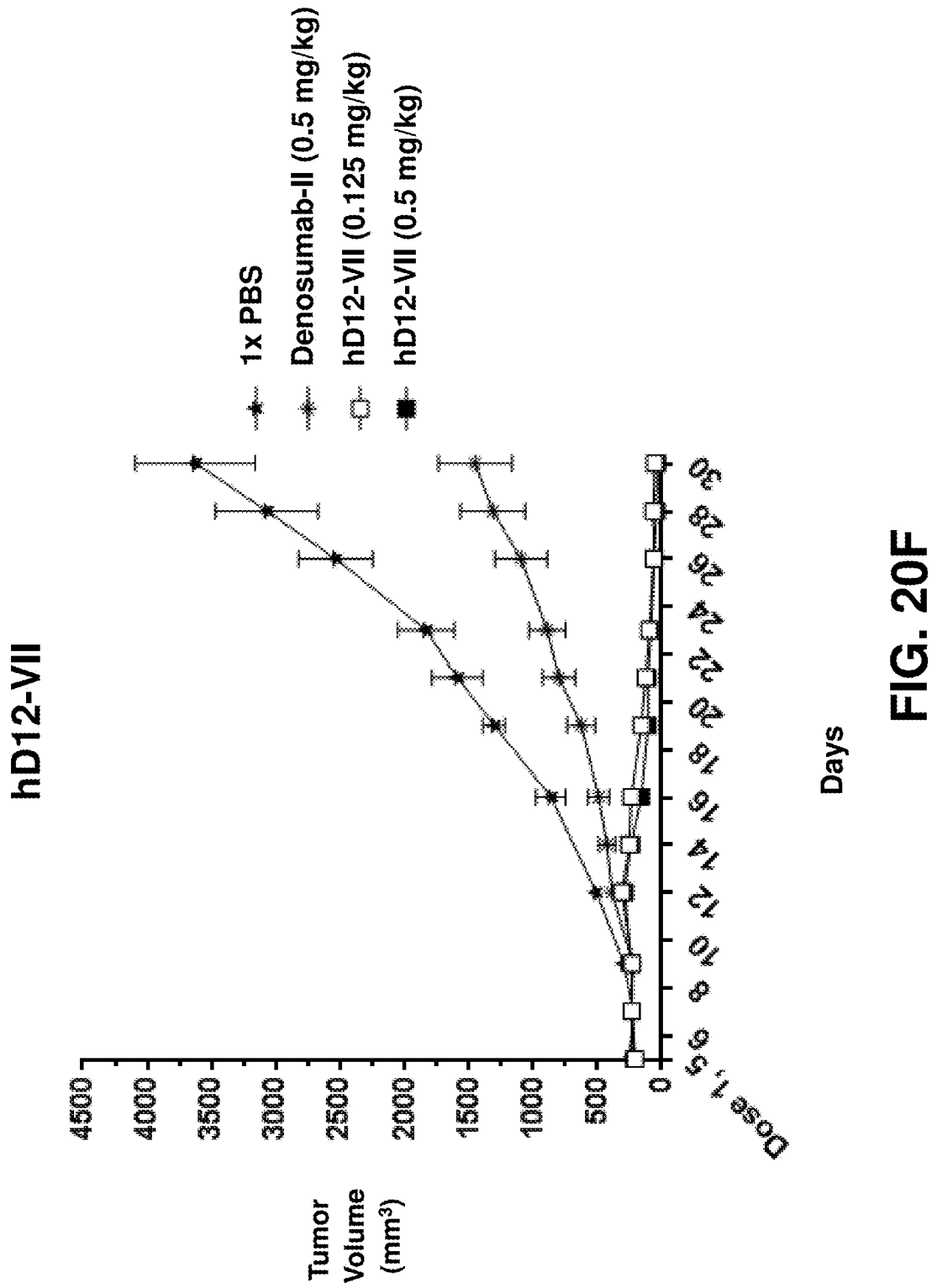
Figure 20G:
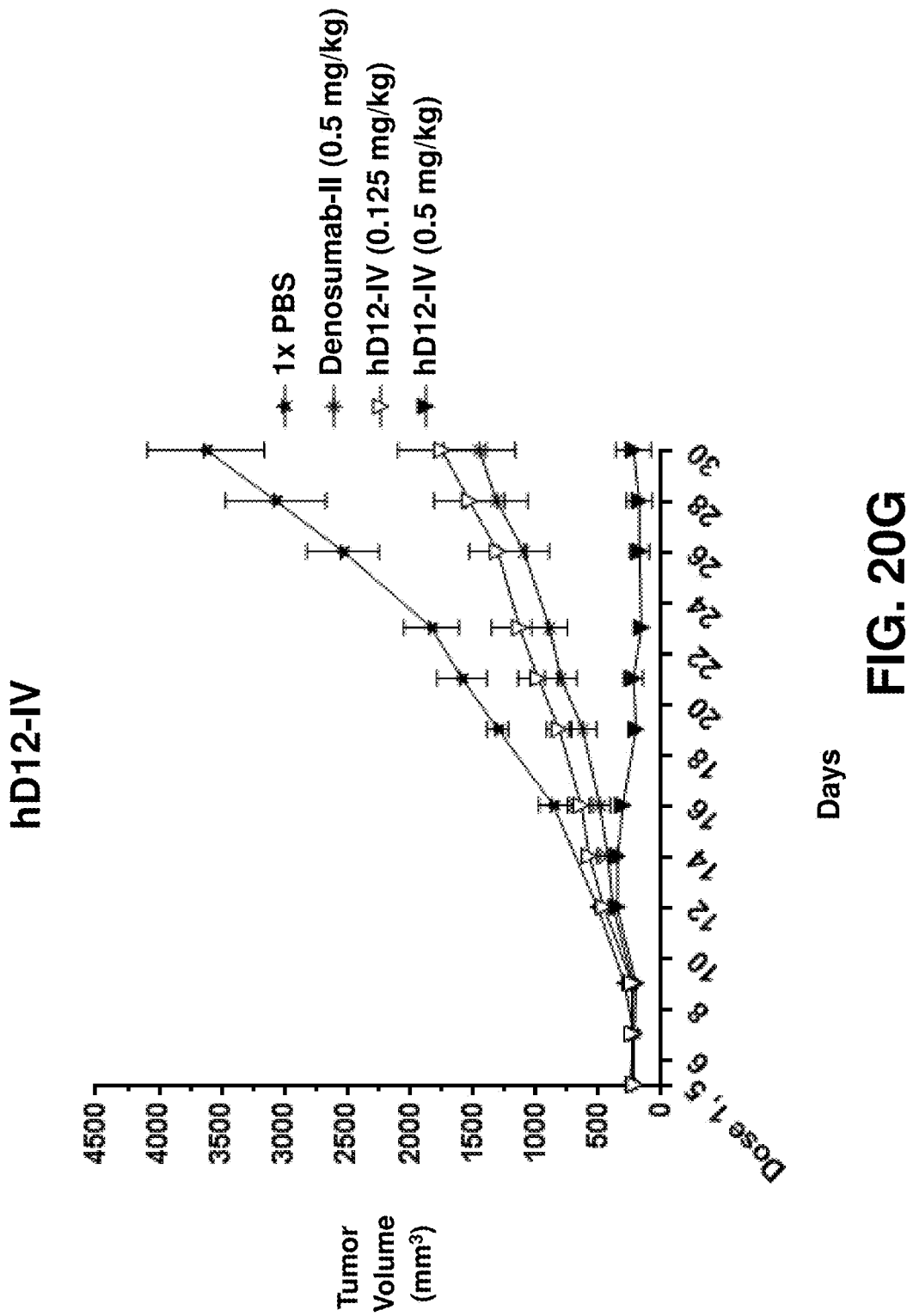

All animals tolerated the antibody drug conjugates well. There was no significant weight loss observed in any of the groups (e.g., see FIG. 20B). hD12-VII showed the highest efficacy at both dose concentrations of all ADCs tested (FIGS. 20A and 20F). hD12-II and hD12-VI were slightly less efficacious in the low dose group (0.125 mg/kg)(FIGS. 20E and 20D) than hD12-VII. hD12-3315 and hD12-XI were least efficacious in the low dose group (FIGS. 20G and 20C). The isotype control Denosumab-II showed some efficacy at the 0.5 mg/kg dose. It is possible that Denosumab showed tumor growth inhibition because H1975 has a RANK-RANKL signaling pathway (Journal of Thoracic Oncol., 2014, 9(3) 345-54). In summary, all five hD12 drug conjugates showed significant efficacy against the H1975 xenografts. hD12-VII, hD12-II and hD12-VI showed the highest treatment efficacy with VII slightly outperforming the other two.

A second H1373 in vivo xenograft study was conducted to further assess the efficacy of the five hD12 antibody drug conjugates of Example 3 (i.e., hD12-VI, hD12-II, hD12-VII and hD12-XI). The H1373 in vivo xenograft study was set up with ten mice (Nu/nu: (Charles River)) in each group. Each mouse was inoculated with H1373 cells followed by treatment with one of the indicated antibody drug conjugates, or with PBS. Antibody drug conjugates were administered as a single administration by i.v. tail vein injection on day 7. Two different doses (0.5 mg/kg and 0.125 mg/kg) of each antibody drug conjugate was tested. Denosumab-II was used as a negative control. Tumor volume and weight were measured 3 times a week. Results of the H1373 in vivo xenograft study are shown in FIGS. 21A-213 and FIG. 22.

All animals tolerated the antibody drug conjugates well. There was no significant weight loss observed in any of the groups (e.g., see FIG. 22). As seen in the first H1975 xenograft model hD12-VII (FIG. 21D) showed slightly better efficacy in the low dose group (0.125 mg/kg) in comparison to hD12-II and hD12-VI (FIGS. 21C and 21B). hD12-IV was the least efficacious drug, as observed before (FIG. 21E).

Example 6—PK Studies in Mice

Figure 23:
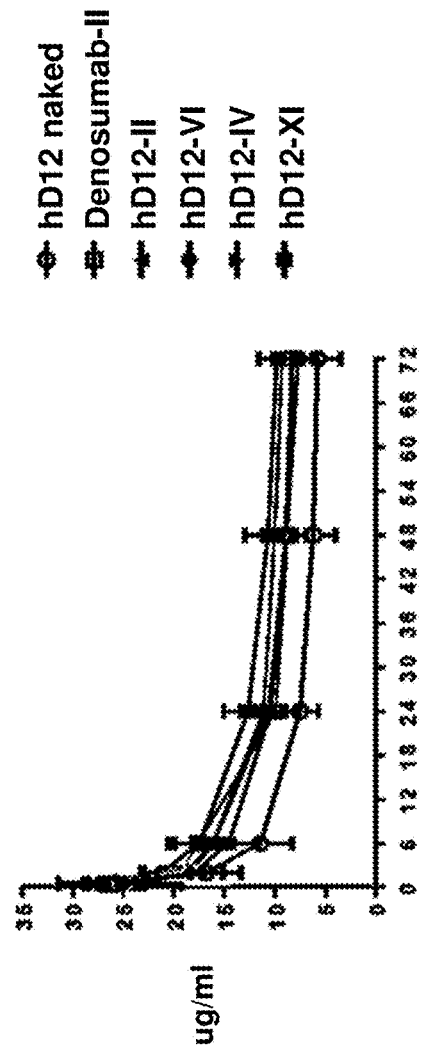
FIG. 23 shows the serum concentration (y-axis) of hD12-XI, hD12-VI, hD12-II, hD12-VII, hD12-IV, and Denosumab-II after i.v. injection in mice. Time (hours) after injection is indicated on the x-axis. The concentration of each antibody-drug conjugate was determined by ELISA.

The circulating half-life of the hD12 drug conjugates of Example 3 (i.e., hD12-VI, hD12-II, hD12-VII and hD12-XI) was assessed in 5 groups of 3 mice over a 72 hour period. Each group of mice received a single i.v. injection with 1 mg/kg of one of hD12-II, hD12-IV, hD12-VI, hD12-XI or Denosumab-II. Blood was drawn after 0.5 h, 2 h, 6 h, 24 h, 48 h, 72 h. Serum samples were prepared and analyzed for the amount of each of the indicated antibody drug conjugates (FIG. 23). Serum antibodies were captured with an anti Fc-specific antibody and detected with goat anti-human IgG (H+L)-HRP.

Example 7—Site-Specific Conjugation of Payloads to hD12

The coding regions of hD12 was mutated at various sites to introduce a cysteine residue into the heavy chain constant region of the IgG2 antibody to obtain the hD12 variant antibodies hD12-T289C (T at position 289 mutated to cysteine), hD12-V442C (V at position 442 mutated to cysteine), hD12-V282C (V at position 282 mutated to cysteine), hD12-S119C (S at position 119 mutated to cysteine). Points of mutation are in the constant region of hD12 and are defined according to the EU numbering system as described in Edelman, G. M. et al. (1969) *Proc. Nal. Acad. USA*, 63, 78-85. PMID: 5257969. The payload of chemical formula II was site-specifically conjugated to each of the mutated cysteine residues using Maleimide chemistry. The quality and extent of conjugation was assessed by a determination of total recovery, aggregate content, monomer content and drug-antibody ratio (DAR). Optimal conjugation was observed for the hD12 conjugates hD12-T289C-II, hD12-V442C-II and hD12-V282C-II. The relative binding affinity of these three site-specific conjugates for cMET was compared to the stochastically conjugated hD12-II using a cMET binding ELISA as described in Example 3. The results of the cMET binding assay are shown in FIGS. 24A and 24B. All of the site-specific compounds successfully bound to human cMET with similar affinities. The site specific conjugates bound with similar, or slightly better, affinity than the stochastically coupled hD12-II.

Figure 25B:
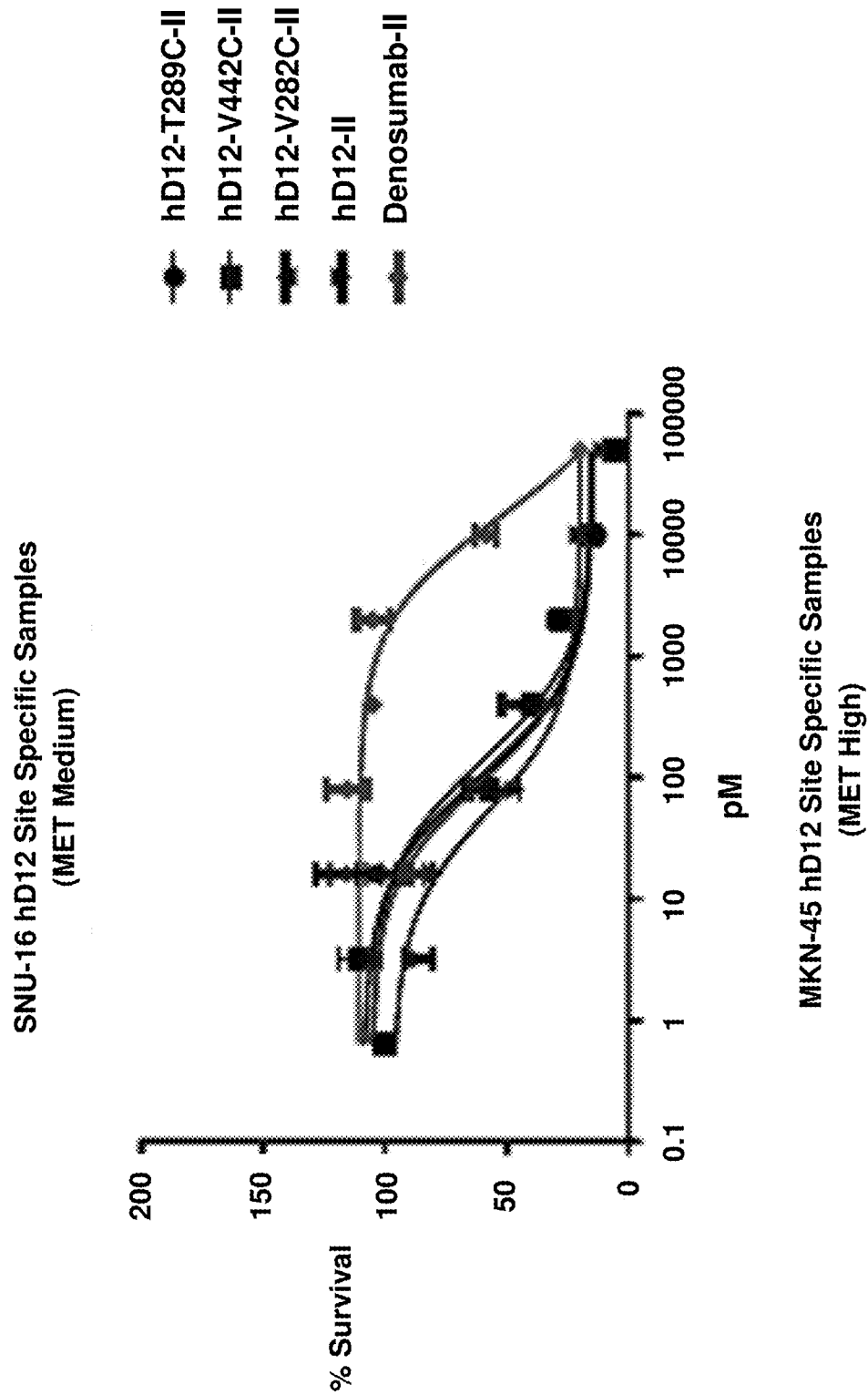
FIG. 25 shows the results of a cytotoxicity assay for the antibody conjugates of FIG. 24 (i.e., hD12-II, hD12-T289C-II, hD12-V442C-II and hD12-V282C-II) on four cell lines that express different amounts of cMET on their cell surface (SNU-1, no expression of cMET (FIG. 25A), SNU-16, medium expression of cMET (FIG. 25B), SNU-620, high expression of cMET (FIG. 25C), MKN-45, high expression of cMET (FIG. 25D), and N87, low expression of cMET (FIG. 25E)). Percent survival is indicated on the y-axis and the amount of antibody drug conjugate added is indicated on the x-axis (pM). The results are summarized in FIG. 25F which shows comparative $IC_{50}$ values. The concentrations of antibody drug conjugate tested are indicated in FIG. 25G.
Figure 25C:
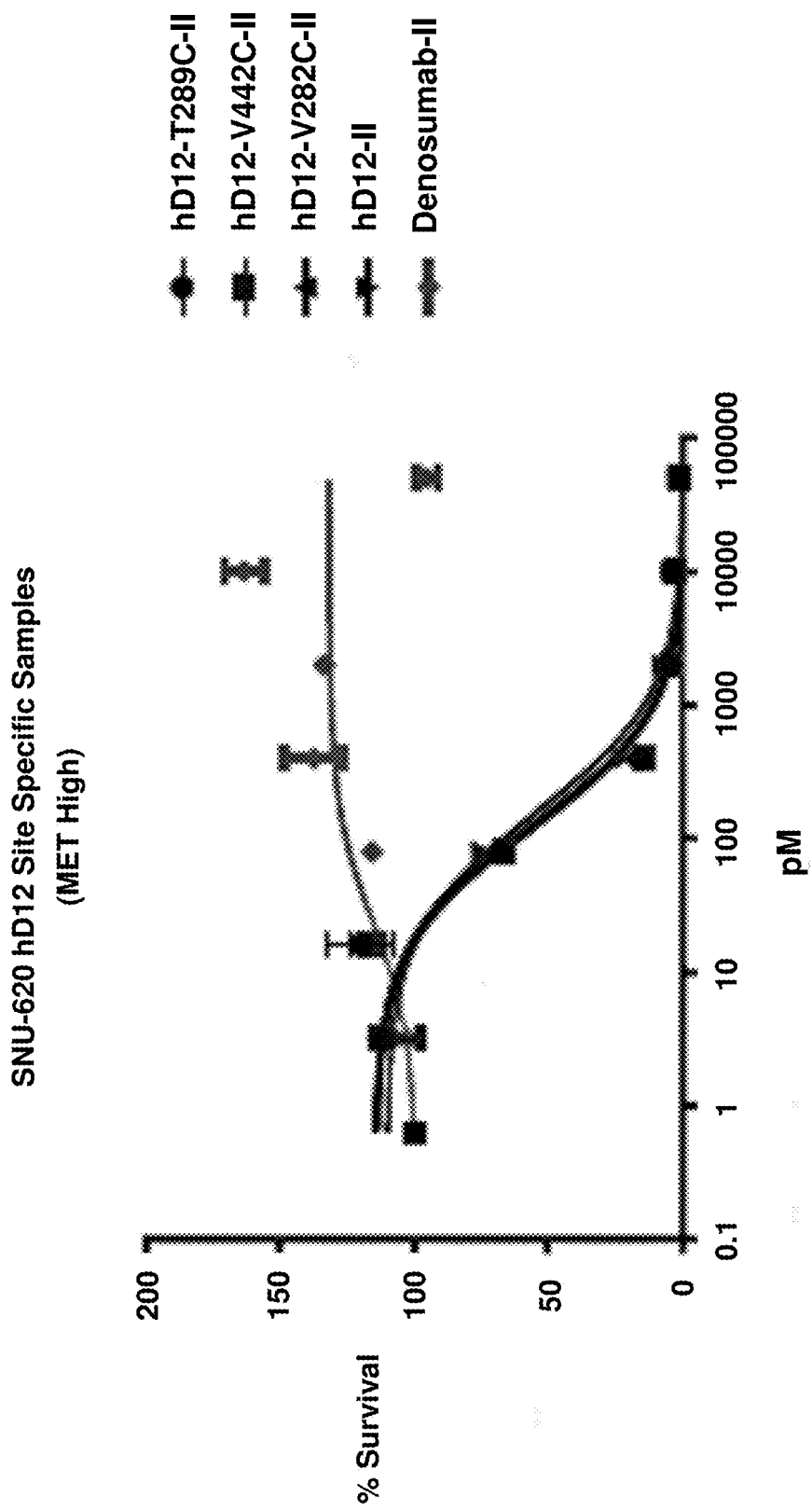
Figure 25D:
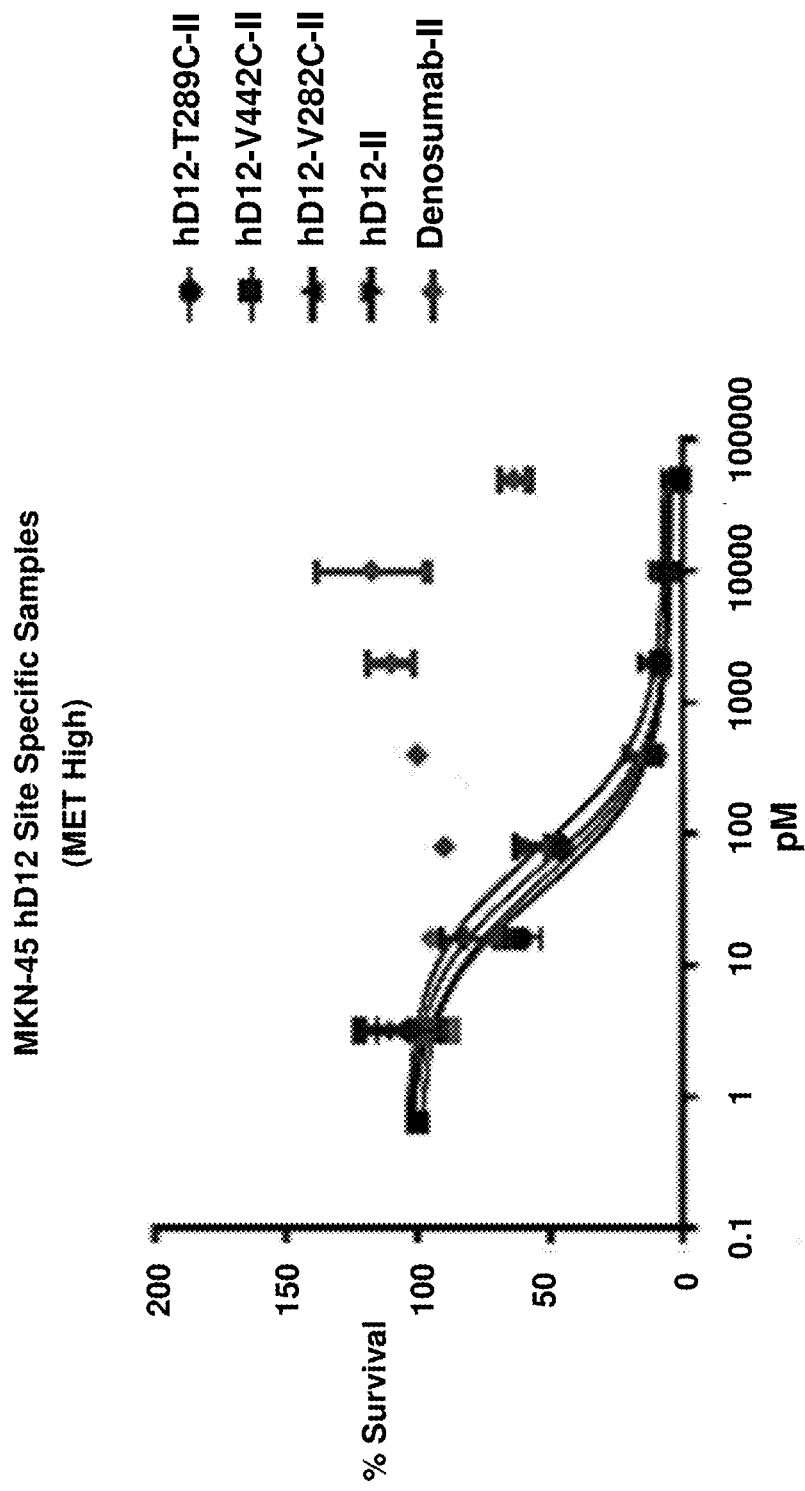
Figure 25E:
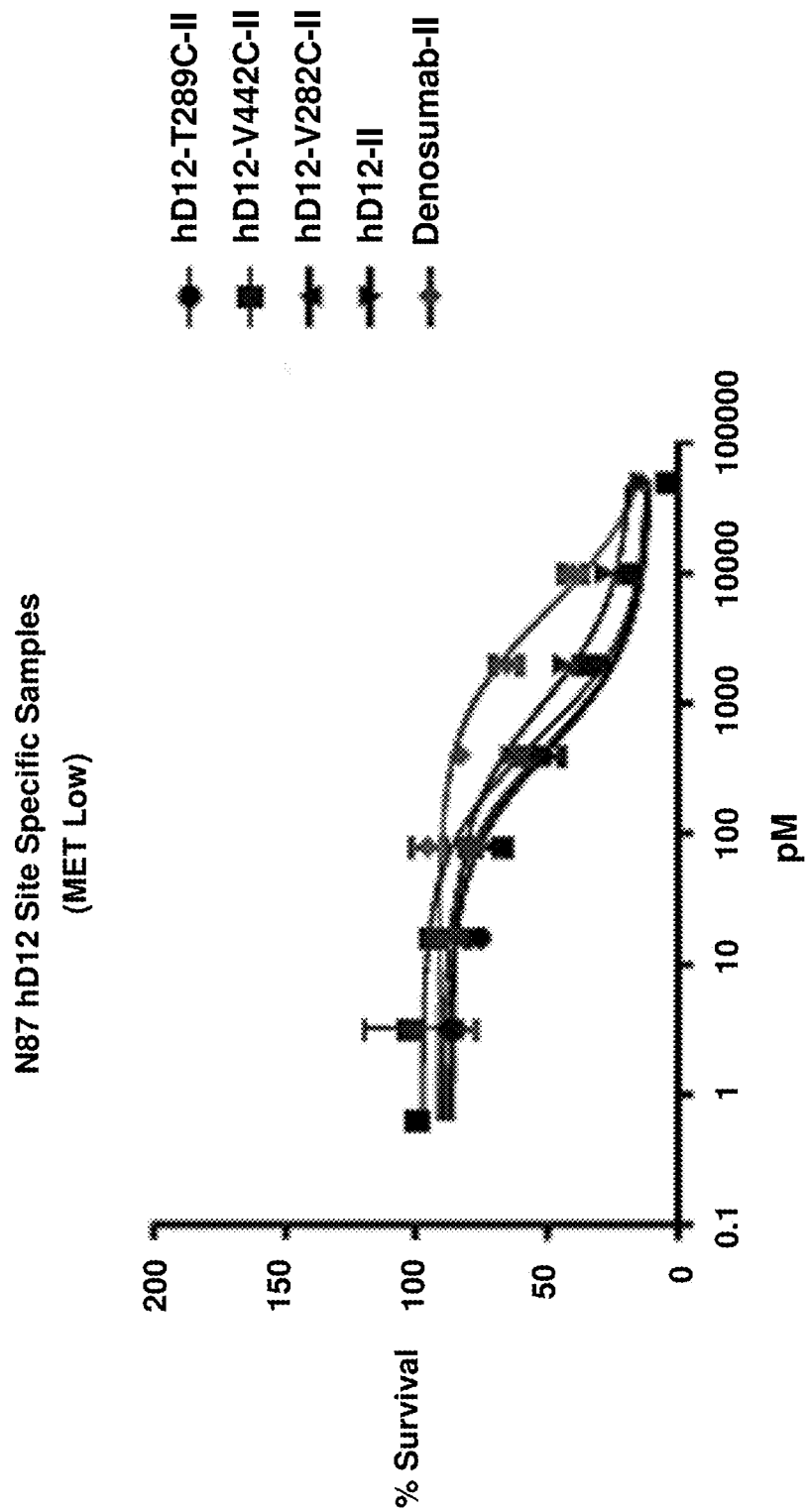
Figures 26A, 26B, 26C:
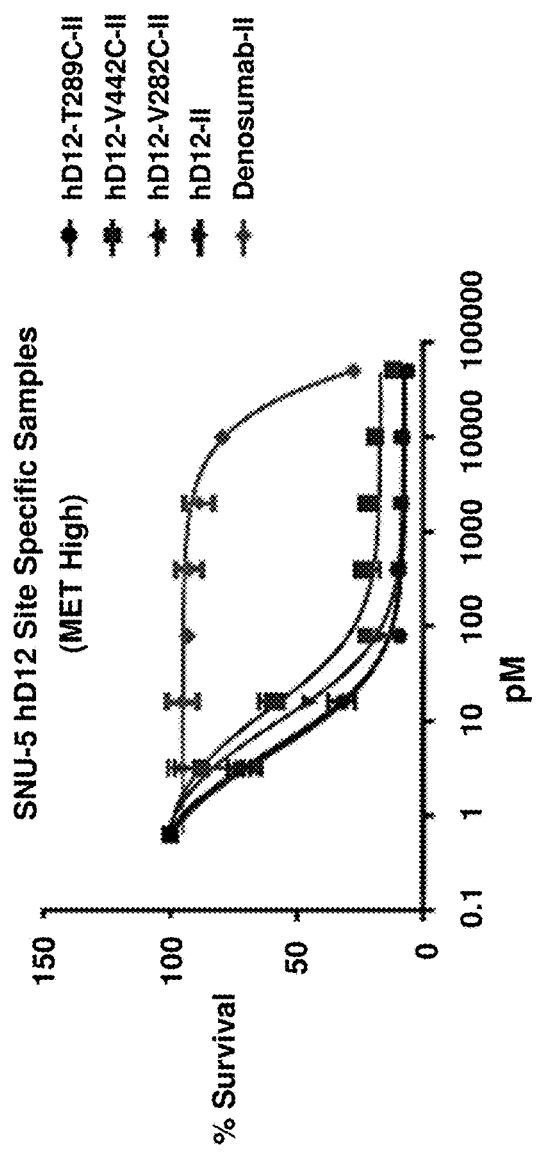
FIG. 26A shows the results of a cytotoxicity assay for the antibody conjugates of FIG. 24 (i.e., hD12-II, hD12-T289C-II, hD12-V442C-II and hD12-V282C-II) on a high cMET expressing cell line (i.e., SNU-5). Percent survival is indicated on the y-axis and the amount of antibody drug conjugate added is indicated on the x-axis (pM). The results are summarized in FIG. 26B which shows comparative $IC_{50}$ values. The concentrations of antibody drug conjugate tested are indicated in FIG. 26C.
Figure 27A:
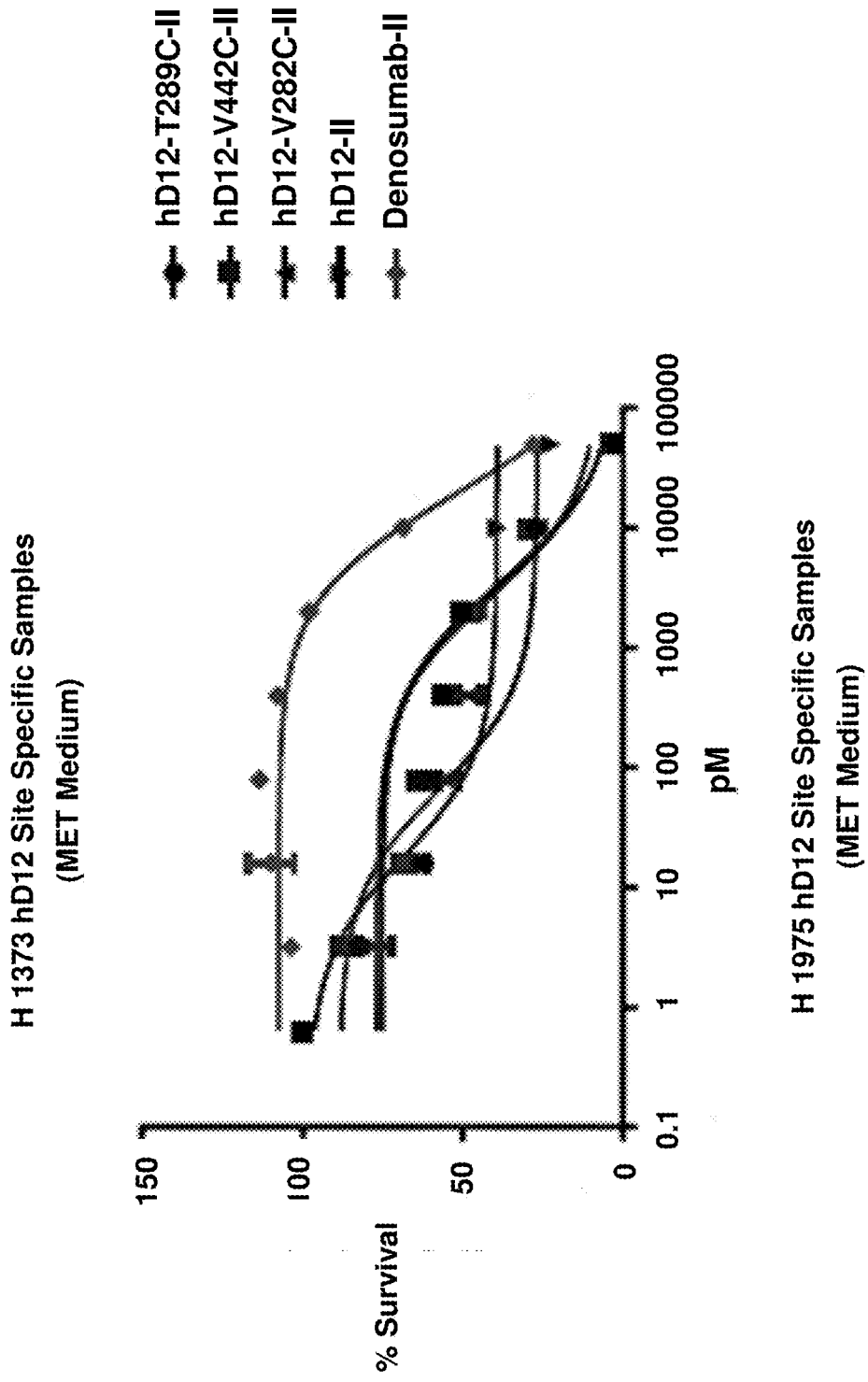
FIG. 27 shows the results of a cytotoxicity assay for the antibody conjugates of FIG. 24 (i.e., hD12-II, hD12-T289C-II, hD12-V442C-II and hD12-V282C-II) on three cell lines expressing medium amounts of cMET on their cell surface (H1373, FIG. 27A, H1573, FIG. 27B, and H1975, FIG. 27C). Percent survival is indicated on the y-axis and the amount of antibody drug conjugate added is indicated on the x-axis (pM). The concentrations of antibody drug conjugate tested are indicated in FIG. 27D. The results are summarized in FIG. 27E which shows comparative $IC_{50}$ values.
Figure 27B:
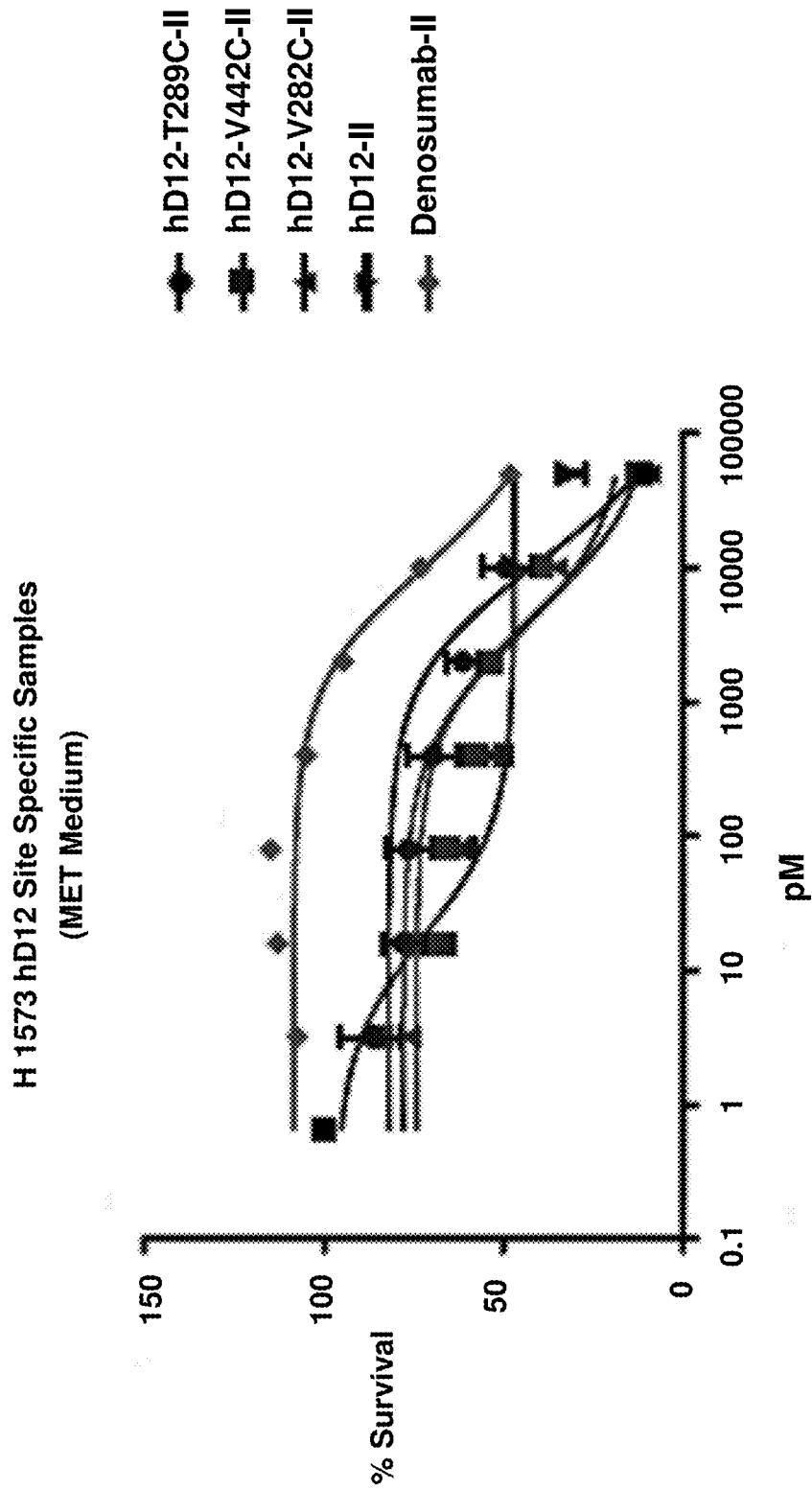
Figure 27C:
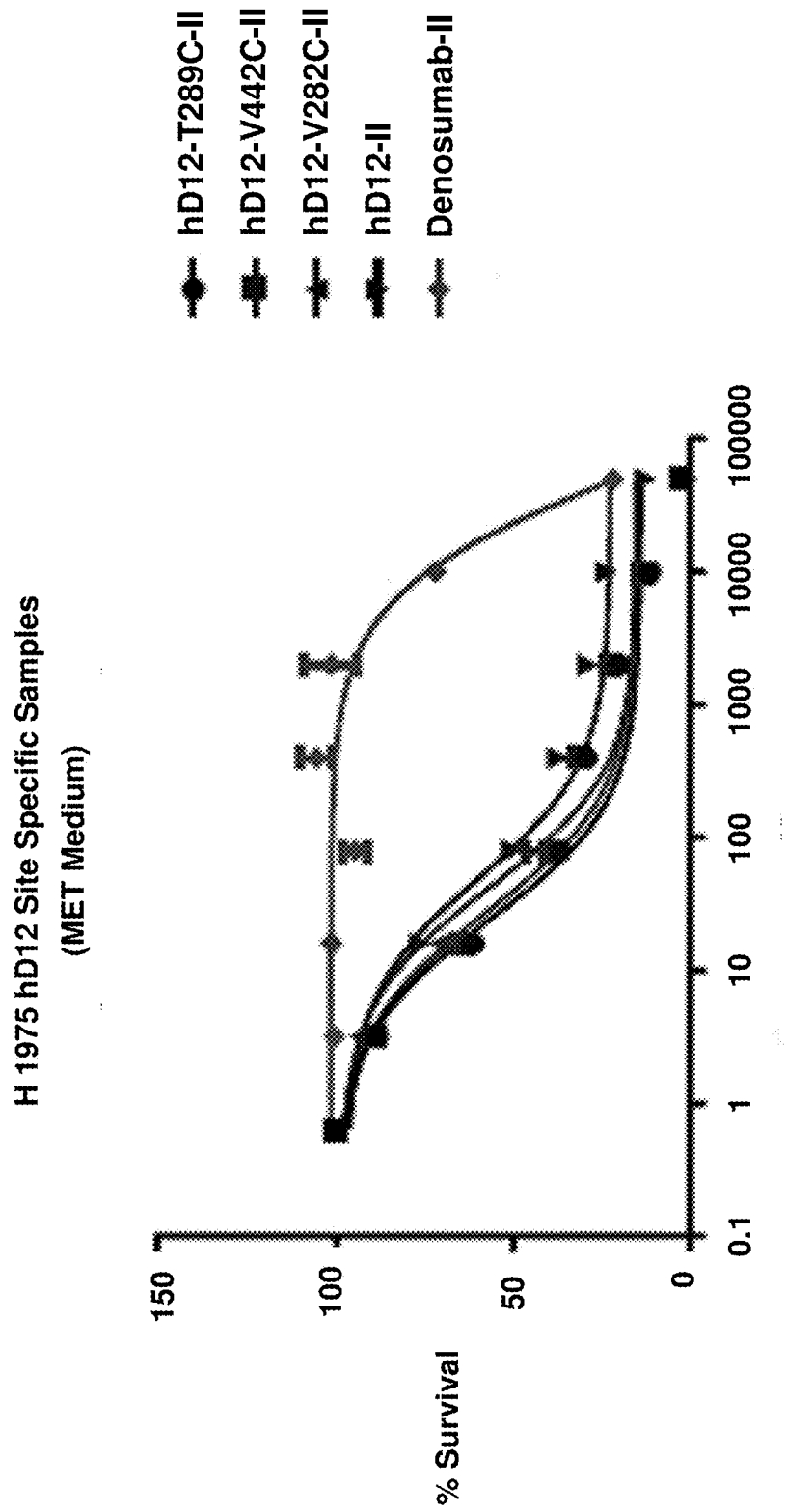

Example 8—Cytotoxicity Assessment of Site-Specific Conjugates to cMET Expression Cell Lines The cytotoxic potency of the site-specifically coupled II conjugates (i.e., hD12-T289C-II, hD12-V442C-II and hD12-V282C-II) was compared to the stochastically coupled hD12-II as a benchmark, against eight cMET expressing cell lines SNU-16 (FIG. 25B), SNU-620 (FIG. 25C), MKN-45 (FIG. 25D), NCI-N87 (FIG. 25E), SNU-5 (FIG. 26A), H1373 (FIG. 27A), H1573 (FIG. 27B), H1975 (FIG. 27C) and the cMET negative cell line SNU-1 (FIG. 25A). Cytotoxicity results are summarized in FIGS. 25F, 26B and 27E. The doses administered are indicated in FIGS. 25G, 26C and 27D.

All site-specific conjugated antibodies showed comparable cytotoxicity to the stochastically coupled hD12-II control against the MKN-45, SNU-620, SNU-5, SNU-16, NCI-N87 and H1975 cell lines. The EC50 for the site-specific conjugates could not be determined for the H1373 and H1573 cell lines due to complex killing curves that differed significantly from sigmoidal curves. The complex shape of the killing curves was more pronounced with the site-specific conjugates, and was repeatable in duplicate experiments. Overall, the cytotoxic potency of the site-specific hD12 conjugates seemed to be better than the stochastically conjugated hD12-II.

Example 9—In Vivo Xenograft Analysis of Site-Specific Conjugates

Figure 28A:
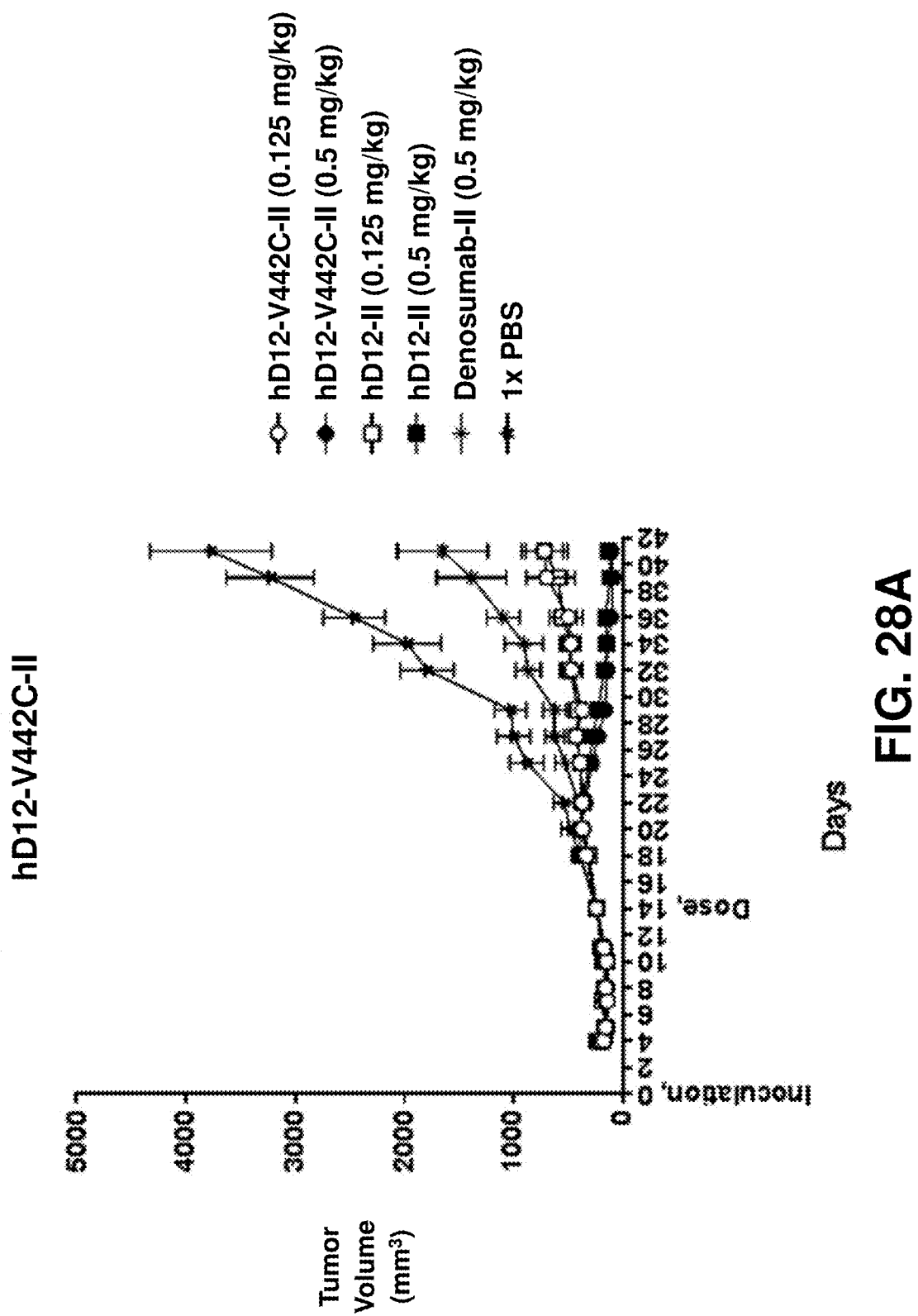
FIG. 28 shows the results of an in vivo xenograft study. Mice were injected with H1975 tumor cells (medium expression of cMET) and treated with hD12-V442C-II (FIG. 28A), hD12-T289C-II (FIG. 28B) and hD12-V282C-II (FIG. 28C) at the indicated concentrations. Mice were treated with stochastically conjugated hD12-II as a positive control. Mice were treated with vehicle (PBS) or Denosumab-II as negative controls. Tumor volume (y-axis) was determined over time (i.e., days, x-axis).
Figure 28B:
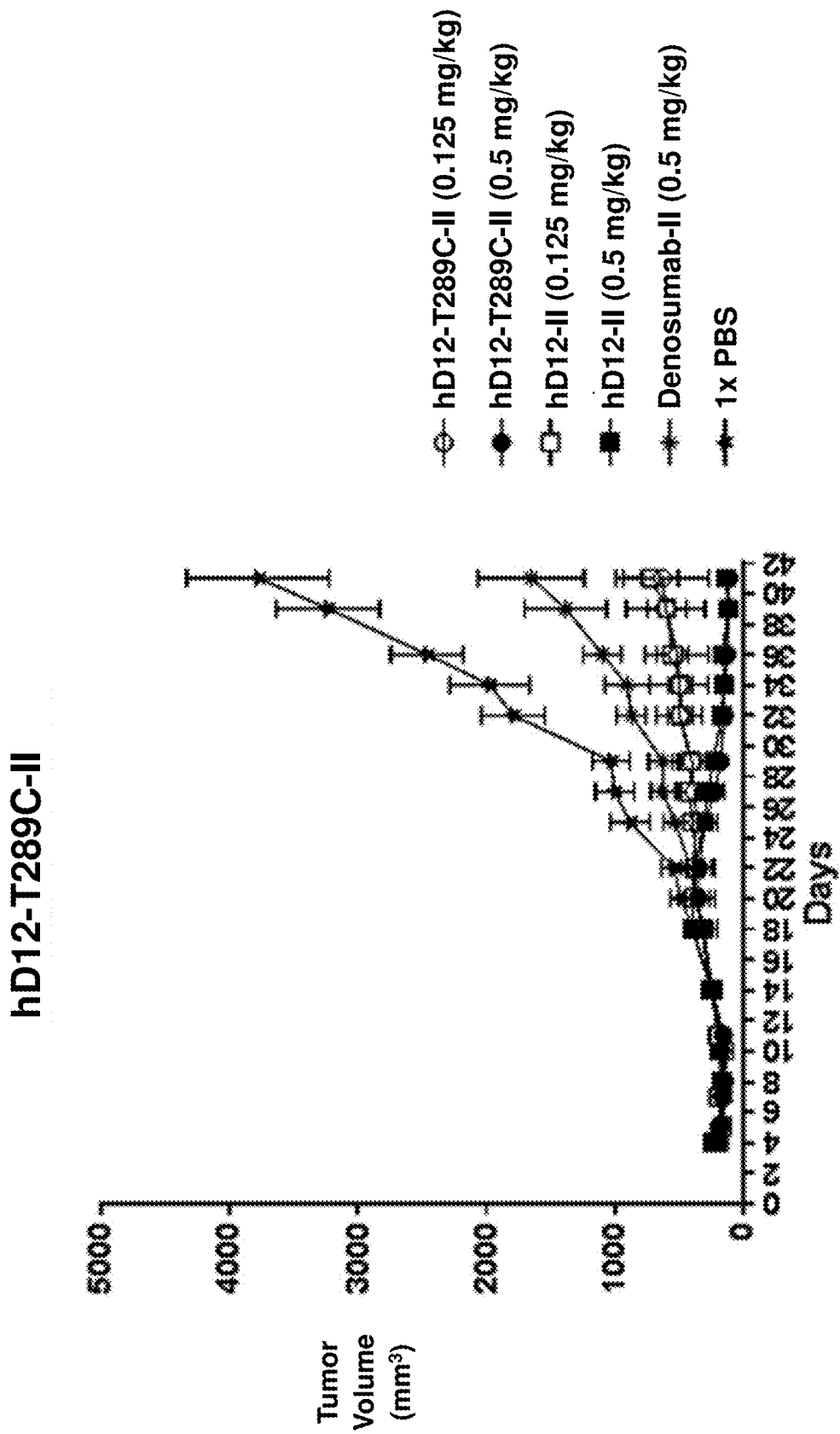
Figure 28C:
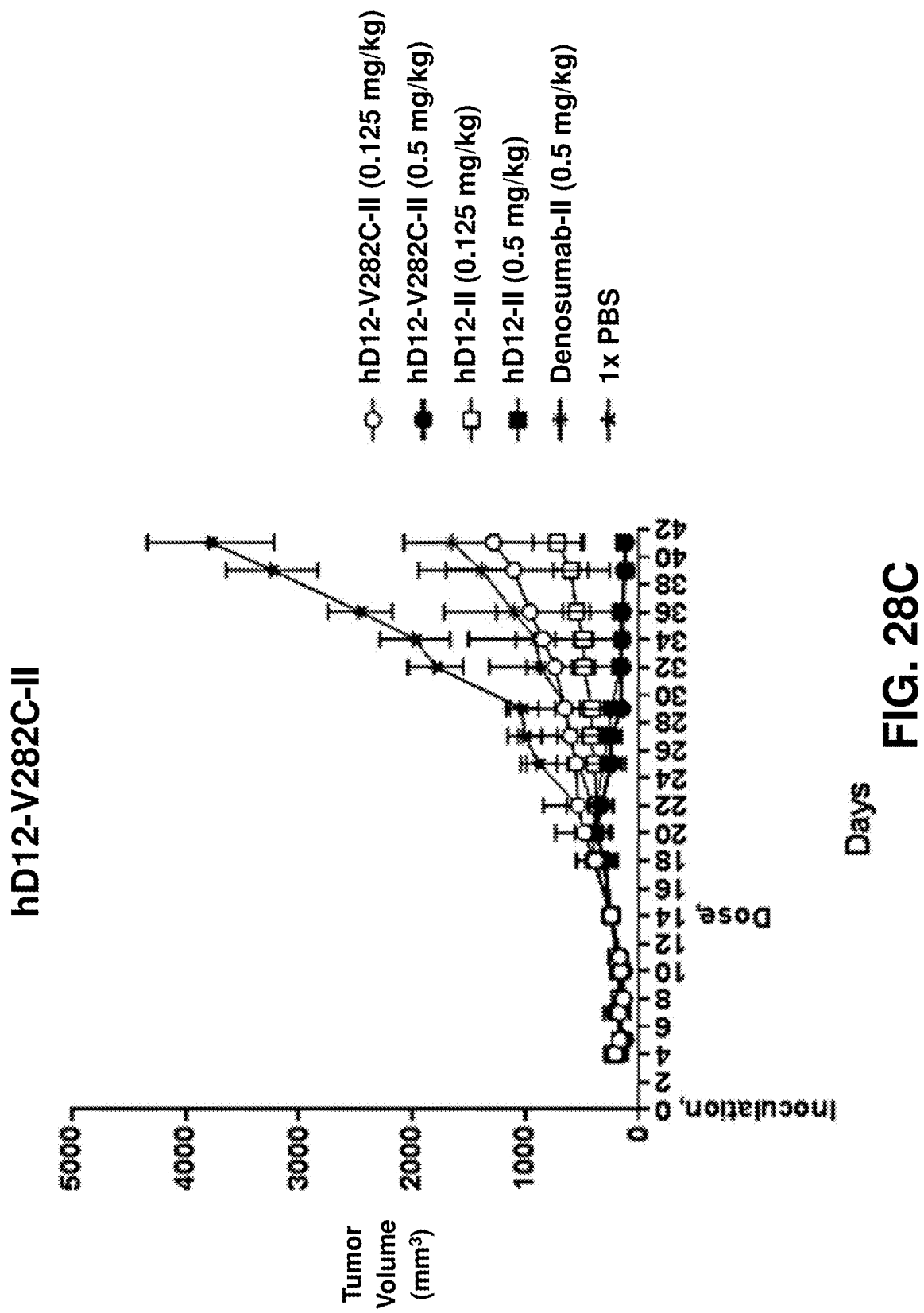

The site-specific conjugates hD12-T289C-II, hD12-V442C-II and hD12-V282C-II and the stochastically coupled hD12-II were assessed in an H1975 (medium cMET expression) xenograft tumor model. Denosumab-II was used as a negative control. Each mouse was inoculated with H1975 cells (Day 0) followed by treatment with one of the indicated antibody drug conjugates, or with PBS. Antibody drug conjugates were administered as a single administration by i.v. tail vein injection on day 14 after tumor cell inoculation. Two different doses (0.5 mg/kg and 0.125 mg/kg) of each antibody drug conjugate were tested. Ten mice were tested for each treatment. Tumor volume and weight were measured 3 times a week. Results of the H1975 in vivo xenograft study are shown in FIGS. 28A-28C.

Figure 29:
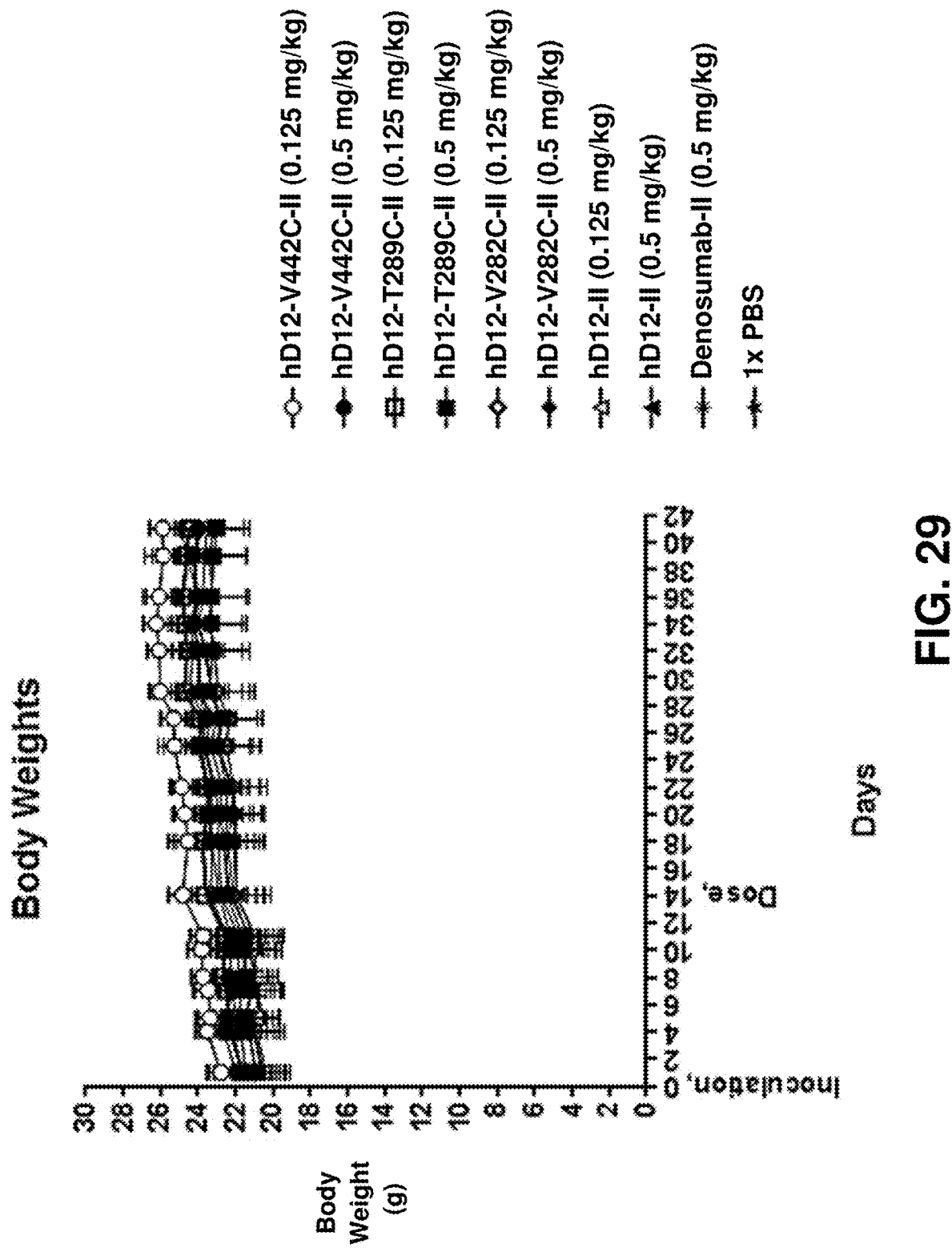
FIG. 29 shows the body weight (y-axis) of the mice treated in FIG. 28 over time (x-axis).

All high dose groups with site-specific ADCs, and the stochastically coupled II (0.5 mg/kg), showed high efficacy in the H1975 model. Tumors regressed completely (FIGS. 28A-28C). The low dose groups (0.125 mg/kg) showed tumor regression with hD12-II (stochastic) and hD12-T289C-II with hD12-V422C-II being the most efficacious. hD12-V282C-II was the least efficacious. The Denosumab control showed mild efficacy in the high dose, which was also seen in the previous H1975 model ran with the stochastically conjugated ADCs. All administered test articles were well tolerated and significant weight loss was not observed (FIG. 29).

Example 10—Pharmacokinetics in Rats with hD12 Site-Specific Conjugates (Total Antibody Detection)

Figure 30:
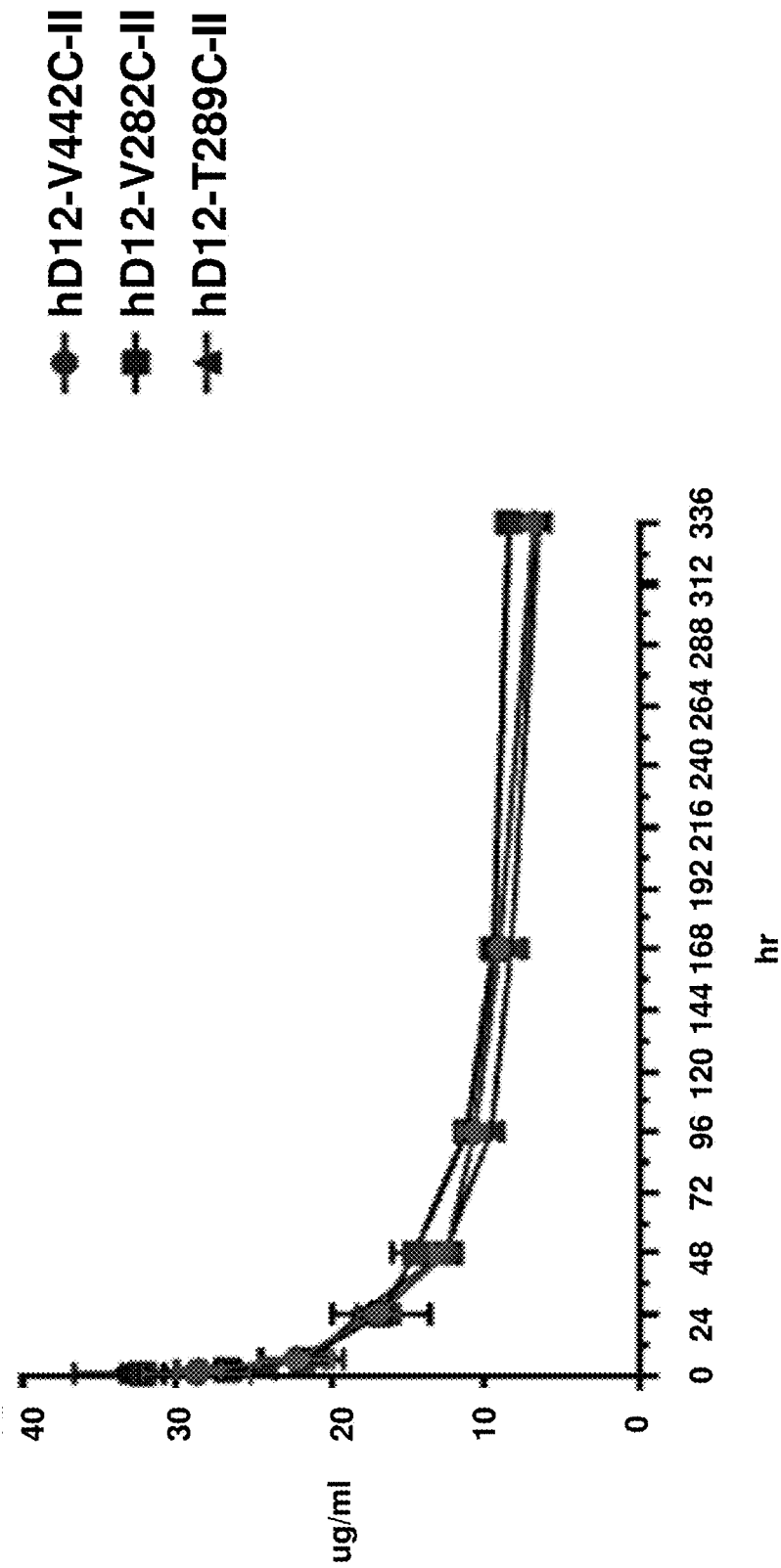
FIG. 30 shows the serum concentration (y-axis) of hD12-V442C-II (FIG. 28A), hD12-T289C-II (FIG. 28B) and hD12-V282C-II (FIG. 28C) after i.v. injection in rats. Time (hours) after injection is indicated on the x-axis. The concentration of each antibody-drug conjugate was determined by ELISA.

The circulating half-life of the site-specific hD12 conjugates hD12-V422C-II, hD12-V282C-II and hD12-T289C-II was assessed in rats for 21 days. Each group of rats (3 rats/group) received a single i.v. injection with 1 mg/kg of the indicated antibody drug conjugate (FIG. 30). Blood was drawn at 0.5 hr, 2 hr, 6 hr, 24 hr, 48 hr, 72 hr, 168 hr, 312 hr, and 480 hr post injection. Antibody levels in serum samples were analyzed in a PK ELISA using a capture antibody (anti Fc-specific) and goat anti-human IgG (H+L)-HRP detection antibody. The results are summarized in FIG. 31. Pharmacokinetic (PK) parameters of the site-specific conjugates was determined with WinNonlin software. All 3 site-specific conjugates showed similar shaped concentration-time curves. The calculated half-life was between 12 and 18 days. The variants could not be distinguished from one another based on the total antibody pharmacokinetic data alone. Based on the results of this experiment there is no significant pharmacokinetic difference between hD12-V422C-II, hD12-V282C-II and hD12-T289C-II.

Example 11—Non-Human Primate Tolerability

Stochastically coupled hD12-II and site-specific variants hD12-V282C-II and hD12-T289C-II were tested at amounts up to 1 mg/kg for tolerability in non-human primates. In general all of the antibody drug conjugates were well tolerated. There was no severe body weight loss observed by study end (day 21).

Example 12—PDX Models, Methods and Results

Patient derived xenografts (PDX) are models of cancer, where tissue or cells from a patient's tumor are implanted into an immunodeficient mouse. PDX models are often used to create an environment that resembles the natural growth of cancer, for the study of cancer progression and treatment. Multiple Crown Bio HuPrime® gastric, colorectal and head and neck (H&N) PDX models were carried out to evaluate the efficacy of hD12-T289C-II. The PDX models were chosen that ranged in their expression of c-Met (low to high).

Briefly, female BALB/c nude mice, 14-15 weeks old, were inoculated subcutaneously in the right flank with a primary human tumor fragment (gastric, colorectal or H&N cancer, 2-3 mm in size) for tumor development. Mice were randomized and grouped (6 treatment groups) when the tumor size reached an average volume of 200 mm$^3$. Each group consisted of 10 mice. Test articles were administered i.v. as a single dose into tumor-bearing mice starting on day 0. If required a second dose was administered. A non-targeting antibody (Secukinumab) linked to the payload of chemical formula II (Secukinumab-II) was administered at a dose of 1 mg/kg. hD12-T289C-II was administered as a single dose of 1.0 mg/kg, 0.5 mg/kg, 0.25 and 0.125 mg/kg, except where noted in FIG. 34. The vehicle control group was administered a single i.v. dose of 1×PBS.

After randomization, tumor size was measured by calipers twice weekly in two dimensions. The tumor volume (mm$^3$) was calculated by TV=0.5a×b$^2$ where a and b are the long and short diameters of the tumor surface. Bodyweight was measured and updated along with tumor measurements.

Tumor size was then used to calculate TGI % according to the following formula: TGI %=((mean(C)−mean(C0))−(mean(T)−mean(T0))/(mean(C)−mean(C0))*100% with T—current group value; T0—current group initial value; C—control group value; C0—control group initial value.

Figures 33A, 33B:
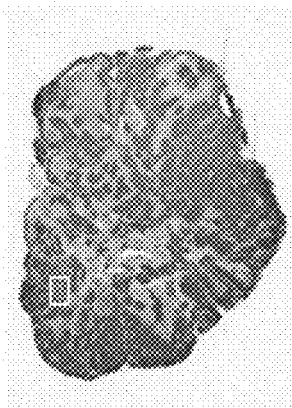
FIG. 33A shows immunohistochemical staining of a cross-section of gastric cancer PDX model GA3121 for human cMET protein.
FIG. 33B shows an amplified view of the area shown in the white inset of FIG. 33A.
Figure 33C:
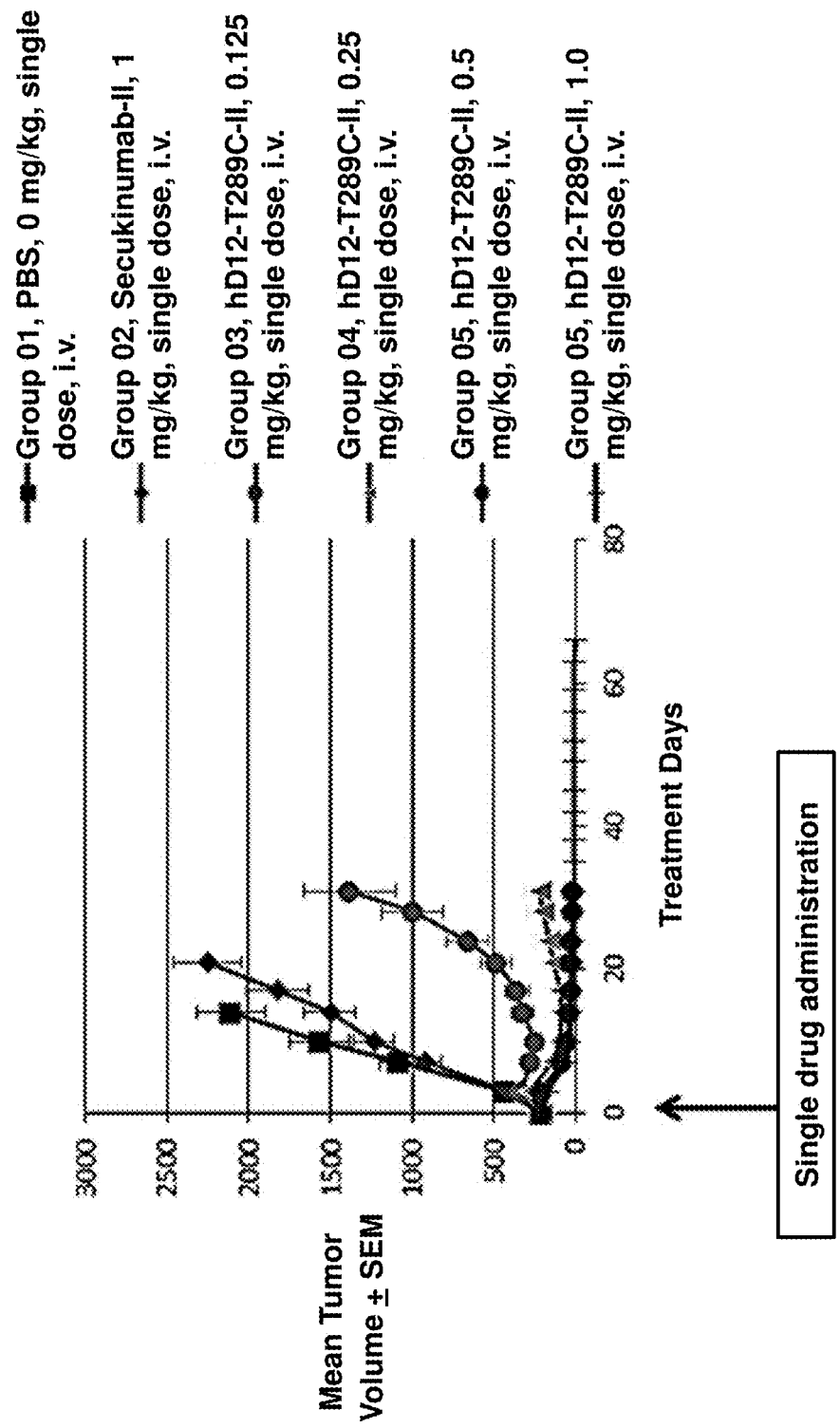
FIG. 33C shows the results of tumor growth inhibition of an in vivo patient-derived xenograft (PDX) model GA3121. Each data point represents 1 group consisting of 10 mice. Mice were treated with vehicle (PBS) or sekukinumab-II as negative controls. Tumor volume (y-axis) was determined over time (i.e., days, x-axis).

Results of the PDX studies are shown in FIGS. 32 and 33. Each data point represents 1 PDX model group consisting of 10 mice inoculated with a single PDX tumor. TGI % was calculated as described above. Mice were treated with vehicle (PBS) or Secukinumab-II as negative controls. Tumor volume (y-axis) was determined over time (i.e., days, x-axis; FIG. 33C). The results of FIGS. 32 and 33 show that hD12-T289C-II effectively inhibits the growth of human tumor tissues derived from gastric, colorectal or H&N cancer in a dose-dependent manner.

Example 13

A human subject presents with multiple metastatic carcinomas of 2 cm or larger, present in liver and lung. A biopsy is performed to determine if the cells of the carcinoma express cMET on their cell surface. The presence of cell surface cMET expression is confirmed from the biopsy results.

The human subject is administered a binding agent-drug conjugate described herein that specifically binds to the extracellular domain of human cMET. The binding agent optionally comprises human kappa and IgG2 heavy-chain constant regions, the light chain variable region of SEQ ID NO: 41 and the heavy chain variable region of SEQ ID NO:98. The binding agent-drug conjugate is administered at a dose of 15 mg/kg, intravenously, in a volume of 100 ml over a period of 1 hour, once a day for six weeks. The presence, size and viability of the tumors are determined by follow-up biopsy and ultrasound. The size and number of the tumors are substantially reduced after 2 weeks of treatment. The subject is determined to be in remission after six weeks of treatment.

Example 14

A human subject presents with colorectal adenocarcinoma having a solid tumor of 2 cm in diameter. The human subject is administered a binding agent-drug conjugate described herein. The binding agent of the binding agent-drug conjugate is a monoclonal humanized antibody of IgG2 isotype comprising a light chain variable region of SEQ ID NO: 47 and a humanized heavy chain variable region of SEQ ID NO: 108. The drug payload has the structure of chemical formula II. The binding agent is administered at a dose of 1 mg/kg, intravenously, in a volume of 50 ml over a period of 30 minutes, once a day for six weeks. After two weeks of treatment, size of the tumor is decreased by more than 50%. The subject is determined to be in remission after six weeks of treatment.

Example 15—cMET Sequences

```
(Human cMET-UniProtKB-P08581 (MET_HUMAN)).
*Residue E168 and N375 are bolded and underlined.
                                             SEQ ID NO: 109
MKAPAVLAPGILVLLFTLVQRSNGECKEALAKSEMNVNMKYQLPNFTAETPIQ

NVILHEHHIFLGATNYIYVLNEEDLQKVAEYKTGPVLEHPDCFPCQDCSSKANLSGGVW

KDNINMALVVDTYYDDQLISCGSVNRGTCQRHVFPHNHTADIQSEVHCIFSPQIEEPSQC

PDCVVSALGAKVLSSVKDRFINFFVGNTINSSYFPDHPLHSISVRRLKETKDGFMFLTDQ

SYIDVLPEFRDSYPIKYVHAFESNNFIYFLTVQRETLDAQTFHTRIIRFCSINSGLHSYMEM

PLECILTEKRKKRSTKKEVFNILQAAYVSKPGAQLARQIGASLNDDILFGVFAQSKPDSA

EPMDRSAMCAFPIKYVNDFFNKIVNKNNVRCLQHFYGPNHEHCFNRTLLRNSSGCEAR

RDEYRTEFTTALQRVDLFMGQFSEVLLTSISTFIKGDLTIANLGTSEGRFMQVVVSRSGPS

TPHVNFLLDSHPVSPEVIVEHTLNQNGYTLVITGKKITKIPLNGLGCRHFQSCSQCLSAPP
```

```
FVQCGWCHDKCVRSEECLSGTWTQQICLPAIYKVFPNSAPLEGGTRLTICGWDFGFRRN

NKFDLKKTRVLLGNESCTLTLSESTMNTLKCTVGPAMNKHFNMSIIISNGHGTTQYSTFS

YVDPVITSISPKYGPMAGGTLLTLTGNYLNSGNSRHISIGGKTCTLKSVSNSILECYTPAQ

TISTEFAVKLKIDLANRETSIFSYREDPIVYEIHPTKSFISGGSTITGVGKNLNSVSVPRMVI

NVHEAGRNFTVACQHRSNSEIICCTTPSLQQLNLQLPLKTKAFFMLDGILSKYFDLIYVH

NPVFKPFEKPVMISMGNENVLEIKGNDIDPEAVKGEVLKVGNKSCENIHLHSEAVLCTV

PNDLLKLNSELNIEWKQAISSTVLGKVIVQPDQNFTGLIAGVVSISTALLLLLGFFLWLKK

RKQIKDLGSELVRYDARVHTPHLDRLVSARSVSPTTEMVSNESVDYRATFPEDQFPNSS

QNGSCRQVQYPLTDMSPILTSGDSDISSPLLQNTVHIDLSALNPELVQAVQHVVIGPSSLI

VHFNEVIGRGHFGCVYHGTLLDNDGKKIHCAVKSLNRITDIGEVSQFLTEGIIMKDFSHP

NVLSLLGICLRSEGSPLVVLPYMKHGDLRNFIRNETHNPTVKDLIGFGLQVAKGMKYLA

SKKFVHRDLAARNCMLDEKFTVKVADFGLARDMYDKEYYSVHNKTGAKLPVKWMAL

ESLQTQKFTTKSDVWSFGVLLWELMTRGAPPYPDVNTFDITVYLLQGRRLLQPEYCPDP

LYEVMLKCWHPKAEMRPSFSELVSRISAIFSTFIGEHYVHVNATYVNVKCVAPYPSLLSS

EDNADDEVDTRPASFWETS (Rat cMET-UniProtKB-P97523 (MET_RAT))
                                            SEQ ID NO: 110
MKAPTALAPGILLLLLTLAQRSHGECKEALVKSEMNVNMKYQLPNFTAETPIH

NVVLPGHHIYLGATNYIYVLNDKDLQKVSEFKTGPVVEHPDCFPCQDCSSKANVSGGV

WKDNVNMALLVDTYYDDQLISCGSVNRGTCQRHVLPPDNAADIQSEVHCMFSPLAEEE

SGQCPDCVVSALGAKVLLSEKDRFINFFVGNTINSSYPPDYSLHSISVRRLKETQDGFKFL

TDQSYIDVLPEFRDSYPIKYIHAFESNHFIYFLTVQKETLDAQTFHTRIIRFCSVDSGLHSY

MEMPLECILTEKRRKRSTREEVFNILQAAYVSKPGANLAKQIGASPYDDILYGVFAQSKP

DSAEPMNRSAVCAFPIKYVNDFFNKIVNKNNVRCLQHFYGPNHEHCFNRTLLRNSSGCE

VRSDEYRTEFTTALQRVDLFMGRLNHVLLTSISTFIKGDLTIANLGTSEGRFMQVVLSRT

AHFTPHVNFLLDSYPVSPEVIVEHPSNQNGYTLVVTGKKITKIPLNGLGCGHFQSCSQCL

SPPYFIQCGWCHNRCVHSNECPSGTWTQEICLPAVYKVFPTSAPLEGGTMLTICGWDFG

FKKNNKFDLRKTKVLLGNESCTLTLSESTTNTLKCTVGPAMSEHFNVSVIVSNSRETTQY

SAFSYVDPVITSISPRYGPHAGGTLLTLTGKYLNSGNSRHISIGGKTCTLKSVSDSILECYT

PGHTVSAEFPVKLKIDLADRVTSSFSYREDPVVSEIHPTKSFISGGSTITGIGKNLNSVSTP

KLVIEVHDVGVNYTVACQHRSSSEIICCTTPSLRQLDLQLPLKTKAFFLLDGILSKHFDLT

YVHDPMFKPFEKPVMISMGNENVVEIKGDDIDPEAVKGEVLKVGNKSCENLHWHSEAL

LCTVPSDLLKLNGGELNIEWKQAVSSTVLGKVIVQPDQNFAGLIIGAVSISVVVLLVSGL

FLWLRKRKHKDLGSELVRYDARVHTPHLDRLVSARSVSPTTEMVSNESVDYRATFPED

QFPNSSQNGACRQVQYLLTDLSPILTSGDSDISSPLLQNTVHIDLSALNPELVQAVPHVVI

GPSSLIVHFNEVIGRGHFGCVYHGTLLDSDGKKIHCAVKSLNRITDIEEVSQFLTEGIIMK

DFSHPNVLSLLGICLRSEGSPLVVLPYMKHGDLRNFIRNETHNPTVKDLIGFGLQVAKG

MKYLVSKKFVHRDLAARNCMLDEKFTVKVADFGLARDMYDKEYYSVHNKTGAKLPV

KWMALESLQTQKFTTKSDVWSFGVLLWELMTRGAPPYPDVNTFDITIYLLQGRRLLQPE

YCPDALYEVMLKCWHPKAEMRPS VSELVSRISSIFSTFIGEHYVHVNATYVNVKCVAPY

PSLLPSQDNIDGEANT (Mouse cMET-UniProtKB-P16056 (MET_MOUSE))
```

```
                                     SEQ ID NO: 111
MKAPTVLAPGILVLLLSLVQRSHGECKEALVKSEMNVNMKYQLPNFTAETPIQ

NVVLHGHHIYLGATNYIYVLNDKDLQKVSEFKTGPVLEHPDCLPCRDCSSKANSSGGV

WKDNINMALLVDTYYDDQLISCGSVNRGTCQRHVLPPDNSADIQSEVHCMFSPEEESGQ

CPDCVVSALGAKVLLSEKDRFINFFVGNTINSSYPPGYSLHSISVRRLKETQDGFKFLTDQ

SYIDVLPEFLDSYPIKYIHAFESNHFIYFLTVQKETLDAQTFHTRIIRFCSVDSGLHSYMEM

PLECILTEKRRKRSTREEVFNILQAAYVSKPGANLAKQIGASPSDDILFGVFAQSKPDSAE

PVNRSAVCAFPIKYVNDFFNKIVNKNNVRCLQHFYGPNHEHCFNRTLLRNSSGCEARSD

EYRTEFTTALQRVDLFMGRLNQVLLTSISTFIKGDLTIANLGTSEGRFMQVVLSRTAHLT

PHVNFLLDSHPVSPEVIVEHPSNQNGYTLVVTGKKITKIPLNGLGCGHFQSCSQCLSAPY

FIQCGWCHNQCVRFDECPSGTWTQEICLPAVYKVFPTSAPLEGGTVLTICGWDFGFRKN

NKFDLRKTKVLLGNESCTLTLSESTTNTLKCTVGPAMSEHFNVSVIISNSRETTQYSAFSY

VDPVITSISPRYGPQAGGTLLTLTGKYLNSGNSRHISIGGKTCTLKSVSDSILECYTPAQTT

SDEFPVKLKIDLANRETSSFSYREDPVVYEIHPTKSFISGGSTITGIGKTLNSVSLPKLVIDV

HEVGVNYTVACQHRSNSEIICCTTPSLKQLGLQLPLKTKAFFLLDGILSKHFDLTYVHNP

VFEPFEKPVMISMGNENVVEIKGNNIDPEAVKGEVLKVGNQSCESLHWHSGAVLCTVPS

DLLKLNSELNIEWKQAVSSTVLGKVIVQPDQNFAGLIIGAVSISVVVLLLSGLFLWMRKR

KHKDLGSELVRYDARVHTPHLDRLVSARSVSPTTEMVSNESVDYRATFPEDQFPNSSQN

GACRQVQYPLTDLSPILTSGDSDISSPLLQNTVHIDLSALNPELVQAVQHVVIGPSSLIVHF

NEVIGRGHFGCVYHGTLLDNDGKKIHCAVKSLNRITDIEEVSQFLTEGIIMKDFSHPNVLS

LLGICLRSEGSPLVVLPYMKHGDLRNFIRNETHNPTVKDLIGFGLQVAKGMKYLASKKF

VHRDLAARNCMLDEKFTVKVADFGLARDMYDKEYYSVHNKTGAKLPVKWMALESLQ

TQKFTTKSDVWSFGVLLWELMTRGAPPYPDVNTFDITIYLLQGRRLLQPEYCPDALYEV

MLKCWHPKAEMRPSFSELVSRISSIFSTFIGEHYVHVNATYVNVKCVAPYPSLLPSQDNI

DGEGNT (Dog cMET)
                                     SEQ ID NO: 112
MKAPAVLAPGILVLLFTLVQKSYGECKEALVKSEMNVNMKYQLPNFTAETPIQ

NVVLHKHHIYLGAVNYIYVLNDKDLQKVAEYKTGPVLEHPDCSPCQDCSHKANLSGGV

WEDNINMALLVDTYYDDQLISCGSVHRGTCQRHILPPSNIADIQSEVHCMYSSQADEEPS

QCPDCVVSALGTKVLISEKDRFINFFVGNTINSSDHPDHSLHSISVRRLKETQDGFKFLTD

QSYIDVLPEFRDSYPIKYVHAFESNHFIYFLTVQRETLDAQTFHTRIIRFCSVDSGLHSYM

EMPLECILTEKRRKRSTREEVFNILQAAYVSKPGAHLAKQIGANLNDDILYGVFAQSKPD

SAEPMNRSAVCAFPIKYVNEFFNKIVNKNNVRCLQHFYGPNHEHCFNRTLLRNSSGCEA

RNDEYRTEFTTALQRVDLFMGQFNQVLLTSISTFIKGDLTIANLGTSEGRFMQVVVSRSG

LSTPHVNFRLDSHPVSPEAIVEHPLNQNGYTLVVTGKKITRIPLNGLGCEHFQSCSQCLSA

PPFVQCGWCHDRCVHLEECPTGAWTQEVCLPAIYEVFPTSAPLEGGTVLTVCGWDFGF

RRNNKFDLKKTKVFLGNESCTLTLSESTTNMLKCTVGPAVNEHFNISIIISNGRGTAQYST

FSYVDPIITSISPSYGPKNGGTLLTLTGKYLNSGNSRHISMGGKTCTLKSVSDSILECYTPA

QATATEFPIKLKIDLANREMNSFSYQEDPIVYAIHPTKSFISGGSTITAVGKNLNSVSVLR

MVIDVHETRRNFTVACQHRSNSEIICCTTPSLQQLNLQLPLKTKAFFMLDGIHSKYFDLIY

VHNPVFKPFEKPVMISIGNENVLEIKGNDIDPEAVKGEVLKVGNKSCETIYSDSKAVLCK
```

-continued

VPNDLLKLNNELNIEWKQAVSSTVLGKVIVQPDQNFTGLIAGVISISTIVLLLLGLFLWLK

RKKQIKDLGSELVRYDARVHTPHLDRLVSARSVSPTTEMVSNESVDYRATFPEDQFPNS

SQNGSCRQVQYPLTDLSPMLTSGDSDISSPLLQNTVHIDLSALNPELVQAVQHVVIGPSS

LIVHFNEVIGRGHFGCVYHGTLLDNDDKKIHCAVKSLNRITDIGEVSQFLTEGIIMKDFSH

PNVLSLLGICLRSEGSPLVVLPYMKHGDLRNFIRNETHNPTVKDLIGFGLQVAKGMKYL

ASKKFVHRDLAARNCMLDEKFTVKVADFGLARDMYDKEYYSVHNKTGAKLPVKWM

ALESLQTQKFTTKSDVWSFGVLLWELMTRGAPPYPDVNTFDITVYLLQGRRLLQPEYCP

DPLYEVMLKCWHPRAELRPSFSELVSRISAIFSTFIGEHYVHVNATYVNVKCVAPYPSLL

SSQDNIDGEGDT (Macaca mulatta, Rhesus cMET-NCBI Reference Sequence:
NP_001162100.1)
SEQ ID NO: 113

MKAPAVLVPGILVLLFTLVQRSNGECKEALAKS EMNVNMKYQLPNFTAETAIQ

NVILHEHHIFLGATNYIYVLNEEDLQKVAEYKTGPVLEHPDCFPCQDCSSKANLSGGVW

KDNINMALVVDTYYDDQLISCGSVNRGTCQRHVFPHNHTADIQSEVHCIFSPQIEEPNQC

PDCVVSALGAKVLSSVKDRFINFFVGNTINSSYFPHHPLHSISVRRLKETKDGFMFLTDQ

SYIDVLPEFRDSYPIKYIHAFESNNFIYFLTVQRETLNAQTFHTRIIRFCSLNSGLHSYMEM

PLECILTEKRKKRSTKKEVFNILQAAYVSKPGAQLARQIGASLNDDILFGVFAQSKPDSA

EPMDRSAMCAFPIKYVNDFFNKIVNKNNVRCLQHFYGPNHEHCFNRTLLRNSSGCEAR

RDEYRAEFTTALQRVDLFMGQFSEVLLTSISTFVKGDLTIANLGTSEGRFMQVVVSRSGP

STPHVNFLLDSHPVSPEVIVEHPLNQNGYTLVVTGKKITKIPLNGLGCRHFQSCSQCLSAP

PFVQCGWCHDKCVRSEECPSGTWTQQICLPAIYKVFPTSAPLEGGTRLTICGWDFGFRR

NNKFDLKKTRVLLGNESCTLTLSESTMNTLKCTVGPAMNKHFNMSIIISNGHGTTQYSTF

SYVDPIITSISPKYGPMAGGTLLTLTGNYLNSGNSRHISIGGKTCTLKSVSNSILECYTPAQ

TISTEFAVKLKIDLANRETSIFSYREDPIVYEIHPTKSFISGGSTITGVGKNLHSVSVPRMVI

NVHEAGRNFTVACQHRSNSEIICCTTPSLQQLNLQLPLKTKAFFMLDGILSKYFDLIYVH

NPVFKPFEKPVMISMGNENVLEIKGNDIDPEAVKGEVLKVGNKSCENIHLHSEAVLCTV

PNDLLKLNSELNIEWKQAISSTVLGKVIVQPDQNFTGLIAGVVSISIALLLLLGLFLWLKK

RKQIKDLGSELVRYDARVHTPHLDRLVSARSVSPTTEMVSNESVDYRATFPEDQFPNSS

QNGSCRQVQYPLTDMSPILTSGDSDISSPLLQNTVHIDLSALNPELVQAVQHVVIGPSSLI

VHFNEVIGRGHFGCVYHGTLLDNDGKKIHCAVKSLNRITDIGEVSQFLTEGIIMKDFSHP

NVLSLLGICLRSEGSPLVVLPYMKHGDLRNFIRNETHNPTVKDLIGFGLQVAKGMKYLA

SKKFVHRDLAARNCMLDEKFTVKVADFGLARDMYDKEYYSVHNKTGAKLPVKWMAL

ESLQTQKFTTKSDVWSFGVLLWELMTRGAPPYPDVNTFDITVYLLQGRRLLQPEYCPDP

LYEVMLKCWHPKAEMRPSFSELVSRISAIFSTFIGEHYVHVNATYVNVKCVAPYPSLLSS

EDNADDEVDT

Heavy Chain sequence of hD12
SEQ ID NO: 114

QVQLVQSGAEVKKPGASVKVSCKASGYTFTSYWMHWVKQAPGQGLDWIGYI

KPSTDNTEYNQKFKDKATLTADKSTSTAYMELSSLRSEDTAVYYCARSYGNYPLMDY

WGQGTTVTVSSASTKGPSVFPLAPCSRSTSESTAALGCLVKDYFPEPVTVSWNSGALTS

GVHTFPAVLQSSGLYSLSSVVTVPSSNFGTQTYTCNVDHKPSNTKVDKTVERKCCVECP

PCPAPPVAGPSVFLFPPKPKDTLMISRTPEVTCVVVDVSHEDPEVQFNWYVDGVEVHNA

-continued

KTKPREEQFNSTFRVVSVLTVVHQDWLNGKEYKCKVSNKGLPAPIEKTISKTKGQPREP

QVYTLPPSREEMTKNQVSLTCLVKGFYPSDIAVEWESNGQPENNYKTTPPMLDSDGSFF

LYSKLTVDKSRWQQGNVFSCSVMHEALHNHYTQKSLSLSPGK

Light Chain sequence of hD12
SEQ ID: 115
QIVLTQSPAILSLSPGERATLSCSASSSVTSNYLYWYQQKPGSSPKLLIYSTSNLA

SGVPARFSGSGSGTSYTLTISSLEAEDAASYFCHQWSSYPPTFGSGTKLEIKRTVAAPSVF

IFPPSDEQLKSGTASVVCLLNNFYPREAKVQWKVDNALQSGNSQESVTEQDSKDSTYSL

SSTLTLSKADYEKHKVYACEVTHQGLSSPVTKSFNRGEC

Heavy Chain sequence of hD12 T289C (Residue C289
is underlined)
SEQ ID NO: 116
QVQLVQSGAEVKKPGASVKVSCKASGYTFTSYWMHWVKQAPGQGLDWIGYI

KPSTDNTEYNQKFKDKATLTADKSTSTAYMELSSLRSEDTAVYYCARSYGNYPLMDY

WGQGTTVTVSSASTKGPSVFPLAPCSRSTSESTAALGCLVKDYFPEPVTVSWNSGALTS

GVHTFPAVLQSSGLYSLSSVVTVPSSNFGTQTYTCNVDHKPSNTKVDKTVERKCCVECP

PCPAPPVAGPSVFLFPPKPKDTLMISRTPEVTCVVVDVSHEDPEVQFNWYVDGVEVHNA

K<u>C</u>KPREEQFNSTFRVVSVLTVVHQDWLNGKEYKCKVSNKGLPAPIEKTISKTKGQPREP

QVYTLPPSREEMTKNQVSLTCLVKGFYPSDIAVEWESNGQPENNYKTTPPMLDSDGSFF

LYSKLTVDKSRWQQGNVFSCSVMHEALHNHYTQKSLSLSPGK

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or segments thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

Thus, it should be understood that although the present technology has been specifically disclosed by representative embodiments and optional features, modification and variation of the concepts herein disclosed can be resorted to by those skilled in the art, and such modifications and variations are considered within the scope of this technology.

What is claimed is:

1. A binding agent-drug conjugate comprising a binding agent and a payload,
   wherein the binding agent comprises:
   a CDR-L1 comprising the amino acid sequence of SEQ ID NO: 9 or 10;
   a CDR-L2 comprising the amino acid sequence of SEQ ID NO: 24 or STS;
   a CDR-L3 comprising the amino acid sequence of SEQ ID NO: 34 or 35;
   a CDR-H1 comprising the amino acid sequence of SEQ ID NO: 58 or 59;
   a CDR-H2 comprising the amino acid sequence of SEQ ID NO: 70 or 71; and
   a CDR-H3 comprising the amino acid sequence of SEQ ID NO: 87 or 88;
   wherein the payload comprises a pyrrolobenzodiazepine toxin and a linking group; and
   wherein the pyrrolobenzodiazepine toxin is covalently linked to the linking group, the linking group is covalently linked to the binding agent, and the binding agent specifically binds to an extracellular domain of mesenchymal epithelial transition factor (cMET).

2. The binding agent-drug conjugate of claim 1, wherein the pyrrolobenzodiazepine toxin comprises the structure of chemical formula I:

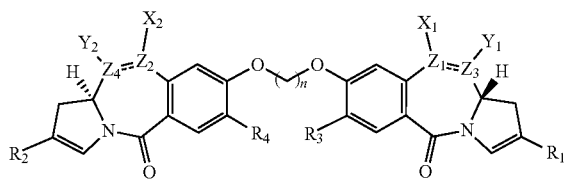

(I)

wherein
$Z_1$ and $Z_2$ are both N;
$Z_3$ and $Z_4$ are both C;
the double-dash lines ===== represent a single bond or a double bond;
n is 1 to 10;
each of $R_3$ and $R_4$ are independently H, or a $C_{1-4}$ alkoxyl; and
each of $R_1$ and $R_2$ are independently selected from the group consisting of H, $C_{1-5}$ alkyl, $C_{3-6}$ cycloalkyl, $C_{2-5}$ alkenyl, and a phenyl optionally substituted with $R_5$, wherein
$R_5$ is selected from the group consisting of —$NH_2$, —$NHR_6$, and a piperazinyl substituted with $R_7$ having the structure

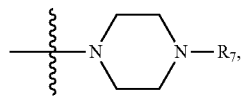

wherein $R_6$ comprises the linking group, and
$R_7$ is H, or a $C_{1-5}$ alkyl;

$X_1$ is null, a protecting group, or comprises the linking group;

$X_2$ is null, a protecting group, or comprises the linking group;

only one of $X_1$, $X_2$, $R_1$, and $R_2$ comprises the linking group; and each of $Y_1$ and $Y_2$ are independently either null, OH, or $SO_3H$;

provided that:

(i) when $X_1$ comprises the linking group, $Z_1$ ===== $Z_3$ is N—C, (ii) when $X_2$ comprises the linking group, $Z_2$ ===== $Z_4$ is N—C, (iii) when $X_1$ comprises the protecting group, $Z_1$ ===== $Z_3$ is N—C, and (iv) when $X_2$ comprises the protecting group, $Z_2$ ===== $Z_4$ is N—C, wherein null indicates the absence of the moiety or the presence of one or more hydrogens to complete a required valency.

3. The binding agent-drug conjugate of claim 1, wherein the linking group comprises the structure of chemical formula A:

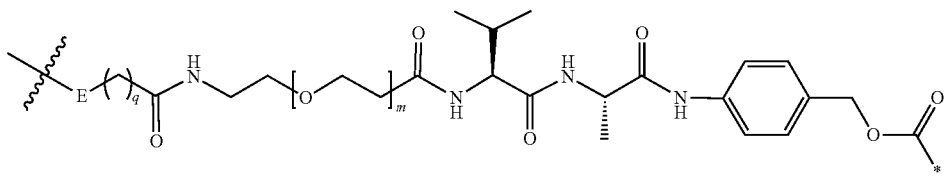

(A)

wherein
the asterisk indicates the point of attachment to the pyrrolobenzodiazepine toxin;
the wavy line indicates the point of attachment to the binding agent;
m is 1 to 20;
q is 0 to 10; and
E is a connecting group.

4. The binding agent-drug conjugate of claim 1, wherein the linking group comprises the structure of chemical formula B:

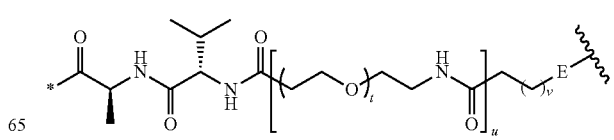

(B)

wherein the asterisk indicates the point of attachment to the pyrrolobenzodiazepine toxin; the wavy line indicates the point of attachment to the binding agent;

E is a connecting group;

v is 0 to 10; and u is 0 or 1; wherein when u is 1, t is 1 to 10.

5. The binding agent-drug conjugate of claim 2, wherein the protecting group has the following structure (D):

(D)

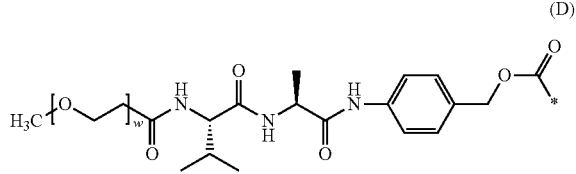

wherein the asterisk indicates the point of attachment to the pyrrolobenzodiazepine toxin; and w is 1 to 5.

6. The binding agent-drug conjugate of claim 1, wherein the payload comprises a structure selected from the group consisting of (II)

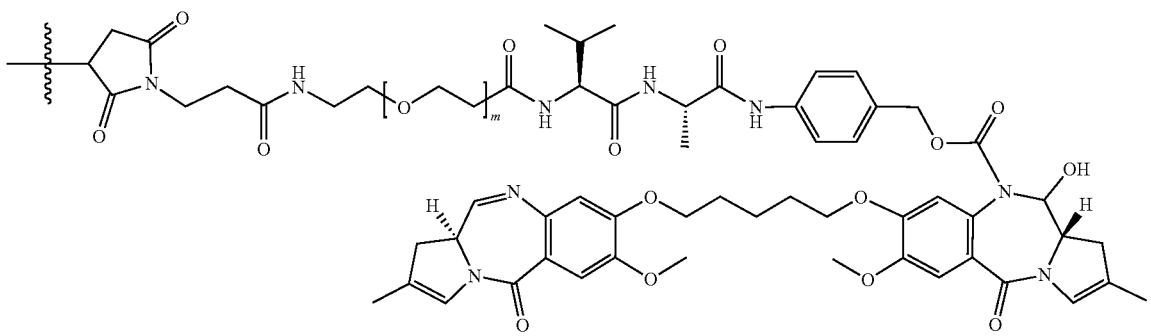

wherein m is 8;

(III)

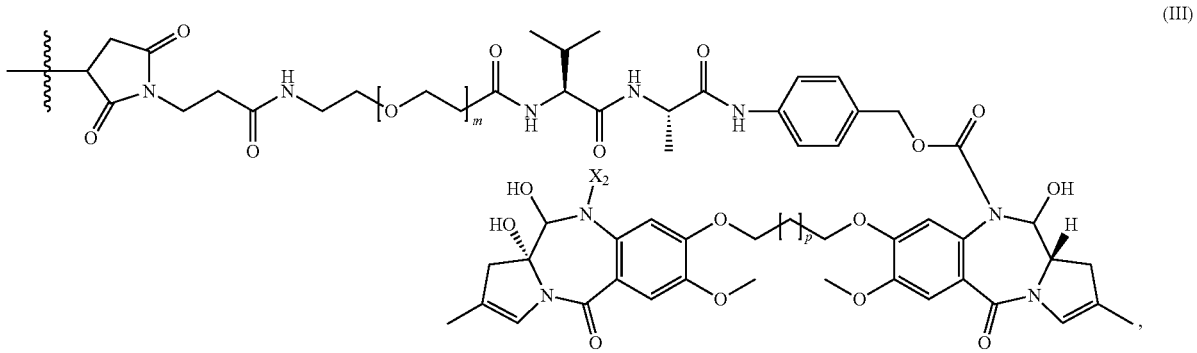

wherein m is 8, p is 3, and $X_2$ is a protecting group;

(V)

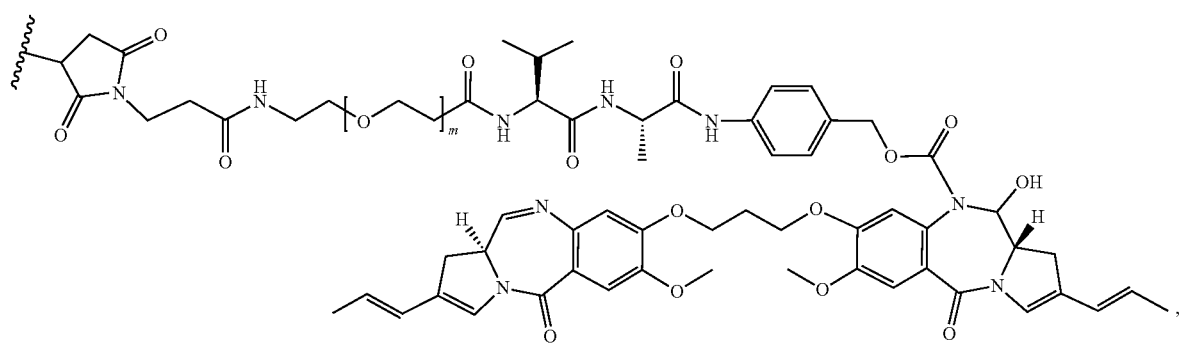

wherein m is 8;

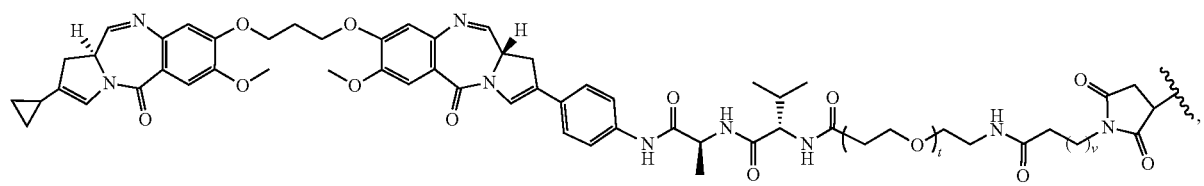

(VI)

wherein t is 8, and v is 1; and

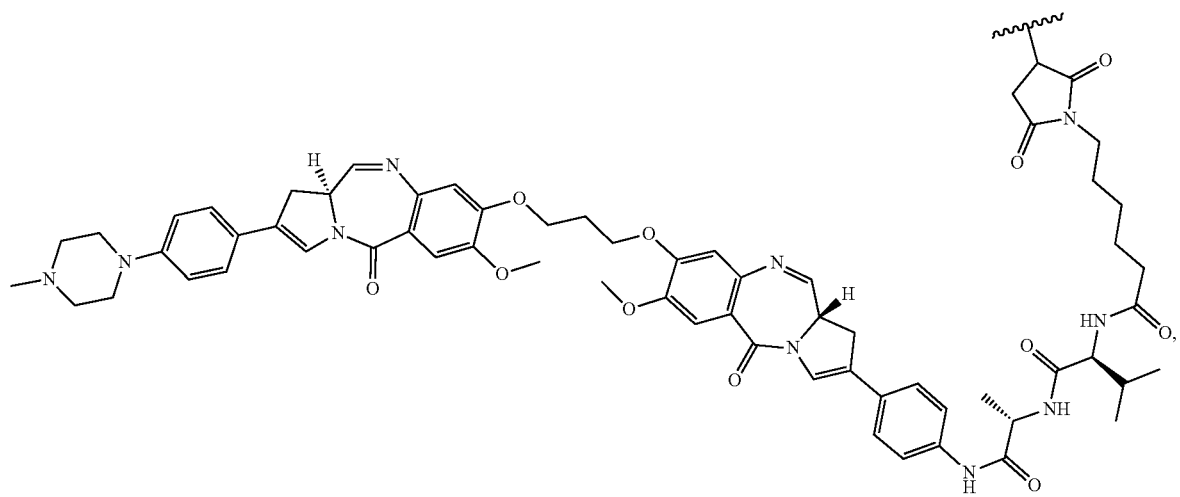

(VII)

wherein the wavy line indicates the point of attachment to the binding agent.

7. The binding agent-drug conjugate of claim 6, wherein the protecting group of $X_2$ has the following structure (D):

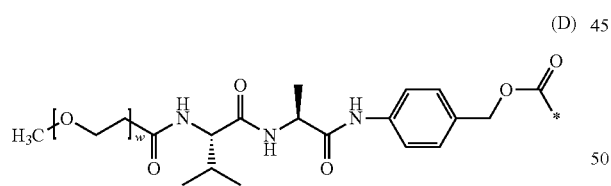

(D)

wherein the asterisk indicates the point of attachment to the payload; and
w is 1 to 5.

8. The binding agent-drug conjugate of claim 1, wherein the binding agent is an antibody, or a binding fragment thereof.

9. The binding agent-drug conjugate of claim 1, wherein the binding agent binds specifically to a human cMET, monkey cMET or rat cMET.

10. The binding agent-drug conjugate of claim 1, wherein the binding agent specifically binds to the extracellular domain of a cMET variant.

11. The binding agent-drug conjugate of claim 1, wherein the binding agent comprises a light chain variable region comprising SEQ ID NO: 47 and a heavy chain variable region comprising SEQ ID NO: 108.

12. A binding agent-drug conjugate comprising a binding agent and a payload,
wherein the binding agent comprises:
a heavy chain variable region comprising an amino acid sequence selected from SEQ ID NOs: 105, 106, 107 and 108, and
a light chain variable region comprising an amino acid sequence selected from SEQ ID NOs: 46, 47, 48 and 49, and
the payload comprises a pyrrolobenzodiazepine toxin and a linking group;
wherein the pyrrolobenzodiazepine toxin is covalently linked to the linking group, the linking group is covalently linked to the binding agent, and the binding agent specifically binds to an extracellular domain of mesenchymal epithelial transition factor (cMET).

13. A method of treating a subject having a neoplastic disorder or cancer comprising:
a) providing a subject having, or suspected of having, a neoplastic disorder or cancer; and
b) administering to the subject a therapeutically effective amount of the binding agent-drug conjugate of claim 1.

14. The method of claim 13, wherein the neoplastic disorder or cancer comprises a carcinoma, sarcoma, neuroblastoma, glioblastoma, myeloma, lymphoma, melanoma or a solid or soft tissue tumor.

15. The method of claim 14, wherein the neoplastic disorder or cancer comprises a bladder cancer, breast cancer, colorectal cancer, gastric cancer, pancreatic cancer, esophageal cancer, liver cancer, hepatocellular cancer, hypopharynx cancer, lung cancer, adenocarcinoma, ovarian cancer or renal cancer.

16. The method of claim 14, wherein the neoplastic disorder or cancer comprises a pancreatic adenocarcinoma, pancreatic neuroendocrine cancer, colorectal adenocarcinoma, small intestinal malignancy, cholangiocarcinoma, non-small cell lung cancer (NSCLC), thyroid carcinoma, esophageal or esophagogastric junction (EGJ) cancer, gastric adenocarcinoma, liver hepatocellular carcinoma, head and neck squamous carcinoma, female genital tract malignancy, breast carcinoma, triple negative breast cancer, lung small cell carcinoma, ovarian surface epithelial carcinoma, retroperitoneal or peritoneal sarcoma, prostatic adenocarcinoma, neuroendocrine tumor, gastrointestinal stromal tumor, glioblastoma or non-epithelial ovarian cancer.

* * * * *